US012473527B2

(12) United States Patent
Lopes Ferreira et al.

(10) Patent No.: US 12,473,527 B2
(45) Date of Patent: Nov. 18, 2025

(54) OPTIMIZED GENETIC TOOL FOR MODIFYING BACTERIA

(71) Applicant: IFP ENERGIES NOUVELLES, Rueil-Malmaison (FR)

(72) Inventors: Nicolas Lopes Ferreira, Croisilles (FR); Rèmi Hocq, Paris (FR); François Wasels, Metz (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 894 days.

(21) Appl. No.: 17/611,962

(22) PCT Filed: May 22, 2020

(86) PCT No.: PCT/FR2020/050853
§ 371 (c)(1),
(2) Date: Nov. 17, 2021

(87) PCT Pub. No.: WO2020/240122
PCT Pub. Date: Dec. 3, 2020

(65) Prior Publication Data

US 2022/0243170 A1 Aug. 4, 2022

(30) Foreign Application Priority Data

May 24, 2019 (FR) ...................................... 1905485

(51) Int. Cl.
*C12N 1/20* (2006.01)
*C12N 9/22* (2006.01)
(Continued)

(52) U.S. Cl.
CPC ............... *C12N 1/205* (2021.05); *C12N 9/22* (2013.01); *C12N 15/102* (2013.01);
(Continued)

(58) Field of Classification Search
CPC ................ C12N 15/74; C12N 2310/20; C12R 2001/145
See application file for complete search history.

(56) References Cited

U.S. PATENT DOCUMENTS

2017/0037415 A1* 2/2017 Krabben ............ C12N 15/1024
2018/0105847 A1 4/2018 Koepke et al.
(Continued)

FOREIGN PATENT DOCUMENTS

WO WO-2019213592 A1 * 11/2019 ........... A61K 35/768
WO WO 2020/128379 6/2020

OTHER PUBLICATIONS

Máté de Gérando H, Wasels F, Bisson A, Clement B, Bidard F, Jourdier E, López-Contreras AM, Lopes Ferreira N. Genome and transcriptome of the natural isopropanol producer Clostridium beijerinckii DSM6423. BMC Genomics. Apr. 10, 2018;19(1):242. doi: 10.1186/s12864-018-4636-7. (Year: 2018).*
(Continued)

*Primary Examiner* — Ram R Shukla
*Assistant Examiner* — Africa M Mcleod
(74) *Attorney, Agent, or Firm* — SALIWANCHIK, LLOYD & EISENSCHENK

(57) ABSTRACT

Methods, tools and kits allowing genetic modification, involving in particular a nucleic acid sequence used to facilitate the transformation of bacteria of the phylum Firmicutes, the sequence comprising i) all or part of the sequence SEQ ID NO: 126 and ii) a sequence allowing the modification of the genetic material of a bacterium and/or expression, within a bacterium, of a DNA sequence partially or totally absent from the genetic material present within the wild-type version of the bacterium are provided. Also pro-
(Continued)

vided are genetically modified bacteria and uses thereof, in particular for producing a solvent, preferably on an industrial scale.

3 Claims, 34 Drawing Sheets

Specification includes a Sequence Listing.

(51) Int. Cl.

| | |
|---|---|
| ***C12N 15/10*** | (2006.01) |
| ***C12N 15/11*** | (2006.01) |
| ***C12N 15/113*** | (2010.01) |
| ***C12N 15/74*** | (2006.01) |
| ***C12N 15/90*** | (2006.01) |
| ***C12R 1/145*** | (2006.01) |

(52) U.S. Cl.
CPC .......... *C12N 15/111* (2013.01); *C12N 15/113* (2013.01); *C12N 15/74* (2013.01); *C12N 15/902* (2013.01); *C12N 2310/20* (2017.05); *C12R 2001/145* (2021.05)

(56) References Cited

U.S. PATENT DOCUMENTS

2018/0305680 A1* 10/2018 Wasels .................. C12N 15/63
2019/0367947 A1* 12/2019 Lopes Ferreira .... C12N 15/902

OTHER PUBLICATIONS

George, H. A., et al. "Acetone, Isopropanol, and Butanol Production by Clostridium Beijerinckii (Syn. Clostridium Butylicum) and Clostridium Aurantibutyricum." Applied and Environmental Microbiology, vol. 45, No. 3, Mar. 1983, pp. 1160-1163, https://doi.org/10.1128/aem.45.3.1160-1163.1983. (Year: 1983).*

Herrero, Javier, et al. "Ensembl Comparative Genomics Resources." Database, vol. 2016, 2016, p. bav096, https://doi.org/10.1093/database/bav096. (Year: 2016).*

"Leibniz Institute DSMZ: Clostridium Beijerinckii DSM 6423." Dsmz.de, 2024, www.dsmz.de/collection/catalogue/details/culture/DSM-6423. Accessed Dec. 17, 2024. (Year: 2024).*

Köpke, Michael, et al. "Clostridium Difficile Is an Autotrophic Bacterial Pathogen." PLoS ONE, vol. 8, No. 4, Apr. 23, 2013, p. e62157, https://doi.org/10.1371/journal.pone.0062157. Accessed Feb. 5, 2020. (Year: 2013).*

Nakamura, Shinichi, et al. "Antimicrobial Susceptibility of Clostridium Difficile from Different Sources." Microbiology and Immunology, vol. 26, No. 1, Jan. 1982, pp. 25-30, https://doi.org/10.1111/j.1348-0421.1982.tb00150.x. Accessed Apr. 10, 2025. (Year: 1982).*

Smits, Wiep Klaas, et al. "Plasmids of Clostridioides Difficile." Current Opinion in Microbiology, vol. 65, Nov. 11, 2021, pp. 87-94, https://doi.org/10.1016/j.mib.2021.10.016. Accessed Apr. 10, 2025. (Year: 2021).*

Dornbusch, K, et al. "Antibiotic Susceptibility of Clostridium Species Isolated from Human Infections." Scandinavian Journal of Infectious Diseases, vol. 7, No. 2, 1975, pp. 127-134, pubmed.ncbi.nlm.nih.gov/170668/, https://doi.org/10.3109/inf.1975.7.issue-2.09. (Year: 1975).*

Skarin, Hanna, and Bo Segerman. "Plasmidome Interchange between Clostridium Botulinum, Clostridium Novyi and Clostridium Haemolyticum Converts Strains of Independent Lineages into Distinctly Different Pathogens." PLoS ONE, vol. 9, No. 9, Sep. 25, 2014, p. e107777. (Year: 2014).*

Diallo, M. et al. "Adaptation and application of a two-plasmid inducible CRISPR-Cas9 system in *Clostridium beijerinckii" Methods*, 2020 (available online Jul. 27, 2019), pp. 51-60, vol. 172.

Gu, Y. et al. "Curing the endogenous megaplasmid in *Clostridium saccharoperbutylacetonicum* N1-4 (HMT) using CRISPR-Cas9 and preliminary investigation of the role of the plasmid for the strain metabolism" *Fuel*, 2019 (available online Oct. 3, 2018), pp. 1559-1566, vol. 236.

Mate de Gerando, H. et al. "Genome and transcriptome of the natural isopropanol producer *Clostridium beijerinckii* DSM6423" *BMC Genomics*, 2018, pp. 1-12. Vol. 19, No. 242.

Wang, Y. et al. "Markerless chromosomal gene deletion in *Clostridium beijerinckii* using CRISPR/Cas9 system" *Journal of Biotechnology*, 2015, pp. 1-5, vol. 200.

Wasels, F. et al. "A two-plasmid inducible CRISPR/Cas9 genome editing tool for *Clostridium acetobutylicum" Journal of Microbiological Methods*, 2017, pp. 5-11, vol. 140.

* cited by examiner

SEQUENCE LISTING

<160> NUMBER OF SEQ ID NOS: 134

<210> SEQ ID NO 1
<211> LENGTH: 50
<212> TYPE: DNA
<213> ORGANISM: Artificial Sequence
<220> FEATURE:
<223> OTHER INFORMATION: Primer deltacatB-fwd

<400> SEQUENCE: 1
tgttatggat tataagcggc tcgaggacgt caaaccatgt taatcattgc 50

<210> SEQ ID NO 2
<211> LENGTH: 50
<212> TYPE: DNA
<213> ORGANISM: Artificial Sequence
<220> FEATURE:
<223> OTHER INFORMATION: Primer deltacatB-rev

<400> SEQUENCE: 2
aatctatcac tgatagggac tcgagcaatt tcaccaaaga attcgctagc 50

<210> SEQ ID NO 3
<211> LENGTH: 28
<212> TYPE: DNA
<213> ORGANISM: Artificial Sequence
<220> FEATURE:
<223> OTHER INFORMATION: Primer RH076

<400> SEQUENCE: 3
catataataa aaggaaacct cttgatcg 28

<210> SEQ ID NO 4
<211> LENGTH: 20
<212> TYPE: DNA
<213> ORGANISM: Artificial Sequence
<220> FEATURE:
<223> OTHER INFORMATION: Primer RH077

<400> SEQUENCE: 4
attgccagcc taacacttgg 20

<210> SEQ ID NO 5
<211> LENGTH: 50
<212> TYPE: DNA
<213> ORGANISM: Artificial Sequence
<220> FEATURE:
<223> OTHER INFORMATION: Primer RH001

<400> SEQUENCE: 5
atctccatgg acgcgtgacg tcgacataag gtaccaggaa ttagagcagc 50

<210> SEQ ID NO 6
<211> LENGTH: 43
<212> TYPE: DNA
<213> ORGANISM: Artificial Sequence
<220> FEATURE:
<223> OTHER INFORMATION: Primer RH002

<400> SEQUENCE: 6
tctatctcca gctctagacc attattattc ctccaagttt gct 43

<210> SEQ ID NO 7
<211> LENGTH: 40
<212> TYPE: DNA
<213> ORGANISM: Artificial Sequence
<220> FEATURE:
<223> OTHER INFORMATION: Primer RH003

<400> SEQUENCE: 7
ataatggtct agagctggag atagattatt tggtactaag 40

<210> SEQ ID NO 8
<211> LENGTH: 50
<212> TYPE: DNA
<213> ORGANISM: Artificial Sequence
<220> FEATURE:
<223> OTHER INFORMATION: Primer RH004

<400> SEQUENCE: 8
tatgaccatg attacgaatt cgagctcgaa gcgcttatta ttgcattagc 50

<210> SEQ ID NO 9
<211> LENGTH: 22
<212> TYPE: DNA
<213> ORGANISM: Artificial Sequence
<220> FEATURE:
<223> OTHER INFORMATION: Primer pEX-fwd

<400> SEQUENCE: 9
cagattgtac tgagagtgca cc 22

<210> SEQ ID NO 10
<211> LENGTH: 23
<212> TYPE: DNA
<213> ORGANISM: Artificial Sequence
<220> FEATURE:
<223> OTHER INFORMATION: Primer pEX-rev

<400> SEQUENCE: 10
gtgagcggat aacaatttca cac 23

<210> SEQ ID NO 11
<211> LENGTH: 32
<212> TYPE: DNA
<213> ORGANISM: Artificial Sequence
<220> FEATURE:
<223> OTHER INFORMATION: Primer pEC750C-fwd

<400> SEQUENCE: 11
caatattcca caatattata ttataagcta gc 32

<210> SEQ ID NO 12
<211> LENGTH: 17
<212> TYPE: DNA
<213> ORGANISM: Artificial Sequence
<220> FEATURE:

<223> OTHER INFORMATION: Primer M13-rev

<400> SEQUENCE: 12
caggaaacag ctatgac 17

<210> SEQ ID NO 13
<211> LENGTH: 22
<212> TYPE: DNA
<213> ORGANISM: Artificial Sequence
<220> FEATURE:
<223> OTHER INFORMATION: Primer RH010

<400> SEQUENCE: 13
cggatattgc attaccagta gc 22

<210> SEQ ID NO 14
<211> LENGTH: 24
<212> TYPE: DNA
<213> ORGANISM: Artificial Sequence
<220> FEATURE:
<223> OTHER INFORMATION: Primer RH011

<400> SEQUENCE: 14
ttatcaatct cttacacatg gagc 24

<210> SEQ ID NO 15
<211> LENGTH: 24
<212> TYPE: DNA
<213> ORGANISM: Artificial Sequence
<220> FEATURE:
<223> OTHER INFORMATION: Primer RH025

<400> SEQUENCE: 15
tagtatgccg ccattattac gaca 24

<210> SEQ ID NO 16
<211> LENGTH: 20
<212> TYPE: DNA
<213> ORGANISM: Artificial Sequence
<220> FEATURE:
<223> OTHER INFORMATION: Primer RH134

<400> SEQUENCE: 16
gtcgacgtgg aattgtgagc 20

<210> SEQ ID NO 17
<211> LENGTH: 3658
<212> TYPE: DNA
<213> ORGANISM: Artificial Sequence
<220> FEATURE:
<223> OTHER INFORMATION: pEX-A258-deltacatB

<400> SEQUENCE: 17
ctcgagctgc agcaaaaaaa gcaccgactc ggtgccactt tttcaagttg ataacggact 60
agccttattt taacttgcta tttctagctc taaaactgtg gtctctcttt tcgttgatgg 120
tggaatgata agggtttgca ccttaatttc tcctattgag aaaatcgtct cttctcagac 180
gtcaaaccat gttaatcatt gcttttatca aaaataggat ccactctatc attgatagag 240
tttgaaactc tatcattgat agagtataat atctttgttc atgtacatca tgctatctgt 300
gagttttaga gctagaaata gcaagttaaa ataaggctag tccgttatca acttgaaaaa 360
gtggcaccga gtcggtgctt tttttgaagc ttgtctttac acttttgccc attaattttt 420
gagttcctta tttttaggga gcttttatta tttttatcat gaaaatttca taaaatactc 480

```
ataaactaag gatgtcttca taatcagatt agtactccat tttcaatcca tttaatctgg    540
gaatatgata ttttaattac gtattattta agatatatta acgtgtaata taataccccg    600
caaatattaa ttatcacata catatccccc ctttattggg gcattttttg tacccattat    660
tttagtattg tgcagtactt aaataaaaaa atgccgcaaa ttcattttta ttgaataatg    720
cggtatttct tctattcttt atttttatta ctctataaat aatgtaatca agacatgact    780
atctaaatat atgatatctt aattcataat tcgggcctcc taaaaatttt cgtaattcta    840
ttttagaagg ctttttttccg tgacctagcc atttcaatct cctttttaca atgatattta   900
cgctttagtt tattatagca cattctgtaa taccgaacta ttcaattttc agagaccatt    960
ttttattgat tcataactta agaatactac gaattactct aatattttac tttttcttat   1020
ctcttgttat tttaacatcg gaattactac taatattaat ttttattttt ccatccgcat   1080
ttgctccaac attttttttaa ctatactttc cttttgttaa taaattatgt tattgttgaa  1140
caatataaga aaagtgcgta acattttttta ttaaaaataa ttaggtattt ctatctgtgg  1200
ggtaccctcg aggtggcagc tctagagcta gcgaattctt tggtgaaatt gttatccgct   1260
cacaattcca cacaacatac gagccggaag cataaagtgt aaagcctggg gtgcctaatg   1320
agtgagctaa ctcacattaa ttgcgttgcg ctcactgccc gctttccagt cgggaaacct   1380
gtcgtgccag ctgcattaat gaatcggcca acgcgcgggg agaggcggtt tgcgtattgg   1440
gcgctcttcc gcttcctcgc tcactgactc gctgcgctcg gtcgttcggc tgcggcgagc   1500
ggtatcagct cactcaaagg cggtaatacg gttatccaca gaatcagggg ataacgcagg   1560
aaagaacatg tgagcaaaag gccagcaaaa ggccaggaac cgtaaaaagg ccgcgttgct   1620
ggcgtttttc cataggctcc gcccccctga cgagcatcac aaaaatcgac gctcaagtca   1680
gaggtggcga aacccgacag gactataaag ataccaggcg tttccccctg gaagctccct   1740
cgtgcgctct cctgttccga ccctgccgct taccggatac ctgtccgcct ttctcccttc   1800
gggaagcgtg gcgctttctc atagctcacg ctgtaggtat ctcagttcgg tgtaggtcgt   1860
tcgctccaag ctgggctgtg tgcacgaacc ccccgttcag cccgaccgct gcgccttatc   1920
cggtaactat cgtcttgagt ccaacccggt aagacacgac ttatcgccac tggcagcagc   1980
cactggtaac aggattagca gagcgaggta tgtaggcggt gctacagagt tcttgaagtg   2040
gtggcctaac tacggctaca ctagaagaac agtatttggt atctgcgctc tgctgaagcc   2100
agttaccttc ggaaaaagag ttggtagctc ttgatccggc aaacaaacca ccgctggtag   2160
cggtggtttt tttgtttgca agcagcagat tacgcgcaga aaaaaaggat ctcaagaaga   2220
tcctttgatc ttttctacgg ggtctgacgc tcagtggaac gaaaactcac gttaagggat   2280
tttggtcatg agattatcaa aaaggatctt cacctagatc cttttaaatt aaaaatgaag   2340
ttttaaatca atctaaagta tatatgagta aacttggtct gacagttacc aatgcttaat   2400
cagtgaggca cctatctcag cgatctgtct atttcgttca tccatagttg cctgactccc   2460
cgtcgtgtag ataactacga tacgggaggg cttaccatct ggccccagtg ctgcaatgat   2520
accgcgcgaa ccacgctcac cggctccaga tttatcagca ataaaccagc cagccggaag   2580
ggccgagcgc agaagtggtc ctgcaacttt atccgcctcc atccagtcta ttaattgttg   2640
ccgggaagct agagtaagta gttcgccagt taatagtttg cgcaacgttg ttgccattgc   2700
tacaggcatc gtggtgtcac gctcgtcgtt tggtatggct tcattcagct ccggttccca   2760
acgatcaagg cgagttacat gatcccccat gttgtgcaaa aaagcggtta gctccttcgg   2820
```

-continued

```
tcctccgatc gttgtcagaa gtaagttggc cgcagtgtta tcactcatgg ttatggcagc   2880

actgcataat tctcttactg tcatgccatc cgtaagatgc ttttctgtga ctggtgagta   2940

ctcaaccaag tcattctgag aatagtgtat gcggcgaccg agttgctctt gcccggcgtc   3000

aatacgggat aataccgcgc cacatagcag aactttaaaa gtgctcatca ttggaaaacg   3060

ttcttcgggg cgaaaactct caaggatctt accgctgttg agatccagtt cgatgtaacc   3120

cactcgtgca cccaactgat cttcagcatc ttttactttc accagcgttt ctgggtgagc   3180

aaaaacagga aggcaaaatg ccgcaaaaaa gggaataagg gcgacacgga aatgttgaat   3240

actcatactc ttcctttttc aatattattg aagcatttat cagggttatt gtctcatgag   3300

cggatacata tttgaatgta tttagaaaaa taaacaaata ggggttccgc gcacatttcc   3360

ccgaaaagtg ccacctgacg tctaagaaac cattattatc atgacattaa cctataaaaa   3420

taggcgtatc acgaggccct ttcgtctcgc gcgtttcggt gatgacggtg aaaacctctg   3480

acacatgcag ctcccggaga cggtcacagc ttgtctgtaa gcggatgccg ggagcagaca   3540

agcccgtcag ggcgcgtcag cgggtgttgg cgggtgtcgg ggctggctta actatgcggc   3600

atcagagcag attgtactga gagtttggca attggtcgac ctcgagggcg cgcccgta     3658
```

<210> SEQ ID NO 18
<211> LENGTH: 660
<212> TYPE: DNA
<213> ORGANISM: Clostridium beijerinckii

<400> SEQUENCE: 18

```
atgaatttta atttgataga tattaatcat tggagtagaa agccatactt tgaacattat     60

ttaaacaatg tgaaatgtac ttatagtatg actgccaata tagaaataac tgatttattg    120

tatgaaatta aacttaaaaa tattaaattt tatcctaccc ttatttatat gattgcaact    180

gtggttaata agcataaaga attccgtatt tgttttgatc atgaaggtag tttaggatat    240

tgggatagca tgaatccaag ctatactatt tttcataaag aaaacgaaac attttcaagt    300

atttggacgg aatataacaa aagtttttta cgtttttata gtgattatct tgacgatata    360

aaaaactatg gaaatatcat gaagtttact ccgaaatcaa atgaacctga caatacattt    420

tctgtatcaa gcattccttg ggtgagtttt acaggattta acttgaatgt gtataatgaa    480

ggaacatatt taattcctat ttttactgca ggaaagtatt tcaaacaaga aaataaaata    540

tttattccta tatcaataca agtacatcat gctatctgtg acggttatca tgctagtaga    600

tttattaatg aaatgcaaga attagcattt agttttcaag aatggttaga aaataaataa    660
```

<210> SEQ ID NO 19
<211> LENGTH: 160
<212> TYPE: DNA
<213> ORGANISM: Artificial Sequence
<220> FEATURE:
<223> OTHER INFORMATION: gRNA expression cassette

<400> SEQUENCE: 19

```
actctatcat tgatagagtt tgaaactcta tcattgatag agtataatat ctttgttcat     60

gtacatcatg ctatctgtga gttttagagc tagaaatagc aagttaaaat aaggctagtc    120

cgttatcaac ttgaaaaagt ggcaccgagt cggtgctttt                          160
```

<210> SEQ ID NO 20
<211> LENGTH: 808
<212> TYPE: DNA
<213> ORGANISM: Artificial Sequence
<220> FEATURE:
<223> OTHER INFORMATION: Editing template

<400> SEQUENCE: 20
gtctttacac ttttgcccat taatttttga gttccttatt tttagggagc ttttattatt 60
tttatcatga aaatttcata aaatactcat aaactaagga tgtcttcata atcagattag 120
tactccattt tcaatccatt taatctggga atatgatatt ttaattacgt attatttaag 180
atatattaac gtgtaatata ataccccgca aatattaatt atcacataca tatccccccct 240 ttattggggc attttttgta cccattattt tagtattgtg cagtacttaa ataaaaaaat 300
gccgcaaatt catttttatt gaataatgcg gtatttcttc tattctttat ttttattact 360
ctataaataa tgtaatcaag acatgactat ctaaatatat gatatcttaa ttcataattc 420
gggcctccta aaaattttcg taattctatt ttagaaggct tttttccgtg acctagccat 480
ttcaatctcc tttttacaat gatatttacg ctttagttta ttatagcaca ttctgtaata 540
ccgaactatt caattttcag agaccatttt ttattgattc ataacttaag aatactacga 600
attactctaa tattttactt tttcttatct cttgttattt taacatcgga attactacta 660
atattaattt ttatttttcc atccgcattt gctccaacat ttttttaact atactttcct 720
tttgttaata aattatgtta ttgttgaaca atataagaaa agtgcgtaac atttttttatt 780 aaaaataatt aggtatttct atctgtgg 808

<210> SEQ ID NO 21
<211> LENGTH: 9954
<212> TYPE: DNA
<213> ORGANISM: Artificial Sequence
<220> FEATURE:
<223> OTHER INFORMATION: pCas9ind-deltacatB

<400> SEQUENCE: 21
catggataaa aagtacagta ttggtctaga cataggaact aactctgttg ggtgggctgt 60
tataacagat gaatataaag ttccatcaaa aaaatttaaa gtattaggaa acactgatag 120
acattcaata aaaaaaaact tgataggtgc tttattattc gattcaggag agactgctga 180
agctacacgt ttaaaaagaa cagctagacg tagatataca agaagaaaaa ataggatatg 240
ttatcttcaa gaaattttta gtaatgaaat ggcaaaagtt gatgattcat tctttcacag 300
actagaagaa agtttcttag ttgaagaaga taagaagcat gaaagacacc ctatttttgg 360
taatatcgta gatgaagtag catatcatga gaagtatcca actatctatc atttaagaaa 420
gaaattagtt gattctacag ataaagctga tctgagatta atatatttag ctttagctca 480
tatgattaaa tttagaggac attttttaat agaaggtgat ttaaacccag acaacagcga 540
tgtagataaa ttatttatcc aattagttca aacttataat caattattcg aagagaatcc 600
aattaatgca agtggtgtag acgctaaggc tatattatca gctagattat caaaatctag 660
aagattagaa aatctaatag ctcaacttcc tggagaaaag aaaaatggac tttttgggaa 720
cctaatagct ctctcactcg gactaacacc aaattttaaa agcaattttg atcttgctga 780
agacgcaaag ttacaactat caaaggatac atacgatgat gatttagata atttgttagc 840
tcaaataggt gatcaatatg ctgatttgtt tcttgcagca aaaaacttaa gtgatgcaat 900
tttactatca gatatactta gagtaaatac agaaataaca aaggctcctt tatcagcaag 960
tatgattaaa cgatatgatg agcatcatca agatttaaca ttattaaagg cacttgtaag 1020
acaacaatta ccagaaaaat ataaagaaat tttctttgat caatctaaaa atggatatgc 1080

```
tggatatata gacggtggag caagtcaaga agagttttat aaatttataa agcctatttt   1140
agaaaaaatg gatggaactg aagaattact tgttaaactt aacagagaag atttacttag   1200
aaaacaaaga acttttgata atggttcaat tcctcaccaa attcatttag gagaattaca   1260
tgctatacta agaagacaag aagattttta tccatttctt aaagataata gagaaaaaat   1320
tgaaaaaatt ttaactttta gaataccata ttatgtagga ccacttgcaa ggggaaattc   1380
aagatttgca tggatgacta gaaaatcaga agaaactata accccgtgga attttgaaga   1440
agtagtagat aaaggagcta gtgctcaatc atttatagaa agaatgacaa attttgataa   1500
gaatcttcct aacgaaaagg ttttgccaaa gcatagcctt ctttatgagt attttacagt   1560
ttataatgag cttactaaag taaaatacgt tacagaagga atgagaaaac cagcattttt   1620
gtctggtgaa caaaagaaag caatagtaga cctattattt aaaacaaata ggaaggttac   1680
cgtaaagcaa cttaaagaag attacttcaa aaaaattgaa tgctttgata gtgttgaaat   1740
atcaggagtt gaagatagat ttaatgcttc acttggtaca tatcacgatc tcttaaaaat   1800
tataaaagat aaggattttt tagataatga agaaaatgaa gatattcttg aagatatagt   1860
attaacattg acactttttg aagatagaga aatgatagaa gaaagattaa aaacatatgc   1920
acatcttttt gatgataagg ttatgaagca acttaaaaga agaagatata caggttgggg   1980
acgtttgtca agaaagctaa ttaatggtat tagagataaa caatcaggaa agactattct   2040
cgattttctt aaatcagatg gatttgctaa tagaaacttt atgcaattaa ttcatgatga   2100
ttctcttact ttcaaagagg atattcaaaa ggctcaagtt tctggacaag gcgatagctt   2160
acacgaacac attgctaacc ttgcagggag ccccgctatc aaaaaaggaa ttttacaaac   2220
agttaaagtt gtagatgaac ttgttaaagt tatgggaaga cacaaacctg agaatatagt   2280
tatagaaatg gccagagaaa atcaaacaac acaaaaagga caaaaaaatt ctagagagag   2340
aatgaagaga attgaagaag gaataaaaga gctaggatca caaatattaa aagaacatcc   2400
agttgaaaat actcaattgc aaaatgaaaa gttatatttg tattacttac aaaatggaag   2460
agatatgtat gttgatcaag aactcgatat taatagatta agtgactatg atgttgatca   2520
tattgttcct caatcatttt taaaagatga ttcaatcgat aacaaagtat taactagatc   2580
agataaaaat agaggaaagt cagataatgt accatctgaa gaagttgtta aaaaaatgaa   2640
gaactattgg agacaacttt taaatgcaaa gctaattaca caaagaaaat ttgacaattt   2700
aacaaaagca gaaagaggag gattaagcga attagacaaa gctggattta taaaaagaca   2760
acttgttgag acaagacaaa taactaagca tgttgctcaa atacttgatt caagaatgaa   2820
tacaaaatat gatgaaaatg ataaattaat cagagaagta aaagtaataa cattaaagtc   2880
aaaattagta tcagatttca gaaaggattt tcaattttac aaagttcgtg aaataaataa   2940
ctatcatcat gctcatgatg catacttaaa tgctgttgta ggaactgctc ttattaagaa   3000
atatcctaaa ctagaaagcg aatttgttta tggagattat aaagtttatg atgtgcgcaa   3060
aatgatcgcg aaatccgaac aagaaatcgg taaggctaca gcaaaatatt tcttttatag   3120
taatataatg aatttttta agacagaaat aactttggct aatggtgaaa tcagaaaaag   3180
accacttatc gaaacaaatg gagagacagg agaaatagta tgggataaag gaagagattt   3240
tgctactgtt agaaaagtac taagtatgcc acaagtaaat atcgtaaaga aaactgaagt   3300
tcaaactgga ggtttctcta aggaatcaat tttacctaag agaaattcag ataagttaat   3360
tgcaaggaaa aaagattggg acccaaaaaa atacggtggt tttgatagtc caacagttgc   3420
ctatagtgtt cttgtagtag cgaaagttga gaaaggtaag tcaaaaaagt tgaaaagcgt   3480
```

-continued

```
aaaagaactt cttggtatca caattatgga aagatcttca tttgaaaaaa atccaattga   3540
ctttttagaa gctaagggtt ataaagaagt taaaaaggat ttaatcataa aactaccaaa   3600
gtatagtcta tttgaactcg aaaacggaag aaaacgaatg ctcgctagcg caggagaact   3660
tcaaaaagga aatgaacttg cgctgccatc aaagtatgta aatttcttat atttagcttc   3720
tcattatgag aaattaaaag gatcaccaga ggataatgaa caaaagcaac tatttgtaga   3780
acaacacaaa cattatttag atgaaataat agaacaaata tctgaatttt ctaaaagagt   3840
tatacttgcc gacgcaaatc tagataaggt gctttcagcg tataataaac acagagataa   3900
accaataaga gaacaagcag aaaacattat ccatcttttt acattaacta atcttggtgc   3960
accagctgca tttaagtact ttgatacaac aatagataga aaaagataca catctactaa   4020
agaagtatta gacgcaactt taatacatca atctattaca gggctttatg aaacaagaat   4080
tgatttaagt caactaggcg gagattaagt cgacaaagta ttgttaaaaa taactctgta   4140
gaattataaa ttagttctac agagttattt tttgacccgg gtatattgat aaaaataata   4200
atagtgggta taattaagtt gttaggaggt tagttagaat gatgtcaaga ttagataaaa   4260
gtaaagtgat taacagcgca ttagagctgc ttaatgaggt cggaatcgaa ggtttaacaa   4320
cccgtaaact cgcccagaag ctaggtgtag agcagcctac attgtattgg catgtaaaaa   4380
ataagcgggc tttgctcgac gccttagcca ttgagatgtt agataggcac catactcact   4440
tttgcccttt agaaggggaa agctggcaag atttttttacg taataacgct aaaagtttta   4500
gatgtgcttt actaagtcat cgcgatggag caaaagtaca tttaggtaca cggcctacag   4560
aaaaacagta tgaaactctc gaaaatcaat tagccttttt atgccaacaa ggtttttcac   4620
tagagaatgc attatatgca ctcagcgctg tggggcattt tactttaggt tgcgtattgg   4680
aagatcaaga gcatcaagtc gctaaagaag aaagggaaac acctactact gatagtatgc   4740
cgccattatt acgacaagct atcgaattat ttgatcacca aggtgcagag ccagccttct   4800
tattcggcct tgaattgatc atatgcggat tagaaaaaca acttaaatgt gaaagtgggt   4860
cttaaaagca gcataacctt tttccgtgat ggtaacttca cggtaaccaa gatgtcgagt   4920
tgagctcgaa ttcgtaatca tggtcatagc tgtttcctgt gtgaaattgt tatccgctca   4980
caattccaca caacatacga gccggaagca taaagtgtaa agcctggggt gcctaatgag   5040
tgagctaact cacattaatt gcgttgcgct cactgcccgc tttccagtcg ggaaacctgt   5100
cgtgccagct gcattaatga atcggccaac gcgcggggag aggcggtttg cgtattgggc   5160
gctcttccgc ttcctcgctc actgactcgc tgcgctcggt cgttcggctg cggcgagcgg   5220
tatcagctca ctcaaaggcg gtaatacggt tatccacaga atcaggggat aacgcaggaa   5280
agaacatgtg agcaaaaggc cagcaaaagg ccaggaaccg taaaaaggcc gcgttgctgg   5340
cgtttttcca taggctccgc ccccctgacg agcatcacaa aaatcgacgc tcaagtcaga   5400
ggtggcgaaa cccgacagga ctataaagat accaggcgtt tccccctgga agctccctcg   5460
tgcgctctcc tgttccgacc ctgccgctta ccggatacct gtccgccttt ctcccttcgg   5520
gaagcgtggc gctttctcat agctcacgct gtaggtatct cagttcggtg taggtcgttc   5580
gctccaagct gggctgtgtg cacgaacccc ccgttcagcc cgaccgctgc gccttatccg   5640
gtaactatcg tcttgagtcc aacccggtaa gacacgactt atcgccactg gcagcagcca   5700
ctggtaacag gattagcaga gcgaggtatg taggcggtgc tacagagttc ttgaagtggt   5760
ggcctaacta cggctacact agaaggacag tatttggtat ctgcgctctg ctgaagccag   5820
```

ttaccttcgg aaaaagagtt ggtagctctt gatccggcaa acaaaccacc gctggtagcg 5880
gtggtttttt tgtttgcaag cagcagatta cgcgcagaaa aaaaggatct caagaagatc 5940
ctttgatctt ttctacgggg tctgacgctc agtggaacga aaactcacgt taagggattt 6000
tggtcatgag attatcaaaa aggatcttca cctagatcct tttaaattaa aaatgaagtt 6060
ttaaatcaat ctaaagtata tatgagtaaa cttggtctga cagttaccag gtccactgcc 6120
gggcctcttg cgggatcaaa agaaaaacga aatgatacac caatcagtgc aaaaaaagat 6180
ataatgggag ataagacggt tcgtgttcgt gctgacttgc accatatcat aaaaatcgaa 6240
acagcaaaga atggcggaaa cgtaaaagaa gttatggaaa taagacttag aagcaaactt 6300
aagagtgtgt tgatagtgca gtatcttaaa attttgtata ataggaattg aagttaaatt 6360
agatgctaaa aatttgtaat taagaaggag tgattacatg aacaaaaata taaaatattc 6420
tcaaaacttt ttaacgagtg aaaaagtact caaccaaata ataaaacaat tgaatttaaa 6480
agaaaccgat accgtttacg aaattggaac aggtaaaggg catttaacga cgaaactggc 6540
taaaataagt aaacaggtaa cgtctattga attagacagt catctattca acttatcgtc 6600
agaaaaatta aaactgaata ctcgtgtcac tttaattcac caagatattc tacagtttca 6660
attccctaac aaacagaggt ataaaattgt tgggagtatt ccttaccatt taagcacaca 6720
aattattaaa aaagtggttt ttgaaagcca tgcgtctgac atctatctga ttgttgaaga 6780
aggattctac aagcgtacct tggatattca ccgaacacta gggttgctct tgcacactca 6840
agtctcgatt cagcaattgc ttaagctgcc agcggaatgc tttcatccta aaccaaaagt 6900
aaacagtgtc ttaataaaac ttacccgcca taccacagat gttccagata aatattggaa 6960
gctatatacg tactttgttt caaaatgggt caatcgagaa tatcgtcaac tgtttactaa 7020
aaatcagttt catcaagcaa tgaaacacgc caaagtaaac aatttaagta ccgttactta 7080
tgagcaagta ttgtctattt ttaatagtta tctattattt aacgggagga aataattcta 7140
tgagtcccta ggcaggcctc cgccattatt tttttgaaca attgacaatt catttcttat 7200
tttttattaa gtgatagtca aaaggcataa cagtgctgaa tagaaagaaa tttacagaaa 7260
agaaaattat agaatttagt atgattaatt atactcattt atgaatgttt aattgaatac 7320
aaaaaaaaat acttgttatg tattcaatta cgggttaaaa tatagacaag ttgaaaaatt 7380
taataaaaaa ataagtcctc agctcttata tattaagcta ccaacttagt atataagcca 7440
aaacttaaat gtgctaccaa cacatcaagc cgttagagaa ctctatctat agcaatattt 7500
caaatgtacc gacatacaag agaaacatta actatatata ttcaatttat gagattatct 7560
taacagatat aaatgtaaat tgcaataagt aagatttaga agtttatagc ctttgtgtat 7620
tggaagcagt acgcaaaggc tttttttattt gataaaaatt agaagtatat ttattttttc 7680
ataattaatt tatgaaaatg aaagggggtg agcaaagtga cagaggaaag cagtatctta 7740
tcaaataaca aggtattagc aatatcatta ttgactttag cagtaaacat tatgactttt 7800
atagtgcttg tagctaagta gtacgaaagg gggagcttta aaaagctcct tggaatacat 7860
agaattcata aattaattta tgaaaagaag ggcgtatatg aaaacttgta aaaattgcaa 7920
agagtttatt aaagatactg aaatatgcaa aatacattcg ttgatgattc atgataaaac 7980
agtagcaacc tattgcagta aatacaatga gtcaagatgt ttacataaag ggaaagtcca 8040
atgtattaat tgttcaaaga tgaaccgata tggatggtgt gccataaaaa tgagatgttt 8100
tacagaggaa gaacagaaaa aagaacgtac atgcattaaa tattatgcaa ggagctttaa 8160
aaaagctcat gtaaagaaga gtaaaaagaa aaaataattt atttattaat ttaatattga 8220

```
gagtgccgac acagtatgca ctaaaaaata tatctgtggt gtagtgagcc gatacaaaag   8280

gatagtcact cgcattttca taatacatct tatgttatga ttatgtgtcg gtgggacttc   8340

acgacgaaaa cccacaataa aaaaagagtt cggggtaggg ttaagcatag ttgaggcaac   8400

taaacaatca agctaggata tgcagtagca gaccgtaagg tcgttgttta ggtgtgttgt   8460

aatacatacg ctattaagat gtaaaaatac ggataccaat gaagggaaaa gtataatttt   8520

tggatgtagt ttgtttgttc atctatgggc aaactacgtc caaagccgtt tccaaatctg   8580

ctaaaaagta tatcctttct aaaatcaaag tcaagtatga aatcataaat aaagtttaat   8640

tttgaagtta ttatgatatt atgtttttct attaaaataa attaagtata tagaatagtt   8700

taataatagt atatacttaa tgtgataagt gtctgacagt gtcacagaaa ggatgattgt   8760

tatggattat aagcggctcg aggacgtcaa accatgttaa tcattgcttt tatcaaaaat   8820

aggatccact ctatcattga tagagtttga aactctatca ttgatagagt ataatatctt   8880

tgttcatgta catcatgcta tctgtgagtt ttagagctag aaatagcaag ttaaaataag   8940

gctagtccgt tatcaacttg aaaaagtggc accgagtcgg tgcttttttt gaagcttgtc   9000

tttacacttt tgcccattaa tttttgagtt ccttattttt agggagcttt tattattttt   9060

atcatgaaaa tttcataaaa tactcataaa ctaaggatgt cttcataatc agattagtac   9120

tccattttca atccatttaa tctgggaata tgatatttta attacgtatt atttaagata   9180

tattaacgtg taatataata ccccgcaaat attaattatc acatacatat ccccccttta   9240

ttggggcatt ttttgtaccc attattttag tattgtgcag tacttaaata aaaaaatgcc   9300

gcaaattcat ttttattgaa taatgcggta tttcttctat tctttatttt tattactcta   9360

taaataatgt aatcaagaca tgactatcta aatatatgat atcttaattc ataattcggg   9420

cctcctaaaa attttcgtaa ttctatttta gaaggctttt ttccgtgacc tagccatttc   9480

aatctccttt ttacaatgat atttacgctt tagtttatta tagcacattc tgtaataccg   9540

aactattcaa ttttcagaga ccattttttta ttgattcata acttaagaat actacgaatt   9600

actctaatat tttacttttt cttatctctt gttattttaa catcggaatt actactaata   9660

ttaattttta tttttccatc cgcatttgct ccaacatttt tttaactata ctttcctttt   9720

gttaataaat tatgttattg ttgaacaata taagaaaagt gcgtaacatt ttttattaaa   9780

aataattagg tatttctatc tgtggggtac cctcgaggtg gcagctctag agctagcgaa   9840

ttctttggtg aaattgctcg agtccctatc agtgatagat tgaaactcta tcattgatag   9900

agtataatat ctttgttcat tagagcgata aacttgaatt tgagagggaa cttc         9954
```

<210> SEQ ID NO 22
<211> LENGTH: 8874
<212> TYPE: DNA
<213> ORGANISM: Artificial Sequence
<220> FEATURE:
<223> OTHER INFORMATION: pCas9ind

<400> SEQUENCE: 22

```
catggataaa aagtacagta ttggtctaga cataggaact aactctgttg ggtgggctgt     60

tataacagat gaatataaag ttccatcaaa aaaatttaaa gtattaggaa acactgatag    120

acattcaata aaaaaaaact tgataggtgc tttattattc gattcaggag agactgctga    180

agctacacgt ttaaaaagaa cagctagacg tagatataca agaagaaaaa ataggatatg    240

ttatcttcaa gaaattttta gtaatgaaat ggcaaaagtt gatgattcat tctttcacag    300
```

```
actagaagaa agtttcttag ttgaagaaga taagaagcat gaaagacacc ctatttttgg    360
taatatcgta gatgaagtag catatcatga gaagtatcca actatctatc atttaagaaa    420
gaaattagtt gattctacag ataaagctga tctgagatta atatatttag ctttagctca    480
tatgattaaa tttagaggac atttttttaat agaaggtgat ttaaacccag acaacagcga    540
tgtagataaa ttatttatcc aattagttca aacttataat caattattcg aagagaatcc    600
aattaatgca agtggtgtag acgctaaggc tatattatca gctagattat caaaatctag    660
aagattagaa aatctaatag ctcaacttcc tggagaaaag aaaaatggac tttttgggaa    720
cctaatagct ctctcactcg gactaacacc aaattttaaa agcaattttg atcttgctga    780
agacgcaaag ttacaactat caaaggatac atacgatgat gatttagata atttgttagc    840
tcaaataggt gatcaatatg ctgatttgtt tcttgcagca aaaaacttaa gtgatgcaat    900
tttactatca gatatactta gagtaaatac agaaataaca aaggctcctt tatcagcaag    960
tatgattaaa cgatatgatg agcatcatca agatttaaca ttattaaagg cacttgtaag   1020
acaacaatta ccagaaaaat ataaagaaat tttctttgat caatctaaaa atggatatgc   1080
tggatatata gacggtggag caagtcaaga agagttttat aaatttataa agcctatttt   1140
agaaaaaatg gatggaactg aagaattact tgttaaactt aacagagaag atttacttag   1200
aaaacaaaga acttttgata atggttcaat tcctcaccaa attcatttag gagaattaca   1260
tgctatacta agaagacaag aagattttta tccatttctt aaagataata gagaaaaaat   1320
tgaaaaaatt ttaactttta gaataccata ttatgtagga ccacttgcaa ggggaaattc   1380
aagatttgca tggatgacta gaaaatcaga agaaactata accccgtgga attttgaaga   1440
agtagtagat aaaggagcta gtgctcaatc atttatagaa agaatgacaa attttgataa   1500
gaatcttcct aacgaaaagg ttttgccaaa gcatagcctt ctttatgagt attttacagt   1560
ttataatgag cttactaaag taaaatacgt tacagaagga atgagaaaac cagcattttt   1620
gtctggtgaa caaaagaaag caatagtaga cctattattt aaaacaaata ggaaggttac   1680
cgtaaagcaa cttaaagaag attacttcaa aaaaattgaa tgctttgata gtgttgaaat   1740
atcaggagtt gaagatagat ttaatgcttc acttggtaca tatcacgatc tcttaaaaat   1800
tataaaagat aaggattttt tagataatga agaaaatgaa gatattcttg aagatatagt   1860
attaacattg acacttttttg aagatagaga aatgatagaa gaaagattaa aaacatatgc   1920
acatcttttt gatgataagg ttatgaagca acttaaaaga agaagatata caggttgggg   1980
acgtttgtca agaaagctaa ttaatggtat tagagataaa caatcaggaa agactattct   2040
cgattttctt aaatcagatg gatttgctaa tagaaacttt atgcaattaa ttcatgatga   2100
ttctcttact ttcaaagagg atattcaaaa ggctcaagtt tctggacaag gcgatagctt   2160
acacgaacac attgctaacc ttgcagggag ccccgctatc aaaaaaggaa ttttacaaac   2220
agttaaagtt gtagatgaac ttgttaaagt tatgggaaga cacaaacctg agaatatagt   2280
tatagaaatg gccagagaaa atcaaacaac acaaaaagga caaaaaaatt ctagagagag   2340
aatgaagaga attgaagaag gaataaaaga gctaggatca caaatattaa aagaacatcc   2400
agttgaaaat actcaattgc aaaatgaaaa gttatatttg tattacttac aaaatggaag   2460
agatatgtat gttgatcaag aactcgatat taatagatta agtgactatg atgttgatca   2520
tattgttcct caatcatttt taaaagatga ttcaatcgat aacaaagtat taactagatc   2580
agataaaaat agaggaaagt cagataatgt accatctgaa gaagttgtta aaaaaatgaa   2640
gaactattgg agacaacttt taaatgcaaa gctaattaca caaagaaaat ttgacaattt   2700
```

```
aacaaaagca gaaagaggag gattaagcga attagacaaa gctggattta taaaaagaca   2760
acttgttgag acaagacaaa taactaagca tgttgctcaa atacttgatt caagaatgaa   2820
tacaaaatat gatgaaaatg ataaattaat cagagaagta aaagtaataa cattaaagtc   2880
aaaattagta tcagatttca gaaaggattt tcaattttac aaagttcgtg aaataaataa   2940
ctatcatcat gctcatgatg catacttaaa tgctgttgta ggaactgctc ttattaagaa   3000
atatcctaaa ctagaaagcg aatttgttta tggagattat aaagtttatg atgtgcgcaa   3060
aatgatcgcg aaatccgaac aagaaatcgg taaggctaca gcaaaatatt tcttttatag   3120
taatataatg aatttttta agacagaaat aactttggct aatggtgaaa tcagaaaaag   3180
accacttatc gaaacaaatg gagagacagg agaaatagta tgggataaag gaagagattt   3240
tgctactgtt agaaaagtac taagtatgcc acaagtaaat atcgtaaaga aaactgaagt   3300
tcaaactgga ggtttctcta aggaatcaat tttacctaag agaaattcag ataagttaat   3360
tgcaaggaaa aaagattggg acccaaaaaa atacggtggt tttgatagtc caacagttgc   3420
ctatagtgtt cttgtagtag cgaaagttga gaaaggtaag tcaaaaaagt tgaaaagcgt   3480
aaaagaactt cttggtatca caattatgga aagatcttca tttgaaaaaa atccaattga   3540
ctttttagaa gctaagggtt ataaagaagt taaaaaggat ttaatcataa aactaccaaa   3600
gtatagtcta tttgaactcg aaaacggaag aaaacgaatg ctcgctagcg caggagaact   3660
tcaaaaagga aatgaacttg cgctgccatc aaagtatgta aatttcttat atttagcttc   3720
tcattatgag aaattaaaag gatcaccaga ggataatgaa caaaagcaac tatttgtaga   3780
acaacacaaa cattatttag atgaaataat agaacaaata tctgaatttt ctaaaagagt   3840
tatacttgcc gacgcaaatc tagataaggt gctttcagcg tataataaac acagagataa   3900
accaataaga gaacaagcag aaaacattat ccatcttttt acattaacta atcttggtgc   3960
accagctgca tttaagtact ttgatacaac aatagataga aaaagataca catctactaa   4020
agaagtatta gacgcaactt taatacatca atctattaca gggctttatg aaacaagaat   4080
tgatttaagt caactaggcg gagattaagt cgacaaagta ttgttaaaaa taactctgta   4140
gaattataaa ttagttctac agagttattt tttgacccgg gtatattgat aaaaataata   4200
atagtgggta taattaagtt gttaggaggt tagttagaat gatgtcaaga ttagataaaa   4260
gtaaagtgat taacagcgca ttagagctgc ttaatgaggt cggaatcgaa ggtttaacaa   4320
cccgtaaact cgcccagaag ctaggtgtag agcagcctac attgtattgg catgtaaaaa   4380
ataagcgggc tttgctcgac gccttagcca ttgagatgtt agataggcac catactcact   4440
tttgcccttt agaaggggaa agctggcaag attttttacg taataacgct aaaagtttta   4500
gatgtgcttt actaagtcat cgcgatggag caaaagtaca tttaggtaca cggcctacag   4560
aaaaacagta tgaaactctc gaaaatcaat tagccttttt atgccaacaa ggtttttcac   4620
tagagaatgc attatatgca ctcagcgctg tggggcattt tactttaggt tgcgtattgg   4680
aagatcaaga gcatcaagtc gctaaagaag aaagggaaac acctactact gatagtatgc   4740
cgccattatt acgacaagct atcgaattat ttgatcacca aggtgcagag ccagccttct   4800
tattcggcct tgaattgatc atatgcggat tagaaaaaca acttaaatgt gaaagtgggt   4860
cttaaaagca gcataacctt tttccgtgat ggtaacttca cggtaaccaa gatgtcgagt   4920
tgagctcgaa ttcgtaatca tggtcatagc tgtttcctgt gtgaaattgt tatccgctca   4980
caattccaca caacatacga gccggaagca taaagtgtaa agcctggggt gcctaatgag   5040
```

tgagctaact cacattaatt gcgttgcgct cactgcccgc tttccagtcg ggaaacctgt 5100
cgtgccagct gcattaatga atcggccaac gcgcggggag aggcggtttg cgtattgggc 5160
gctcttccgc ttcctcgctc actgactcgc tgcgctcggt cgttcggctg cggcgagcgg 5220
tatcagctca ctcaaaggcg gtaatacggt tatccacaga atcaggggat aacgcaggaa 5280
agaacatgtg agcaaaaggc cagcaaaagg ccaggaaccg taaaaaggcc gcgttgctgg 5340
cgtttttcca taggctccgc ccccctgacg agcatcacaa aaatcgacgc tcaagtcaga 5400
ggtggcgaaa cccgacagga ctataaagat accaggcgtt tccccctgga agctccctcg 5460
tgcgctctcc tgttccgacc ctgccgctta ccggatacct gtccgccttt ctcccttcgg 5520
gaagcgtggc gctttctcat agctcacgct gtaggtatct cagttcggtg taggtcgttc 5580
gctccaagct gggctgtgtg cacgaacccc ccgttcagcc cgaccgctgc gccttatccg 5640
gtaactatcg tcttgagtcc aacccggtaa gacacgactt atcgccactg gcagcagcca 5700
ctggtaacag gattagcaga gcgaggtatg taggcggtgc tacagagttc ttgaagtggt 5760
ggcctaacta cggctacact agaaggacag tatttggtat ctgcgctctg ctgaagccag 5820
ttaccttcgg aaaaagagtt ggtagctctt gatccggcaa acaaaccacc gctggtagcg 5880
gtggtttttt tgtttgcaag cagcagatta cgcgcagaaa aaaaggatct caagaagatc 5940
ctttgatctt ttctacgggg tctgacgctc agtggaacga aaactcacgt taagggattt 6000
tggtcatgag attatcaaaa aggatcttca cctagatcct tttaaattaa aaatgaagtt 6060
ttaaatcaat ctaaagtata tatgagtaaa cttggtctga cagttaccag gtccactgcc 6120
gggcctcttg cgggatcaaa agaaaaacga aatgatacac caatcagtgc aaaaaaagat 6180
ataatgggag ataagacggt tcgtgttcgt gctgacttgc accatatcat aaaaatcgaa 6240
acagcaaaga atggcggaaa cgtaaaagaa gttatggaaa taagacttag aagcaaactt 6300
aagagtgtgt tgatagtgca gtatcttaaa attttgtata ataggaattg aagttaaatt 6360
agatgctaaa aatttgtaat taagaaggag tgattacatg aacaaaaata taaaatattc 6420
tcaaaacttt ttaacgagtg aaaaagtact caaccaaata ataaaacaat tgaatttaaa 6480
agaaaccgat accgtttacg aaattggaac aggtaaaggg catttaacga cgaaactggc 6540
taaaataagt aaacaggtaa cgtctattga attagacagt catctattca acttatcgtc 6600
agaaaaatta aaactgaata ctcgtgtcac tttaattcac caagatattc tacagtttca 6660
attccctaac aaacagaggt ataaaattgt tgggagtatt ccttaccatt taagcacaca 6720
aattattaaa aaagtggttt ttgaaagcca tgcgtctgac atctatctga ttgttgaaga 6780
aggattctac aagcgtacct tggatattca ccgaacacta gggttgctct tgcacactca 6840
agtctcgatt cagcaattgc ttaagctgcc agcggaatgc tttcatccta aaccaaaagt 6900
aaacagtgtc ttaataaaac ttacccgcca taccacagat gttccagata aatattggaa 6960
gctatatacg tactttgttt caaaatgggt caatcgagaa tatcgtcaac tgtttactaa 7020
aaatcagttt catcaagcaa tgaaacacgc caaagtaaac aatttaagta ccgttactta 7080
tgagcaagta ttgtctattt ttaatagtta tctattattt aacgggagga aataattcta 7140
tgagtcccta ggcaggcctc cgccattatt tttttgaaca attgacaatt catttcttat 7200
tttttattaa gtgatagtca aaaggcataa cagtgctgaa tagaaagaaa tttacagaaa 7260
agaaaattat agaatttagt atgattaatt atactcattt atgaatgttt aattgaatac 7320
aaaaaaaaat acttgttatg tattcaatta cgggttaaaa tatagacaag ttgaaaaatt 7380
taataaaaaa ataagtcctc agctcttata tattaagcta ccaacttagt atataagcca 7440

```
aaacttaaat gtgctaccaa cacatcaagc cgttagagaa ctctatctat agcaatattt   7500

caaatgtacc gacatacaag agaaacatta actatatata ttcaatttat gagattatct   7560

taacagatat aaatgtaaat tgcaataagt aagatttaga agtttatagc ctttgtgtat   7620

tggaagcagt acgcaaaggc tttttttattt gataaaaatt agaagtatat ttatttttttc   7680

ataattaatt tatgaaaatg aaaggggggtg agcaaagtga cagaggaaag cagtatctta   7740

tcaaataaca aggtattagc aatatcatta ttgactttag cagtaaacat tatgactttt   7800

atagtgcttg tagctaagta gtacgaaagg gggagcttta aaaagctcct tggaatacat   7860

agaattcata aattaattta tgaaaagaag ggcgtatatg aaaacttgta aaaattgcaa   7920

agagtttatt aaagatactg aaatatgcaa aatacattcg ttgatgattc atgataaaac   7980

agtagcaacc tattgcagta aatacaatga gtcaagatgt ttacataaag ggaaagtcca   8040

atgtattaat tgttcaaaga tgaaccgata tggatggtgt gccataaaaa tgagatgttt   8100

tacagaggaa gaacagaaaa aagaacgtac atgcattaaa tattatgcaa ggagctttaa   8160

aaaagctcat gtaaagaaga gtaaaaagaa aaaataattt atttattaat ttaatattga   8220

gagtgccgac acagtatgca ctaaaaaata tatctgtggt gtagtgagcc gatacaaaag   8280

gatagtcact cgcattttca taatacatct tatgttatga ttatgtgtcg gtgggacttc   8340

acgacgaaaa cccacaataa aaaaagagtt cggggtaggg ttaagcatag ttgaggcaac   8400

taaacaatca agctaggata tgcagtagca gaccgtaagg tcgttgttta ggtgtgttgt   8460

aatacatacg ctattaagat gtaaaaatac ggataccaat gaagggaaaa gtataatttt   8520

tggatgtagt ttgtttgttc atctatgggc aaactacgtc caaagccgtt tccaaatctg   8580

ctaaaaagta tatcctttct aaaatcaaag tcaagtatga aatcataaat aaagtttaat   8640

tttgaagtta ttatgatatt atgtttttct attaaaataa attaagtata tagaatagtt   8700

taataatagt atatacttaa tgtgataagt gtctgacagt gtcacagaaa ggatgattgt   8760

tatggattat aagcggctcg agtccctatc agtgatagat tgaaactcta tcattgatag   8820

agtataatat ctttgttcat tagagcgata aacttgaatt tgagagggaa cttc         8874
```

<210> SEQ ID NO 23
<211> LENGTH: 10534
<212> TYPE: DNA
<213> ORGANISM: Artificial Sequence
<220> FEATURE:
<223> OTHER INFORMATION: pCas9acr

<400> SEQUENCE: 23

```
cgaattcgta atcatggtca tagctgtttc ctgtgtgaaa ttgttatccg ctcacaattc     60

cacacaacat acgagccgga agcataaagt gtaaagcctg gggtgcctaa tgagtgagct    120

aactcacatt aattgcgttg cgctcactgc ccgctttcca gtcgggaaac ctgtcgtgcc    180

agctgcatta atgaatcggc caacgcgcgg ggagaggcgg tttgcgtatt gggcgctctt    240

ccgcttcctc gctcactgac tcgctgcgct cggtcgttcg gctgcggcga gcggtatcag    300

ctcactcaaa ggcggtaata cggttatcca cagaatcagg ggataacgca ggaaagaaca    360

tgtgagcaaa aggccagcaa aaggccagga accgtaaaaa ggccgcgttg ctggcgtttt    420

tccataggct ccgcccccct gacgagcatc acaaaaatcg acgctcaagt cagaggtggc    480

gaaacccgac aggactataa agataccagg cgtttccccc tggaagctcc ctcgtgcgct    540

ctcctgttcc gaccctgccg cttaccggat acctgtccgc ctttctccct tcgggaagcg    600
```

-continued

```
tggcgctttc tcatagctca cgctgtaggt atctcagttc ggtgtaggtc gttcgctcca    660
agctgggctg tgtgcacgaa ccccccgttc agcccgaccg ctgcgcctta tccggtaact    720
atcgtcttga gtccaacccg gtaagacacg acttatcgcc actggcagca gccactggta    780
acaggattag cagagcgagg tatgtaggcg gtgctacaga gttcttgaag tggtggccta    840
actacggcta cactagaagg acagtatttg gtatctgcgc tctgctgaag ccagttacct    900
tcggaaaaag agttggtagc tcttgatccg gcaaacaaac caccgctggt agcggtggtt    960
tttttgtttg caagcagcag attacgcgca gaaaaaaagg atctcaagaa gatcctttga   1020
tcttttctac ggggtctgac gctcagtgga acgaaaactc acgttaaggg attttggtca   1080
tgagattatc aaaaaggatc ttcacctaga tccttttaaa ttaaaaatga agttttaaat   1140
caatctaaag tatatatgag taaacttggt ctgacagtta ccaggtccac tgccgggcct   1200
cttgcgggat caaaagaaaa acgaaatgat acaccaatca gtgcaaaaaa agatataatg   1260
ggagataaga cggttcgtgt tcgtgctgac ttgcaccata tcataaaaat cgaaacagca   1320
aagaatggcg gaaacgtaaa agaagttatg gaaataagac ttagaagcaa acttaagagt   1380
gtgttgatag tgcagtatct taaaattttg tataatagga attgaagtta aattagatgc   1440
taaaaatttg taattaagaa ggagtgatta catgaacaaa aatataaaat attctcaaaa   1500
ctttttaacg agtgaaaaag tactcaacca aataataaaa caattgaatt taaaagaaac   1560
cgataccgtt tacgaaattg gaacaggtaa agggcattta acgacgaaac tggctaaaat   1620
aagtaaacag gtaacgtcta ttgaattaga cagtcatcta ttcaacttat cgtcagaaaa   1680
attaaaactg aatactcgtg tcactttaat tcaccaagat attctacagt ttcaattccc   1740
taacaaacag aggtataaaa ttgttgggag tattccttac catttaagca cacaaattat   1800
taaaaaagtg gtttttgaaa gccatgcgtc tgacatctat ctgattgttg aagaaggatt   1860
ctacaagcgt accttggata ttcaccgaac actagggttg ctcttgcaca ctcaagtctc   1920
gattcagcaa ttgcttaagc tgccagcgga atgctttcat cctaaaccaa aagtaaacag   1980
tgtcttaata aaacttaccc gccataccac agatgttcca gataaatatt ggaagctata   2040
tacgtacttt gtttcaaaat gggtcaatcg agaatatcgt caactgttta ctaaaaatca   2100
gtttcatcaa gcaatgaaac acgccaaagt aaacaattta agtaccgtta cttatgagca   2160
agtattgtct atttttaata gttatctatt atttaacggg aggaaataat tctatgagtc   2220
cctaggcagg cctccgccat tatttttttg aacaattgac aattcatttc ttattttta   2280
ttaagtgata gtcaaaaggc ataacagtgc tgaatagaaa gaaatttaca gaaaagaaaa   2340
ttatagaatt tagtatgatt aattatactc atttatgaat gtttaattga atacaaaaaa   2400
aaatacttgt tatgtattca attacgggtt aaaatataga caagttgaaa aatttaataa   2460
aaaaataagt cctcagctct tatatattaa gctaccaact tagtatataa gccaaaactt   2520
aaatgtgcta ccaacacatc aagccgttag agaactctat ctatagcaat atttcaaatg   2580
taccgacata caagagaaac attaactata tatattcaat ttatgagatt atcttaacag   2640
atataaatgt aaattgcaat aagtaagatt tagaagttta tagcctttgt gtattggaag   2700
cagtacgcaa aggctttttt atttgataaa aattagaagt atatttattt tttcataatt   2760
aatttatgaa aatgaaaggg ggtgagcaaa gtgacagagg aaagcagtat cttatcaaat   2820
aacaaggtat tagcaatatc attattgact ttagcagtaa acattatgac ttttatagtg   2880
cttgtagcta agtagtacga aagggggagc tttaaaaagc tccttggaat acatagaatt   2940
cataaattaa tttatgaaaa gaagggcgta tatgaaaact tgtaaaaatt gcaaagagtt   3000
```

```
tattaaagat actgaaatat gcaaaataca ttcgttgatg attcatgata aaacagtagc   3060
aacctattgc agtaaataca atgagtcaag atgtttacat aaagggaaag tccaatgtat   3120
taattgttca aagatgaacc gatatggatg gtgtgccata aaaatgagat gttttacaga   3180
ggaagaacag aaaaaagaac gtacatgcat taaatattat gcaaggagct ttaaaaaagc   3240
tcatgtaaag aagagtaaaa agaaaaaata atttatttat taatttaata ttgagagtgc   3300
cgacacagta tgcactaaaa aatatatctg tggtgtagtg agccgataca aaaggatagt   3360
cactcgcatt ttcataatac atcttatgtt atgattatgt gtcggtggga cttcacgacg   3420
aaaacccaca ataaaaaaag agttcggggt agggttaagc atagttgagg caactaaaca   3480
atcaagctag gatatgcagt agcagaccgt aaggtcgttg tttaggtgtg ttgtaataca   3540
tacgctatta agatgtaaaa atacggatac caatgaaggg aaaagtataa tttttggatg   3600
tagtttgttt gttcatctat gggcaaacta cgtccaaagc cgtttccaaa tctgctaaaa   3660
agtatatcct ttctaaaatc aaagtcaagt atgaaatcat aaataaagtt taattttgaa   3720
gttattatga tattatgttt ttctattaaa ataaattaag tatatagaat agtttaataa   3780
tagtatatac ttaatgtgat aagtgtctga cagtgtcaca gaaaggatga ttgttatgga   3840
ttataagcgg ctcgagtccc tatcagtgat agattgaaac tctatcattg atagagtata   3900
atatctttgt tcattagagc gataaacttg aatttgagag ggaacttcca tggataaaaa   3960
gtacagtatt ggtctagaca taggaactaa ctctgttggg tgggctgtta taacagatga   4020
atataaagtt ccatcaaaaa aatttaaagt attaggaaac actgatagac attcaataaa   4080
aaaaaacttg ataggtgctt tattattcga ttcaggagag actgctgaag ctacacgttt   4140
aaaaagaaca gctagacgta gatatacaag aagaaaaaat aggatatgtt atcttcaaga   4200
aatttttagt aatgaaatgg caaaagttga tgattcattc tttcacagac tagaagaaag   4260
tttcttagtt gaagaagata agaagcatga aagacaccct atttttggta atatcgtaga   4320
tgaagtagca tatcatgaga agtatccaac tatctatcat ttaagaaaga aattagttga   4380
ttctacagat aaagctgatc tgagattaat atatttagct ttagctcata tgattaaatt   4440
tagaggacat tttttaatag aaggtgattt aaacccagac aacagcgatg tagataaatt   4500
atttatccaa ttagttcaaa cttataatca attattcgaa gagaatccaa ttaatgcaag   4560
tggtgtagac gctaaggcta tattatcagc tagattatca aaatctagaa gattagaaaa   4620
tctaatagct caacttcctg gagaaaagaa aaatggactt tttgggaacc taatagctct   4680
ctcactcgga ctaacaccaa attttaaaag caattttgat cttgctgaag acgcaaagtt   4740
acaactatca aaggatacat acgatgatga tttagataat ttgttagctc aaataggtga   4800
tcaatatgct gatttgtttc ttgcagcaaa aaacttaagt gatgcaattt tactatcaga   4860
tatacttaga gtaaatacag aaataacaaa ggctccttta tcagcaagta tgattaaacg   4920
atatgatgag catcatcaag atttaacatt attaaaggca cttgtaagac aacaattacc   4980
agaaaaatat aaagaaattt tctttgatca atctaaaaat ggatatgctg gatatataga   5040
cggtggagca agtcaagaag agttttataa atttataaag cctattttag aaaaaatgga   5100
tggaactgaa gaattacttg ttaaacttaa cagagaagat ttacttagaa aacaaagaac   5160
ttttgataat ggttcaattc ctcaccaaat tcatttagga gaattacatg ctatactaag   5220
aagacaagaa gatttttatc catttcttaa agataataga gaaaaaattg aaaaaatttt   5280
aacttttaga ataccatatt atgtaggacc acttgcaagg ggaaattcaa gatttgcatg   5340
```

```
gatgactaga aaatcagaag aaactataac cccgtggaat tttgaagaag tagtagataa   5400
aggagctagt gctcaatcat ttatagaaag aatgacaaat tttgataaga atcttcctaa   5460
cgaaaaggtt ttgccaaagc atagccttct ttatgagtat tttacagttt ataatgagct   5520
tactaaagta aaatacgtta cagaaggaat gagaaaacca gcatttttgt ctggtgaaca   5580
aaagaaagca atagtagacc tattatttaa aacaaatagg aaggttaccg taaagcaact   5640
taaagaagat tacttcaaaa aaattgaatg ctttgatagt gttgaaatat caggagttga   5700
agatagattt aatgcttcac ttggtacata tcacgatctc ttaaaaatta taaaagataa   5760
ggattttta gataatgaag aaaatgaaga tattcttgaa gatatagtat taacattgac    5820
actttttgaa gatagagaaa tgatagaaga aagattaaaa acatatgcac atctttttga   5880
tgataaggtt atgaagcaac ttaaaagaag aagatataca ggttggggac gtttgtcaag   5940
aaagctaatt aatggtatta gagataaaca atcaggaaag actattctcg attttcttaa   6000
atcagatgga tttgctaata gaaactttat gcaattaatt catgatgatt ctcttacttt   6060
caaagaggat attcaaaagg ctcaagtttc tggacaaggc gatagcttac acgaacacat   6120
tgctaacctt gcagggagcc ccgctatcaa aaaaggaatt ttacaaacag ttaaagttgt   6180
agatgaactt gttaaagtta tgggaagaca caaacctgag aatatagtta tagaaatggc   6240
cagagaaaat caaacaacac aaaaaggaca aaaaaattct agagagagaa tgaagagaat   6300
tgaagaagga ataaaagagc taggatcaca aatattaaaa gaacatccag ttgaaaatac   6360
tcaattgcaa aatgaaaagt tatatttgta ttacttacaa aatggaagag atatgtatgt   6420
tgatcaagaa ctcgatatta atagattaag tgactatgat gttgatcata ttgttcctca   6480
atcattttta aaagatgatt caatcgataa caaagtatta actagatcag ataaaaatag   6540
aggaaagtca gataatgtac catctgaaga agttgttaaa aaaatgaaga actattggag   6600
acaactttta aatgcaaagc taattacaca aagaaaattt gacaatttaa caaaagcaga   6660
aagaggagga ttaagcgaat tagacaaagc tggatttata aaaagacaac ttgttgagac   6720
aagacaaata actaagcatg ttgctcaaat acttgattca agaatgaata caaaatatga   6780
tgaaaatgat aaattaatca gagaagtaaa agtaataaca ttaaagtcaa aattagtatc   6840
agatttcaga aaggattttc aattttacaa agttcgtgaa ataaataact atcatcatgc   6900
tcatgatgca tacttaaatg ctgttgtagg aactgctctt attaagaaat atcctaaact   6960
agaaagcgaa tttgtttatg gagattataa agtttatgat gtgcgcaaaa tgatcgcgaa   7020
atccgaacaa gaaatcggta aggctacagc aaaatatttc ttttatagta atataatgaa   7080
ttttttaag acagaaataa ctttggctaa tggtgaaatc agaaaaagac cacttatcga    7140
aacaaatgga gagacaggag aaatagtatg ggataaagga agagattttg ctactgttag   7200
aaaagtacta agtatgccac aagtaaatat cgtaaagaaa actgaagttc aaactggagg   7260
tttctctaag gaatcaattt tacctaagag aaattcagat aagttaattg caaggaaaaa   7320
agattgggac ccaaaaaaat acggtggttt tgatagtcca acagttgcct atagtgttct   7380
tgtagtagcg aaagttgaga aaggtaagtc aaaaaagttg aaaagcgtaa aagaacttct   7440
tggtatcaca attatggaaa gatcttcatt tgaaaaaaat ccaattgact ttttagaagc   7500
taagggttat aaagaagtta aaaaggattt aatcataaaa ctaccaaagt atagtctatt   7560
tgaactcgaa aacggaagaa aacgaatgct cgctagcgca ggagaacttc aaaaaggaaa   7620
tgaacttgcg ctgccatcaa agtatgtaaa tttcttatat ttagcttctc attatgagaa   7680
attaaaagga tcaccagagg ataatgaaca aaagcaacta tttgtagaac aacacaaaca   7740
```

-continued

```
ttatttagat gaaataatag aacaaatatc tgaattttct aaaagagtta tacttgccga   7800
cgcaaatcta gataaggtgc tttcagcgta taataaacac agagataaac caataagaga   7860
acaagcagaa aacattatcc atctttttac attaactaat cttggtgcac cagctgcatt   7920
taagtacttt gatacaacaa tagatagaaa aagatacaca tctactaaag aagtattaga   7980
cgcaacttta atacatcaat ctattacagg gctttatgaa acaagaattg atttaagtca   8040
actaggcgga gattaagtcg acaaagtatt gttaaaaata actctgtaga attataaatt   8100
agttctacag agttattttt tgacccgggt atattgataa aaataataat agtgggtata   8160
attaagttgt taggaggtta gttagaatga tgtcaagatt agataaaagt aaagtgatta   8220
acagcgcatt agagctgctt aatgaggtcg gaatcgaagg tttaacaacc cgtaaactcg   8280
cccagaagct aggtgtagag cagcctacat tgtattggca tgtaaaaaat aagcgggctt   8340
tgctcgacgc cttagccatt gagatgttag ataggcacca tactcacttt tgccctttag   8400
aaggggaaag ctggcaagat tttttacgta ataacgctaa aagttttaga tgtgctttac   8460
taagtcatcg cgatggagca aaagtacatt taggtacacg gcctacagaa aaacagtatg   8520
aaactctcga aaatcaatta gcctttttat gccaacaagg tttttcacta gagaatgcat   8580
tatatgcact cagcgctgtg gggcatttta ctttaggttg cgtattggaa gatcaagagc   8640
atcaagtcgc taaagaagaa agggaaacac ctactactga tagtatgccg ccattattac   8700
gacaagctat cgaattattt gatcaccaag gtgcagagcc agccttctta ttcggccttg   8760
aattgatcat atgcggatta gaaaaacaac ttaaatgtga aagtgggtct taaaagcagc   8820
ataacctttt tccgtgatgg taacttcacg gtaaccaaga tgtcgagttg agctcttagt   8880
tcaactcact tttaaggtg attgtttgca tgtcattata aaattcttct tcatcctcgt   8940
attcttgatt ccaaccgttt ttaaatgcag atatgaattt ttcaactatt gattcatttt   9000
cactttcaga aattacatac tcgtttccat cattattaac tctaataatt agctgtgtta   9060
tactattgct atccgtacca ctcaatttca ctgtgtaatc tttgtttttt atttctctaa   9120
ttaagtcatt aatattcatt tcagccctcc tgtgaaattg ttatccgctc acaattccac   9180
gtcgactacc gcggattcta gattctgcag tatcttcatg gtattcattt tttaatatca   9240
ttttaccctc ccaatacatt taaaataatt atgtattcat gaaacatgat tgtatattta   9300
agaaacataa ttccatataa atcatttttc aaaatagttt ttacccataa ttaaatgtta   9360
atatgtaaat taatctttta gaatagttaa aaagttctaa aatatgttat aatgtttctt   9420
ataatcttat aaattttaat aactaatata taaagatatt tctttaaaat attcttatat   9480
ttagaagaat ttattttaaa ataaaaagct tttatgttga taaactgctt tgcaaagctc   9540
tcatgtaaat gtttaatata agactactat aaaattggct aattttatag gttaggaggt   9600
agaaatgcaa atattgtgga aaaagtatgt taaagaaaac tttgaaatga atgtagatga   9660
atgtggtata gaacaaggta taccaggatt aggatataac tatgaagtat tgaaaaatgc   9720
tgttattcat tacgtaacta agggatatgg aacttttaaa tttaatggta aggtatataa   9780
cttaaaacaa ggtgatattt ttatactact aaaaggtatg caagttgagt atgtggcttc   9840
tattgatgat ccttgggaat actactggat aggatttagt ggttcaaatg ctaatgagta   9900
tttaaataga acttctatta ctaactcctg tgttgctaat tgtgaagaaa actcaaaaat   9960
tccacagata atattaaata tgtgcgaaat atcaaaaact tataatcctt caagatctga  10020
tgacatacta ttactaaaag aactttactc attattgtac gcacttatag aagaattccc  10080
```

```
aaaacctttt gaatacaaag ataaggaatt acacacatat attcaagatg ctcttaattt  10140

cattaattct aattacatgc atagcataac tgttcaagaa attgctgatt atgtgaactt  10200

aagtagaagt tatttatata aaatgttcat aaaaaacctt ggaatttctc ctcaaagata  10260

tttaataaac cttagaatgt acaaagccac ccttttatta aaaagcacta aacttcctat  10320

aggagaagtc gcaagtagtg taggttatag tgactccctg ttattttcaa aaactttttc  10380

aaaacatttt tcaatgtctc cactaaatta cagaaataat caagtaaata aaccaagtat  10440

ataaatttaa aatacagctt taaaacaaaa aaatttcaaa aataaaaagt ataacagagg  10500

cgtaaattaa aacctctgtt atactttttg agct                              10534
```

<210> SEQ ID NO 24
<211> LENGTH: 5754
<212> TYPE: DNA
<213> ORGANISM: Artificial Sequence
<220> FEATURE:
<223> OTHER INFORMATION: pEC750S-uppHR

<400> SEQUENCE: 24

```
ataaggtacc aggaattaga gcagcgctat gttcagatac atttagtgct catgcaacaa    60

gagaacataa taatgctaat atattaacta tgggtcaaag ggttgttgga gcaggtcttg   120

ctttagatat agtaaaaaca tttatatcag ctaaatttga aggagatagg caccaaaaaa   180

gaatagataa gatttcagat attgaaaaaa agtatacaca ttagaaaaaa gcagctatgc   240

tgcaaataag atcaatttat attagaaaaa agcagctatg ctgcaaataa gatcaattta   300

tattagaaaa aagcagctat gctgcaaata agatcaattt atattagaaa aaagcagcta   360

tgctacaaat aagatcaatt tatattagaa aaaagtagct atgctgcaac aatattaatt   420

tatattacta gaaagctaaa tggggtatat aaatataaag ggctataaat actaaaagca   480

aacttggagg aataataatg gtctagagct ggagatagat tatttggtac taagtaatta   540

gtaatctatt agaattaaaa gctatctaca taagtttctg aatgacccaa gataatttta   600

ctggggggaa tatagaaaat ggagagacga gataagaaaa attattactt ggatattgct   660

gaaacagttt tagagagagg aacctgtcta aggagaaact atggttctat aattgttaaa   720

aatgatgaaa taatttctac tggatacaca ggagcaccta gaggtagaaa aaattgcatg   780

gatttgaata gttgcataag agaaaagttg aaagttccaa gaggtactca ttatgagttg   840

tgtaggagtg tacatagtga agctaatgca ataataagcg cttcgagctc gaattcgtaa   900

tcatggtcat agctgtttcc tgtgtgaaat tgttatccgc tcacaattcc acacaacata   960

cgagccggaa gcataaagtg taaagcctgg ggtgcctaat gagtgagcta actcacatta  1020

attgcgttgc gctcactgcc cgctttccag tcgggaaacc tgtcgtgcca gctgcattaa  1080

tgaatcggcc aacgcgcggg gagaggcggt ttgcgtattg ggcgctcttc cgcttcctcg  1140

ctcactgact cgctgcgctc ggtcgttcgg ctgcggcgag cggtatcagc tcactcaaag  1200

gcggtaatac ggttatccac agaatcaggg gataacgcag gaaagaacat gtgagcaaaa  1260

ggccagcaaa aggccaggaa ccgtaaaaag gccgcgttgc tggcgttttt ccataggctc  1320

cgcccccctg acgagcatca caaaaatcga cgctcaagtc agaggtggcg aaacccgaca  1380

ggactataaa gataccaggc gtttccccct ggaagctccc tcgtgcgctc tcctgttccg  1440

accctgccgc ttaccggata cctgtccgcc tttctccctt cgggaagcgt ggcgctttct  1500

catagctcac gctgtaggta tctcagttcg gtgtaggtcg ttcgctccaa gctgggctgt  1560

gtgcacgaac cccccgttca gcccgaccgc tgcgccttat ccggtaacta tcgtcttgag  1620
```

```
tccaacccgg taagacacga cttatcgcca ctggcagcag ccactggtaa caggattagc   1680
agagcgaggt atgtaggcgg tgctacagag ttcttgaagt ggtggcctaa ctacggctac   1740
actagaagaa cagtatttgg tatctgcgct ctgctgaagc cagttacctt cggaaaaaga   1800
gttggtagct cttgatccgg caaacaaacc accgctggta gcggtggttt ttttgtttgc   1860
aagcagcaga ttacgcgcag aaaaaaagga tctcaagaag atcctttgat cttttctacg   1920
gggtctgacg ctcagtggaa cgaaaactca cgttaaggga ttttggtcat gagattatca   1980
aaaaggatct tcacctagat ccttttaaat taaaaatgaa gttttaaatc aatctaaagt   2040
atatatgagt aaacttggtc tgacagttac caaagctagc ttaatactag tatatactta   2100
atgtgataag tgtctgacag ctgaccggtc taaagaggtc cgccaatgaa atctataaat   2160
aaactaaatt aagtttattt aattaacaac tatggatata aaataggtac taatcaaaat   2220
agtgaggagg atatatttga atacatacga acaaattaat aaagtgaaaa aaatacttcg   2280
gaaacattta aaaaataacc ttattggtac ttacatgttt ggatcaggag ttgagagtgg   2340
actaaaacca aatagtgatc ttgacttttt agtcgtcgta tctgaaccat tgacagatca   2400
aagtaaagaa atacttatac aaaaaattag acctatttca aagaaaatag gagataaaag   2460
caacttacga tatattgaat taacaattat tattcagcaa gaaatggtac cgtggaatca   2520
tcctcccaaa caagaattta tttatggaga atggttacaa gagctttatg aacaaggata   2580
cattcctcag aaggaattaa attcagattt aaccataatg ctttaccaag caaaacgaaa   2640
aaataaaaga atatacggaa attatgactt agaggaatta ctacctgata ttccattttc   2700
tgatgtgaga agagccatta tggattcgtc agaggaatta atagataatt atcaggatga   2760
tgaaaccaac tctatattaa ctttatgccg tatgatttta actatggaca cgggtaaaat   2820
cataccaaaa gatattgcgg gaaatgcagt ggctgaatct tctccattag aacataggga   2880
gagaattttg ttagcagttc gtagttatct tggagagaat attgaatgga ctaatgaaaa   2940
tgtaaattta actataaact atttaaataa cagattaaaa aaattataaa aaaattgaaa   3000
aaatggtgga aacacttttt tcaatttttt tgttttatta tttaatattt gggaaatatt   3060
cattctaatt ggtaatcaga ttttagaagt tgttaacttc aggtttgtct gtaactaaaa   3120
actagtattt aacctaggat caaaaaaatt tccaataatc ccactctaag ccacaaacac   3180
gccctataaa atcccgcttt aatcccactt tgagacacat gtaatattac tttacgccct   3240
agtatagtga taattttta cattcaatgc cacgcaaaaa aataaagggg cactataata   3300
aaagttcctt cggaactaac taaagtaaaa aattatcttt acaacctccc caaaaaaaag   3360
aacaggtaca aagtacccta taatacaagc gtaaaaaaaa tgagggtaaa aataaaaaaa   3420
taaaaaaata aaaaaataaa aaaataaaaa aataaaaaaa taaaaaaata taaaaataaa   3480
aaaatataaa aataaaaaaa tataaaaata aaaaaataaa aaaatataaa aataaaaaaa   3540
taaaaaaata taaaaatatt ttttatttaa agtttgaaaa aaattttttt atattatata   3600
atctttgaag aaaagaatat aaaaaatgag cctttataaa agcccatttt ttttcatata   3660
cgtaatatga cgttctaatg tttttattgg tacttctaac attagagtaa tttctttatt   3720
tttaaagcct ttttctttaa gggcttttat tttttttctt aatacattta attcctcttt   3780
ttttgttgct tttcctttag cttttaattg ctcttgataa ttttttttac ctctaatatt   3840
ttctcttctc ttatattcct ttttagaaat tattattgtc atatattttt gttcttcttc   3900
tgtaatttct aataactcta taagagtttc attcttatac ttatattgct tatttttatc   3960
```

```
taaataacat ctttcagcac ttctagttgc tcttataact tctctttcac ttaaatgttg   4020

tctaaacata ctattaagtt ctaaaacatc atttaatgcc ttctcaatgt cttctgtaaa   4080

gctacaaaga taatatctat ataaaaataa tataagctct ctgtgtcctt ttaaatcata   4140

ttctcttagt tcacaaagtt ttattatgtc ttgtattctt ccataatata aacttctttc   4200

tctataaata taatttattt tgcttggtct accctttttc ctttcatatg gttttaattc   4260

aggtaaaaat ccattttgta tttctcttaa gtcataaata tattcgtact catctaatat   4320

attgactact gtttttgatt tagagtttat acttcctgga actcttaata ttctcgttgc   4380

atctaaggct tgtctatctg ctccaaagta ttttaattga ttatataaat attcttgaac   4440

cgctttccat aatggtaatg ctttactagg tactgcattt attatccata ttaaatacat   4500

tcctcttcca ctatctatta catagtttgg tataggaata ctttgattaa aataattctt   4560

ttctaagtcc attaatacct ggtctttagt tttgccagtt ttataataat ccaagtctat   4620

aaacagtgta tttaactctt ttatatttc taatcgccta cacggcttat aaaaggtatt   4680

tagagttata tagatatttt catcactcat atctaaatct tttaattcag cgtatttata   4740

gtgccattgg ctatatcctt ttttatctat aacgctcctg gttatccacc ctttacttct   4800

actatgaata ttatctatat agttcttttt attcagcttt aatgcgtttc tcacttattc   4860

acctcccctt ctgtaaaact aagaaaatta tatcatattt tcaataatta ttaactattc   4920

ttaaactctt aataaaaaat agagtaagtc cccaattgaa acttaatcta tttttttatgt   4980

tttaatttat tatttttatt aaaatatttt aaactaaatt aaatgattct ttttaatttt   5040

ttactatttc attccataat atattactat aattatttac aaataatatt tcttcatttg   5100

taatatttag atgatttact aattttagtt tttatatatt aaataattaa tgtataattt   5160

atataaaaaa tcaaaggagc ttataaatta tgattatttc caaagatact aaagatttaa   5220

ttttttttcaa ttttaacaat actttttgta atattatgtt taaatttaat tgtatttttt   5280

tcatataata aagccgttga agtaaaccaa tccattttcc ttatgatgtt attattaaat   5340

ttaagtttta taataatatc tttattatat ttattgtttt taaaaaaact agtgaaattt   5400

ctagtgaaat ttccggcttt attaaactta tttttaggaa ttttattttc attttcatct   5460

ttacaggatt tgattatatc tttaaatatg ttttatcaaa tattatcttt ttctaaattt   5520

atatatattt ttattatatt tattattata tatattttat ttttaagttt ctttctaaca   5580

gctattaaaa agaaacttaa aaataaaaac acgtactcta aaccaataaa taaaactatt   5640

tttattattg ctgccttgat tggaatagtt tttagtaaaa ttaatttcaa tattccacaa   5700

tattatatta taagctagca ggcctcgaga tctccatgga cgcgtgacgt cgac         5754
```

<210> SEQ ID NO 25
<211> LENGTH: 884
<212> TYPE: DNA
<213> ORGANISM: Artificial Sequence
<220> FEATURE:
<223> OTHER INFORMATION: Repair template

<400> SEQUENCE: 25

```
ataaggtacc aggaattaga gcagcgctat gttcagatac atttagtgct catgcaacaa     60

gagaacataa taatgctaat atattaacta tgggtcaaag ggttgttgga gcaggtcttg    120

ctttagatat agtaaaaaca tttatatcag ctaaatttga aggagatagg caccaaaaaa    180

gaatagataa gatttcagat attgaaaaaa agtatacaca ttagaaaaaa gcagctatgc    240

tgcaaataag atcaatttat attagaaaaa agcagctatg ctgcaaataa gatcaattta    300
```

```
tattagaaaa aagcagctat gctgcaaata agatcaattt atattagaaa aaagcagcta    360

tgctacaaat aagatcaatt tatattagaa aaaagtagct atgctgcaac aatattaatt    420

tatattacta gaaagctaaa tggggtatat aaatataaag ggctataaat actaaaagca    480

aacttggagg aataataatg gtctagagct ggagatagat tatttggtac taagtaatta    540

gtaatctatt agaattaaaa gctatctaca taagtttctg aatgacccaa gataatttta    600

ctgggggaa tatagaaaat ggagagacga gataagaaaa attattactt ggatattgct    660

gaaacagttt tagagagagg aacctgtcta aggagaaact atggttctat aattgttaaa    720

aatgatgaaa taatttctac tggatacaca ggagcaccta gaggtagaaa aaattgcatg    780

gatttgaata gttgcataag agaaaagttg aaagttccaa gaggtactca ttatgagttg    840

tgtaggagtg tacatagtga agctaatgca ataataagcg cttc                      884


<210> SEQ ID NO 26
<211> LENGTH: 500
<212> TYPE: DNA
<213> ORGANISM: Artificial Sequence
<220> FEATURE:
<223> OTHER INFORMATION: upp gene upstream fragment

<400> SEQUENCE: 26

ataaggtacc aggaattaga gcagcgctat gttcagatac atttagtgct catgcaacaa     60

gagaacataa taatgctaat atattaacta tgggtcaaag ggttgttgga gcaggtcttg    120

ctttagatat agtaaaaaca tttatatcag ctaaatttga aggagatagg caccaaaaaa    180

gaatagataa gatttcagat attgaaaaaa agtatacaca ttagaaaaaa gcagctatgc    240

tgcaaataag atcaatttat attagaaaaa agcagctatg ctgcaaataa gatcaattta    300

tattagaaaa aagcagctat gctgcaaata agatcaattt atattagaaa aaagcagcta    360

tgctacaaat aagatcaatt tatattagaa aaaagtagct atgctgcaac aatattaatt    420

tatattacta gaaagctaaa tggggtatat aaatataaag ggctataaat actaaaagca    480

aacttggagg aataataatg                                                 500


<210> SEQ ID NO 27
<211> LENGTH: 377
<212> TYPE: DNA
<213> ORGANISM: Artificial Sequence
<220> FEATURE:
<223> OTHER INFORMATION: upp gene downstream fragment

<400> SEQUENCE: 27

gctggagata gattatttgg tactaagtaa ttagtaatct attagaatta aaagctatct     60

acataagttt ctgaatgacc caagataatt ttactggggg gaatatagaa aatggagaga    120

cgagataaga aaaattatta cttggatatt gctgaaacag ttttagagag aggaacctgt    180

ctaaggagaa actatggttc tataattgtt aaaaatgatg aaataatttc tactggatac    240

acaggagcac ctagaggtag aaaaaattgc atggatttga atagttgcat aagagaaaag    300

ttgaaagttc caagaggtac tcattatgag ttgtgtagga gtgtacatag tgaagctaat    360

gcaataataa gcgcttc                                                    377


<210> SEQ ID NO 28
<211> LENGTH: 2666
<212> TYPE: DNA
<213> ORGANISM: Artificial Sequence
<220> FEATURE:
```

<223> OTHER INFORMATION: pEX-A2-gRNA-upp

<400> SEQUENCE: 28

```
ctcgagtatt tttgataaaa gcaatgatta acatggtttg acgtctgaga agagacgatt     60
ttctcaatag gagaaattaa ggtgcaaacc cttatcattc caccatgatc cacctgtagc    120
aagcatgttt tagagctaga aatagcaagt taaaataagg ctagtccgtt atcaacttga    180
aaaagtggca ccgagtcggt gctttttttg ccatggacct gcttttgctc gcttggatcc    240
gaattcctgt gtgaaattgt tatccgctca caattccaca caacatacga gccggaagca    300
taaagtgtaa agcctggggt gcctaatgag tgagctaact cacattaatt gcgttgcgct    360
cactgcccgc tttccagtcg ggaaacctgt cgtgccagct gcattaatga atcggccaac    420
gcgcggggag aggcggtttg cgtattgggc gctcttccgc ttcctcgctc actgactcgc    480
tgcgctcggt cgttcggctg cggcgagcgg tatcagctca ctcaaaggcg gtaatacggt    540
tatccacaga atcaggggat aacgcaggaa agaacatgtg agcaaaaggc cagcaaaagg    600
ccaggaaccg taaaaaggcc gcgttgctgg cgtttttcca taggctccgc ccccctgacg    660
agcatcacaa aaatcgacgc tcaagtcaga ggtggcgaaa cccgacagga ctataaagat    720
accaggcgtt tccccctgga agctccctcg tgcgctctcc tgttccgacc ctgccgctta    780
ccggatacct gtccgccttt ctcccttcgg gaagcgtggc gctttctcat agctcacgct    840
gtaggtatct cagttcggtg taggtcgttc gctccaagct gggctgtgtg cacgaacccc    900
ccgttcagcc cgaccgctgc gccttatccg gtaactatcg tcttgagtcc aacccggtaa    960
gacacgactt atcgccactg gcagcagcca ctggtaacag gattagcaga gcgaggtatg   1020
taggcggtgc tacagagttc ttgaagtggt ggcctaacta cggctacact agaagaacag   1080
tatttggtat ctgcgctctg ctgaagccag ttaccttcgg aaaaagagtt ggtagctctt   1140
gatccggcaa acaaaccacc gctggtagcg gtggtttttt tgtttgcaag cagcagatta   1200
cgcgcagaaa aaaaggatct caagaagatc ctttgatctt ttctacgggg tctgacgctc   1260
agtggaacga aaactcacgt taagggattt tggtcatgag attatcaaaa aggatcttca   1320
cctagatcct tttaaattaa aaatgaagtt ttaaatcaat ctaaagtata tatgagtaaa   1380
cttggtctga cagttaccaa tgcttaatca gtgaggcacc tatctcagcg atctgtctat   1440
ttcgttcatc catagttgcc tgactccccg tcgtgtagat aactacgata cgggagggct   1500
taccatctgg ccccagtgct gcaatgatac cgcgactccc acgctcaccg gctccagatt   1560
tatcagcaat aaaccagcca gccggaaggg ccgagcgcag aagtggtcct gcaactttat   1620
ccgcctccat ccagtctatt aattgttgcc gggaagctag agtaagtagt tcgccagtta   1680
atagtttgcg caacgttgtt gccattgcta caggcatcgt ggtgtcacgc tcgtcgtttg   1740
gtatggcttc attcagctcc ggttcccaac gatcaaggcg agttacatga tcccccatgt   1800
tgtgcaaaaa agcggttagc tccttcggtc ctccgatcgt tgtcagaagt aagttggccg   1860
cagtgttatc actcatggtt atggcagcac tgcataattc tcttactgtc atgccatccg   1920
taagatgctt ttctgtgact ggtgagtact caaccaagtc attctgagaa tagtgtatgc   1980
ggcgaccgag ttgctcttgc ccggcgtcaa tacgggataa taccgcgcca catagcagaa   2040
ctttaaaagt gctcatcatt ggaaaacgtt cttcggggcg aaaactctca aggatcttac   2100
cgctgttgag atccagttcg atgtaaccca ctcgtgcacc caactgatct tcagcatctt   2160
ttactttcac cagcgtttct gggtgagcaa aaacaggaag gcaaaatgcc gcaaaaaagg   2220
gaataagggc gacacggaaa tgttgaatac tcatactctt cctttttcaa tattattgaa   2280
```

gcatttatca gggttattgt ctcatgagcg gatacatatt tgaatgtatt tagaaaaata 2340
aacaaatagg ggttccgcgc acatttcccc gaaaagtgcc acctgacgtc taagaaacca 2400
ttattatcat gacattaacc tataaaaata ggcgtatcac gaggcccttt cgtctcgcgc 2460
gtttcggtga tgacggtgaa aacctctgac acatgcagct cccggagacg gtcacagctt 2520
gtctgtaagc ggatgccggg agcagacaag cccgtcaggg cgcgtcagcg ggtgttggcg 2580
ggtgtcgggg ctggcttaac tatgcggcat cagagcagat tgtactgaga gtgcaccaat 2640
tgggtaccga gctcgcggcc gcaagc 2666

<210> SEQ ID NO 29
<211> LENGTH: 203
<212> TYPE: DNA
<213> ORGANISM: Artificial Sequence
<220> FEATURE:
<223> OTHER INFORMATION: gRNA expression cassette

<400> SEQUENCE: 29
tatttttgat aaaagcaatg attaacatgg tttgacgtct gagaagagac gattttctca 60
ataggagaaa ttaaggtgca aacccttatc attccaccat gatccacctg tagcaagcat 120
gttttagagc tagaaatagc aagttaaaat aaggctagtc cgttatcaac ttgaaaaagt 180
ggcaccgagt cggtgctttt ttt 203

<210> SEQ ID NO 30
<211> LENGTH: 100
<212> TYPE: DNA
<213> ORGANISM: Artificial Sequence
<220> FEATURE:
<223> OTHER INFORMATION: Constitutive promoter

<400> SEQUENCE: 30
tatttttgat aaaagcaatg attaacatgg tttgacgtct gagaagagac gattttctca 60
ataggagaaa ttaaggtgca aacccttatc attccaccat 100

<210> SEQ ID NO 31
<211> LENGTH: 20
<212> TYPE: DNA
<213> ORGANISM: Artificial Sequence
<220> FEATURE:
<223> OTHER INFORMATION: Protospacer targeting upp

<400> SEQUENCE: 31
gatccacctg tagcaagcat 20

<210> SEQ ID NO 32
<211> LENGTH: 5954
<212> TYPE: DNA
<213> ORGANISM: Artificial Sequence
<220> FEATURE:
<223> OTHER INFORMATION: pEC750S-deltaupp

<400> SEQUENCE: 32
ataaggtacc aggaattaga gcagcgctat gttcagatac atttagtgct catgcaacaa 60
gagaacataa taatgctaat atattaacta tgggtcaaag ggttgttgga gcaggtcttg 120
ctttagatat agtaaaaaca tttatatcag ctaaatttga aggagatagg caccaaaaaa 180
gaatagataa gatttcagat attgaaaaaa agtatacaca ttagaaaaaa gcagctatgc 240
tgcaaataag atcaatttat attagaaaaa agcagctatg ctgcaaataa gatcaattta 300

-continued

```
tattagaaaa aagcagctat gctgcaaata agatcaattt atattagaaa aaagcagcta    360
tgctacaaat aagatcaatt tatattagaa aaaagtagct atgctgcaac aatattaatt    420
tatattacta gaaagctaaa tggggtatat aaatataaag ggctataaat actaaaagca    480
aacttggagg aataataatg gtctagagct ggagatagat tatttggtac taagtaatta    540
gtaatctatt agaattaaaa gctatctaca taagtttctg aatgacccaa gataatttta    600
ctggggggaa tatagaaaat ggagagacga gataagaaaa attattactt ggatattgct    660
gaaacagttt tagagagagg aacctgtcta aggagaaact atggttctat aattgttaaa    720
aatgatgaaa taatttctac tggatacaca ggagcaccta gaggtagaaa aaattgcatg    780
gatttgaata gttgcataag agaaaagttg aaagttccaa gaggtactca ttatgagttg    840
tgtaggagtg tacatagtga agctaatgca ataataagcg cttcgagctc gaattcgtaa    900
tcatggtcat agctgtttcc tgtgtgaaat tgttatccgc tcacaattcc acacaacata    960
cgagccggaa gcataaagtg taaagcctgg ggtgcctaat gagtgagcta actcacatta   1020
attgcgttgc gctcactgcc cgctttccag tcgggaaacc tgtcgtgcca gctgcattaa   1080
tgaatcggcc aacgcgcggg gagaggcggt ttgcgtattg ggcgctcttc cgcttcctcg   1140
ctcactgact cgctgcgctc ggtcgttcgg ctgcggcgag cggtatcagc tcactcaaag   1200
gcggtaatac ggttatccac agaatcaggg gataacgcag gaaagaacat gtgagcaaaa   1260
ggccagcaaa aggccaggaa ccgtaaaaag gccgcgttgc tggcgttttt ccataggctc   1320
cgcccccctg acgagcatca caaaaatcga cgctcaagtc agaggtggcg aaacccgaca   1380
ggactataaa gataccaggc gtttccccct ggaagctccc tcgtgcgctc tcctgttccg   1440
accctgccgc ttaccggata cctgtccgcc tttctccctt cgggaagcgt ggcgctttct   1500
catagctcac gctgtaggta tctcagttcg gtgtaggtcg ttcgctccaa gctgggctgt   1560
gtgcacgaac cccccgttca gcccgaccgc tgcgccttat ccggtaacta tcgtcttgag   1620
tccaacccgg taagacacga cttatcgcca ctggcagcag ccactggtaa caggattagc   1680
agagcgaggt atgtaggcgg tgctacagag ttcttgaagt ggtggcctaa ctacggctac   1740
actagaagaa cagtatttgg tatctgcgct ctgctgaagc cagttacctt cggaaaaaga   1800
gttggtagct cttgatccgg caaacaaacc accgctggta gcggtggttt ttttgtttgc   1860
aagcagcaga ttacgcgcag aaaaaaagga tctcaagaag atcctttgat cttttctacg   1920
gggtctgacg ctcagtggaa cgaaaactca cgttaaggga ttttggtcat gagattatca   1980
aaaaggatct tcacctagat ccttttaaat taaaaatgaa gttttaaatc aatctaaagt   2040
atatatgagt aaacttggtc tgacagttac caaagctagc ttaatactag tatatactta   2100
atgtgataag tgtctgacag ctgaccggtc taaagaggtc cgccaatgaa atctataaat   2160
aaactaaatt aagtttattt aattaacaac tatggatata aaataggtac taatcaaaat   2220
agtgaggagg atatatttga atacatacga acaaattaat aaagtgaaaa aaatacttcg   2280
gaaacattta aaaaataacc ttattggtac ttacatgttt ggatcaggag ttgagagtgg   2340
actaaaacca aatagtgatc ttgacttttt agtcgtcgta tctgaaccat tgacagatca   2400
aagtaaagaa atacttatac aaaaaattag acctatttca aagaaaatag gagataaaag   2460
caacttacga tatattgaat taacaattat tattcagcaa gaaatggtac cgtggaatca   2520
tcctcccaaa caagaattta tttatggaga atggttacaa gagctttatg aacaaggata   2580
cattcctcag aaggaattaa attcagattt aaccataatg ctttaccaag caaaacgaaa   2640
aaataaaaga atatacggaa attatgactt agaggaatta ctacctgata ttccattttc   2700
```

```
tgatgtgaga agagccatta tggattcgtc agaggaatta atagataatt atcaggatga   2760
tgaaaccaac tctatattaa ctttatgccg tatgatttta actatggaca cgggtaaaat   2820
cataccaaaa gatattgcgg gaaatgcagt ggctgaatct tctccattag aacataggga   2880
gagaattttg ttagcagttc gtagttatct tggagagaat attgaatgga ctaatgaaaa   2940
tgtaaattta actataaact atttaaataa cagattaaaa aaattataaa aaaattgaaa   3000
aaatggtgga aacacttttt tcaatttttt tgttttatta tttaatattt gggaaatatt   3060
cattctaatt ggtaatcaga ttttagaagt tgttaacttc aggtttgtct gtaactaaaa   3120
actagtattt aacctaggat caaaaaaatt tccaataatc ccactctaag ccacaaacac   3180
gccctataaa atcccgcttt aatcccactt tgagacacat gtaatattac tttacgccct   3240
agtatagtga taatttttta cattcaatgc cacgcaaaaa aataaagggg cactataata   3300
aaagttcctt cggaactaac taaagtaaaa aattatcttt acaacctccc caaaaaaaag   3360
aacaggtaca aagtacccta taatacaagc gtaaaaaaaa tgagggtaaa aataaaaaaa   3420
taaaaaaata aaaaaataaa aaaataaaaa aataaaaaaa taaaaaaata taaaaataaa   3480
aaaatataaa aataaaaaaa tataaaaata aaaaaataaa aaaatataaa aataaaaaaa   3540
taaaaaaata taaaaatatt ttttatttaa agtttgaaaa aaattttttt atattatata   3600
atctttgaag aaaagaatat aaaaaatgag cctttataaa agcccatttt ttttcatata   3660
cgtaatatga cgttctaatg tttttattgg tacttctaac attagagtaa tttctttatt   3720
tttaaagcct ttttctttaa gggcttttat ttttttttctt aatacattta attcctcttt   3780
ttttgttgct tttcctttag cttttaattg ctcttgataa ttttttttac ctctaatatt   3840
ttctcttctc ttatattcct ttttagaaat tattattgtc atatattttt gttcttcttc   3900
tgtaatttct aataactcta taagagtttc attcttatac ttatattgct tatttttatc   3960
taaataacat ctttcagcac ttctagttgc tcttataact tctctttcac ttaaatgttg   4020
tctaaacata ctattaagtt ctaaaacatc atttaatgcc ttctcaatgt cttctgtaaa   4080
gctacaaaga taatatctat ataaaaataa tataagctct ctgtgtcctt ttaaatcata   4140
ttctcttagt tcacaaagtt ttattatgtc ttgtattctt ccataatata aacttctttc   4200
tctataaata taatttattt tgcttggtct acccttttttc ctttcatatg gttttaattc   4260
aggtaaaaat ccattttgta tttctcttaa gtcataaata tattcgtact catctaatat   4320
attgactact gtttttgatt tagagtttat acttcctgga actcttaata ttctcgttgc   4380
atctaaggct tgtctatctg ctccaaagta ttttaattga ttatataaat attcttgaac   4440
cgctttccat aatggtaatg ctttactagg tactgcattt attatccata ttaaatacat   4500
tcctcttcca ctatctatta catagtttgg tataggaata ctttgattaa aataattctt   4560
ttctaagtcc attaatacct ggtctttagt tttgccagtt ttataataat ccaagtctat   4620
aaacagtgta tttaactctt ttatattttc taatcgccta cacggcttat aaaaggtatt   4680
tagagttata tagatatttt catcactcat atctaaatct tttaattcag cgtatttata   4740
gtgccattgg ctatatcctt ttttatctat aacgctcctg gttatccacc ctttacttct   4800
actatgaata ttatctatat agttcttttt attcagcttt aatgcgtttc tcacttattc   4860
acctcccctt ctgtaaaact aagaaaatta tatcatattt tcaataatta ttaactattc   4920
ttaaactctt aataaaaaat agagtaagtc cccaattgaa acttaatcta tttttttatgt   4980
tttaatttat tatttttatt aaaatatttt aaactaaatt aaatgattct ttttaatttt   5040
```

```
ttactatttc attccataat atattactat aattatttac aaataatatt tcttcatttg   5100

taatatttag atgatttact aattttagtt tttatatatt aaataattaa tgtataattt   5160

atataaaaaa tcaaaggagc ttataaatta tgattatttc caaagatact aaagatttaa   5220

ttttttcaa ttttaacaat actttttgta atattatgtt taaatttaat tgtatttttt   5280

tcatataata aagccgttga agtaaaccaa tccattttcc ttatgatgtt attattaaat   5340

ttaagtttta taataatatc tttattatat ttattgtttt taaaaaaact agtgaaattt   5400

ctagtgaaat ttccggcttt attaaactta tttttaggaa ttttattttc attttcatct   5460

ttacaggatt tgattatatc tttaaatatg ttttatcaaa tattatcttt ttctaaattt   5520

atatatattt ttattatatt tattattata tatattttat ttttaagttt ctttctaaca   5580

gctattaaaa agaaacttaa aaataaaaac acgtactcta aaccaataaa taaaactatt   5640

tttattattg ctgccttgat tggaatagtt tttagtaaaa ttaatttcaa tattccacaa   5700

tattatatta taagctagca cgcctcgagt atttttgata aaagcaatga ttaacatggt   5760

ttgacgtctg agaagagacg attttctcaa taggagaaat taaggtgcaa acccttatca   5820

ttccaccatg atccacctgt agcaagcatg ttttagagct agaaatagca agttaaaata   5880

aggctagtcc gttatcaact tgaaaaagtg gcaccgagtc ggtgcttttt ttgccatgga   5940

cgcgtgacgt cgac                                                      5954
```

<210> SEQ ID NO 33
<211> LENGTH: 5853
<212> TYPE: DNA
<213> ORGANISM: Artificial Sequence
<220> FEATURE:
<223> OTHER INFORMATION: pEC750C-deltaupp

<400> SEQUENCE: 33

```
atcaaaaaaa tttccaataa tcccactcta agccacaaac acgccctata aaatcccgct     60

ttaatcccac tttgagacac atgtaatatt actttacgcc ctagtatagt gataattttt    120

tacattcaat gccacgcaaa aaaataaagg ggcactataa taaaagttcc ttcggaacta    180

actaaagtaa aaaattatct ttacaacctc cccaaaaaaa agaacaggta caaagtaccc    240

tataatacaa gcgtaaaaaa aatgagggta aaaataaaaa aataaaaaaa taaaaaaata    300

aaaaaataaa aaaataaaaa aataaaaaaa tataaaaata aaaaaatata aaaataaaaa    360

aatataaaaa taaaaaaata aaaaaatata aaaataaaaa aataaaaaaa tataaaaata    420

ttttttattt aaagtttgaa aaaaattttt ttatattata taatctttga agaaaagaat    480

ataaaaaatg agcctttata aaagcccatt ttttttcata tacgtaatat gacgttctaa    540

tgtttttatt ggtacttcta acattagagt aatttcttta tttttaaagc ctttttcttt    600

aagggctttt attttttttc ttaatacatt taattcctct ttttttgttg cttttccttt    660

agcttttaat tgctcttgat aatttttttt acctctaata ttttctcttc tcttatattc    720

ctttttagaa attattattg tcatatattt ttgttcttct tctgtaattt ctaataactc    780

tataagagtt tcattcttat acttatattg cttattttta tctaaataac atctttcagc    840

acttctagtt gctcttataa cttctctttc acttaaatgt tgtctaaaca tactattaag    900

ttctaaaaca tcatttaatg ccttctcaat gtcttctgta aagctacaaa gataatatct    960

atataaaaat aatataagct ctctgtgtcc ttttaaatca tattctctta gttcacaaag   1020

ttttattatg tcttgtattc ttccataata taaacttctt tctctataaa tataatttat   1080

tttgcttggt ctacccttttt tcctttcata tggttttaat tcaggtaaaa atccattttg   1140
```

```
tatttctctt aagtcataaa tatattcgta ctcatctaat atattgacta ctgtttttga   1200
tttagagttt atacttcctg gaactcttaa tattctcgtt gcatctaagg cttgtctatc   1260
tgctccaaag tattttaatt gattatataa atattcttga accgctttcc ataatggtaa   1320
tgctttacta ggtactgcat ttattatcca tattaaatac attcctcttc cactatctat   1380
tacatagttt ggtataggaa tactttgatt aaaataattc ttttctaagt ccattaatac   1440
ctggtcttta gttttgccag ttttataata atccaagtct ataaacagtg tatttaactc   1500
ttttatattt tctaatcgcc tacacggctt ataaaaggta tttagagtta tatagatatt   1560
ttcatcactc atatctaaat cttttaattc agcgtattta tagtgccatt ggctatatcc   1620
tttttatct ataacgctcc tggttatcca ccctttactt ctactatgaa tattatctat    1680
atagttcttt ttattcagct ttaatgcgtt tctcacttat tcacctcccc ttctgtaaaa   1740
ctaagaaaat tatatcatat tttcaataat tattaactat tcttaaactc ttaataaaaa   1800
atagagtaag tccccaattg aaacttaatc tattttttat gttttaattt attattttta   1860
ttaaaatatt ttaaactaaa ttaaatgatt ctttttaatt ttttactatt tcattccata   1920
atatattact ataattattt acaaataata tttcttcatt tgtaatattt agatgattta   1980
ctaattttag tttttatata ttaaataatt aatgtataat ttatataaaa aatcaaagga   2040
gcttataaat tatgattatt tccaaagata ctaaagattt aatttttttc aattttaaca   2100
atactttttg taatattatg tttaaattta attgtatttt tttcatataa taaagccgtt   2160
gaagtaaacc aatccatttt ccttatgatg ttattattaa atttaagttt tataataata   2220
tctttattat atttattgtt tttaaaaaaa ctagtgaaat ttctagtgaa atttccggct   2280
ttattaaact tatttttagg aattttattt tcattttcat ctttacagga tttgattata   2340
tctttaaata tgttttatca aatattatct ttttctaaat ttatatatat ttttattata   2400
tttattatta tatatatttt atttttaagt ttctttctaa cagctattaa aaagaaactt   2460
aaaaataaaa acacgtactc taaaccaata aataaaacta tttttattat tgctgccttg   2520
attggaatag tttttagtaa aattaatttc aatattccac aatattatat tataagctag   2580
cacgcctcga gtatttttga taaaagcaat gattaacatg gtttgacgtc tgagaagaga   2640
cgatttttctc aataggagaa attaaggtgc aaacccttat cattccacca tgatccacct   2700
gtagcaagca tgttttagag ctagaaatag caagttaaaa taaggctagt ccgttatcaa   2760
cttgaaaaag tggcaccgag tcggtgcttt ttttgccatg gacgcgtgac gtcgacataa   2820
ggtaccagga attagagcag cgctatgttc agatacattt agtgctcatg caacaagaga   2880
acataataat gctaatatat taactatggg tcaaagggtt gttggagcag gtcttgcttt   2940
agatatagta aaaacattta tatcagctaa atttgaagga gataggcacc aaaaaagaat   3000
agataagatt tcagatattg aaaaaaagta tacacattag aaaaaagcag ctatgctgca   3060
aataagatca atttatatta gaaaaaagca gctatgctgc aaataagatc aatttatatt   3120
agaaaaaagc agctatgctg caaataagat caatttatat tagaaaaaag cagctatgct   3180
acaaataaga tcaatttata ttagaaaaaa gtagctatgc tgcaacaata ttaatttata   3240
ttactagaaa gctaaatggg gtatataaat ataaagggct ataaatacta aaagcaaact   3300
tggaggaata ataatggtct agagctggag atagattatt tggtactaag taattagtaa   3360
tctattagaa ttaaaagcta tctacataag tttctgaatg acccaagata attttactgg   3420
ggggaatata gaaaatggag agacgagata agaaaaatta ttacttggat attgctgaaa   3480
```

```
cagttttaga gagaggaacc tgtctaagga gaaactatgg ttctataatt gttaaaaatg   3540
atgaaataat ttctactgga tacacaggag cacctagagg tagaaaaaat tgcatggatt   3600
tgaatagttg cataagagaa aagttgaaag ttccaagagg tactcattat gagttgtgta   3660
ggagtgtaca tagtgaagct aatgcaataa taagcgcttc gagctcgaat tcgtaatcat   3720
ggtcatagct gtttcctgtg tgaaattgtt atccgctcac aattccacac aacatacgag   3780
ccggaagcat aaagtgtaaa gcctggggtg cctaatgagt gagctaactc acattaattg   3840
cgttgcgctc actgcccgct ttccagtcgg gaaacctgtc gtgccagctg cattaatgaa   3900
tcggccaacg cgcggggaga ggcggtttgc gtattgggcg ctcttccgct tcctcgctca   3960
ctgactcgct gcgctcggtc gttcggctgc ggcgagcggt atcagctcac tcaaaggcgg   4020
taatacggtt atccacagaa tcaggggata acgcaggaaa gaacatgtga gcaaaaggcc   4080
agcaaaaggc caggaaccgt aaaaaggccg cgttgctggc gtttttccat aggctccgcc   4140
cccctgacga gcatcacaaa aatcgacgct caagtcagag gtggcgaaac ccgacaggac   4200
tataaagata ccaggcgttt ccccctggaa gctccctcgt gcgctctcct gttccgaccc   4260
tgccgcttac cggatacctg tccgcctttc tcccttcggg aagcgtggcg ctttctcata   4320
gctcacgctg taggtatctc agttcggtgt aggtcgttcg ctccaagctg ggctgtgtgc   4380
acgaaccccc cgttcagccc gaccgctgcg ccttatccgg taactatcgt cttgagtcca   4440
acccggtaag acacgactta tcgccactgg cagcagccac tggtaacagg attagcagag   4500
cgaggtatgt aggcggtgct acagagttct tgaagtggtg gcctaactac ggctacacta   4560
gaagaacagt atttggtatc tgcgctctgc tgaagccagt taccttcgga aaaagagttg   4620
gtagctcttg atccggcaaa caaaccaccg ctggtagcgg tggttttttt gtttgcaagc   4680
agcagattac gcgcagaaaa aaaggatctc aagaagatcc tttgatcttt tctacggggt   4740
ctgacgctca gtggaacgaa aactcacgtt aagggatttt ggtcatgaga ttatcaaaaa   4800
ggatcttcac ctagatcctt ttaaattaaa aatgaagttt taaatcaatc taaagtatat   4860
atgagtaaac ttggtctgac agttaccaaa gctagcttaa tactagtata tacttaatgt   4920
gataagtgtc tgacagctga ccggtctaaa gaggtcccta gcgcctacgg ggaatttgta   4980
tcgataaggg gtacaaattc ccactaagcg ctcggccggg gatcgatccc cgggtacgta   5040
cccggcagtt tttctttttc ggcaagtgtt caagaagtta ttaagtcggg agtgcagtcg   5100
aagtgggcaa gttgaaaaat tcacaaaaat gtggtataat atctttgttc attagagcga   5160
taaacttgaa tttgagaggg aacttagatg gtatttgaaa aaattgataa aaatagttgg   5220
aacagaaaag agtattttga ccactacttt gcaagtgtac cttgtaccta cagcatgacc   5280
gttaaagtgg atatcacaca aataaaggaa aagggaatga aactatatcc tgcaatgctt   5340
tattatattg caatgattgt aaaccgccat tcagagttta ggacggcaat caatcaagat   5400
ggtgaattgg ggatatatga tgagatgata ccaagctata caatatttca caatgatact   5460
gaaacatttt ccagcctttg gactgagtgt aagtctgact ttaaatcatt tttagcagat   5520
tatgaaagtg atacgcaacg gtatggaaac aatcatagaa tggaaggaaa gccaaatgct   5580
ccggaaaaca tttttaatgt atctatgata ccgtggtcaa ccttcgatgg ctttaatctg   5640
aatttgcaga aaggatatga ttatttgatt cctattttta ctatggggaa atattataaa   5700
gaagataaca aaattatact tcctttggca attcaagttc atcacgcagt atgtgacgga   5760
tttcacattt gccgttttgt aaacgaattg caggaattga taaatagtta acttcaggtt   5820
tgtctgtaac taaaaactag tatttaacct agg                                5853
```

<210> SEQ ID NO 34
<211> LENGTH: 4966
<212> TYPE: DNA
<213> ORGANISM: Artificial Sequence
<220> FEATURE:
<223> OTHER INFORMATION: pGRNA-pNF2

<400> SEQUENCE: 34
agctcggtac ccggggatcc tctagagtcg acgtcacgcg tccatggaga tctcgaggcg 60
tgctagctta taatataata ttgtggaata ttgaaattaa ttttactaaa aactattcca 120
atcaaggcag caataataaa aatagtttta tttattggtt tagagtacgt gtttttattt 180
ttaagtttct ttttaatagc tgttagaaag aaacttaaaa ataaaatata tataataata 240
aatataataa aaatatatat aaatttagaa aaagataata tttgataaaa catatttaaa 300
gatataatca aatcctgtaa agatgaaaat gaaaataaaa ttcctaaaaa taagtttaat 360
aaagccggaa atttcactag aaatttcact agttttttta aaaacaataa atataataaa 420
gatattatta taaaacttaa atttaataat aacatcataa ggaaaatgga ttggtttact 480
tcaacggctt tattatatga aaaaaataca attaaattta aacataatat tacaaaaagt 540
attgttaaaa ttgaaaaaaa ttaaatcttt agtatctttg gaaataatca taatttataa 600
gctcctttga ttttttatat aaattataca ttaattattt aatatataaa aactaaaatt 660
agtaaatcat ctaaatatta caaatgaaga aatattattt gtaaataatt atagtaatat 720
attatggaat gaaatagtaa aaaattaaaa agaatcattt aatttagttt aaaatatttt 780
aataaaaata ataaattaaa acataaaaaa tagattaagt ttcaattggg gacttactct 840 atttttttatt aagagtttaa gaatagttaa taattattga aaatatgata taattttctt 900
agttttacag aaggggaggt gaataagtga gaaacgcatt aaagctgaat aaaaagaact 960
atatagataa tattcatagt agaagtaaag ggtggataac caggagcgtt atagataaaa 1020
aaggatatag ccaatggcac tataaatacg ctgaattaaa agatttagat atgagtgatg 1080
aaaatatcta tataactcta aataccttttt ataagccgtg taggcgatta gaaaatataa 1140
aagagttaaa tacactgttt atagacttgg attattataa aactggcaaa actaaagacc 1200
aggtattaat ggacttagaa aagaattatt ttaatcaaag tattcctata ccaaactatg 1260
taatagatag tggaagagga atgtatttaa tatggataat aaatgcagta cctagtaaag 1320
cattaccatt atggaaagcg gttcaagaat atttatataa tcaattaaaa tactttggag 1380
cagatagaca agccttagat gcaacgagaa tattaagagt tccaggaagt ataaactcta 1440
aatcaaaaac agtagtcaat atattagatg agtacgaata tatttatgac ttaagagaaa 1500
tacaaaatgg atttttacct gaattaaaac catatgaaag gaaaaagggt agaccaagca 1560
aaataaatta tatttataga gaaagaagtt tatattatgg aagaatacaa gacataataa 1620
aactttgtga actaagagaa tatgatttaa aaggacacag agagcttata ttatttttat 1680
atagatatta tctttgtagc tttacagaag acattgagaa ggcattaaat gatgttttag 1740
aacttaatag tatgtttaga caacatttaa gtgaaagaga agttataaga gcaactagaa 1800
gtgctgaaag atgttattta gataaaaata agcaatataa gtataagaat gaaactctta 1860
tagagttatt agaaattaca gaagaagaac aaaaatatat gacaataata atttctaaaa 1920
aggaatataa gagaagagaa aatattagag gtaaaaaaaa ttatcaagag caattaaaag 1980
ctaaaggaaa agcaacaaaa aaagaggaat taaatgtatt aagaaaaaaa ataaaagccc 2040

```
ttaaagaaaa aggctttaaa aataaagaaa ttactctaat gttagaagta ccaataaaaa   2100

cattagaacg tcatattacg tatatgaaaa aaaatgggct tttataaagg ctcatttttt   2160

atattctttt cttcaaagat tatataatat aaaaaaattt ttttcaaact ttaaataaaa   2220

aatattttta tattttttta ttttttatt tttatatttt tttattttt tatttttata   2280

ttttttatt tttatatttt tttattttta tattttttta ttttttatt tttttatttt   2340

tttattttt tattttttta ttttttatt tttaccctca tttttttac gcttgtatta   2400

tagggtactt tgtacctgtt ctttttttg gggaggttgt aaagataatt ttttacttta   2460

gttagttccg aaggaacttt tattatagtg ccccttatt tttttgcgtg gcattgaatg   2520

taaaaaatta tcactatact agggcgtaaa gtaatattac atgtgtctca aagtgggatt   2580

aaagcgggat tttatagggc gtgtttgtgg cttagagtgg gattattgga aatttttttg   2640

atcctaggtt aaatactagt ttttagttac agacaaacct gaagttaact atttatcaat   2700

tcctgcaatt cgtttacaaa acggcaaatg tgaaatccgt cacatactgc gtgatgaact   2760

tgaattgcca aaggaagtat aattttgtta tcttctttat aatatttccc catagtaaaa   2820

ataggaatca aataatcata tcctttctgc aaattcagat taaagccatc gaaggttgac   2880

cacggtatca tagatacatt aaaaatgttt tccggagcat ttggctttcc ttccattcta   2940

tgattgtttc cataccgttg cgtatcactt tcataatctg ctaaaaatga tttaaagtca   3000

gacttacact cagtccaaag gctggaaaat gtttcagtat cattgtgaaa tattgtatag   3060

cttggtatca tctcatcata tatccccaat tcaccatctt gattgattgc cgtcctaaac   3120

tctgaatggc ggtttacaat cattgcaata taataaagca ttgcaggata tagtttcatt   3180

ccctttcct ttatttgtgt gatatccact ttaacggtca tgctgtaggt acaaggtaca   3240

cttgcaaagt agtggtcaaa atactctttt ctgttccaac tatttttatc aatttttca   3300

aataccatct aagttccctc tcaaattcaa gtttatcgct ctaatgaaca aagatattat   3360

accacatttt tgtgaatttt tcaacttgcc cacttcgact gcactcccga cttaataact   3420

tcttgaacac ttgccgaaaa agaaaaactg ccgggtacgt acccggggat cgatccccgg   3480

ccgagcgctt agtgggaatt tgtacccctt atcgatacaa attccccgta ggcgctaggg   3540

acctctttag accggtcagc tgtcagacac ttatcacatt aagtatatac tagtattaag   3600

ctagctttgg taactgtcag accaagttta ctcatatata ctttagattg atttaaaact   3660

tcatttttaa tttaaaagga tctaggtgaa gatccttttt gataatctca tgaccaaaat   3720

cccttaacgt gagttttcgt tccactgagc gtcagacccc gtagaaaaga tcaaaggatc   3780

ttcttgagat ccttttttc tgcgcgtaat ctgctgcttg caaacaaaaa aaccaccgct   3840

accagcggtg gtttgtttgc cggatcaaga gctaccaact ctttttccga aggtaactgg   3900

cttcagcaga gcgcagatac caaatactgt tcttctagtg tagccgtagt taggccacca   3960

cttcaagaac tctgtagcac cgcctacata cctcgctctg ctaatcctgt taccagtggc   4020

tgctgccagt ggcgataagt cgtgtcttac cgggttggac tcaagacgat agttaccgga   4080

taaggcgcag cggtcgggct gaacgggggg ttcgtgcaca cagcccagct tggagcgaac   4140

gacctacacc gaactgagat acctacagcg tgagctatga gaaagcgcca cgcttcccga   4200

agggagaaag gcggacaggt atccggtaag cggcagggtc ggaacaggag agcgcacgag   4260

ggagcttcca gggggaaacg cctggtatct ttatagtcct gtcgggtttc gccacctctg   4320

acttgagcgt cgatttttgt gatgctcgtc aggggggcgg agcctatgga aaaacgccag   4380

caacgcggcc tttttacggt tcctggcctt ttgctggcct tttgctcaca tgttctttcc   4440
```

```
tgcgttatcc cctgattctg tggataaccg tattaccgcc tttgagtgag ctgataccgc   4500

tcgccgcagc cgaacgaccg agcgcagcga gtcagtgagc gaggaagcgg aagagcgccc   4560

aatacgcaaa ccgcctctcc ccgcgcgttg gccgattcat taatgcagct ggcacgacag   4620

gtttcccgac tggaaagcgg gcagtgagcg caacgcaatt aatgtgagtt agctcactca   4680

ttaggcaccc caggctttac actttatgct tccggctcgt atgttgtgtg gaattgtgag   4740

cggataacaa tttcacacag gaaacagcta tgaccatgat tacgaattcg agctcactct   4800

atcattgata gagtttgaaa ctctatcatt gatagagtat aatatctttg ttcatttaag   4860

ccatctacta aacaagtttt agagctagaa atagcaagtt aaaataaggc tagtccgtta   4920

tcaacttgaa aaagtggcac cgagtcggtg cttttttga agcttg                   4966
```

<210> SEQ ID NO 35
<211> LENGTH: 400
<212> TYPE: DNA
<213> ORGANISM: Artificial Sequence
<220> FEATURE:
<223> OTHER INFORMATION: catB gene upstream fragment

<400> SEQUENCE: 35

```
gtctttacac ttttgcccat taatttttga gttccttatt tttagggagc ttttattatt     60

tttatcatga aaatttcata aaatactcat aaactaagga tgtcttcata atcagattag    120

tactccattt tcaatccatt taatctggga atatgatatt ttaattacgt attatttaag    180

atatattaac gtgtaatata ataccccgca aatattaatt atcacataca tatccccccct    240

ttattggggc attttttgta cccattattt tagtattgtg cagtacttaa ataaaaaaat    300

gccgcaaatt catttttatt gaataatgcg gtatttcttc tattctttat ttttattact    360

ctataaataa tgtaatcaag acatgactat ctaaatatat                         400
```

<210> SEQ ID NO 36
<211> LENGTH: 400
<212> TYPE: DNA
<213> ORGANISM: Artificial Sequence
<220> FEATURE:
<223> OTHER INFORMATION: catB gene downstream fragment

<400> SEQUENCE: 36

```
aattcataat tcgggcctcc taaaaatttt cgtaattcta ttttagaagg ctttttttccg     60

tgacctagcc atttcaatct cctttttaca atgatattta cgctttagtt tattatagca    120

cattctgtaa taccgaacta ttcaattttc agagaccatt ttttattgat tcataactta    180

agaatactac gaattactct aatattttac tttttcttat ctcttgttat tttaacatcg    240

gaattactac taatattaat ttttattttt ccatccgcat ttgctccaac attttttttaa    300

ctatactttc cttttgttaa taaattatgt tattgttgaa caatataaga aaagtgcgta    360

acattttta ttaaaaataa ttaggtattt ctatctgtgg                          400
```

<210> SEQ ID NO 37
<211> LENGTH: 218
<212> TYPE: PRT
<213> ORGANISM: Clostridium beijerinckii

<400> SEQUENCE: 37

```
Met Asn Phe Asn Leu Ile Asp Ile Asn His Trp Ser Arg Lys Pro Tyr
1               5                   10                  15

Phe Glu His Tyr Leu Asn Asn Val Lys Cys Thr Tyr Ser Met Thr Ala
```

```
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Lys
    50                  55                  60

His Lys Glu Phe Arg Ile Cys Asp His Glu Gly Ser Leu Gly Tyr Trp
65                  70                  75                  80

Asp Ser Met Asn Pro Ser Tyr Thr Ile Phe His Lys Glu Asn Glu Thr
                85                  90                  95

Phe Ser Ser Ile Trp Thr Glu Tyr Asn Lys Ser Phe Leu Arg Phe Tyr
            100                 105                 110

Ser Asp Tyr Leu Asp Asp Ile Lys Asn Tyr Gly Asn Ile Met Lys Phe
        115                 120                 125

Thr Pro Lys Ser Asn Glu Pro Asp Asn Thr Phe Ser Val Ser Ser Ile
    130                 135                 140

Pro Trp Val Ser Phe Thr Gly Phe Asn Leu Asn Val Tyr Asn Glu Gly
145                 150                 155                 160

Thr Tyr Leu Ile Pro Ile Phe Thr Ala Gly Lys Tyr Phe Lys Gln Glu
                165                 170                 175

Asn Lys Ile Phe Ile Pro Ile Ser Ile Gln Val His His Ala Ile Cys
            180                 185                 190

Asp Gly Tyr His Ala Ser Arg Phe Ile Asn Glu Met Gln Glu Leu Ala
        195                 200                 205

Phe Ser Phe Gln Glu Trp Leu Glu Asn Lys
    210                 215
```

<210> SEQ ID NO 38
<211> LENGTH: 9113
<212> TYPE: DNA
<213> ORGANISM: Artificial Sequence
<220> FEATURE:
<223> OTHER INFORMATION: pCas9ind-gRNA_catB

<400> SEQUENCE: 38

```
catggataaa aagtacagta ttggtctaga cataggaact aactctgttg ggtgggctgt     60

tataacagat gaatataaag ttccatcaaa aaaatttaaa gtattaggaa acactgatag    120

acattcaata aaaaaaaact tgataggtgc tttattattc gattcaggag agactgctga    180

agctacacgt ttaaaaagaa cagctagacg tagatataca agaagaaaaa ataggatatg    240

ttatcttcaa gaaatttttta gtaatgaaat ggcaaaagtt gatgattcat tctttcacag    300

actagaagaa agtttcttag ttgaagaaga taagaagcat gaaagacacc ctatttttgg    360

taatatcgta gatgaagtag catatcatga gaagtatcca actatctatc atttaagaaa    420

gaaattagtt gattctacag ataaagctga tctgagatta atatatttag ctttagctca    480

tatgattaaa tttagaggac atttttttaat agaaggtgat ttaaacccag acaacagcga    540

tgtagataaa ttatttatcc aattagttca aacttataat caattattcg aagagaatcc    600

aattaatgca agtggtgtag acgctaaggc tatattatca gctagattat caaaatctag    660

aagattagaa aatctaatag ctcaacttcc tggagaaaag aaaaatggac tttttgggaa    720

cctaatagct ctctcactcg gactaacacc aaattttaaa agcaattttg atcttgctga    780

agacgcaaag ttacaactat caaaggatac atacgatgat gatttagata atttgttagc    840

tcaaataggt gatcaatatg ctgatttgtt tcttgcagca aaaaacttaa gtgatgcaat    900

tttactatca gatatactta gagtaaatac agaaataaca aaggctcctt tatcagcaag    960
```

```
tatgattaaa cgatatgatg agcatcatca agatttaaca ttattaaagg cacttgtaag   1020
acaacaatta ccagaaaaat ataaagaaat tttctttgat caatctaaaa atggatatgc   1080
tggatatata gacggtggag caagtcaaga agagttttat aaatttataa agcctatttt   1140
agaaaaaatg gatggaactg aagaattact tgttaaactt aacagagaag atttacttag   1200
aaaacaaaga actttttgata atggttcaat tcctcaccaa attcatttag gagaattaca   1260
tgctatacta agaagacaag aagattttta tccatttctt aaagataata gagaaaaaat   1320
tgaaaaaatt ttaactttta gaataccata ttatgtagga ccacttgcaa ggggaaattc   1380
aagatttgca tggatgacta gaaaatcaga agaaactata accccgtgga attttgaaga   1440
agtagtagat aaaggagcta gtgctcaatc atttatagaa agaatgacaa attttgataa   1500
gaatcttcct aacgaaaagg ttttgccaaa gcatagcctt ctttatgagt attttacagt   1560
ttataatgag cttactaaag taaaatacgt tacagaagga atgagaaaac cagcattttt   1620
gtctggtgaa caaaagaaag caatagtaga cctattattt aaaacaaata ggaaggttac   1680
cgtaaagcaa cttaaagaag attacttcaa aaaaattgaa tgctttgata gtgttgaaat   1740
atcaggagtt gaagatagat ttaatgcttc acttggtaca tatcacgatc tcttaaaaat   1800
tataaaagat aaggattttt tagataatga agaaaatgaa gatattcttg aagatatagt   1860
attaacattg acacttttttg aagatagaga aatgatagaa gaaagattaa aaacatatgc   1920
acatcttttt gatgataagg ttatgaagca acttaaaaga agaagatata caggttgggg   1980
acgtttgtca agaaagctaa ttaatggtat tagagataaa caatcaggaa agactattct   2040
cgattttctt aaatcagatg gatttgctaa tagaaacttt atgcaattaa ttcatgatga   2100
ttctcttact ttcaaagagg atattcaaaa ggctcaagtt tctggacaag gcgatagctt   2160
acacgaacac attgctaacc ttgcagggag ccccgctatc aaaaaaggaa ttttacaaac   2220
agttaaagtt gtagatgaac ttgttaaagt tatgggaaga cacaaacctg agaatatagt   2280
tatagaaatg gccagagaaa atcaaacaac acaaaaagga caaaaaaatt ctagagagag   2340
aatgaagaga attgaagaag gaataaaaga gctaggatca caaatattaa aagaacatcc   2400
agttgaaaat actcaattgc aaaatgaaaa gttatatttg tattacttac aaaatggaag   2460
agatatgtat gttgatcaag aactcgatat taatagatta agtgactatg atgttgatca   2520
tattgttcct caatcatttt taaaagatga ttcaatcgat aacaaagtat taactagatc   2580
agataaaaat agaggaaagt cagataatgt accatctgaa gaagttgtta aaaaaatgaa   2640
gaactattgg agacaacttt taaatgcaaa gctaattaca caaagaaaat ttgacaattt   2700
aacaaaagca gaaagaggag gattaagcga attagacaaa gctggattta taaaaagaca   2760
acttgttgag acaagacaaa taactaagca tgttgctcaa atacttgatt caagaatgaa   2820
tacaaaatat gatgaaaatg ataaattaat cagagaagta aaagtaataa cattaaagtc   2880
aaaattagta tcagatttca gaaaggattt tcaattttac aaagttcgtg aaataaataa   2940
ctatcatcat gctcatgatg catacttaaa tgctgttgta ggaactgctc ttattaagaa   3000
atatcctaaa ctagaaagcg aatttgttta tggagattat aaagtttatg atgtgcgcaa   3060
aatgatcgcg aaatccgaac aagaaatcgg taaggctaca gcaaaatatt tcttttatag   3120
taatataatg aatttttttta agacagaaat aactttggct aatggtgaaa tcagaaaaag   3180
accacttatc gaaacaaatg gagagacagg agaaatagta tgggataaag gaagagattt   3240
tgctactgtt agaaaagtac taagtatgcc acaagtaaat atcgtaaaga aaactgaagt   3300
```

```
tcaaactgga ggtttctcta aggaatcaat tttacctaag agaaattcag ataagttaat   3360
tgcaaggaaa aaagattggg acccaaaaaa atacggtggt tttgatagtc caacagttgc   3420
ctatagtgtt cttgtagtag cgaaagttga gaaaggtaag tcaaaaaagt tgaaaagcgt   3480
aaaagaactt cttggtatca caattatgga aagatcttca tttgaaaaaa atccaattga   3540
ctttttagaa gctaagggtt ataaagaagt taaaaaggat ttaatcataa aactaccaaa   3600
gtatagtcta tttgaactcg aaaacggaag aaaacgaatg ctcgctagcg caggagaact   3660
tcaaaaagga aatgaacttg cgctgccatc aaagtatgta aatttcttat atttagcttc   3720
tcattatgag aaattaaaag gatcaccaga ggataatgaa caaaagcaac tatttgtaga   3780
acaacacaaa cattatttag atgaaataat agaacaaata tctgaatttt ctaaaagagt   3840
tatacttgcc gacgcaaatc tagataaggt gctttcagcg tataataaac acagagataa   3900
accaataaga gaacaagcag aaaacattat ccatcttttt acattaacta atcttggtgc   3960
accagctgca tttaagtact ttgatacaac aatagataga aaaagataca catctactaa   4020
agaagtatta gacgcaactt taatacatca atctattaca gggctttatg aaacaagaat   4080
tgatttaagt caactaggcg gagattaagt cgacaaagta ttgttaaaaa taactctgta   4140
gaattataaa ttagttctac agagttattt tttgacccgg gtatattgat aaaaataata   4200
atagtgggta taattaagtt gttaggaggt tagttagaat gatgtcaaga ttagataaaa   4260
gtaaagtgat taacagcgca ttagagctgc ttaatgaggt cggaatcgaa ggtttaacaa   4320
cccgtaaact cgcccagaag ctaggtgtag agcagcctac attgtattgg catgtaaaaa   4380
ataagcgggc tttgctcgac gccttagcca ttgagatgtt agataggcac catactcact   4440
tttgcccttt agaaggggaa agctggcaag atttttacg taataacgct aaaagtttta    4500
gatgtgcttt actaagtcat cgcgatggag caaaagtaca tttaggtaca cggcctacag   4560
aaaaacagta tgaaactctc gaaaatcaat tagccttttt atgccaacaa ggtttttcac   4620
tagagaatgc attatatgca ctcagcgctg tggggcattt tactttaggt tgcgtattgg   4680
aagatcaaga gcatcaagtc gctaaagaag aaagggaaac acctactact gatagtatgc   4740
cgccattatt acgacaagct atcgaattat ttgatcacca aggtgcagag ccagccttct   4800
tattcggcct tgaattgatc atatgcggat tagaaaaaca acttaaatgt gaaagtgggt   4860
cttaaaagca gcataacctt tttccgtgat ggtaacttca cggtaaccaa gatgtcgagt   4920
tgagctcgaa ttcgtaatca tggtcatagc tgtttcctgt gtgaaattgt tatccgctca   4980
caattccaca caacatacga gccggaagca taaagtgtaa agcctggggt gcctaatgag   5040
tgagctaact cacattaatt gcgttgcgct cactgcccgc tttccagtcg ggaaacctgt   5100
cgtgccagct gcattaatga atcggccaac gcgcggggag aggcggtttg cgtattgggc   5160
gctcttccgc ttcctcgctc actgactcgc tgcgctcggt cgttcggctg cggcgagcgg   5220
tatcagctca ctcaaaggcg gtaatacggt tatccacaga atcaggggat aacgcaggaa   5280
agaacatgtg agcaaaaggc cagcaaaagg ccaggaaccg taaaaaggcc gcgttgctgg   5340
cgtttttcca taggctccgc ccccctgacg agcatcacaa aaatcgacgc tcaagtcaga   5400
ggtggcgaaa cccgacagga ctataaagat accaggcgtt tccccctgga agctccctcg   5460
tgcgctctcc tgttccgacc ctgccgctta ccggatacct gtccgccttt ctcccttcgg   5520
gaagcgtggc gctttctcat agctcacgct gtaggtatct cagttcggtg taggtcgttc   5580
gctccaagct gggctgtgtg cacgaacccc ccgttcagcc cgaccgctgc gccttatccg   5640
gtaactatcg tcttgagtcc aacccggtaa gacacgactt atcgccactg gcagcagcca   5700
```

ctggtaacag gattagcaga gcgaggtatg taggcggtgc tacagagttc ttgaagtggt 5760
ggcctaacta cggctacact agaaggacag tatttggtat ctgcgctctg ctgaagccag 5820
ttaccttcgg aaaaagagtt ggtagctctt gatccggcaa acaaaccacc gctggtagcg 5880
gtggtttttt tgtttgcaag cagcagatta cgcgcagaaa aaaggatctc aagaagatcc 5940
ctttgatctt ttctacgggg tctgacgctc agtggaacga aaactcacgt taagggattt 6000
tggtcatgag attatcaaaa aggatcttca cctagatcct tttaaattaa aaatgaagtt 6060
ttaaatcaat ctaaagtata tatgagtaaa cttggtctga cagttaccag gtccactgcc 6120
gggcctcttg cgggatcaaa agaaaaacga aatgatacac caatcagtgc aaaaaaagat 6180
ataatgggag ataagacggt tcgtgttcgt gctgacttgc accatatcat aaaaatcgaa 6240
acagcaaaga atggcggaaa cgtaaaagaa gttatggaaa taagacttag aagcaaactt 6300
aagagtgtgt tgatagtgca gtatcttaaa attttgtata ataggaattg aagttaaatt 6360
agatgctaaa aatttgtaat taagaaggag tgattacatg aacaaaaata taaaatattc 6420
tcaaaacttt ttaacgagtg aaaaagtact caaccaaata ataaaacaat tgaatttaaa 6480
agaaaccgat accgtttacg aaattggaac aggtaaaggg catttaacga cgaaactggc 6540
taaaataagt aaacaggtaa cgtctattga attagacagt catctattca acttatcgtc 6600
agaaaaatta aaactgaata ctcgtgtcac tttaattcac caagatattc tacagtttca 6660
attccctaac aaacagaggt ataaaattgt tgggagtatt ccttaccatt taagcacaca 6720
aattattaaa aaagtggttt ttgaaagcca tgcgtctgac atctatctga ttgttgaaga 6780
aggattctac aagcgtacct tggatattca ccgaacacta gggttgctct tgcacactca 6840
agtctcgatt cagcaattgc ttaagctgcc agcggaatgc tttcatccta aaccaaaagt 6900
aaacagtgtc ttaataaaac ttacccgcca taccacagat gttccagata aatattggaa 6960
gctatatacg tactttgttt caaaatgggt caatcgagaa tatcgtcaac tgtttactaa 7020
aaatcagttt catcaagcaa tgaaacacgc caaagtaaac aatttaagta ccgttactta 7080
tgagcaagta ttgtctattt ttaatagtta tctattattt aacgggagga aataattcta 7140
tgagtcccta ggcaggcctc cgccattatt tttttgaaca attgacaatt catttcttat 7200
tttttattaa gtgatagtca aaaggcataa cagtgctgaa tagaaagaaa tttacagaaa 7260
agaaaattat agaatttagt atgattaatt atactcattt atgaatgttt aattgaatac 7320
aaaaaaaaat acttgttatg tattcaatta cgggttaaaa tatagacaag ttgaaaaatt 7380
taataaaaaa ataagtcctc agctcttata tattaagcta ccaacttagt atataagcca 7440
aaacttaaat gtgctaccaa cacatcaagc cgttagagaa ctctatctat agcaatattt 7500
caaatgtacc gacatacaag agaaacatta actatatata ttcaatttat gagattatct 7560
taacagatat aaatgtaaat tgcaataagt aagatttaga agtttatagc ctttgtgtat 7620
tggaagcagt acgcaaaggc ttttttattt gataaaaatt agaagtatat ttattttttc 7680
ataattaatt tatgaaaatg aaagggggtg agcaaagtga cagaggaaag cagtatctta 7740
tcaaataaca aggtattagc aatatcatta ttgactttag cagtaaacat tatgactttt 7800
atagtgcttg tagctaagta gtacgaaagg gggagcttta aaaagctcct tggaatacat 7860
agaattcata aattaattta tgaaaagaag ggcgtatatg aaaacttgta aaaattgcaa 7920
agagtttatt aaagatactg aaatatgcaa aatacattcg ttgatgattc atgataaaac 7980
agtagcaacc tattgcagta aatacaatga gtcaagatgt ttacataaag ggaaagtcca 8040
atgtattaat tgttcaaaga tgaaccgata tggatggtgt gccataaaaa tgagatgttt 8100
tacagaggaa gaacagaaaa aagaacgtac atgcattaaa tattatgcaa ggagctttaa 8160
aaaagctcat gtaaagaaga gtaaaaagaa aaaataattt atttattaat ttaatattga 8220
gagtgccgac acagtatgca ctaaaaaata tatctgtggt gtagtgagcc gatacaaaag 8280
gatagtcact cgcattttca taatacatct tatgttatga ttatgtgtcg gtgggacttc 8340
acgacgaaaa cccacaataa aaaaagagtt cggggtaggg ttaagcatag ttgaggcaac 8400
taaacaatca agctaggata tgcagtagca gaccgtaagg tcgttgttta ggtgtgttgt 8460
aatacatacg ctattaagat gtaaaaatac ggataccaat gaagggaaaa gtataatttt 8520
tggatgtagt ttgtttgttc atctatgggc aaactacgtc caaagccgtt tccaaatctg 8580
ctaaaaagta tatcctttct aaaatcaaag tcaagtatga aatcataaat aaagtttaat 8640
tttgaagtta ttatgatatt atgtttttct attaaaataa attaagtata tagaatagtt 8700
taataatagt atatacttaa tgtgataagt gtctgacagt gtcacagaaa ggatgattgt 8760
tatggattat aagcggctcg aggacgtcaa accatgttaa tcattgcttt tatcaaaaat 8820
aggatccact ctatcattga tagagtttga aactctatca ttgatagagt ataatatctt 8880
tgttcatgta catcatgcta tctgtgagtt ttagagctag aaatagcaag ttaaaataag 8940
gctagtccgt tatcaacttg aaaaagtggc accgagtcgg tgcttttttt gaagcttgtc 9000
tttacacttt tgcccctcga gtccctatca gtgatagatt gaaactctat cattgataga 9060
gtataatatc tttgttcatt agagcgataa acttgaattt gagagggaac ttc 9113

<210> SEQ ID NO 39
<211> LENGTH: 20
<212> TYPE: DNA
<213> ORGANISM: Artificial Sequence
<220> FEATURE:
<223> OTHER INFORMATION: Primer pNF2

<400> SEQUENCE: 39
gggcgcactt atacaccacc 20

<210> SEQ ID NO 40
<211> LENGTH: 20
<212> TYPE: DNA
<213> ORGANISM: Artificial Sequence
<220> FEATURE:
<223> OTHER INFORMATION: Primer pNF2

<400> SEQUENCE: 40
tgctacgcac cccctaaagg 20

<210> SEQ ID NO 41
<211> LENGTH: 50
<212> TYPE: DNA
<213> ORGANISM: Artificial Sequence
<220> FEATURE:
<223> OTHER INFORMATION: DeltacatB_gRNA_rev

<400> SEQUENCE: 41
aatctatcac tgatagggac tcgaggggca aaagtgtaaa gacaagcttc 50

<210> SEQ ID NO 42
<211> LENGTH: 20
<212> TYPE: DNA
<213> ORGANISM: Artificial Sequence
<220> FEATURE:
<223> OTHER INFORMATION: Primer pCas9ind_fwd

<400> SEQUENCE: 42
agctcttgat ccggcaaaca 20

<210> SEQ ID NO 43
<211> LENGTH: 20
<212> TYPE: DNA
<213> ORGANISM: Artificial Sequence
<220> FEATURE:
<223> OTHER INFORMATION: Primer pCas9ind _rev

<400> SEQUENCE: 43
gcaaccctag tgttcggtga 20

<210> SEQ ID NO 44
<211> LENGTH: 219
<212> TYPE: PRT
<213> ORGANISM: Clostridium butyricum

<400> SEQUENCE: 44

Met Asn Phe Asn Leu Ile Asp Ile Asn His Trp Ser Arg Lys Pro Tyr
1 5 10 15

Phe Glu His Tyr Leu Asn Asn Val Lys Cys Thr Tyr Ser Met Thr Ala
20 25 30

Asn Ile Glu Ile Thr Asp Leu Leu Tyr Glu Ile Lys Leu Lys Asn Ile
35 40 45

Lys Phe Tyr Pro Thr Leu Ile Tyr Met Ile Ala Thr Val Val Asn Asn
50 55 60

His Lys Glu Phe Arg Ile Cys Phe Asp His Lys Gly Ser Leu Gly Tyr
65 70 75 80

Trp Asp Ser Met Asn Pro Ser Tyr Thr Ile Phe His Lys Glu Asn Glu
85 90 95

Thr Phe Ser Ser Ile Trp Thr Glu Tyr Asn Lys Ser Phe Leu Arg Phe
100 105 110

Tyr Ser Asp Tyr Leu Asp Asp Ile Lys Asn Tyr Gly Asn Ile Met Lys
115 120 125

Phe Thr Pro Lys Ser Asn Glu Pro Asp Asn Thr Phe Ser Val Ser Ser
130 135 140

Ile Pro Trp Val Ser Phe Thr Gly Phe Asn Leu Asn Val Tyr Asn Glu
145 150 155 160

Gly Thr Tyr Leu Ile Pro Ile Phe Thr Ala Gly Lys Tyr Phe Lys Gln
165 170 175

Glu Asn Lys Ile Phe Ile Pro Ile Ser Ile Gln Val His His Ala Ile
180 185 190

Cys Asp Gly Tyr His Ala Ser Arg Phe Ile Asn Glu Met Gln Glu Leu
195 200 205

Ala Phe Ser Phe Gln Glu Trp Leu Glu Asn Lys
210 215

<210> SEQ ID NO 45
<211> LENGTH: 219
<212> TYPE: PRT
<213> ORGANISM: Clostridium beijerinckii

<400> SEQUENCE: 45

Met Asn Phe Asn Leu Ile Asp Ile Asn His Trp Ile Arg Lys Pro Tyr
1 5 10 15

Phe Glu His Tyr Leu Asn Asn Val Lys Cys Thr Tyr Ser Met Thr Ala

```
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Lys Glu Phe Arg Ile Cys Phe Asp His Lys Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Lys Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Glu Pro Asp Asn Thr Phe Ser Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Glu Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215


<210> SEQ ID NO 46
<211> LENGTH: 219
<212> TYPE: PRT
<213> ORGANISM: Clostridium beijerinckii

<400> SEQUENCE: 46

Met Asn Phe Asn Leu Ile Asp Ile Asn His Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Glu Glu Phe Arg Ile Cys Phe Asp His Glu Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Lys Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Glu Pro Asp Asn Thr Phe Ser Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175
```

```
Gly Asn Lys Val Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215


<210> SEQ ID NO 47
<211> LENGTH: 219
<212> TYPE: PRT
<213> ORGANISM: Clostridium beijerinckii

<400> SEQUENCE: 47

Met Asn Phe Asn Leu Ile Asp Ile Asn His Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Lys Glu Phe Ser Ile Cys Phe Asp His Glu Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Glu Pro Asp Asn Thr Phe Ser Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Gly Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215


<210> SEQ ID NO 48
<211> LENGTH: 219
<212> TYPE: PRT
<213> ORGANISM: Artificial Sequence
<220> FEATURE:
<223> OTHER INFORMATION: Clostridium sp.2-1

<400> SEQUENCE: 48

Met Asn Phe Asn Leu Ile Asp Ile Asn His Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Asn Val Val Asn Asn
```

```
    50                  55                  60

His Lys Glu Phe Arg Ile Cys Phe Asp His Asn Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Gln Pro Asp Asn Thr Phe Ser Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Glu Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215


<210> SEQ ID NO 49
<211> LENGTH: 219
<212> TYPE: PRT
<213> ORGANISM: Artificial Sequence
<220> FEATURE:
<223> OTHER INFORMATION: Clostridium diolis

<400> SEQUENCE: 49

Met Asn Phe Asn Leu Ile Asp Ile Asn His Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Asn Val Val Asn Asn
    50                  55                  60

His Lys Glu Phe Arg Ile Cys Phe Asp His Asn Gly Ser Leu Gly Tyr
65                  70                  75                  80

Trp Asp Ser Met Asn Pro Ser Tyr Thr Val Phe His Lys Glu Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Glu Pro Asp Asn Thr Phe Ser Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Gly Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
```

```
        195                 200                 205

Ala Phe Ser Phe Gln Glu Trp Leu Glu Asn Lys
    210                 215


<210> SEQ ID NO 50
<211> LENGTH: 219
<212> TYPE: PRT
<213> ORGANISM: Clostridium beijerinckii

<400> SEQUENCE: 50

Met Asn Phe Asn Leu Ile Asp Ile Asn His Trp Ile Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Lys Glu Phe Arg Ile Cys Phe Asp His Lys Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Lys Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Gln Pro Asp Asn Thr Phe Ser Val Ser Ser
    130                 135                 140

Ile Pro Trp Val Ser Phe Thr Gly Phe Asn Leu Asn Val Asn Asn Glu
145                 150                 155                 160

Gly Thr Tyr Leu Ile Pro Ile Phe Thr Ala Gly Lys Tyr Phe Lys Gln
                165                 170                 175

Glu Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Lys Glu Trp Leu Glu Asn Lys
    210                 215


<210> SEQ ID NO 51
<211> LENGTH: 221
<212> TYPE: PRT
<213> ORGANISM: Clostridium beijerinckii

<400> SEQUENCE: 51

Met Asn Phe Asn Leu Ile Asp Ile Asn Asn Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Asn Val Val Asn Asn
    50                  55                  60

His Lys Glu Phe Arg Ile Cys Phe Asp His Glu Gly Ser Leu Gly Tyr
65                  70                  75                  80

Trp Asp Ser Met Asn Pro Ser Tyr Thr Ile Phe His Lys Glu Asn Glu
```

```
                85                  90                  95

Thr Phe Ser Ser Ile Trp Thr Glu Tyr Asn Glu Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Glu Pro Asp Asn Thr Phe Pro Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Gly Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys Tyr Ile
    210                 215                 220


<210> SEQ ID NO 52
<211> LENGTH: 219
<212> TYPE: PRT
<213> ORGANISM: Clostridium beijerinckii

<400> SEQUENCE: 52

Met Asn Phe Asn Leu Ile Asp Ile Asn Asn Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Lys Glu Phe Arg Ile Cys Phe Asp His Asn Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Glu Pro Asp Asn Thr Phe Pro Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Gly Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Arg Glu Trp Leu Glu Asn Lys
    210                 215


<210> SEQ ID NO 53
<211> LENGTH: 219
```

<212> TYPE: PRT
<213> ORGANISM: Clostridium saccharoperbutylacetonicum

<400> SEQUENCE: 53

```
Met Asn Phe Asn Leu Ile Asp Ile Asn His Trp Ser Arg Lys Pro Tyr
1               5                   10                  15

Phe Glu His Tyr Leu Asn Thr Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Lys Glu Phe Arg Ile Cys Phe Asp His Lys Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Ile Asp Asp Ile Lys Asn Tyr Gly Asn Ile Met Lys
        115                 120                 125

Phe Thr Pro Lys Ser Asn Glu Pro Asp Asn Ile Phe Pro Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Glu Asn Lys Ile Phe Ile Pro Ile Ser Ile Gln Val His His Ala Val
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215
```

<210> SEQ ID NO 54
<211> LENGTH: 219
<212> TYPE: PRT
<213> ORGANISM: Clostridium saccharoperbutylacetonicum

<400> SEQUENCE: 54

```
Met Asn Phe Asn Leu Ile Asp Ile Asn His Trp Ser Arg Lys Pro Tyr
1               5                   10                  15

Phe Glu His Tyr Leu Asn Thr Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Lys Glu Phe Arg Ile Cys Phe Asp His Lys Gly Ser Leu Gly Tyr
65                  70                  75                  80

Trp Asp Ser Met Asn Pro Ser Tyr Thr Ile Phe Tyr Lys Glu Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Ile Asp Asp Ile Lys Asn Tyr Gly Asn Ile Met Lys
        115                 120                 125
```

```
Phe Thr Pro Lys Ser Asn Glu Pro Asp Asn Ile Phe Pro Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Glu Asn Lys Ile Phe Ile Pro Ile Ser Ile Gln Val His His Ala Val
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys
    210                 215


<210> SEQ ID NO 55
<211> LENGTH: 219
<212> TYPE: PRT
<213> ORGANISM: Clostridium beijerinckii

<400> SEQUENCE: 55

Met Asn Phe Asn Leu Ile Asp Ile Asn Asn Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Lys Glu Phe Arg Ile Cys Phe Asp His Asn Gly Ser Leu Gly Tyr
65                  70                  75                  80

Trp Asp Ser Met Asn Pro Ser Tyr Thr Ile Phe His Lys Glu Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Arg Ser Asp Asn Thr Phe Pro Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Ala Gly Lys Tyr Phe Lys Gln
                165                 170                 175

Gly Asn Lys Ile Phe Ile Pro Ile Ser Ile Gln Val His His Ala Ile
            180                 185                 190

Cys Asp Gly Tyr His Ala Ser Arg Phe Ile Asn Glu Met Gln Glu Leu
        195                 200                 205

Ala Phe Ser Phe Arg Glu Trp Leu Glu Asn Lys
    210                 215


<210> SEQ ID NO 56
<211> LENGTH: 221
<212> TYPE: PRT
<213> ORGANISM: Clostridium beijerinckii

<400> SEQUENCE: 56

Met Asn Phe Asn Leu Ile Asp Ile Asn His Trp Asn Arg Lys Pro Phe
1               5                   10                  15
```

```
Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Lys Leu Lys Asn Ile
        35                  40                  45

Lys Phe Tyr Pro Thr Leu Ile Tyr Met Ile Ala Thr Val Val Asn Asn
    50                  55                  60

His Lys Glu Phe Arg Ile Cys Phe Asp His Lys Gly Ser Leu Gly Tyr
65                  70                  75                  80

Trp Asp Ser Met Asn Pro Ser Tyr Thr Ile Phe His Glu Glu Asn Glu
                85                  90                  95

Thr Phe Ser Ser Ile Trp Thr Glu Tyr Asn Glu Ser Phe Leu Arg Phe
            100                 105                 110

Tyr Ser Asp Tyr Leu Asp Asp Ile Lys Asn Tyr Gly Asn Ile Met Lys
        115                 120                 125

Phe Thr Pro Lys Ser Asn Glu Pro Asp Asn Thr Phe Pro Val Ser Ser
    130                 135                 140

Ile Pro Trp Val Ser Phe Thr Gly Phe Asn Leu Asn Val Cys Asn Glu
145                 150                 155                 160

Gly Thr Tyr Leu Thr Pro Ile Phe Thr Ala Gly Lys Tyr Phe Lys Gln
                165                 170                 175

Glu Asn Lys Ile Phe Ile Pro Ile Ser Ile Gln Val His His Ser Ile
            180                 185                 190

Cys Asp Gly Tyr His Ala Ser Arg Phe Ile Asn Glu Met Gln Glu Leu
        195                 200                 205

Ala Phe Ser Phe Gln Glu Trp Leu Glu Asn Lys Tyr Ile
    210                 215                 220
```

<210> SEQ ID NO 57
<211> LENGTH: 219
<212> TYPE: PRT
<213> ORGANISM: Clostridium beijerinckii

<400> SEQUENCE: 57

```
Met Asn Phe Asn Leu Ile Asp Ile Lys His Trp Ser Arg Lys Pro Tyr
1               5                   10                  15

Phe Glu His Tyr Leu Asn Asn Val Lys Cys Thr Tyr Ser Met Thr Ala
            20                  25                  30

Asn Ile Glu Ile Thr Asp Leu Leu Tyr Glu Ile Arg Leu Lys Asn Ile
        35                  40                  45

Lys Leu Tyr Pro Thr Leu Ile Tyr Met Ile Ala Thr Val Val Asn Asn
    50                  55                  60

His Lys Glu Phe Arg Thr Cys Phe Asp His Ser Gly Ser Leu Gly Tyr
65                  70                  75                  80

Trp Asp Ser Met Ser Pro Ser Tyr Thr Ile Phe His Lys Glu Asn Glu
                85                  90                  95

Thr Phe Ser Ser Ile Trp Thr Glu Tyr Asn Glu Ser Phe Pro Arg Phe
            100                 105                 110

Tyr Ser Asp Tyr Phe Asp Asp Ile Lys Asn Tyr Gly Asn Ile Met Lys
        115                 120                 125

Phe Thr Pro Lys Leu Asn Glu Pro Asp Asn Thr Phe Pro Val Ser Ser
    130                 135                 140

Ile Pro Trp Val Ser Phe Thr Gly Phe Asn Leu Asn Val Tyr Asn Glu
145                 150                 155                 160

Gly Thr Tyr Leu Ile Pro Ile Phe Thr Thr Gly Lys Tyr Phe Lys Gln
                165                 170                 175
```

Glu Asn Lys Met Phe Ile Pro Ile Ser Ile Gln Val His His Ala Ile
180 185 190

Cys Asp Gly Tyr His Ala Ser Arg Phe Ile Asn Glu Met Gln Glu Leu
195 200 205

Ala Phe Ser Phe Gln Asp Trp Leu Glu Asn Lys
210 215

<210> SEQ ID NO 58
<211> LENGTH: 219
<212> TYPE: PRT
<213> ORGANISM: Clostridium botulinum

<400> SEQUENCE: 58

Met Lys Phe Asn Leu Ile Asp Ile Glu His Trp Asn Arg Lys Pro Tyr
1 5 10 15

Phe Glu Tyr Tyr Leu His Ser Val Arg Cys Thr Tyr Ser Met Thr Ala
20 25 30

Asn Ile Glu Ile Thr Asn Leu Leu His Glu Ile Lys Leu Lys Lys Leu
35 40 45

Lys Leu Tyr Pro Thr Leu Ile Tyr Ile Ile Ala Thr Val Val Asn Asn
50 55 60

His Lys Glu Phe Arg Thr Cys Phe Asp Glu Asn Gly Asn Leu Gly Tyr
65 70 75 80

Trp Asp Ser Met Ser Pro Ser Tyr Thr Ile Phe His Lys Asp Asn Glu
85 90 95

Thr Phe Ser Ser Ile Trp Thr Asp Tyr Asp Glu Ser Phe Ser Cys Phe
100 105 110

Tyr Asn Asp Tyr Leu Asp Asp Ile Lys Asn Tyr Gly Ala Ile Met Lys
115 120 125

Phe Thr Pro Lys Leu Asn Glu Pro Ala Asn Thr Phe Pro Val Ser Ser
130 135 140

Ile Pro Trp Val Asn Phe Thr Gly Phe Asn Leu Asn Val Tyr Asn Asn
145 150 155 160

Gly Thr Tyr Leu Val Pro Ile Phe Thr Met Gly Lys Tyr Phe Glu Gln
165 170 175

Asn Asn Lys Ile Phe Ile Pro Met Ser Ile Gln Val His His Ala Val
180 185 190

Cys Asp Gly Tyr His Ile Ser Arg Phe Ile Asn Glu Val Gln Glu Leu
195 200 205

Ala Leu Asn Ser Gln Thr Trp Leu Lys His Lys
210 215

<210> SEQ ID NO 59
<211> LENGTH: 219
<212> TYPE: PRT
<213> ORGANISM: Artificial Sequence
<220> FEATURE:
<223> OTHER INFORMATION: Anaerocolumna aminovalerica

<400> SEQUENCE: 59

Met Lys Phe Asn Leu Ile Asp Ile Glu Asn Trp Asn Arg Lys Pro Tyr
1 5 10 15

Phe Glu His Tyr Leu Asn Ser Val Arg Cys Thr Tyr Ser Met Thr Ala
20 25 30

Asn Ile Glu Ile Thr Asn Leu Leu His Glu Ile Lys Leu Lys Asp Leu
35 40 45

Lys Leu Tyr Pro Thr Leu Ile Tyr Ile Leu Ala Thr Val Val Asn Asn
    50                  55                  60

His Lys Glu Phe Arg Thr Cys Phe Asp Glu Asn Gly Asn Leu Gly Tyr
65                  70                  75                  80

Trp Asp Ser Met Ser Pro Ser Tyr Thr Ile Phe His Lys Glu Asn Glu
                85                  90                  95

Thr Phe Ser Ser Ile Trp Thr Glu Tyr Asp Glu Ser Phe Ser Arg Phe
            100                 105                 110

Tyr Thr Ala Tyr Leu Asp Asp Ile Lys Asn His Gly Asn Ile Met Lys
        115                 120                 125

Phe Thr Pro Lys Leu Asn Glu Pro Ala Asn Thr Phe Pro Ile Ser Ser
    130                 135                 140

Ile Pro Trp Val Ser Phe Thr Gly Phe Asn Leu Asn Val Tyr Asn Asp
145                 150                 155                 160

Gly Lys Tyr Leu Leu Pro Ile Phe Thr Thr Gly Lys Tyr Phe Glu Gln
                165                 170                 175

Asn Ser Lys Ile Phe Ile Pro Met Ser Val Gln Val His His Ala Val
            180                 185                 190

Cys Asp Gly Tyr His Ile Ser Arg Phe Ile Asn Glu Val Gln Glu Val
        195                 200                 205

Ile Leu Asn Tyr Gln Thr Trp Leu Gly Asp Lys
    210                 215

<210> SEQ ID NO 60
<211> LENGTH: 219
<212> TYPE: PRT
<213> ORGANISM: Artificial Sequence
<220> FEATURE:
<223> OTHER INFORMATION: Desnuesiella massiliensis

<400> SEQUENCE: 60

Met Lys Phe Asn Leu Ile Asp Ile Glu His Trp Asn Arg Lys Pro Tyr
1               5                   10                  15

Phe Glu His Tyr Leu Asn Ser Val Arg Cys Thr Tyr Ser Met Thr Ala
            20                  25                  30

Asn Ile Glu Ile Thr Asn Leu Leu His Asp Ile Lys Leu Lys Lys Leu
        35                  40                  45

Lys Leu Tyr Pro Thr Leu Ile Tyr Ile Ile Ala Thr Val Val Asn Asn
    50                  55                  60

His Glu Glu Phe Arg Thr Cys Phe Tyr Glu Asn Gly Asn Leu Gly Tyr
65                  70                  75                  80

Trp Asp Ser Met Ser Pro Ser Tyr Thr Ile Phe His Lys Asp Asn Glu
                85                  90                  95

Thr Phe Ser Glu Ile Trp Ser Glu Tyr Asp Glu Ser Phe Ser Cys Phe
            100                 105                 110

Tyr Ser Lys Tyr Leu Asp Asp Ile Lys Asn Tyr Gly Asp Ile Met Arg
        115                 120                 125

Phe Thr Pro Lys Leu Asn Glu Pro Ala Asn Thr Phe Pro Ile Ser Cys
    130                 135                 140

Ile Pro Trp Val Ser Phe Thr Gly Phe Asn Leu Asn Val Tyr Asn Asp
145                 150                 155                 160

Gly Arg Tyr Leu Val Pro Ile Phe Thr Ile Gly Lys Tyr Phe Glu Gln
                165                 170                 175

Asn Asn Lys Ile Phe Ile Pro Met Ser Ile Gln Val His His Ala Val
            180                 185                 190

```
Cys Asp Gly Tyr His Thr Ser Arg Phe Ile Asn Glu Val Gln Glu Leu
        195                 200                 205

Ala Leu Asn Ser Gln Thr Trp Leu Arg His Lys
    210                 215


<210> SEQ ID NO 61
<211> LENGTH: 219
<212> TYPE: PRT
<213> ORGANISM: Artificial Sequence
<220> FEATURE:
<223> OTHER INFORMATION: Clostridium sp. HMP27

<400> SEQUENCE: 61

Met Lys Phe Asn Leu Ile Asp Thr Glu His Trp Asn Arg Lys Pro Tyr
1               5                   10                  15

Phe Glu His Tyr Leu Asn Ser Val Arg Cys Thr Tyr Ser Ile Thr Ala
            20                  25                  30

Asn Ile Glu Ile Thr Asn Leu Leu His Asp Ile Lys Gln Lys Lys Leu
        35                  40                  45

Lys Leu Tyr Pro Thr Phe Ile Tyr Ile Ile Ala Thr Val Val Asn Thr
    50                  55                  60

His Lys Glu Phe Arg Thr Cys Phe Asp Glu Ser Gly Asn Leu Gly Tyr
65                  70                  75                  80

Trp Asp Ser Met Ser Pro Ser Tyr Thr Ile Phe His Lys Asp Asn Glu
                85                  90                  95

Thr Phe Ser Ser Ile Trp Thr Glu Tyr Asp Lys Ser Phe Ser Cys Phe
            100                 105                 110

Tyr Ser Lys Tyr Leu His Asp Ile Lys Asn Tyr Gly Asp Ile Met Ser
        115                 120                 125

Phe Thr Pro Lys Leu Asn Glu Pro Ala Asn Thr Phe Pro Ile Ser Cys
    130                 135                 140

Ile Pro Trp Val Ser Phe Thr Gly Phe Asn Leu Asn Ile Tyr Asn Asp
145                 150                 155                 160

Gly Thr Tyr Leu Val Pro Ile Phe Thr Ile Gly Lys Tyr Phe Lys Gln
                165                 170                 175

Ala Asp Lys Ile Leu Ile Pro Ile Ser Ile Gln Val His His Ala Val
            180                 185                 190

Cys Asp Gly Tyr His Thr Ser Arg Phe Ile Asn Glu Val Gln Glu Leu
        195                 200                 205

Ile Leu Asn Tyr Gln Thr Trp Leu Lys His Lys
    210                 215


<210> SEQ ID NO 62
<211> LENGTH: 219
<212> TYPE: PRT
<213> ORGANISM: Artificial Sequence
<220> FEATURE:
<223> OTHER INFORMATION: Clostridium drakei

<400> SEQUENCE: 62

Met Lys Phe Asn Leu Ile Asp Ile Glu Asn Trp Asn Arg Lys Pro Tyr
1               5                   10                  15

Phe Glu His Tyr Leu Asn Ala Val Arg Cys Thr Tyr Ser Met Thr Ala
            20                  25                  30

Asn Ile Glu Ile Thr Gly Leu Leu Arg Glu Ile Lys Leu Lys Gly Leu
        35                  40                  45

Lys Leu Tyr Pro Thr Leu Ile Tyr Ile Ile Thr Ala Val Ile Asn Arg
    50                  55                  60
```

```
His Lys Glu Phe Arg Thr Cys Phe Asp Glu Asn Arg Lys Leu Gly Tyr
65                  70                  75                  80

Trp Asp Ser Met Ser Pro Ser Tyr Thr Val Phe His Lys Glu Asp Glu
                85                  90                  95

Thr Phe Ser Ser Ile Trp Thr Glu Tyr Asp Glu Ser Phe Pro Arg Phe
            100                 105                 110

Tyr Asp Asn Tyr Leu Asp Asp Ile Lys Ser Tyr Gly Asp Val Leu Lys
        115                 120                 125

Phe Met Pro Lys Pro Asp Glu Pro Gly Asn Thr Phe Asn Val Ser Ser
    130                 135                 140

Ile Pro Trp Val Asn Phe Thr Gly Phe Asn Leu Asn Ile Tyr Asn Asp
145                 150                 155                 160

Ala Thr Tyr Leu Ile Pro Ile Phe Thr Met Gly Lys Phe Phe His Gln
                165                 170                 175

Asp Asn Lys Ile Phe Ile Pro Met Ser Ile Gln Val His His Ala Val
            180                 185                 190

Cys Asp Gly Tyr His Thr Ser Arg Phe Phe Asn Glu Val Gln Glu Leu
        195                 200                 205

Ser Ser Asn Phe Glu Thr Trp Leu Asp Glu Lys
    210                 215


<210> SEQ ID NO 63
<211> LENGTH: 219
<212> TYPE: PRT
<213> ORGANISM: Clostridium scatologenes

<400> SEQUENCE: 63

Met Lys Phe Asn Leu Ile Asp Ile Glu Asp Trp Asn Arg Lys Pro Tyr
1               5                   10                  15

Phe Glu His Tyr Leu Asn Ala Val Arg Cys Thr Tyr Ser Met Thr Ala
            20                  25                  30

Asn Ile Glu Ile Thr Gly Leu Leu Arg Glu Ile Lys Leu Lys Gly Leu
        35                  40                  45

Lys Leu Tyr Pro Thr Leu Ile Tyr Ile Ile Thr Ala Val Ile Asn Arg
    50                  55                  60

His Lys Glu Phe Arg Thr Cys Phe Asp Glu Asn Arg Lys Leu Gly Tyr
65                  70                  75                  80

Trp Asp Ser Met Ser Pro Ser Tyr Thr Val Phe His Lys Glu Asp Glu
                85                  90                  95

Thr Phe Ser Ser Ile Trp Thr Glu Tyr Asp Glu Ser Phe Pro Arg Phe
            100                 105                 110

Tyr Asp Asn Tyr Leu Asp Asp Ile Lys Ser Tyr Gly Asp Val Leu Lys
        115                 120                 125

Phe Met Pro Lys Pro Asp Glu Pro Gly Asn Thr Phe Asn Val Ser Ser
    130                 135                 140

Ile Pro Trp Val Asn Phe Thr Gly Phe Asn Leu Asn Ile Tyr Asn Asp
145                 150                 155                 160

Ala Thr Tyr Leu Ile Pro Ile Phe Thr Met Gly Lys Phe Phe His Gln
                165                 170                 175

Asp Asn Lys Ile Phe Ile Pro Met Ser Ile Gln Val His His Ala Val
            180                 185                 190

Cys Asp Gly Tyr His Thr Ser Arg Phe Phe Asn Glu Val Gln Glu Leu
        195                 200                 205

Ser Ser Asn Phe Glu Thr Trp Leu Gly Glu Lys
```

210 215

<210> SEQ ID NO 64
<211> LENGTH: 219
<212> TYPE: PRT
<213> ORGANISM: Artificial Sequence
<220> FEATURE:
<223> OTHER INFORMATION: Clostridium tunisiense

<400> SEQUENCE: 64

Met Lys Phe Asn Leu Ile Asp Thr Glu His Trp Asp Arg Lys Pro Tyr
1 5 10 15

Phe Glu His Tyr Phe Asn Ser Val Lys Cys Thr Tyr Ser Met Thr Ala
20 25 30

Asn Ile Glu Ile Thr Asn Leu Leu Asn His Ile Arg Leu Lys Lys Leu
35 40 45

Lys Leu Tyr Pro Thr Leu Ile Tyr Ile Ile Ala Thr Val Val Asn Asn
50 55 60

His Glu Glu Phe Arg Ile Cys Phe Asp Glu Asn Asn Asn Leu Gly Tyr
65 70 75 80

Trp Asp Ser Met Ser Pro Asn Tyr Thr Ile Phe His Glu Asp Asn Lys
85 90 95

Thr Phe Ser Ser Ile Trp Thr Glu Tyr Glu Glu Ser Phe Ser Gly Phe
100 105 110

Tyr Asn Lys Tyr Leu Glu Asp Ile Lys Thr Tyr Gly His Ile Met Ser
115 120 125

Phe Glu Pro Lys Leu Asn Glu Ser Thr Asn Thr Phe Pro Ile Ser Cys
130 135 140

Ile Pro Trp Val Ser Phe Thr Gly Phe Asn Leu Asn Ile Gln Asp Asp
145 150 155 160

Gly Thr Tyr Leu Thr Pro Ile Phe Thr Leu Gly Lys Tyr Phe Glu Gln
165 170 175

Asn Asn Lys Thr Phe Ile Pro Ile Ser Ile Gln Val His His Ala Val
180 185 190

Cys Asp Gly Tyr His Thr Ser Arg Phe Ile Asn Glu Val Gln Glu Leu
195 200 205

Ala Ser Asp Phe Gln Ile Trp Leu Thr Tyr Lys
210 215

<210> SEQ ID NO 65
<211> LENGTH: 219
<212> TYPE: PRT
<213> ORGANISM: Artificial Sequence
<220> FEATURE:
<223> OTHER INFORMATION: Lachnospiraceae

<400> SEQUENCE: 65

Met Lys Phe Asn Leu Ile Asp Ile Glu Asp Trp Asn Arg Lys Pro Tyr
1 5 10 15

Phe Glu His Tyr Leu Asn Ala Val Arg Cys Thr Tyr Ser Met Thr Ala
20 25 30

Asn Ile Glu Ile Thr Gly Leu Leu Arg Glu Ile Lys Leu Lys Gly Leu
35 40 45

Lys Leu Tyr Pro Thr Leu Ile Tyr Ile Ile Thr Thr Val Val Asn Arg
50 55 60

His Lys Glu Phe Arg Thr Cys Phe Asp Gln Lys Gly Lys Leu Gly Tyr
65 70 75 80

```
Trp Asp Ser Met Asn Pro Ser Tyr Thr Val Phe His Lys Asp Asn Glu
                85                  90                  95

Thr Phe Ser Ser Ile Trp Thr Glu Tyr Asp Glu Asn Phe Pro Arg Phe
            100                 105                 110

Tyr Tyr Asn Tyr Leu Glu Asp Ile Arg Asn Tyr Ser Asp Val Leu Asn
        115                 120                 125

Phe Met Pro Lys Thr Gly Glu Pro Ala Asn Thr Ile Asn Val Ser Ser
    130                 135                 140

Ile Pro Trp Val Asn Phe Thr Gly Phe Asn Leu Asn Ile Tyr Asn Asp
145                 150                 155                 160

Ala Thr Tyr Leu Ile Pro Ile Phe Thr Leu Gly Lys Tyr Phe Gln Gln
                165                 170                 175

Asp Asn Lys Ile Leu Leu Pro Met Ser Val Gln Val His His Ala Val
            180                 185                 190

Cys Asp Gly Tyr His Thr Ser Arg Phe Phe Asn Glu Ala Gln Glu Leu
        195                 200                 205

Ala Ser Asn Tyr Glu Thr Trp Leu Gly Glu Lys
    210                 215
```

<210> SEQ ID NO 66
<211> LENGTH: 219
<212> TYPE: PRT
<213> ORGANISM: Clostridium perfringens

<400> SEQUENCE: 66

```
Met Lys Phe Asn Leu Ile Asp Ile Glu Asp Trp Asn Arg Lys Pro Tyr
1               5                   10                  15

Phe Glu His Tyr Leu Asn Ala Val Arg Cys Thr Tyr Ser Met Thr Ala
            20                  25                  30

Asn Ile Glu Ile Thr Gly Leu Leu Arg Glu Ile Lys Leu Lys Gly Leu
        35                  40                  45

Lys Leu Tyr Pro Thr Leu Ile Tyr Ile Ile Thr Thr Val Val Asn Arg
    50                  55                  60

His Lys Glu Phe Arg Thr Cys Phe Asp Gln Lys Gly Lys Leu Gly Tyr
65                  70                  75                  80

Trp Asp Ser Met Asn Pro Ser Tyr Thr Val Phe His Lys Asp Asn Glu
                85                  90                  95

Thr Phe Ser Ser Ile Trp Thr Glu Tyr Asp Glu Asn Phe Pro Arg Phe
            100                 105                 110

Tyr Tyr Asn Tyr Leu Glu Asp Ile Arg Asn Tyr Ser Asp Val Leu Asn
        115                 120                 125

Phe Met Pro Lys Thr Gly Glu Pro Ala Asn Thr Ile Asn Val Ser Ser
    130                 135                 140

Ile Pro Trp Val Asn Phe Thr Gly Phe Asn Leu Asn Ile Tyr Asn Asp
145                 150                 155                 160

Ala Thr Tyr Leu Ile Pro Ile Phe Thr Leu Gly Lys Tyr Phe Gln Gln
                165                 170                 175

Asp Asn Lys Ile Leu Leu Pro Met Ser Val Gln Val His His Ala Val
            180                 185                 190

Cys Asp Gly Tyr His Ile Ser Arg Phe Phe Asn Glu Ala Gln Glu Leu
        195                 200                 205

Ala Ser Asn Tyr Glu Thr Trp Leu Gly Glu Lys
    210                 215
```

<210> SEQ ID NO 67

<211> LENGTH: 218
<212> TYPE: PRT
<213> ORGANISM: Artificial Sequence
<220> FEATURE:
<223> OTHER INFORMATION: Clostrdium sp. BL8

<400> SEQUENCE: 67

```
Met Lys Phe Asn Leu Ile Asp Ile Asp Gln Trp Asp Arg Lys Pro Tyr
1               5                   10                  15

Phe Glu His Tyr Phe Asn Ser Val Lys Cys Thr Tyr Ser Ile Thr Ala
            20                  25                  30

Asn Ile Glu Ile Thr Asn Leu Leu Lys Asp Ile Lys Ile Thr Lys Leu
        35                  40                  45

Lys Leu Tyr Pro Thr Leu Ile Tyr Ile Ile Ala Thr Val Ile Asn Asn
    50                  55                  60

His Glu Glu Phe Arg Thr Cys Phe Asp Glu Asn Asn Asn Leu Gly Tyr
65                  70                  75                  80

Trp Asp Ser Met Ser Pro Asn Tyr Thr Ile Phe His Glu Glu Thr Lys
                85                  90                  95

Thr Phe Ser Asn Ile Trp Thr Glu Tyr Asp Lys Ser Phe Ser Gly Phe
            100                 105                 110

Tyr Asn Lys Tyr Val Glu Asp Asn Lys Asn Tyr Gly Asn Ile Met Asn
        115                 120                 125

Phe Asp Pro Lys Leu Asn Glu Pro Ala Asn Thr Phe Pro Ile Ser Cys
    130                 135                 140

Ile Pro Trp Val Ser Phe Thr Gly Phe Asn Leu Asn Ile Gln Asp His
145                 150                 155                 160

Gly Thr Tyr Leu Thr Pro Ile Phe Thr Leu Gly Lys Tyr Phe Glu Glu
                165                 170                 175

Asn Asn Lys Val Phe Ile Pro Met Ser Ile Gln Val His His Ala Val
            180                 185                 190

Cys Asp Gly Tyr His Thr Ser Arg Phe Ile Asn Glu Val Gln Glu Leu
        195                 200                 205

Ala Ser Asn Ser Gln Ser Trp Leu Lys His
    210                 215
```

<210> SEQ ID NO 68
<211> LENGTH: 660
<212> TYPE: DNA
<213> ORGANISM: Clostridium perfringens

<400> SEQUENCE: 68

```
atgaaattta atttgataga tattgaggat tggaatagaa agccatactt tgagcattat     60

ttaaatgcgg ttaggtgcac ttacagtatg actgcaaata tagagataac tggtttactg    120

cgtgaaatta aacttaaggg cctgaaactg taccctacgc ttatttatat catcacaact    180

gtggttaacc gtcacaagga gttccgcacc tgttttgatc aaaaaggtaa gttaggatac    240

tgggatagta tgaacccaag ttatactgtc tttcataagg ataacgaaac tttttcaagt    300

atttggacag agtatgacga gaacttccca cgtttttact ataattacct tgaggatatt    360

agaaactata gcgacgtttt gaatttcatg cctaagacag gtgaacctgc taatacaatt    420

aatgtgtcca gcattccttg ggtgaatttt accggattca acctgaatat atacaatgat    480

gcaacatatc taatccctat ttttactttg ggtaagtatt ttcagcagga taataaaatt    540

ttattaccta tgtctgtaca ggtgcatcat gcggtttgcg acggttatca tataagcaga    600

tttttaatg aggcacagga attagcgtca aattatgaga catggttagg agaaaaataa    660
```

<210> SEQ ID NO 69
<211> LENGTH: 624
<212> TYPE: DNA
<213> ORGANISM: Clostridium difficile

<400> SEQUENCE: 69
atggtatttg aaaaaattga taaaaatagt tggaacagaa aagagtattt tgaccactac 60
tttgcaagtg taccttgtac atacagcatg accgttaaag tggatatcac acaaataaag 120
gaaaagggaa tgaaactata tcctgcaatg ctttattata ttgcaatgat tgtaaaccgc 180
cattcagagt ttaggacggc aatcaatcaa gatggtgaat tggggatata tgatgagatg 240
ataccaagct atacaatatt tcacaatgat actgaaacat tttccagcct ttggactgag 300
tgtaagtctg actttaaatc atttttagca gattatgaaa gtgatacgca acggtatgga 360
aacaatcata gaatggaagg aaagccaaat gctccggaaa acatttttaa tgtatctatg 420
ataccgtggt caaccttcga tggctttaat ctgaatttgc agaaaggata tgattatttg 480
attcctattt ttactatggg gaaatattat aaagaagata acaaaattat acttcctttg 540
gcaattcaag ttcatcacgc agtatgtgac ggatttcaca tttgccgttt tgtaaacgaa 600
ttgcaggaat tgataaatag ttaa 624

<210> SEQ ID NO 70
<211> LENGTH: 624
<212> TYPE: DNA
<213> ORGANISM: Clostridium perfringens

<400> SEQUENCE: 70
atggtatttg aaaaaattga taaaaatagt tggaacagaa aagagtattt tgaccactac 60
tttgcaagtg taccttgtac atacagcatg accgttaaag tggatatcac acaaataaag 120
gaaaagggaa tgaaactata tcctgcaatg ctttattata ttgcaatgat tgtaaaccgc 180
cattcagagt ttaggacggc aatcaatcaa gatggtgaat tggggatata tgatgagatg 240
ataccaagct atacaatatt tcacaatgat actgaaacat tttccagcct ttggactgag 300
tgtaagtctg actttaaatc atttttagca gattatgaaa gtgatacgca acggtatgga 360
aacaatcata gaatggaagg aaagccaaat gctccggaaa acatttttaa tgtatctatg 420
ataccgtggt caaccttcga tggctttaat ctgaatttgc agaaaggata tgattatttg 480
attcctattt ttactatggg gaaatattat aaagaagata acaaaattat acttcctttg 540
gcaattcaag ttcatcacgc agtatgtgac ggatttcaca tttgccgttt tgtaaacgaa 600
ttgcaggaat tgataaatag ttaa 624

<210> SEQ ID NO 71
<211> LENGTH: 3897
<212> TYPE: DNA
<213> ORGANISM: Artificial Sequence
<220> FEATURE:
<223> OTHER INFORMATION: Optimized MAD7

<400> SEQUENCE: 71
ctcgagtccc tatcagtgat agattgaaac tctatcattg atagagtata atatctttgt 60
tcattagagc gataaacttg aatttgagag ggaacttaga tgaacaacgg cacaaataat 120
tttcagaact tcatagggat atcaagtttg cagaaaacgt taagaaatgc tttaataccc 180
acggaaacca cgcaacagtt catagttaag aacggaataa ttaaagaaga tgagttaaga 240

```
ggcgagaaca gacagatttt aaaagatata atggatgact actacagagg attcatatct    300
gagactttaa gttctattga tgacatagat tggactagct tattcgaaaa aatggaaatt    360
cagttaaaaa atggtgataa taaagatacc ttaattaagg aacagacaga gtatagaaaa    420
gcaatacata aaaaatttgc gaacgacgat agatttaaga acatgtttag cgccaaatta    480
attagtgaca tattacctga atttgttata cacaacaata attattcggc atcagagaaa    540
gaggaaaaaa cccaggtgat aaaattgttt tcgagatttg cgactagctt taaagattac    600
ttcaagaaca gagcaaattg cttttcagcg gacgatattt catcaagcag ctgccataga    660
atagttaacg acaatgcaga gatattcttt tcaaatgcgt tagtttacag aagaatagta    720
aaatcgttaa gcaatgacga tataaacaaa atttcgggcg atatgaaaga ttcattaaaa    780
gaaatgagtt tagaagaaat atattcttac gagaagtatg ggaatttat tacccaggaa    840
ggcattagct tctataatga tatatgtggg aaagtgaatt cttttatgaa cttatattgt    900
cagaaaaata aagaaaacaa aaatttatac aaacttcaga aacttcacaa acagattcta    960
tgcattgcgg acactagcta tgaggttccg tataaatttg aaagtgacga ggaagtgtac   1020
caatcagtta acggcttcct tgataacatt agcagcaaac atatagttga aagattaaga   1080
aaaataggcg ataactataa cggctacaac ttagataaaa tttatatagt gtccaaattt   1140
tacgagagcg ttagccaaaa aacctacaga gactgggaaa caattaatac cgccttagaa   1200
attcattaca ataatatatt gccgggtaac ggtaaaagta aagccgacaa agtaaaaaaa   1260
gcggttaaga atgatttaca gaaatccata accgaaataa atgaactagt gtcaaactat   1320
aagttatgca gtgacgacaa cataaaagcg gagacttata tacatgagat tagccatata   1380
ttgaataact ttgaagcaca ggaattgaaa tacaatccgg aaattcacct agttgaatcc   1440
gagttaaaag cgagtgagct taaaaacgtg ttagacgtga taatgaatgc gtttcattgg   1500
tgttcggttt ttatgactga ggaacttgtt gataaagaca acaattttta tgcggaatta   1560
gaggagattt acgatgaaat ttatccagta attagtttat acaacttagt tagaaactac   1620
gttacccaga aaccgtacag cacgaaaaag attaaattga actttggaat accgacgtta   1680
gcagacggtt ggtcaaagtc caaagagtat tctaataacg ctataatatt aatgagagac   1740
aatttatatt atttaggcat atttaatgcg aagaataaac cggacaagaa gattatagag   1800
ggtaatacgt cagaaaataa gggtgactac aaaaagatga tttataattt gttaccgggt   1860
cccaacaaaa tgataccgaa agttttcttg agcagcaaga cgggggtgga aacgtataaa   1920
ccgagcgcct atatactaga ggggtataaa cagaataaac atataaagtc ttcaaaagac   1980
tttgatataa ctttctgtca tgatttaata gactacttca aaaactgtat tgcaattcat   2040
cccgagtgga aaaacttcgg ttttgatttt agcgacacca gtacttatga agacatttcc   2100
gggttttata gagaggtaga gttacaaggt tacaagattg attggacata cattagcgaa   2160
aaagacattg atttattaca ggaaaaaggt caattatatt tattccagat atataacaaa   2220
gatttttcga aaaaatcaac cgggaatgac aaccttcaca ccatgtactt aaaaaatctt   2280
ttctcagaag aaaatcttaa ggatatagtt ttaaaactta acggcgaagc ggaaatattc   2340
ttcaggaaga gcagcataaa gaacccaata attcataaaa aaggctcgat tttagttaac   2400
agaacctacg aagcagaaga aaaagaccag tttggcaaca ttcaaattgt gagaaaaaat   2460
attccggaaa acatttatca ggagttatac aaatacttca acgataaaag cgacaaagag   2520
ttatctgatg aagcagccaa attaaagaat gtagtgggac accacgaggc agcgacgaat   2580
atagttaagg actatagata cacgtatgat aaatacttcc ttcatatgcc tattacgata   2640
```

aatttcaaag ccaataaaac gggttttatt aatgatagga tattacagta tatagctaaa 2700
gaaaaagact tacatgtgat aggcattgat agaggcgaga gaaacttaat atacgtgtcc 2760
gtgattgata cttgtggtaa tatagttgaa cagaaaagct ttaacattgt aaacggctac 2820
gactatcaga taaaattaaa acaacaggag ggcgctagac agattgcgag aaaagaatgg 2880
aaagaaattg gtaaaattaa agagataaaa gagggctact taagcttagt aatacacgag 2940
atatctaaaa tggtaataaa atacaatgca attatagcga tggaggattt gtcttatggt 3000
tttaaaaaag ggagatttaa ggttgaaaga caagtttacc agaaatttga aaccatgtta 3060
ataaataaat taaactattt agtatttaaa gatatttcga ttaccgagaa tggcggttta 3120
ttaaaaggtt atcagttaac atacattcct gataaactta aaaacgtggg tcatcagtgc 3180
ggctgcattt tttatgtgcc tgctgcatac acgagcaaaa ttgatccgac caccggcttt 3240
gtgaatatat ttaaatttaa agacttaaca gtggacgcaa aaagagaatt cattaaaaaa 3300
tttgactcaa ttagatatga cagtgaaaaa aatttattct gctttacatt tgactacaat 3360
aactttatta cgcaaaacac ggttatgagc aaatcatcgt ggagtgtgta tacatacggc 3420
gtgagaataa aaagaagatt tgtgaacggc agattctcaa acgaaagtga taccattgac 3480
ataaccaaag atatggagaa aacgttggaa atgacggaca ttaactggag agatggccac 3540
gatcttagac aagacattat agattatgaa attgttcagc acatattcga aattttcaga 3600
ttaacagtgc aaatgagaaa ctccttgtct gaattagagg acagagatta cgatagatta 3660
atttcacctg tattaaacga aaataacatt ttttatgaca gcgcgaaagc gggggatgca 3720
cttcctaagg atgccgatgc aaatggtgcg tattgtattg cattaaaagg gttatatgaa 3780
attaaacaaa ttaccgaaaa ttggaaagaa gatggtaaat tttcgagaga taaattaaaa 3840
ataagcaata aagattggtt cgactttata cagaataaga gatatttata agtcgac 3897

<210> SEQ ID NO 72
<211> LENGTH: 1263
<212> TYPE: PRT
<213> ORGANISM: Artificial Sequence
<220> FEATURE:
<223> OTHER INFORMATION: MAD7

<400> SEQUENCE: 72

Met Asn Asn Gly Thr Asn Asn Phe Gln Asn Phe Ile Gly Ile Ser Ser
1 5 10 15

Leu Gln Lys Thr Leu Arg Asn Ala Leu Ile Pro Thr Glu Thr Thr Gln
20 25 30

Gln Phe Ile Val Lys Asn Gly Ile Ile Lys Glu Asp Glu Leu Arg Gly
35 40 45

Glu Asn Arg Gln Ile Leu Lys Asp Ile Met Asp Asp Tyr Tyr Arg Gly
50 55 60

Phe Ile Ser Glu Thr Leu Ser Ser Ile Asp Asp Ile Asp Trp Thr Ser
65 70 75 80

Leu Phe Glu Lys Met Glu Ile Gln Leu Lys Asn Gly Asp Asn Lys Asp
85 90 95

Thr Leu Ile Lys Glu Gln Thr Glu Tyr Arg Lys Ala Ile His Lys Lys
100 105 110

Phe Ala Asn Asp Asp Arg Phe Lys Asn Met Phe Ser Ala Lys Leu Ile
115 120 125

Ser Asp Ile Leu Pro Glu Phe Val Ile His Asn Asn Asn Tyr Ser Ala
130 135 140

```
Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
    290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560
```

```
Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Ile Gln Ile Val
    770                 775                 780

Arg Lys Asn Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
        835                 840                 845

Phe Lys Ala Asn Lys Thr Gly Phe Ile Asn Asp Arg Ile Leu Gln Tyr
    850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
        915                 920                 925

Glu Ile Gly Lys Ile Lys Glu Ile Lys Glu Gly Tyr Leu Ser Leu Val
    930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
```

```
            980                 985                 990

Tyr Leu Val Phe Lys Asp Ile Ser  Ile Thr Glu Asn Gly  Gly Leu Leu
        995                 1000                1005

Lys Gly  Tyr Gln Leu Thr Tyr  Ile Pro Asp Lys Leu  Lys Asn Val
    1010                 1015                 1020

Gly His  Gln Cys Gly Cys Ile  Phe Tyr Val Pro Ala  Ala Tyr Thr
    1025                 1030                 1035

Ser Lys  Ile Asp Pro Thr Thr  Gly Phe Val Asn Ile  Phe Lys Phe
    1040                 1045                 1050

Lys Asp  Leu Thr Val Asp Ala  Lys Arg Glu Phe Ile  Lys Lys Phe
    1055                 1060                 1065

Asp Ser  Ile Arg Tyr Asp Ser  Glu Lys Asn Leu Phe  Cys Phe Thr
    1070                 1075                 1080

Phe Asp  Tyr Asn Asn Phe Ile  Thr Gln Asn Thr Val  Met Ser Lys
    1085                 1090                 1095

Ser Ser  Trp Ser Val Tyr Thr  Tyr Gly Val Arg Ile  Lys Arg Arg
    1100                 1105                 1110

Phe Val  Asn Gly Arg Phe Ser  Asn Glu Ser Asp Thr  Ile Asp Ile
    1115                 1120                 1125

Thr Lys  Asp Met Glu Lys Thr  Leu Glu Met Thr Asp  Ile Asn Trp
    1130                 1135                 1140

Arg Asp  Gly His Asp Leu Arg  Gln Asp Ile Ile Asp  Tyr Glu Ile
    1145                 1150                 1155

Val Gln  His Ile Phe Glu Ile  Phe Arg Leu Thr Val  Gln Met Arg
    1160                 1165                 1170

Asn Ser  Leu Ser Glu Leu Glu  Asp Arg Asp Tyr Asp  Arg Leu Ile
    1175                 1180                 1185

Ser Pro  Val Leu Asn Glu Asn  Asn Ile Phe Tyr Asp  Ser Ala Lys
    1190                 1195                 1200

Ala Gly  Asp Ala Leu Pro Lys  Asp Ala Asp Ala Asn  Gly Ala Tyr
    1205                 1210                 1215

Cys Ile  Ala Leu Lys Gly Leu  Tyr Glu Ile Lys Gln  Ile Thr Glu
    1220                 1225                 1230

Asn Trp  Lys Glu Asp Gly Lys  Phe Ser Arg Asp Lys  Leu Lys Ile
    1235                 1240                 1245

Ser Asn  Lys Asp Trp Phe Asp  Phe Ile Gln Asn Lys  Arg Tyr Leu
    1250                 1255                 1260
```

<210> SEQ ID NO 73
<211> LENGTH: 363
<212> TYPE: DNA
<213> ORGANISM: Artificial Sequence
<220> FEATURE:
<223> OTHER INFORMATION: CatB promoter

<400> SEQUENCE: 73

```
taaaaaatgt tacgcacttt tcttatattg ttcaacaata acataattta ttaacaaaag     60

gaaagtatag ttaaaaaaat gttggagcaa atgcggatgg aaaaataaaa attaatatta    120

gtagtaattc cgatgttaaa ataacaagag ataagaaaaa gtaaaatatt agagtaattc    180

gtagtattct taagttatga atcaataaaa aatggtctct gaaaattgaa tagttcggta    240

ttacagaatg tgctataata aactaaagcg taaatatcat tgtaaaaagg agattgaaat    300

ggctaggtca cggaaaaaag ccttctaaaa tagaattacg aaaattttta ggaggcccga    360

att                                                                  363
```

<210> SEQ ID NO 74
<211> LENGTH: 322
<212> TYPE: DNA
<213> ORGANISM: Artificial Sequence
<220> FEATURE:
<223> OTHER INFORMATION: CATQ promoter

<400> SEQUENCE: 74
ctgcgtacac atccagacat cgctttagag tatggtgaat taaagatgga gcgggcttat 60
cgattctcag aggatattga aggctactgc actggtaagg atgcatttgt aaagcaacta 120
gaaaaggatg ctttgcgatg gtggcaaact gtctgttagg aggttattct caaaggattg 180
caagaagcag ttgaggataa tccgtataac taactattac acattcttaa cattgctggt 240
ttgtatcggt agaataacac gaattaacaa aggatatatt ttgtagtagc aagtgtattt 300
gttttatatt ctatgaacct at 322

<210> SEQ ID NO 75
<211> LENGTH: 1368
<212> TYPE: PRT
<213> ORGANISM: Streptococcus pyogenes

<400> SEQUENCE: 75

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

-continued

```
Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
```

```
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095
```

```
Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 76
<211> LENGTH: 4107
<212> TYPE: DNA
<213> ORGANISM: Streptococcus pyogenes

<400> SEQUENCE: 76

```
atggataaga aatactcaat aggcttagat atcggcacaa atagcgtcgg atgggcggtg     60

atcactgatg aatataaggt tccgtctaaa aagttcaagg ttctgggaaa tacagaccgc    120

cacagtatca aaaaaaatct tataggggct cttttatttg acagtggaga gacagcggaa    180

gcgactcgtc tcaaacggac agctcgtaga aggtatacac gtcggaagaa tcgtatttgt    240

tatctacagg agatttttc aaatgagatg gcgaaagtag atgatagttt ctttcatcga     300

cttgaagagt ctttttggt ggaagaagac aagaagcatg aacgtcatcc tatttttgga     360

aatatagtag atgaagttgc ttatcatgag aaatatccaa ctatctatca tctgcgaaaa    420

aaattggtag attctactga taaagcggat ttgcgcttaa tctatttggc cttagcgcat    480
```

```
atgattaagt ttcgtggtca ttttttgatt gagggagatt taaatcctga taatagtgat    540
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taaagaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
```

```
aaattagttt ctgacttccg aaaagatttc caattctata aagtacgtga gattaacaat   2940

taccatcatg cccatgatgc gtatctaaat gccgtcgttg gaactgcttt gattaagaaa   3000

tatccaaaac ttgaatcgga gtttgtctat ggtgattata aagtttatga tgttcgtaaa   3060

atgattgcta agtctgagca agaaataggc aaagcaaccg caaaatattt cttttactct   3120

aatatcatga acttcttcaa aacagaaatt acacttgcaa atggagagat tcgcaaacgc   3180

cctctaatcg aaactaatgg ggaaactgga gaaattgtct gggataaagg gcgagatttt   3240

gccacagtgc gcaaagtatt gtccatgccc caagtcaata ttgtcaagaa aacagaagta   3300

cagacaggcg gattctccaa ggagtcaatt ttaccaaaaa gaaattcgga caagcttatt   3360

gctcgtaaaa aagactggga tccaaaaaaa tatggtggtt ttgatagtcc aacggtagct   3420

tattcagtcc tagtggttgc taaggtggaa aaagggaaat cgaagaagtt aaaatccgtt   3480

aaagagttac tagggatcac aattatggaa agaagttcct ttgaaaaaaa tccgattgac   3540

tttttagaag ctaaaggata taaggaagtt aaaaaagact taatcattaa actacctaaa   3600

tatagtcttt ttgagttaga aaacggtcgt aaacggatgc tggctagtgc cggagaatta   3660

caaaaaggaa atgagctggc tctgccaagc aaatatgtga atttttttata tttagctagt   3720

cattatgaaa agttgaaggg tagtccagaa gataacgaac aaaaacaatt gtttgtggag   3780

cagcataagc attatttaga tgagattatt gagcaaatca gtgaattttc taagcgtgtt   3840

attttagcag atgccaattt agataaagtt cttagtgcat ataacaaaca tagagacaaa   3900

ccaatacgtg aacaagcaga aaatattatt catttattta cgttgacgaa tcttggagct   3960

cccgctgctt ttaaatattt tgatacaaca attgatcgta aacgatatac gtctacaaaa   4020

gaagttttag atgccactct tatccatcaa tccatcactg gtctttatga aacacgcatt   4080

gatttgagtc agctaggagg tgactga                                       4107
```

<210> SEQ ID NO 77
<211> LENGTH: 1170
<212> TYPE: DNA
<213> ORGANISM: Artificial Sequence
<220> FEATURE:
<223> OTHER INFORMATION: bdhA

<400> SEQUENCE: 77

```
atgctaagtt ttgattattc aataccaact aaagtttttt ttggaaaagg aaaaatagac     60

gtaattggag aagaaattaa gaaatatggc tcaagagtgc ttatagttta tggcggagga    120

agtataaaaa ggaacggtat atatgataga gcaacagcta tattaaaaga aaacaatata    180

gctttctatg aactttcagg agtagagcca aatcctagga taacaacagt aaaaaaaggc    240

atagaaatat gtagagaaaa taatgtggat ttagtattag caatagggggg aggaagtgca    300

atagactgtt ctaaggtaat tgcagctgga gtttattatg atggcgatac atgggacatg    360

gttaaagatc catctaaaat aactaaagtt cttccaattg caagtatact tactctttca    420

gcaacagggt ctgaaatgga tcaaattgca gtaatttcaa atatggagac taatgaaaag    480

cttggagtag gacatgatga tatgagacct aaattttcag tgttagatcc tacatatact    540

tttacagtac ctaaaaatca aacagcagcg ggaacagctg acattatgag tcacaccttt    600

gaatcttact ttagtggtgt tgaaggtgct tatgtgcagg acggtatagc agaagcaatc    660

ttaagaacat gtataaagta tggaaaaata gcaatggaga agactgatga ttacgaggct    720

agagctaatt tgatgtgggc ttcaagttta gctataaatg gtctattatc acttggtaag    780
```

gatagaaaat ggagttgtca tcctatggaa cacgagttaa gtgcatatta tgatataaca 840
catggtgtag gacttgcaat tttaacacct aattggatgg aatatattct aaatgacgat 900
acacttcata aatttgtttc ttatggaata aatgtttggg gaatagacaa gaacaaagat 960
aactatgaaa tagcacgaga ggctattaaa aatacgagag aatactttaa ttcattgggt 1020
attccttcaa agcttagaga agttggaata ggaaaagata aactagaact aatggcaaag 1080
caagctgtta gaaattctgg aggaacaata ggaagtttaa gaccaataaa tgcagaggat 1140
gttcttgaga tatttaaaaa atcttattaa 1170

<210> SEQ ID NO 78
<211> LENGTH: 1173
<212> TYPE: DNA
<213> ORGANISM: Artificial Sequence
<220> FEATURE:
<223> OTHER INFORMATION: bdhB

<400> SEQUENCE: 78
gtggttgatt tcgaatattc aataccaact agaatttttt tcggtaaaga taagataaat 60
gtacttggaa gagagcttaa aaaatatggt tctaaagtgc ttatagttta tggtggagga 120
agtataaaga gaaatggaat atatgataaa gctgtaagta tacttgaaaa aaacagtatt 180
aaattttatg aacttgcagg agtagagcca aatccaagag taactacagt tgaaaaagga 240
gttaaaatat gtagagaaaa tggagttgaa gtagtactag ctataggtgg aggaagtgca 300
atagattgcg caaaggttat agcagcagca tgtgaatatg atggaaatcc atgggatatt 360
gtgttagatg gctcaaaaat aaaaagggtg cttcctatag ctagtatatt aaccattgct 420
gcaacaggat cagaaatgga tacgtgggca gtaataaata atatggatac aaacgaaaaa 480
ctaattgcgg cacatccaga tatggctcct aagttttcta tattagatcc aacgtatacg 540
tataccgtac ctaccaatca aacagcagca ggaacagctg atattatgag tcatatattt 600
gaggtgtatt ttagtaatac aaaaacagca tatttgcagg atagaatggc agaagcgtta 660
ttaagaactt gtattaaata tggaggaata gctcttgaga agccggatga ttatgaggca 720
agagccaatc taatgtgggc ttcaagtctt gcgataaatg gacttttaac atatggtaaa 780
gacactaatt ggagtgtaca cttaatggaa catgaattaa gtgcttatta cgacataaca 840
cacggcgtag ggcttgcaat tttaacacct aattggatgg agtatatttt aaataatgat 900
acagtgtaca agtttgttga atatggtgta aatgtttggg gaatagacaa agaaaaaaat 960
cactatgaca tagcacatca agcaatacaa aaaacaagag attactttgt aaatgtacta 1020
ggtttaccat ctagactgag agatgttgga attgaagaag aaaaattgga cataatggca 1080
aaggaatcag taaagcttac aggaggaacc ataggaaacc taagaccagt aaacgcctcc 1140
gaagtcctac aaatattcaa aaaatctgtg taa 1173

<210> SEQ ID NO 79
<211> LENGTH: 6560
<212> TYPE: DNA
<213> ORGANISM: Artificial Sequence
<220> FEATURE:
<223> OTHER INFORMATION: pGRNA-deltabdhB

<400> SEQUENCE: 79
gatccccggg taccgagctc gaattcgtaa tcatggtcat agctgtttcc tgtgtgaaat 60
tgttatccgc tcacaattcc acacaacata cgagccggaa gcataaagtg taaagcctgg 120
ggtgcctaat gagtgagcta actcacatta attgcgttgc gctcactgcc cgctttccag 180

```
tcgggaaacc tgtcgtgcca gctgcattaa tgaatcggcc aacgcgcggg gagaggcggt    240
ttgcgtattg ggcgctcttc cgcttcctcg ctcactgact cgctgcgctc ggtcgttcgg    300
ctgcggcgag cggtatcagc tcactcaaag gcggtaatac ggttatccac agaatcaggg    360
gataacgcag gaaagaacat gtgagcaaaa ggccagcaaa aggccaggaa ccgtaaaaag    420
gccgcgttgc tggcgttttt ccataggctc cgcccccctg acgagcatca caaaaatcga    480
cgctcaagtc agaggtggcg aaacccgaca ggactataaa gataccaggc gtttccccct    540
ggaagctccc tcgtgcgctc tcctgttccg accctgccgc ttaccggata cctgtccgcc    600
tttctccctt cgggaagcgt ggcgctttct catagctcac gctgtaggta tctcagttcg    660
gtgtaggtcg ttcgctccaa gctgggctgt gtgcacgaac cccccgttca gcccgaccgc    720
tgcgccttat ccggtaacta tcgtcttgag tccaacccgg taagacacga cttatcgcca    780
ctggcagcag ccactggtaa caggattagc agagcgaggt atgtaggcgg tgctacagag    840
ttcttgaagt ggtggcctaa ctacggctac actagaagaa cagtatttgg tatctgcgct    900
ctgctgaagc cagttacctt cggaaaaaga gttggtagct cttgatccgg caaacaaacc    960
accgctggta gcggtggttt ttttgtttgc aagcagcaga ttacgcgcag aaaaaaagga   1020
tctcaagaag atcctttgat cttttctacg gggtctgacg ctcagtggaa cgaaaactca   1080
cgttaaggga ttttggtcat gagattatca aaaaggatct tcacctagat ccttttaaat   1140
taaaaatgaa gttttaaatc aatctaaagt atatatgagt aaacttggtc tgacagttac   1200
caaagctagc ttaatactag tatatactta atgtgataag tgtctgacag ctgaccggtc   1260
taaagaggtc cctagcgcct acggggaatt tgtatcgata aggggtacaa attcccacta   1320
agcgctcggc cggggatcga tccccgggta cgtacccggc agtttttctt tttcggcaag   1380
tgttcaagaa gttattaagt cgggagtgca gtcgaagtgg gcaagttgaa aaattcacaa   1440
aaatgtggta taatatcttt gttcattaga gcgataaact tgaatttgag agggaactta   1500
gatggtattt gaaaaaattg ataaaaatag ttggaacaga aaagagtatt ttgaccacta   1560
ctttgcaagt gtaccttgta cctacagcat gaccgttaaa gtggatatca cacaaataaa   1620
ggaaaaggga atgaaactat atcctgcaat gctttattat attgcaatga ttgtaaaccg   1680
ccattcagag tttaggacgg caatcaatca agatggtgaa ttggggatat atgatgagat   1740
gataccaagc tatacaatat ttcacaatga tactgaaaca ttttccagcc tttggactga   1800
gtgtaagtct gactttaaat catttttagc agattatgaa agtgatacgc aacggtatgg   1860
aaacaatcat agaatggaag gaaagccaaa tgctccggaa aacattttta atgtatctat   1920
gataccgtgg tcaaccttcg atggctttaa tctgaatttg cagaaaggat atgattattt   1980
gattcctatt tttactatgg ggaaatatta taaagaagat aacaaaatta tacttccttt   2040
ggcaattcaa gttcatcacg cagtatgtga cggatttcac atttgccgtt ttgtaaacga   2100
attgcaggaa ttgataaata gttaacttca ggtttgtctg taactaaaaa ctagtattta   2160
acctaggatc aaaaaaattt ccaataatcc cactctaagc cacaaacacg ccctataaaa   2220
tcccgcttta atcccacttt gagacacatg taatattact ttacgcccta gtatagtgat   2280
aattttttac attcaatgcc acgcaaaaaa ataaaggggc actataataa aagttccttc   2340
ggaactaact aaagtaaaaa attatcttta caacctcccc aaaaaaaaga acaggtacaa   2400
agtaccctat aatacaagcg taaaaaaaat gagggtaaaa ataaaaaaat aaaaaaataa   2460
aaaaataaaa aaataaaaaa ataaaaaaat aaaaaaatat aaaaataaaa aaatataaaa   2520
```

```
ataaaaaaat ataaaaataa aaaaataaaa aaatataaaa ataaaaaaat aaaaaaatat   2580
aaaaatattt tttatttaaa gtttgaaaaa aattttttta tattatataa tctttgaaga   2640
aaagaatata aaaaatgagc ctttataaaa gcccattttt tttcatatac gtaatatgac   2700
gttctaatgt ttttattggt acttctaaca ttagagtaat ttctttattt ttaaagcctt   2760
tttctttaag ggcttttatt ttttttctta atacatttaa ttcctctttt tttgttgctt   2820
ttcctttagc ttttaattgc tcttgataat ttttttttacc tctaatattt tctcttctct   2880
tatattcctt tttagaaatt attattgtca tatatttttg ttcttcttct gtaatttcta   2940
ataactctat aagagtttca ttcttatact tatattgctt atttttatct aaataacatc   3000
tttcagcact tctagttgct cttataactt ctctttcact taaatgttgt ctaaacatac   3060
tattaagttc taaaacatca tttaatgcct tctcaatgtc ttctgtaaag ctacaaagat   3120
aatatctata taaaaataat ataagctctc tgtgtccttt taaatcatat tctcttagtt   3180
cacaaagttt tattatgtct tgtattcttc cataatataa acttctttct ctataaatat   3240
aatttatttt gcttggtcta ccctttttcc tttcatatgg ttttaattca ggtaaaaatc   3300
cattttgtat ttctcttaag tcataaatat attcgtactc atctaatata ttgactactg   3360
tttttgattt agagtttata cttcctggaa ctcttaatat tctcgttgca tctaaggctt   3420
gtctatctgc tccaaagtat tttaattgat tatataaata ttcttgaacc gctttccata   3480
atggtaatgc tttactaggt actgcattta ttatccatat taaatacatt cctcttccac   3540
tatctattac atagtttggt ataggaatac tttgattaaa ataattcttt tctaagtcca   3600
ttaatacctg gtctttagtt ttgccagttt tataataatc caagtctata aacagtgtat   3660
ttaactcttt tatattttct aatcgcctac acggcttata aaaggtattt agagttatat   3720
agatattttc atcactcata tctaaatctt ttaattcagc gtatttatag tgccattggc   3780
tatatccttt tttatctata acgctcctgg ttatccaccc tttacttcta ctatgaatat   3840
tatctatata gttcttttta ttcagcttta atgcgtttct cacttattca cctccccttc   3900
tgtaaaacta agaaaattat atcatatttt caataattat taactattct taaactctta   3960
ataaaaaata gagtaagtcc ccaattgaaa cttaatctat tttttatgtt ttaatttatt   4020
atttttatta aaatatttta aactaaatta aatgattctt tttaattttt tactatttca   4080
ttccataata tattactata attatttaca aataatattt cttcatttgt aatatttaga   4140
tgatttacta attttagttt ttatatatta aataattaat gtataattta tataaaaaat   4200
caaaggagct tataaattat gattatttcc aaagatacta aagatttaat ttttttcaat   4260
tttaacaata ctttttgtaa tattatgttt aaatttaatt gtattttttt catataataa   4320
agccgttgaa gtaaaccaat ccatttttcct tatgatgtta ttattaaatt taagttttat   4380
aataatatct ttattatatt tattgttttt aaaaaaacta gtgaaatttc tagtgaaatt   4440
tccggcttta ttaaacttat ttttaggaat tttattttca ttttcatctt tacaggattt   4500
gattatatct ttaaatatgt tttatcaaat attatctttt tctaaattta tatatatttt   4560
tattatattt attattatat atattttatt tttaagtttc tttctaacag ctattaaaaa   4620
gaaacttaaa aataaaaaca cgtactctaa accaataaat aaaactattt ttattattgc   4680
tgccttgatt ggaatagttt ttagtaaaat taatttcaat attccacaat attatattat   4740
aagctagcac gcctcgagac tctatcattg atagagtttg aaactctatc attgatagag   4800
tataatatct ttgttcatgc ttattacgac ataacacagt tttagagcta gaaatagcaa   4860
gttaaaataa ggctagtccg ttatcaactt gaaaaagtgg caccgagtcg gtgctttttt   4920
```

```
tgaagcttct cgagatctcc atggacgcgt gacgtcgact cttaagaaca tgtataaagt   4980

atggaaaaat agcaatggag aagactgatg attacgaggc tagagctaat ttgatgtggg   5040

cttcaagttt agctataaat ggtctattat cacttggtaa ggatagaaaa tggagttgtc   5100

atcctatgga acacgagtta agtgcatatt atgatataac acatggtgta ggacttgcaa   5160

ttttaacacc taattggatg gaatatattc taaatgacga tacacttcat aaatttgttt   5220

cttatggaat aaatgtttgg ggaatagaca agaacaaaga taactatgaa atagcacgag   5280

aggctattaa aaatacgaga gaatacttta attcattggg tattccttca aagcttagag   5340

aagttggaat aggaaaagat aaactagaac taatggcaaa gcaagctgtt agaaattctg   5400

gaggaacaat aggaagttta agaccaataa atgcagagga tgttcttgag atatttaaaa   5460

aatcttatta atagaaactg tagaggtatt tttataattt aaaagatgtt aaagagtgag   5520

gagtaatttt gttctaacgc ctcactcttt tcattttatg attaaatgta tgctgattta   5580

cgctaactta aatcctaaat aataacctaa tgttaatatt ttgtaacaaa tggataaaag   5640

cgtaaaaata ttattgtaat aattttaagt aggtttaaaa tatatataat gtagaagcat   5700

tcctacatta tattatttaa ataataatct aaacaggagg ggttaaagtg gttgatttca   5760

aatctgtgta aacctaccgg ggtttgggcg tagccattat attcatgaac tccaagaaag   5820

cagtatgcta gcaaagaaat aaaactcaaa gcagagagaa aatttagaca ttcaactata   5880

aataaaaaat accccccaaa gcattaatat cttggggagt attttttatt ttgaagtatt   5940

ctgttcagct aaatattctt ctaaggtaat acctctgttc ataatttctt gtgaggcagg   6000

aagaccgata tatcttacat gccatggctc aaaattatac tttgttatgt tttctttatc   6060

cttaggatat cttattatga aaccatattt accacaattt tgttgaagcc atttataaga   6120

atttgtattc ataaatccat catctaaaga agagtattcg gttgatagta agtccattgc   6180

caatccagtt tgatgctcac ttgtaccagg ttcagctaca tatttatcag cttcggcttt   6240

tccgtctcgt gctacttttt cattatataa tttttgctga tacgaataag gtctataacc   6300

tgaaacagct agaagtgtaa gaccatcctt tgatgctgca ttaaacatat tttcaagtcc   6360

tgttgcagct tcgctctcca tttgatttac attaggatca gaactactaa taaatttaac   6420

gttaggagtt ctcaaatttt gaggtatata gtttcctgat aatttacttt gcttgtttac   6480

aagtaggatg ttctgtttct ttacctcggg tttcttggct tgttttttag gtgtagaaac   6540

tttctttttg ggttcgtttg                                               6560
```

```
<210> SEQ ID NO 80
<211> LENGTH: 6560
<212> TYPE: DNA
<213> ORGANISM: Artificial Sequence
<220> FEATURE:
<223> OTHER INFORMATION: pGRNA_deltabdhA_deltabdhB

<400> SEQUENCE: 80

gatccccggg taccgagctc gaattcgtaa tcatggtcat agctgtttcc tgtgtgaaat     60

tgttatccgc tcacaattcc acacaacata cgagccggaa gcataaagtg taaagcctgg    120

ggtgcctaat gagtgagcta actcacatta attgcgttgc gctcactgcc cgctttccag    180

tcgggaaacc tgtcgtgcca gctgcattaa tgaatcggcc aacgcgcggg gagaggcggt    240

ttgcgtattg ggcgctcttc cgcttcctcg ctcactgact cgctgcgctc ggtcgttcgg    300

ctgcggcgag cggtatcagc tcactcaaag gcggtaatac ggttatccac agaatcaggg    360
```

-continued

```
gataacgcag gaaagaacat gtgagcaaaa ggccagcaaa aggccaggaa ccgtaaaaag    420
gccgcgttgc tggcgttttt ccataggctc cgcccccctg acgagcatca caaaaatcga    480
cgctcaagtc agaggtggcg aaacccgaca ggactataaa gataccaggc gtttccccct    540
ggaagctccc tcgtgcgctc tcctgttccg accctgccgc ttaccggata cctgtccgcc    600
tttctccctt cgggaagcgt ggcgctttct catagctcac gctgtaggta tctcagttcg    660
gtgtaggtcg ttcgctccaa gctgggctgt gtgcacgaac cccccgttca gcccgaccgc    720
tgcgccttat ccggtaacta tcgtcttgag tccaacccgg taagacacga cttatcgcca    780
ctggcagcag ccactggtaa caggattagc agagcgaggt atgtaggcgg tgctacagag    840
ttcttgaagt ggtggcctaa ctacggctac actagaagaa cagtatttgg tatctgcgct    900
ctgctgaagc cagttacctt cggaaaaaga gttggtagct cttgatccgg caaacaaacc    960
accgctggta gcggtggttt ttttgtttgc aagcagcaga ttacgcgcag aaaaaaagga   1020
tctcaagaag atcctttgat cttttctacg gggtctgacg ctcagtggaa cgaaaactca   1080
cgttaaggga ttttggtcat gagattatca aaaaggatct tcacctagat ccttttaaat   1140
taaaaatgaa gttttaaatc aatctaaagt atatatgagt aaacttggtc tgacagttac   1200
caaagctagc ttaatactag tatatactta atgtgataag tgtctgacag ctgaccggtc   1260
taaagaggtc cctagcgcct acggggaatt tgtatcgata aggggtacaa attcccacta   1320
agcgctcggc cggggatcga tccccgggta cgtacccggc agtttttctt tttcggcaag   1380
tgttcaagaa gttattaagt cgggagtgca gtcgaagtgg gcaagttgaa aaattcacaa   1440
aaatgtggta taatatcttt gttcattaga gcgataaact tgaatttgag agggaactta   1500
gatggtattt gaaaaaattg ataaaaatag ttggaacaga aaagagtatt ttgaccacta   1560
ctttgcaagt gtaccttgta cctacagcat gaccgttaaa gtggatatca cacaaataaa   1620
ggaaaaggga atgaaactat atcctgcaat gctttattat attgcaatga ttgtaaaccg   1680
ccattcagag tttaggacgg caatcaatca agatggtgaa ttggggatat atgatgagat   1740
gataccaagc tatacaatat ttcacaatga tactgaaaca ttttccagcc tttggactga   1800
gtgtaagtct gactttaaat catttttagc agattatgaa agtgatacgc aacggtatgg   1860
aaacaatcat agaatggaag gaaagccaaa tgctccggaa aacattttta atgtatctat   1920
gataccgtgg tcaaccttcg atggctttaa tctgaatttg cagaaaggat atgattattt   1980
gattcctatt tttactatgg ggaaatatta taaagaagat aacaaaatta tacttccttt   2040
ggcaattcaa gttcatcacg cagtatgtga cggatttcac atttgccgtt ttgtaaacga   2100
attgcaggaa ttgataaata gttaacttca ggtttgtctg taactaaaaa ctagtattta   2160
acctaggatc aaaaaaattt ccaataatcc cactctaagc cacaaacacg ccctataaaa   2220
tcccgcttta atcccacttt gagacacatg taatattact ttacgcccta gtatagtgat   2280
aattttttac attcaatgcc acgcaaaaaa ataaaggggc actataataa aagttccttc   2340
ggaactaact aaagtaaaaa attatcttta caacctcccc aaaaaaaaga acaggtacaa   2400
agtaccctat aatacaagcg taaaaaaaat gagggtaaaa ataaaaaaat aaaaaaataa   2460
aaaaataaaa aaataaaaaa ataaaaaaat aaaaaaatat aaaaataaaa aaatataaaa   2520
ataaaaaaat ataaaaataa aaaaataaaa aaatataaaa ataaaaaaat aaaaaaatat   2580
aaaaatattt tttatttaaa gtttgaaaaa aatttttttta tattatataa tctttgaaga   2640
aaagaatata aaaaatgagc ctttataaaa gcccattttt tttcatatac gtaatatgac   2700
gttctaatgt ttttattggt acttctaaca ttagagtaat ttctttattt ttaaagcctt   2760
```

```
tttctttaag ggcttttatt ttttttctta atacatttaa ttcctctttt tttgttgctt   2820

ttcctttagc ttttaattgc tcttgataat tttttttacc tctaatattt tctcttctct   2880

tatattcctt tttagaaatt attattgtca tatattttg ttcttcttct gtaatttcta    2940

ataactctat aagagtttca ttcttatact tatattgctt atttttatct aaataacatc   3000

tttcagcact tctagttgct cttataactt ctctttcact taaatgttgt ctaaacatac   3060

tattaagttc taaaacatca tttaatgcct tctcaatgtc ttctgtaaag ctacaaagat   3120

aatatctata taaaaataat ataagctctc tgtgtccttt taaatcatat tctcttagtt   3180

cacaaagttt tattatgtct tgtattcttc cataatataa acttctttct ctataaatat   3240

aatttatttt gcttggtcta cccttttttcc tttcatatgg ttttaattca ggtaaaaatc  3300

cattttgtat ttctcttaag tcataaatat attcgtactc atctaatata ttgactactg   3360

tttttgattt agagtttata cttcctggaa ctcttaatat tctcgttgca tctaaggctt   3420

gtctatctgc tccaaagtat tttaattgat tatataaata ttcttgaacc gctttccata   3480

atggtaatgc tttactaggt actgcattta ttatccatat taaatacatt cctcttccac   3540

tatctattac atagtttggt ataggaatac tttgattaaa ataattcttt tctaagtcca   3600

ttaatacctg gtctttagtt ttgccagttt tataataatc caagtctata aacagtgtat   3660

ttaactcttt tatattttct aatcgcctac acggcttata aaaggtattt agagttatat   3720

agatattttc atcactcata tctaaatctt ttaattcagc gtatttatag tgccattggc   3780

tatatccttt tttatctata acgctcctgg ttatccaccc tttacttcta ctatgaatat   3840

tatctatata gttcttttta ttcagcttta atgcgtttct cacttattca cctccccttc   3900

tgtaaaacta agaaaattat atcatatttt caataattat taactattct taaactctta   3960

ataaaaaata gagtaagtcc ccaattgaaa cttaatctat tttttatgtt ttaatttatt   4020

atttttatta aaatatttta aactaaatta aatgattctt tttaattttt tactatttca   4080

ttccataata tattactata attatttaca aataatattt cttcatttgt aatatttaga   4140

tgatttacta attttagttt ttatatatta aataattaat gtataattta tataaaaaat   4200

caaaggagct tataaattat gattatttcc aaagatacta aagatttaat ttttttcaat   4260

tttaacaata ctttttgtaa tattatgttt aaatttaatt gtattttttt catataataa   4320

agccgttgaa gtaaaccaat ccattttcct tatgatgtta ttattaaatt taagttttat   4380

aataatatct ttattatatt tattgttttt aaaaaaacta gtgaaatttc tagtgaaatt   4440

tccggcttta ttaaacttat ttttaggaat tttattttca ttttcatctt tacaggattt   4500

gattatatct ttaaatatgt tttatcaaat attatctttt tctaaattta tatatatttt   4560

tattatattt attattatat atattttatt tttaagtttc tttctaacag ctattaaaaa   4620

gaaacttaaa aataaaaaca cgtactctaa accaataaat aaaactattt ttattattgc   4680

tgccttgatt ggaatagttt ttagtaaaat taatttcaat attccacaat attatattat   4740

aagctagcac gcctcgagac tctatcattg atagagtttg aaactctatc attgatagag   4800

tataatatct ttgttcatgc ttattacgac ataacacagt tttagagcta gaaatagcaa   4860

gttaaaataa ggctagtccg ttatcaactt gaaaaagtgg caccgagtcg gtgctttttt   4920

tgaagcttct cgagatctcc atggacgcgt gacgtcgacc ttctaatctc ctctactatt   4980

ttagggttag ctacattagc taaataggta atagctacag ttgtctttga attctcacct   5040

aaagtaagtt cttccacttt aaaatcagtg cttctaattt tttttcttaa aagggctaca   5100
```

```
tttgtggtta aagattcagt gaagccctct ctaggacctc ttattacagt ttcaacagtt   5160
ggttctgtta tagctctttc agggggtttt ccaatactta taataattgc tttactttca   5220
ccatctagga ataatgctat acttcctttt aaaatggaca atataacatc atccatgctt   5280
ttatatacat ttttatcatt aacagcaaaa attgattttg tatattcaaa tatgtttaaa   5340
tggggatggt tattgtaatc ttcttctata agttttttta taacagagga ttctattaca   5400
tcagattgga taagattatt tatgtagaca atcattgcag aaaaatttct attattagct   5460
attttaaatt ctctaatcgt taaatctgag caatttgtaa ataaggtttc tatagtatgt   5520
ttatttgttt taaggctagt tgaaaccgtc ttcgcgttat ttttagatgc ttcttcttta   5580
ttaaaaattt tattaaacaa cgaaaaattc accccctcaa tttatttata taatagtagt   5640
ttgcatgaaa tttcgttgtt tattcatatt agatgcttgt attaaaataa taaaatagta   5700
aaatataagt agacaaacta taaatctatt actaggaggt aagaagtatg ctaagtttta   5760
aatctgtgta aacctaccgg ggtttgggcg tagccattat attcatgaac tccaagaaag   5820
cagtatgcta gcaaagaaat aaaactcaaa gcagagagaa aatttagaca ttcaactata   5880
aataaaaaat accccccaaa gcattaatat cttggggagt atttttttatt ttgaagtatt  5940
ctgttcagct aaatattctt ctaaggtaat acctctgttc ataatttctt gtgaggcagg   6000
aagaccgata tatcttacat gccatggctc aaaattatac tttgttatgt tttctttatc   6060
cttaggatat cttattatga aaccatattt accacaattt tgttgaagcc atttataaga   6120
atttgtattc ataaatccat catctaaaga agagtattcg gttgatagta agtccattgc   6180
caatccagtt tgatgctcac ttgtaccagg ttcagctaca tatttatcag cttcggcttt   6240
tccgtctcgt gctacttttt cattatataa tttttgctga tacgaataag gtctataacc   6300
tgaaacagct agaagtgtaa gaccatcctt tgatgctgca ttaaacatat tttcaagtcc   6360
tgttgcagct tcgctctcca tttgatttac attaggatca gaactactaa taaatttaac   6420
gttaggagtt ctcaaatttt gaggtatata gtttcctgat aatttacttt gcttgtttac   6480
aagtaggatg ttctgtttct ttacctcggg tttcttggct tgttttttag gtgtagaaac   6540
tttctttttg ggttcgtttg                                               6560
```

<210> SEQ ID NO 81
<211> LENGTH: 1654
<212> TYPE: DNA
<213> ORGANISM: Artificial Sequence
<220> FEATURE:
<223> OTHER INFORMATION: bgaR acrIIA4 cassette

<400> SEQUENCE: 81

```
aaaaagtata acagaggttt taatttacgc ctctgttata ctttttattt ttgaaatttt     60
tttgttttaa agctgtattt taaatttata tacttggttt atttacttga ttatttctgt    120
aatttagtgg agacattgaa aaatgttttg aaaaagtttt tgaaaataac agggagtcac    180
tataacctac actacttgcg acttctccta taggaagttt agtgcttttt aataaaaggg    240
tggctttgta cattctaagg tttattaaat atctttgagg agaaattcca aggtttttta    300
tgaacatttt atataaataa cttctactta agttcacata atcagcaatt tcttgaacag    360
ttatgctatg catgtaatta gaattaatga aattaagagc atcttgaata tatgtgtgta    420
attccttatc tttgtattca aaaggttttg ggaattcttc tataagtgcg tacaataatg    480
agtaaagttc ttttagtaat agtatgtcat cagatcttga aggattataa gtttttgata    540
tttcgcacat atttaatatt atctgtggaa tttttgagtt ttcttcacaa ttagcaacac    600
```

aggagttagt aatagaagtt ctatttaaat actcattagc atttgaacca ctaaatccta 660
tccagtagta ttcccaagga tcatcaatag aagccacata ctcaacttgc ataccttttta 720 gtagtataaa aatatcacct tgttttaagt tatatacctt accattaaat ttaaaagttc 780
catatccctt agttacgtaa tgaataacag catttttcaa tacttcatag ttatatccta 840
atcctggtat accttgttct ataccacatt catctacatt catttcaaag ttttctttaa 900
catacttttt ccacaatatt tgcatttcta cctcctaacc tataaaatta gccaatttta 960
tagtagtctt atattaaaca tttacatgag agctttgcaa agcagtttat caacataaaa 1020 gcttttttatt ttaaaataaa ttcttctaaa tataagaata ttttaaagaa atatctttat 1080
atattagtta ttaaaattta taagattata agaaacatta taacatattt tagaactttt 1140
taactattct aaaagattaa tttacatatt aacatttaat tatgggtaaa aactattttg 1200
aaaaatgatt tatatggaat tatgtttctt aaatatacaa tcatgtttca tgaatacata 1260
attattttaa atgtattggg agggtaaaat gatattaaaa aatgaatacc atgaagatac 1320
tgcagaatct agaatccgcg gtagtcgacg tggaattgtg agcggataac aatttcacag 1380
gagggctgaa atgaatatta atgacttaat tagagaaata aaaaacaaag attacacagt 1440
gaaattgagt ggtacggata gcaatagtat aacacagcta attattagag ttaataatga 1500
tggaaacgag tatgtaattt ctgaaagtga aaatgaatca atagttgaaa aattcatatc 1560
tgcatttaaa aacggttgga atcaagaata cgaggatgaa gaagaatttt ataatgacat 1620
gcaaacaatc accttaaaaa gtgagttgaa ctaa 1654

<210> SEQ ID NO 82
<211> LENGTH: 4984
<212> TYPE: DNA
<213> ORGANISM: Artificial Sequence
<220> FEATURE:
<223> OTHER INFORMATION: pGRNAind

<400> SEQUENCE: 82
caagcttcaa aaaaagcacc gactcggtgc cactttttca agttgataac ggactagcct 60
tattttaact tgctatttct agctctaaaa cagagaccgc tagcgatatc cccgggagat 120
ctggtctcaa tgaacaaaga tattatactc tatcaatgat agagtttcaa actctatcaa 180
tgatagagtg agctcgaatt cgtaatcatg gtcatagctg tttcctgtgt gaaattgtta 240
tccgctcaca attccacaca acatacgagc cggaagcata aagtgtaaag cctggggtgc 300
ctaatgagtg agctaactca cattaattgc gttgcgctca ctgcccgctt tccagtcggg 360
aaacctgtcg tgccagctgc attaatgaat cggccaacgc gcggggagag gcggtttgcg 420
tattgggcgc tcttccgctt cctcgctcac tgactcgctg cgctcggtcg ttcggctgcg 480
gcgagcggta tcagctcact caaaggcggt aatacggtta tccacagaat caggggataa 540
cgcaggaaag aacatgtgag caaaaggcca gcaaaaggcc aggaaccgta aaaaggccgc 600
gttgctggcg tttttccata ggctccgccc ccctgacgag catcacaaaa atcgacgctc 660
aagtcagagg tggcgaaacc cgacaggact ataaagatac caggcgtttc cccctggaag 720
ctccctcgtg cgctctcctg ttccgaccct gccgcttacc ggatacctgt ccgcctttct 780
cccttcggga agcgtggcgc tttctcatag ctcacgctgt aggtatctca gttcggtgta 840
ggtcgttcgc tccaagctgg gctgtgtgca cgaacccccc gttcagcccg accgctgcgc 900
cttatccggt aactatcgtc ttgagtccaa cccggtaaga cacgacttat cgccactggc 960

```
agcagccact ggtaacagga ttagcagagc gaggtatgta ggcggtgcta cagagttctt   1020
gaagtggtgg cctaactacg gctacactag aagaacagta tttggtatct gcgctctgct   1080
gaagccagtt accttcggaa aaagagttgg tagctcttga tccggcaaac aaaccaccgc   1140
tggtagcggt ggtttttttg tttgcaagca gcagattacg cgcagaaaaa aaggatctca   1200
agaagatcct ttgatctttt ctacggggtc tgacgctcag tggaacgaaa actcacgtta   1260
agggattttg gtcatgagat tatcaaaaag gatcttcacc tagatccttt taaattaaaa   1320
atgaagtttt aaatcaatct aaagtatata tgagtaaact tggtctgaca gttaccaaag   1380
ctagcttaat actagtatat acttaatgtg ataagtgtct gacagctgac cggtctaaag   1440
aggtccctag cgcctacggg gaatttgtat cgataagggg tacaaattcc cactaagcgc   1500
tcggccgggg atcgatcccc gggtacgtac ccggcagttt ttctttttcg gcaagtgttc   1560
aagaagttat taagtcggga gtgcagtcga agtgggcaag ttgaaaaatt cacaaaaatg   1620
tggtataata tctttgttca ttagagcgat aaacttgaat ttgagaggga acttagatgg   1680
tatttgaaaa aattgataaa aatagttgga acagaaaaga gtattttgac cactactttg   1740
caagtgtacc ttgtacctac agcatgaccg ttaaagtgga tatcacacaa ataaaggaaa   1800
agggaatgaa actatatcct gcaatgcttt attatattgc aatgattgta aaccgccatt   1860
cagagtttag gacggcaatc aatcaagatg gtgaattggg gatatatgat gagatgatac   1920
caagctatac aatatttcac aatgatactg aaacattttc cagcctttgg actgagtgta   1980
agtctgactt taaatcattt ttagcagatt atgaaagtga tacgcaacgg tatggaaaca   2040
atcatagaat ggaaggaaag ccaaatgctc cggaaaacat ttttaatgta tctatgatac   2100
cgtggtcaac cttcgatggc tttaatctga atttgcagaa aggatatgat tatttgattc   2160
ctatttttac tatggggaaa tattataaag aagataacaa aattatactt cctttggcaa   2220
ttcaagttca tcacgcagta tgtgacggat ttcacatttg ccgttttgta aacgaattgc   2280
aggaattgat aaatagttaa cttcaggttt gtctgtaact aaaaactagt atttaaccta   2340
ggatcaaaaa aatttccaat aatcccactc taagccacaa acacgcccta taaaatcccg   2400
ctttaatccc actttgagac acatgtaata ttactttacg ccctagtata gtgataattt   2460
tttacattca atgccacgca aaaaaataaa ggggcactat aataaaagtt ccttcggaac   2520
taactaaagt aaaaaattat ctttacaacc tccccaaaaa aaagaacagg tacaaagtac   2580
cctataatac aagcgtaaaa aaaatgaggg taaaaataaa aaaataaaaa aataaaaaaa   2640
taaaaaaata aaaaaataaa aaaataaaaa aatataaaaa taaaaaaata taaaaataaa   2700
aaaatataaa aataaaaaaa taaaaaaata taaaaataaa aaaataaaaa aatataaaaa   2760
tatttttat ttaaagtttg aaaaaaattt ttttatatta tataatcttt gaagaaaaga   2820
atataaaaaa tgagccttta taaaagccca ttttttttca tatacgtaat atgacgttct   2880
aatgttttta ttggtacttc taacattaga gtaatttctt tatttttaaa gccttttttct   2940
ttaagggctt ttattttttt tcttaataca tttaattcct ctttttttgt tgcttttcct   3000
ttagctttta attgctcttg ataatttttt ttacctctaa tattttctct tctcttatat   3060
tcctttttag aaattattat tgtcatatat ttttgttctt cttctgtaat ttctaataac   3120
tctataagag tttcattctt atacttatat tgcttatttt tatctaaata acatctttca   3180
gcacttctag ttgctcttat aacttctctt tcacttaaat gttgtctaaa catactatta   3240
agttctaaaa catcatttaa tgccttctca atgtcttctg taaagctaca aagataatat   3300
ctatataaaa ataatataag ctctctgtgt ccttttaaat catattctct tagttcacaa   3360
```

agttttatta tgtcttgtat tcttccataa tataaacttc tttctctata aatataattt 3420
attttgcttg gtctaccctt tttcctttca tatggtttta attcaggtaa aaatccattt 3480
tgtatttctc ttaagtcata aatatattcg tactcatcta atatattgac tactgttttt 3540
gatttagagt ttatacttcc tggaactctt aatattctcg ttgcatctaa ggcttgtcta 3600
tctgctccaa agtattttaa ttgattatat aaatattctt gaaccgcttt ccataatggt 3660
aatgctttac taggtactgc atttattatc catattaaat acattcctct tccactatct 3720
attacatagt ttggtatagg aatactttga ttaaaataat tcttttctaa gtccattaat 3780
acctggtctt tagttttgcc agttttataa taatccaagt ctataaacag tgtatttaac 3840
tcttttatat tttctaatcg cctacacggc ttataaaagg tatttagagt tatatagata 3900
ttttcatcac tcatatctaa atcttttaat tcagcgtatt tatagtgcca ttggctatat 3960 cctttttat ctataacgct cctggttatc cacccttac ttctactatg aatattatct 4020
atatagttct ttttattcag ctttaatgcg tttctcactt attcacctcc ccttctgtaa 4080
aactaagaaa attatatcat attttcaata attattaact attcttaaac tcttaataaa 4140
aaatagagta agtccccaat tgaaacttaa tctatttttt atgttttaat ttattatttt 4200
tattaaaata ttttaaacta aattaaatga ttctttttaa ttttttacta tttcattcca 4260
taatatatta ctataattat ttacaaataa tatttcttca tttgtaatat ttagatgatt 4320
tactaatttt agtttttata tattaaataa ttaatgtata atttatataa aaaatcaaag 4380
gagcttataa attatgatta tttccaaaga tactaaagat ttaatttttt tcaattttaa 4440
caatactttt tgtaatatta tgtttaaatt taattgtatt tttttcatat aataaagccg 4500
ttgaagtaaa ccaatccatt ttccttatga tgttattatt aaatttaagt tttataataa 4560
tatctttatt atatttattg tttttaaaaa aactagtgaa atttctagtg aaatttccgg 4620
ctttattaaa cttattttta ggaattttat tttcattttc atctttacag gatttgatta 4680
tatctttaaa tatgttttat caaatattat ctttttctaa atttatatat atttttatta 4740
tatttattat tatatatatt ttatttttaa gtttctttct aacagctatt aaaaagaaac 4800
ttaaaaataa aaacacgtac tctaaaccaa taaataaaac tatttttatt attgctgcct 4860
tgattggaat agtttttagt aaaattaatt tcaatattcc acaatattat attataagct 4920
agcacgcctc gagatctcca tggacgcgtg acgtcgactc tagaggatcc ccgggtaccg 4980
agct 4984

<210> SEQ ID NO 83
<211> LENGTH: 200
<212> TYPE: DNA
<213> ORGANISM: Artificial Sequence
<220> FEATURE:
<223> OTHER INFORMATION: gRNA cassette

<400> SEQUENCE: 83
gagctcactc tatcattgat agagtttgaa actctatcat tgatagagta taatatcttt 60
gttcattgag accagatctc ccggggatat cgctagcggt ctctgtttta gagctagaaa 120
tagcaagtta aaataaggct agtccgttat caacttgaaa aagtggcacc gagtcggtgc 180 ttttttgaa gcttgagctc 200

<210> SEQ ID NO 84
<211> LENGTH: 24
<212> TYPE: DNA

<213> ORGANISM: Artificial Sequence
<220> FEATURE:
<223> OTHER INFORMATION: Primer

<400> SEQUENCE: 84
tcatgatttc tccatattag ctag 24

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
aaacctagct aatatggaga aatc 24

<210> SEQ ID NO 86
<211> LENGTH: 24
<212> TYPE: DNA
<213> ORGANISM: Artificial Sequence
<220> FEATURE:
<223> OTHER INFORMATION: Primer

<400> SEQUENCE: 86
tcatgttaca cttggaacag gcgt 24

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
aaacacgcct gttccaagtg taac 24

<210> SEQ ID NO 88
<211> LENGTH: 24
<212> TYPE: DNA
<213> ORGANISM: Artificial Sequence
<220> FEATURE:
<223> OTHER INFORMATION: Primer

<400> SEQUENCE: 88
tcatttccgg cagtaggatc ccca 24

<210> SEQ ID NO 89
<211> LENGTH: 24
<212> TYPE: DNA
<213> ORGANISM: Artificial Sequence
<220> FEATURE:
<223> OTHER INFORMATION: Primer

<400> SEQUENCE: 89
aaactgggga tcctactgcc ggaa 24

<210> SEQ ID NO 90
<211> LENGTH: 24
<212> TYPE: DNA
<213> ORGANISM: Artificial Sequence
<220> FEATURE:
<223> OTHER INFORMATION: Primer

<400> SEQUENCE: 90
tcatgcttat tacgacataa caca 24

<210> SEQ ID NO 91
<211> LENGTH: 24
<212> TYPE: DNA
<213> ORGANISM: Artificial Sequence
<220> FEATURE:
<223> OTHER INFORMATION: Primer

<400> SEQUENCE: 91
aaactgtgtt atgtcgtaat aagc 24

<210> SEQ ID NO 92
<211> LENGTH: 36
<212> TYPE: DNA
<213> ORGANISM: Artificial Sequence
<220> FEATURE:
<223> OTHER INFORMATION: Primer

<400> SEQUENCE: 92
atgcatggat ccaaacgaac ccaaaaagaa agtttc 36

<210> SEQ ID NO 93
<211> LENGTH: 30
<212> TYPE: DNA
<213> ORGANISM: Artificial Sequence
<220> FEATURE:
<223> OTHER INFORMATION: Primer

<400> SEQUENCE: 93
ggttgatttc aaatctgtgt aaacctaccg 30

<210> SEQ ID NO 94
<211> LENGTH: 30
<212> TYPE: DNA
<213> ORGANISM: Artificial Sequence
<220> FEATURE:
<223> OTHER INFORMATION: Primer

<400> SEQUENCE: 94
acacagattt gaaatcaacc actttaaccc 30

<210> SEQ ID NO 95
<211> LENGTH: 37
<212> TYPE: DNA
<213> ORGANISM: Artificial Sequence
<220> FEATURE:
<223> OTHER INFORMATION: Primer

<400> SEQUENCE: 95
atgcatgtcg actcttaaga acatgtataa agtatgg 37

<210> SEQ ID NO 96
<211> LENGTH: 36
<212> TYPE: DNA
<213> ORGANISM: Artificial Sequence
<220> FEATURE:
<223> OTHER INFORMATION: Primer

<400> SEQUENCE: 96
atgcatggat ccaaacgaac ccaaaaagaa agtttc 36

<210> SEQ ID NO 97
<211> LENGTH: 30
<212> TYPE: DNA
<213> ORGANISM: Artificial Sequence
<220> FEATURE:

<223> OTHER INFORMATION: Primer

<400> SEQUENCE: 97
gctaagtttt aaatctgtgt aaacctaccg 30

<210> SEQ ID NO 98
<211> LENGTH: 32
<212> TYPE: DNA
<213> ORGANISM: Artificial Sequence
<220> FEATURE:
<223> OTHER INFORMATION: Primer

<400> SEQUENCE: 98
acacagattt aaaacttagc atacttctta cc 32

<210> SEQ ID NO 99
<211> LENGTH: 37
<212> TYPE: DNA
<213> ORGANISM: Artificial Sequence
<220> FEATURE:
<223> OTHER INFORMATION: Primer

<400> SEQUENCE: 99
atgcatgtcg accttctaat ctcctctact attttag 37

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
acacattgaa gggagctttt 20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
ggcaacaaca tcaggccttt 20

<210> SEQ ID NO 102
<211> LENGTH: 4966
<212> TYPE: DNA
<213> ORGANISM: Artificial Sequence
<220> FEATURE:
<223> OTHER INFORMATION: pGRNA-xylB

<400> SEQUENCE: 102
atcaaaaaaa tttccaataa tcccactcta agccacaaac acgccctata aaatcccgct 60
ttaatcccac tttgagacac atgtaatatt actttacgcc ctagtatagt gataattttt 120
tacattcaat gccacgcaaa aaaataaagg ggcactataa taaaagttcc ttcggaacta 180
actaaagtaa aaaattatct ttacaacctc cccaaaaaaa agaacaggta caaagtaccc 240
tataatacaa gcgtaaaaaa aatgagggta aaaataaaaa aataaaaaaa taaaaaaata 300
aaaaaataaa aaaataaaaa aataaaaaaa tataaaaata aaaaaatata aaaataaaaa 360
aatataaaaa taaaaaaata aaaaaatata aaaataaaaa aataaaaaaa tataaaaata 420
ttttttattt aaagtttgaa aaaaattttt ttatattata taatctttga agaaaagaat 480

```
ataaaaaatg agcctttata aaagcccatt ttttttcata tacgtaatat gacgttctaa    540
tgtttttatt ggtacttcta acattagagt aatttcttta tttttaaagc cttttttcttt    600
aagggctttt attttttttc ttaatacatt taattcctct ttttttgttg cttttccttt    660
agcttttaat tgctcttgat aatttttttt acctctaata ttttctcttc tcttatattc    720
ctttttagaa attattattg tcatatattt ttgttcttct tctgtaattt ctaataactc    780
tataagagtt tcattcttat acttatattg cttattttta tctaaataac atctttcagc    840
acttctagtt gctcttataa cttctctttc acttaaatgt tgtctaaaca tactattaag    900
ttctaaaaca tcatttaatg ccttctcaat gtcttctgta aagctacaaa gataatatct    960
atataaaaat aatataagct ctctgtgtcc ttttaaatca tattctctta gttcacaaag   1020
ttttattatg tcttgtattc ttccataata taaacttctt tctctataaa tataatttat   1080
tttgcttggt ctaccctttt tcctttcata tggttttaat tcaggtaaaa atccattttg   1140
tatttctctt aagtcataaa tatattcgta ctcatctaat atattgacta ctgtttttga   1200
tttagagttt atacttcctg gaactcttaa tattctcgtt gcatctaagg cttgtctatc   1260
tgctccaaag tattttaatt gattatataa atattcttga accgctttcc ataatggtaa   1320
tgctttacta ggtactgcat ttattatcca tattaaatac attcctcttc cactatctat   1380
tacatagttt ggtataggaa tactttgatt aaaataattc ttttctaagt ccattaatac   1440
ctggtcttta gttttgccag ttttataata atccaagtct ataaacagtg tatttaactc   1500
ttttatattt tctaatcgcc tacacggctt ataaaaggta tttagagtta tatagatatt   1560
ttcatcactc atatctaaat cttttaattc agcgtattta tagtgccatt ggctatatcc   1620
tttttatct ataacgctcc tggttatcca ccctttactt ctactatgaa tattatctat   1680
atagttcttt ttattcagct ttaatgcgtt tctcacttat tcacctcccc ttctgtaaaa   1740
ctaagaaaat tatatcatat tttcaataat tattaactat tcttaaactc ttaataaaaa   1800
atagagtaag tccccaattg aaacttaatc tattttttat gttttaattt attattttta   1860
ttaaaatatt ttaaactaaa ttaaatgatt ctttttaatt ttttactatt tcattcccata   1920
atatattact ataattattt acaaataata tttcttcatt tgtaatattt agatgattta   1980
ctaattttag tttttatata ttaaataatt aatgtataat ttatataaaa aatcaaagga   2040
gcttataaat tatgattatt tccaaagata ctaaagattt aattttttttc aattttaaca   2100
atacttttttg taatattatg tttaaattta attgtatttt tttcatataa taaagccgtt   2160
gaagtaaacc aatccatttt ccttatgatg ttattattaa atttaagttt tataataata   2220
tctttattat atttattgtt tttaaaaaaa ctagtgaaat ttctagtgaa atttccggct   2280
ttattaaact tatttttagg aattttattt tcattttcat ctttacagga tttgattata   2340
tctttaaata tgttttatca aatattatct ttttctaaat ttatatatat ttttattata   2400
tttattatta tatatatttt atttttaagt ttctttctaa cagctattaa aaagaaactt   2460
aaaaataaaa acacgtactc taaaccaata aataaaacta tttttattat tgctgccttg   2520
attggaatag tttttagtaa aattaatttc aatattccac aatattatat tataagctag   2580
cacgcctcga gaagcttcaa aaaaagcacc gactcggtgc cactttttca agttgataac   2640
ggactagcct tattttaact tgctatttct agctctaaaa cctagctaat atggagaaat   2700
catgaacaaa gatattatac tctatcaatg atagagtttc aaactctatc aatgatagag   2760
tctcgagatc tccatggacg cgtgacgtcg actctagagg atccccgggt accgagctcg   2820
```

```
aattcgtaat catggtcata gctgtttcct gtgtgaaatt gttatccgct cacaattcca   2880
cacaacatac gagccggaag cataaagtgt aaagcctggg gtgcctaatg agtgagctaa   2940
ctcacattaa ttgcgttgcg ctcactgccc gctttccagt cgggaaacct gtcgtgccag   3000
ctgcattaat gaatcggcca acgcgcgggg agaggcggtt tgcgtattgg gcgctcttcc   3060
gcttcctcgc tcactgactc gctgcgctcg gtcgttcggc tgcggcgagc ggtatcagct   3120
cactcaaagg cggtaatacg gttatccaca gaatcagggg ataacgcagg aaagaacatg   3180
tgagcaaaag gccagcaaaa ggccaggaac cgtaaaaagg ccgcgttgct ggcgtttttc   3240
cataggctcc gcccccctga cgagcatcac aaaaatcgac gctcaagtca gaggtggcga   3300
aacccgacag gactataaag ataccaggcg tttccccctg gaagctccct cgtgcgctct   3360
cctgttccga ccctgccgct taccggatac ctgtccgcct ttctcccttc gggaagcgtg   3420
gcgctttctc atagctcacg ctgtaggtat ctcagttcgg tgtaggtcgt tcgctccaag   3480
ctgggctgtg tgcacgaacc ccccgttcag cccgaccgct gcgccttatc cggtaactat   3540
cgtcttgagt ccaacccggt aagacacgac ttatcgccac tggcagcagc cactggtaac   3600
aggattagca gagcgaggta tgtaggcggt gctacagagt tcttgaagtg gtggcctaac   3660
tacggctaca ctagaagaac agtatttggt atctgcgctc tgctgaagcc agttaccttc   3720
ggaaaaagag ttggtagctc ttgatccggc aaacaaacca ccgctggtag cggtggtttt   3780
tttgtttgca agcagcagat tacgcgcaga aaaaaaggat ctcaagaaga tcctttgatc   3840
ttttctacgg ggtctgacgc tcagtggaac gaaaactcac gttaagggat tttggtcatg   3900
agattatcaa aaaggatctt cacctagatc cttttaaatt aaaaatgaag ttttaaatca   3960
atctaaagta tatatgagta aacttggtct gacagttacc aaagctagct taatactagt   4020
atatacttaa tgtgataagt gtctgacagc tgaccggtct aaagaggtcc ctagcgccta   4080
cggggaattt gtatcgataa ggggtacaaa ttcccactaa gcgctcggcc ggggatcgat   4140
ccccgggtac gtacccggca gtttttcttt ttcggcaagt gttcaagaag ttattaagtc   4200
gggagtgcag tcgaagtggg caagttgaaa aattcacaaa aatgtggtat aatatctttg   4260
ttcattagag cgataaactt gaatttgaga gggaacttag atggtatttg aaaaaattga   4320
taaaaatagt tggaacagaa aagagtattt tgaccactac tttgcaagtg taccttgtac   4380
ctacagcatg accgttaaag tggatatcac acaaataaag gaaaagggaa tgaaactata   4440
tcctgcaatg ctttattata ttgcaatgat tgtaaaccgc cattcagagt ttaggacggc   4500
aatcaatcaa gatggtgaat tggggatata tgatgagatg ataccaagct atacaatatt   4560
tcacaatgat actgaaacat tttccagcct ttggactgag tgtaagtctg actttaaatc   4620
atttttagca gattatgaaa gtgatacgca acggtatgga aacaatcata gaatggaagg   4680
aaagccaaat gctccggaaa acatttttaa tgtatctatg ataccgtggt caaccttcga   4740
tggctttaat ctgaatttgc agaaaggata tgattatttg attcctattt ttactatggg   4800
gaaatattat aaagaagata acaaaattat acttcctttg gcaattcaag ttcatcacgc   4860
agtatgtgac ggatttcaca tttgccgttt tgtaaacgaa ttgcaggaat tgataaatag   4920
ttaacttcag gtttgtctgt aactaaaaac tagtatttaa cctagg                  4966
```

<210> SEQ ID NO 103
<211> LENGTH: 4966
<212> TYPE: DNA
<213> ORGANISM: Artificial Sequence
<220> FEATURE:
<223> OTHER INFORMATION: pGRNA-xylR

<400> SEQUENCE: 103

```
atcaaaaaaa tttccaataa tcccactcta agccacaaac acgccctata aaatcccgct     60
ttaatcccac tttgagacac atgtaatatt actttacgcc ctagtatagt gataattttt    120
tacattcaat gccacgcaaa aaaataaagg ggcactataa taaaagttcc ttcggaacta    180
actaaagtaa aaaattatct ttacaacctc cccaaaaaaa agaacaggta caaagtaccc    240
tataatacaa gcgtaaaaaa aatgagggta aaaataaaaa aataaaaaaa taaaaaaata    300
aaaaaataaa aaaataaaaa aataaaaaaa tataaaaata aaaaaatata aaaataaaaa    360
aatataaaaa taaaaaaata aaaaaatata aaaataaaaa aataaaaaaa tataaaaata    420
tttttattt aaagtttgaa aaaaattttt ttatattata taatctttga agaaaagaat    480
ataaaaaatg agcctttata aaagcccatt ttttttcata tacgtaatat gacgttctaa    540
tgtttttatt ggtacttcta acattagagt aatttcttta tttttaaagc ctttttcttt    600
aagggctttt attttttttc ttaatacatt taattcctct tttttgttg cttttccttt    660
agcttttaat tgctcttgat aattttttt acctctaata ttttctcttc tcttatattc    720
ctttttagaa attattattg tcatatattt ttgttcttct tctgtaattt ctaataactc    780
tataagagtt tcattcttat acttatattg cttattttta tctaaataac atctttcagc    840
acttctagtt gctcttataa cttctctttc acttaaatgt tgtctaaaca tactattaag    900
ttctaaaaca tcatttaatg ccttctcaat gtcttctgta aagctacaaa gataatatct    960
atataaaaat aatataagct ctctgtgtcc ttttaaatca tattctctta gttcacaaag   1020
ttttattatg tcttgtattc ttccataata taaacttctt tctctataaa tataatttat   1080
tttgcttggt ctaccctttt tcctttcata tggttttaat tcaggtaaaa atccattttg   1140
tatttctctt aagtcataaa tatattcgta ctcatctaat atattgacta ctgtttttga   1200
tttagagttt atacttcctg gaactcttaa tattctcgtt gcatctaagg cttgtctatc   1260
tgctccaaag tattttaatt gattatataa atattcttga accgctttcc ataatggtaa   1320
tgctttacta ggtactgcat ttattatcca tattaaatac attcctcttc cactatctat   1380
tacatagttt ggtataggaa tactttgatt aaaataattc ttttctaagt ccattaatac   1440
ctggtcttta gttttgccag ttttataata atccaagtct ataaacagtg tatttaactc   1500
ttttatattt tctaatcgcc tacacggctt ataaaaggta tttagagtta tatagatatt   1560
ttcatcactc atatctaaat cttttaattc agcgtattta tagtgccatt ggctatatcc   1620
tttttatct ataacgctcc tggttatcca ccctttactt ctactatgaa tattatctat    1680
atagttcttt ttattcagct ttaatgcgtt tctcacttat tcacctcccc ttctgtaaaa   1740
ctaagaaaat tatatcatat tttcaataat tattaactat tcttaaactc ttaataaaaa   1800
atagagtaag tccccaattg aaacttaatc tatttttat gttttaattt attattttta    1860
ttaaaatatt ttaaactaaa ttaaatgatt ctttttaatt ttttactatt tcattccata   1920
atatattact ataattattt acaaataata tttcttcatt tgtaatattt agatgattta   1980
ctaattttag tttttatata ttaaataatt aatgtataat ttatataaaa aatcaaagga   2040
gcttataaat tatgattatt tccaaagata ctaaagattt aattttttc aattttaaca    2100
atacttttg taatattatg tttaaattta attgtatttt tttcatataa taaagccgtt    2160
gaagtaaacc aatccatttt ccttatgatg ttattattaa atttaagttt tataataata   2220
tctttattat atttattgtt tttaaaaaaa ctagtgaaat ttctagtgaa atttccggct   2280
```

```
ttattaaact tatttttagg aattttattt tcattttcat ctttacagga tttgattata   2340
tctttaaata tgttttatca aatattatct ttttctaaat ttatatatat ttttattata   2400
tttattatta tatatatttt atttttaagt ttctttctaa cagctattaa aaagaaactt   2460
aaaaataaaa acacgtactc taaaccaata aataaaacta tttttattat tgctgccttg   2520
attggaatag tttttagtaa aattaatttc aatattccac aatattatat tataagctag   2580
cacgcctcga gactctatca ttgatagagt ttgaaactct atcattgata gagtataata   2640
tctttgttca tgttacactt ggaacaggcg tgttttagag ctagaaatag caagttaaaa   2700
taaggctagt ccgttatcaa cttgaaaaag tggcaccgag tcggtgcttt ttttgaagct   2760
tctcgagatc tccatggacg cgtgacgtcg actctagagg atccccgggt accgagctcg   2820
aattcgtaat catggtcata gctgtttcct gtgtgaaatt gttatccgct cacaattcca   2880
cacaacatac gagccggaag cataaagtgt aaagcctggg gtgcctaatg agtgagctaa   2940
ctcacattaa ttgcgttgcg ctcactgccc gctttccagt cgggaaacct gtcgtgccag   3000
ctgcattaat gaatcggcca acgcgcgggg agaggcggtt tgcgtattgg gcgctcttcc   3060
gcttcctcgc tcactgactc gctgcgctcg gtcgttcggc tgcggcgagc ggtatcagct   3120
cactcaaagg cggtaatacg gttatccaca gaatcagggg ataacgcagg aaagaacatg   3180
tgagcaaaag gccagcaaaa ggccaggaac cgtaaaaagg ccgcgttgct ggcgtttttc   3240
cataggctcc gcccccctga cgagcatcac aaaaatcgac gctcaagtca gaggtggcga   3300
aacccgacag gactataaag ataccaggcg tttccccctg gaagctccct cgtgcgctct   3360
cctgttccga ccctgccgct taccggatac ctgtccgcct ttctcccttc gggaagcgtg   3420
gcgctttctc atagctcacg ctgtaggtat ctcagttcgg tgtaggtcgt tcgctccaag   3480
ctgggctgtg tgcacgaacc ccccgttcag cccgaccgct gcgccttatc cggtaactat   3540
cgtcttgagt ccaacccggt aagacacgac ttatcgccac tggcagcagc cactggtaac   3600
aggattagca gagcgaggta tgtaggcggt gctacagagt tcttgaagtg gtggcctaac   3660
tacggctaca ctagaagaac agtatttggt atctgcgctc tgctgaagcc agttaccttc   3720
ggaaaaagag ttggtagctc ttgatccggc aaacaaacca ccgctggtag cggtggtttt   3780
tttgtttgca agcagcagat tacgcgcaga aaaaaaggat ctcaagaaga tcctttgatc   3840
ttttctacgg ggtctgacgc tcagtggaac gaaaactcac gttaagggat tttggtcatg   3900
agattatcaa aaaggatctt cacctagatc cttttaaatt aaaaatgaag ttttaaatca   3960
atctaaagta tatatgagta aacttggtct gacagttacc aaagctagct taatactagt   4020
atatacttaa tgtgataagt gtctgacagc tgaccggtct aaagaggtcc ctagcgccta   4080
cggggaattt gtatcgataa ggggtacaaa ttcccactaa gcgctcggcc ggggatcgat   4140
ccccgggtac gtacccggca gtttttcttt ttcggcaagt gttcaagaag ttattaagtc   4200
gggagtgcag tcgaagtggg caagttgaaa aattcacaaa aatgtggtat aatatctttg   4260
ttcattagag cgataaactt gaatttgaga gggaacttag atggtatttg aaaaaattga   4320
taaaaatagt tggaacagaa aagagtattt tgaccactac tttgcaagtg taccttgtac   4380
ctacagcatg accgttaaag tggatatcac acaaataaag gaaaagggaa tgaaactata   4440
tcctgcaatg ctttattata ttgcaatgat tgtaaaccgc cattcagagt ttaggacggc   4500
aatcaatcaa gatggtgaat tggggatata tgatgagatg ataccaagct atacaatatt   4560
tcacaatgat actgaaacat tttccagcct ttggactgag tgtaagtctg actttaaatc   4620
atttttagca gattatgaaa gtgatacgca acggtatgga aacaatcata gaatggaagg   4680
```

aaagccaaat gctccggaaa acatttttaa tgtatctatg ataccgtggt caaccttcga 4740
tggctttaat ctgaatttgc agaaaggata tgattatttg attcctattt ttactatggg 4800
gaaatattat aaagaagata acaaaattat acttcctttg gcaattcaag ttcatcacgc 4860
agtatgtgac ggatttcaca tttgccgttt tgtaaacgaa ttgcaggaat tgataaatag 4920
ttaacttcag gtttgtctgt aactaaaaac tagtatttaa cctagg 4966

<210> SEQ ID NO 104
<211> LENGTH: 4966
<212> TYPE: DNA
<213> ORGANISM: Artificial Sequence
<220> FEATURE:
<223> OTHER INFORMATION: pGRNA-glcG

<400> SEQUENCE: 104
agctcggtac ccggggatcc tctagagtcg acgtcacgcg tccatggaga tctcgaggcg 60
tgctagctta taatataata ttgtggaata ttgaaattaa ttttactaaa aactattcca 120
atcaaggcag caataataaa aatagtttta tttattggtt tagagtacgt gtttttattt 180
ttaagtttct ttttaatagc tgttagaaag aaacttaaaa ataaaatata tataataata 240
aatataataa aaatatatat aaatttagaa aaagataata tttgataaaa catatttaaa 300
gatataatca aatcctgtaa agatgaaaat gaaaataaaa ttcctaaaaa taagtttaat 360
aaagccggaa atttcactag aaatttcact agttttttta aaaacaataa atataataaa 420
gatattatta taaaacttaa atttaataat aacatcataa ggaaaatgga ttggtttact 480
tcaacggctt tattatatga aaaaaataca attaaattta aacataatat tacaaaaagt 540
attgttaaaa ttgaaaaaaa ttaaatcttt agtatctttg gaaataatca taatttataa 600
gctcctttga tttttttatat aaattataca ttaattattt aatatataaa aactaaaatt 660
agtaaatcat ctaaatatta caaatgaaga aatattattt gtaaataatt atagtaatat 720
attatggaat gaaatagtaa aaaattaaaa agaatcattt aatttagttt aaaatatttt 780
aataaaaata ataaattaaa acataaaaaa tagattaagt ttcaattggg gacttactct 840
attttttatt aagagtttaa gaatagttaa taattattga aaatatgata taattttctt 900
agttttacag aaggggaggt gaataagtga gaaacgcatt aaagctgaat aaaaagaact 960
atatagataa tattcatagt agaagtaaag ggtggataac caggagcgtt atagataaaa 1020
aaggatatag ccaatggcac tataaatacg ctgaattaaa agatttagat atgagtgatg 1080
aaaatatcta tataactcta aataccttttt ataagccgtg taggcgatta gaaaatataa 1140
aagagttaaa tacactgttt atagacttgg attattataa aactggcaaa actaaagacc 1200
aggtattaat ggacttagaa aagaattatt ttaatcaaag tattcctata ccaaactatg 1260
taatagatag tggaagagga atgtatttaa tatggataat aaatgcagta cctagtaaag 1320
cattaccatt atggaaagcg gttcaagaat atttatataa tcaattaaaa tactttggag 1380
cagatagaca agccttagat gcaacgagaa tattaagagt tccaggaagt ataaactcta 1440
aatcaaaaac agtagtcaat atattagatg agtacgaata tatttatgac ttaagagaaa 1500
tacaaaatgg atttttacct gaattaaaac catatgaaag gaaaaagggt agaccaagca 1560
aaataaatta tatttataga gaaagaagtt tatattatgg aagaatacaa gacataataa 1620
aactttgtga actaagagaa tatgatttaa aaggacacag agagcttata ttatttttat 1680
atagatatta tctttgtagc tttacagaag acattgagaa ggcattaaat gatgttttag 1740

```
aacttaatag tatgtttaga caacatttaa gtgaaagaga agttataaga gcaactagaa   1800
gtgctgaaag atgttattta gataaaaata agcaatataa gtataagaat gaaactctta   1860
tagagttatt agaaattaca gaagaagaac aaaaatatat gacaataata atttctaaaa   1920
aggaatataa gagaagagaa aatattagag gtaaaaaaaa ttatcaagag caattaaaag   1980
ctaaaggaaa agcaacaaaa aaagaggaat taaatgtatt aagaaaaaaa ataaaagccc   2040
ttaaagaaaa aggctttaaa aataaagaaa ttactctaat gttagaagta ccaataaaaa   2100
cattagaacg tcatattacg tatatgaaaa aaaatgggct tttataaagg ctcatttttt   2160
atattctttt cttcaaagat tatataatat aaaaaaattt ttttcaaact ttaaataaaa   2220
aatattttta tattttttta ttttttttatt tttatatttt tttatttttt tatttttata   2280
ttttttttatt tttatatttt tttattttta tattttttta ttttttttatt tttttatttt   2340
tttattttt tattttttta ttttttttatt tttaccctca tttttttttac gcttgtatta   2400
tagggtactt tgtacctgtt cttttttttg gggaggttgt aaagataatt ttttacttta   2460
gttagttccg aaggaacttt tattatagtg cccctttatt tttttgcgtg gcattgaatg   2520
taaaaaatta tcactatact agggcgtaaa gtaatattac atgtgtctca aagtgggatt   2580
aaagcgggat tttatagggc gtgtttgtgg cttagagtgg gattattgga aatttttttg   2640
atcctaggtt aaatactagt ttttagttac agacaaacct gaagttaact atttatcaat   2700
tcctgcaatt cgtttacaaa acggcaaatg tgaaatccgt cacatactgc gtgatgaact   2760
tgaattgcca aaggaagtat aattttgtta tcttctttat aatatttccc catagtaaaa   2820
ataggaatca aataatcata tcctttctgc aaattcagat taaagccatc gaaggttgac   2880
cacggtatca tagatacatt aaaaatgttt tccggagcat ttggctttcc ttccattcta   2940
tgattgtttc cataccgttg cgtatcactt tcataatctg ctaaaaatga tttaaagtca   3000
gacttacact cagtccaaag gctggaaaat gtttcagtat cattgtgaaa tattgtatag   3060
cttggtatca tctcatcata tatccccaat tcaccatctt gattgattgc cgtcctaaac   3120
tctgaatggc ggtttacaat cattgcaata taataaagca ttgcaggata tagtttcatt   3180
ccccttttcct ttatttgtgt gatatccact ttaacggtca tgctgtaggt acaaggtaca   3240
cttgcaaagt agtggtcaaa atactctttt ctgttccaac tatttttatc aatttttttca   3300
aataccatct aagttccctc tcaaattcaa gtttatcgct ctaatgaaca aagatattat   3360
accacatttt tgtgaatttt tcaacttgcc cacttcgact gcactcccga cttaataact   3420
tcttgaacac ttgccgaaaa agaaaaactg ccgggtacgt acccggggat cgatccccgg   3480
ccgagcgctt agtgggaatt tgtacccctt atcgatacaa attccccgta ggcgctaggg   3540
acctctttag accggtcagc tgtcagacac ttatcacatt aagtatatac tagtattaag   3600
ctagctttgg taactgtcag accaagttta ctcatatata ctttagattg atttaaaact   3660
tcatttttaa tttaaaagga tctaggtgaa gatccttttt gataatctca tgaccaaaat   3720
cccttaacgt gagttttcgt tccactgagc gtcagacccc gtagaaaaga tcaaaggatc   3780
ttcttgagat cctttttttc tgcgcgtaat ctgctgcttg caaacaaaaa aaccaccgct   3840
accagcggtg gtttgtttgc cggatcaaga gctaccaact ctttttccga aggtaactgg   3900
cttcagcaga gcgcagatac caaatactgt tcttctagtg tagccgtagt taggccacca   3960
cttcaagaac tctgtagcac cgcctacata cctcgctctg ctaatcctgt taccagtggc   4020
tgctgccagt ggcgataagt cgtgtcttac cgggttggac tcaagacgat agttaccgga   4080
taaggcgcag cggtcgggct gaacgggggg ttcgtgcaca cagcccagct tggagcgaac   4140
```

gacctacacc gaactgagat acctacagcg tgagctatga gaaagcgcca cgcttcccga 4200
agggagaaag gcggacaggt atccggtaag cggcagggtc ggaacaggag agcgcacgag 4260
ggagcttcca gggggaaacg cctggtatct ttatagtcct gtcgggtttc gccacctctg 4320
acttgagcgt cgatttttgt gatgctcgtc aggggggcgg agcctatgga aaaacgccag 4380
caacgcggcc tttttacggt tcctggcctt ttgctggcct tttgctcaca tgttctttcc 4440
tgcgttatcc cctgattctg tggataaccg tattaccgcc tttgagtgag ctgataccgc 4500
tcgccgcagc cgaacgaccg agcgcagcga gtcagtgagc gaggaagcgg aagagcgccc 4560
aatacgcaaa ccgcctctcc ccgcgcgttg gccgattcat taatgcagct ggcacgacag 4620
gtttcccgac tggaaagcgg gcagtgagcg caacgcaatt aatgtgagtt agctcactca 4680
ttaggcaccc caggctttac actttatgct tccggctcgt atgttgtgtg gaattgtgag 4740
cggataacaa tttcacacag gaaacagcta tgaccatgat tacgaattcg agctcactct 4800
atcattgata gagtttgaaa ctctatcatt gatagagtat aatatctttg ttcatttccg 4860
gcagtaggat ccccagtttt agagctagaa atagcaagtt aaaataaggc tagtccgtta 4920
tcaacttgaa aaagtggcac cgagtcggtg ctttttttga agcttg 4966

<210> SEQ ID NO 105
<211> LENGTH: 4938
<212> TYPE: DNA
<213> ORGANISM: Artificial Sequence
<220> FEATURE:
<223> OTHER INFORMATION: pGRNA-bdhB

<400> SEQUENCE: 105
atcaaaaaaa tttccaataa tcccactcta agccacaaac acgccctata aaatcccgct 60
ttaatcccac tttgagacac atgtaatatt actttacgcc ctagtatagt gataattttt 120
tacattcaat gccacgcaaa aaaataaagg ggcactataa taaaagttcc ttcggaacta 180
actaaagtaa aaaattatct ttacaacctc cccaaaaaaa agaacaggta caaagtaccc 240
tataatacaa gcgtaaaaaa aatgagggta aaaataaaaa aataaaaaaa taaaaaaata 300
aaaaaataaa aaaataaaaa aataaaaaaa tataaaaata aaaaaatata aaaataaaaa 360
aatataaaaa taaaaaaata aaaaaatata aaaataaaaa aataaaaaaa tataaaaata 420
ttttttattt aaagtttgaa aaaaattttt ttatattata taatctttga agaaaagaat 480
ataaaaaatg agcctttata aaagcccatt ttttttcata tacgtaatat gacgttctaa 540
tgtttttatt ggtacttcta acattagagt aatttcttta tttttaaagc ctttttcttt 600
aagggctttt atttttttttc ttaatacatt taattcctct ttttttgttg cttttccttt 660
agcttttaat tgctcttgat aattttttt acctctaata ttttctcttc tcttatattc 720
ctttttagaa attattattg tcatatattt ttgttcttct tctgtaattt ctaataactc 780
tataagagtt tcattcttat acttatattg cttattttta tctaaataac atctttcagc 840
acttctagtt gctcttataa cttctctttc acttaaatgt tgtctaaaca tactattaag 900
ttctaaaaca tcatttaatg ccttctcaat gtcttctgta aagctacaaa gataatatct 960
atataaaaat aatataagct ctctgtgtcc ttttaaatca tattctctta gttcacaaag 1020
ttttattatg tcttgtattc ttccataata taaacttctt tctctataaa tataatttat 1080
tttgcttggt ctaccctttt tcctttcata tggttttaat tcaggtaaaa atccattttg 1140
tatttctctt aagtcataaa tatattcgta ctcatctaat atattgacta ctgtttttga 1200

```
tttagagttt atacttcctg gaactcttaa tattctcgtt gcatctaagg cttgtctatc   1260
tgctccaaag tattttaatt gattatataa atattcttga accgctttcc ataatggtaa   1320
tgctttacta ggtactgcat ttattatcca tattaaatac attcctcttc cactatctat   1380
tacatagttt ggtataggaa tactttgatt aaaataattc ttttctaagt ccattaatac   1440
ctggtcttta gttttgccag ttttataata atccaagtct ataaacagtg tatttaactc   1500
ttttatattt tctaatcgcc tacacggctt ataaaaggta tttagagtta tatagatatt   1560
ttcatcactc atatctaaat cttttaattc agcgtattta tagtgccatt ggctatatcc   1620
ttttttatct ataacgctcc tggttatcca ccctttactt ctactatgaa tattatctat   1680
atagttcttt ttattcagct ttaatgcgtt tctcacttat tcacctcccc ttctgtaaaa   1740
ctaagaaaat tatatcatat tttcaataat tattaactat tcttaaactc ttaataaaaa   1800
atagagtaag tccccaattg aaacttaatc tattttttat gttttaattt attattttta   1860
ttaaaatatt ttaaactaaa ttaaatgatt ctttttaatt ttttactatt tcattccata   1920
atatattact ataattattt acaaataata tttcttcatt tgtaatattt agatgattta   1980
ctaattttag tttttatata ttaaataatt aatgtataat ttatataaaa aatcaaagga   2040
gcttataaat tatgattatt tccaaagata ctaaagattt aatttttttc aattttaaca   2100
atacttttttg taatattatg tttaaattta attgtatttt tttcatataa taaagccgtt   2160
gaagtaaacc aatccatttt ccttatgatg ttattattaa atttaagttt tataataata   2220
tctttattat atttattgtt tttaaaaaaa ctagtgaaat ttctagtgaa atttccggct   2280
ttattaaact tatttttagg aattttattt tcattttcat ctttacagga tttgattata   2340
tctttaaata tgttttatca aatattatct ttttctaaat ttatatatat ttttattata   2400
tttattatta tatatatttt atttttaagt ttctttctaa cagctattaa aaagaaactt   2460
aaaaataaaa acacgtactc taaaccaata aataaaacta tttttattat tgctgccttg   2520
attggaatag tttttagtaa aattaatttc aatattccac aatattatat tataagctag   2580
cacgcctcga gtatattgat aaaaataata atagtgggta taattaagtt gttaggaggt   2640
tagttagagc ttattacgac ataacacagt tttagagcta gaaatagcaa gttaaaataa   2700
ggctagtccg ttatcaactt gaaaaagtgg caccgagtcg gtgctttttt tgaagcttgt   2760
cgactctaga ggatccccgg gtaccgagct cgaattcgta atcatggtca tagctgtttc   2820
ctgtgtgaaa ttgttatccg ctcacaattc cacacaacat acgagccgga agcataaagt   2880
gtaaagcctg gggtgcctaa tgagtgagct aactcacatt aattgcgttg cgctcactgc   2940
ccgctttcca gtcgggaaac ctgtcgtgcc agctgcatta atgaatcggc caacgcgcgg   3000
ggagaggcgg tttgcgtatt gggcgctctt ccgcttcctc gctcactgac tcgctgcgct   3060
cggtcgttcg gctgcggcga gcggtatcag ctcactcaaa ggcggtaata cggttatcca   3120
cagaatcagg ggataacgca ggaaagaaca tgtgagcaaa aggccagcaa aaggccagga   3180
accgtaaaaa ggccgcgttg ctggcgtttt tccataggct ccgcccccct gacgagcatc   3240
acaaaaatcg acgctcaagt cagaggtggc gaaacccgac aggactataa agataccagg   3300
cgtttccccc tggaagctcc ctcgtgcgct ctcctgttcc gaccctgccg cttaccggat   3360
acctgtccgc ctttctccct tcgggaagcg tggcgctttc tcatagctca cgctgtaggt   3420
atctcagttc ggtgtaggtc gttcgctcca agctgggctg tgtgcacgaa ccccccgttc   3480
agcccgaccg ctgcgcctta tccggtaact atcgtcttga gtccaacccg gtaagacacg   3540
acttatcgcc actggcagca gccactggta acaggattag cagagcgagg tatgtaggcg   3600
```

gtgctacaga gttcttgaag tggtggccta actacggcta cactagaaga acagtatttg 3660
gtatctgcgc tctgctgaag ccagttacct tcggaaaaag agttggtagc tcttgatccg 3720
gcaaacaaac caccgctggt agcggtggtt tttttgtttg caagcagcag attacgcgca 3780
gaaaaaaagg atctcaagaa gatcctttga tcttttctac ggggtctgac gctcagtgga 3840
acgaaaactc acgttaaggg attttggtca tgagattatc aaaaaggatc ttcacctaga 3900
tccttttaaa ttaaaaatga agttttaaat caatctaaag tatatatgag taaacttggt 3960
ctgacagtta ccaaagctag cttaatacta gtatatactt aatgtgataa gtgtctgaca 4020
gctgaccggt ctaaagaggt ccctagcgcc tacggggaat ttgtatcgat aaggggtaca 4080
aattcccact aagcgctcgg ccggggatcg atccccgggt acgtacccgg cagtttttct 4140
ttttcggcaa gtgttcaaga agttattaag tcgggagtgc agtcgaagtg ggcaagttga 4200
aaaattcaca aaaatgtggt ataatatctt tgttcattag agcgataaac ttgaatttga 4260
gagggaactt agatggtatt tgaaaaaatt gataaaaata gttggaacag aaaagagtat 4320
tttgaccact actttgcaag tgtaccttgt acctacagca tgaccgttaa agtggatatc 4380
acacaaataa aggaaaaggg aatgaaacta tatcctgcaa tgctttatta tattgcaatg 4440
attgtaaacc gccattcaga gtttaggacg gcaatcaatc aagatggtga attggggata 4500
tatgatgaga tgataccaag ctatacaata tttcacaatg atactgaaac attttccagc 4560
ctttggactg agtgtaagtc tgactttaaa tcatttttag cagattatga aagtgatacg 4620
caacggtatg gaaacaatca tagaatggaa ggaaagccaa atgctccgga aaacattttt 4680
aatgtatcta tgataccgtg gtcaaccttc gatggcttta atctgaattt gcagaaagga 4740
tatgattatt tgattcctat ttttactatg ggaaatatt ataaagaaga taacaaaatt 4800
atacttcctt tggcaattca agttcatcac gcagtatgtg acggatttca catttgccgt 4860
tttgtaaacg aattgcagga attgataaat agttaacttc aggtttgtct gtaactaaaa 4920
actagtattt aacctagg 4938

<210> SEQ ID NO 106
<211> LENGTH: 4790
<212> TYPE: DNA
<213> ORGANISM: Artificial Sequence
<220> FEATURE:
<223> OTHER INFORMATION: pEC750C

<400> SEQUENCE: 106
atcaaaaaaa tttccaataa tcccactcta agccacaaac acgccctata aaatcccgct 60
ttaatcccac tttgagacac atgtaatatt actttacgcc ctagtatagt gataattttt 120
tacattcaat gccacgcaaa aaaataaagg ggcactataa taaaagttcc ttcggaacta 180
actaaagtaa aaaattatct ttacaacctc cccaaaaaaa agaacaggta caaagtaccc 240
tataatacaa gcgtaaaaaa aatgagggta aaaataaaaa aataaaaaaa taaaaaaata 300
aaaaaataaa aaaataaaaa aataaaaaaa tataaaaata aaaaaatata aaaataaaaa 360
aatataaaaa taaaaaaata aaaaaatata aaaataaaaa aataaaaaaa tataaaaata 420
ttttttattt aaagtttgaa aaaaattttt ttatattata taatctttga agaaaagaat 480
ataaaaaatg agcctttata aaagcccatt ttttttcata tacgtaatat gacgttctaa 540
tgtttttatt ggtacttcta acattagagt aatttcttta tttttaaagc ctttttcttt 600
aagggctttt attttttttc ttaatacatt taattcctct ttttttgttg cttttccttt 660

```
agcttttaat tgctcttgat aatttttttt acctctaata ttttctcttc tcttatattc    720
ctttttagaa attattattg tcatatattt ttgttcttct tctgtaattt ctaataactc    780
tataagagtt tcattcttat acttatattg cttattttta tctaaataac atctttcagc    840
acttctagtt gctcttataa cttctctttc acttaaatgt tgtctaaaca tactattaag    900
ttctaaaaca tcatttaatg ccttctcaat gtcttctgta aagctacaaa gataatatct    960
atataaaaat aatataagct ctctgtgtcc ttttaaatca tattctctta gttcacaaag   1020
ttttattatg tcttgtattc ttccataata taaacttctt tctctataaa tataatttat   1080
tttgcttggt ctaccctttt tcctttcata tggttttaat tcaggtaaaa atccattttg   1140
tatttctctt aagtcataaa tatattcgta ctcatctaat atattgacta ctgtttttga   1200
tttagagttt atacttcctg gaactcttaa tattctcgtt gcatctaagg cttgtctatc   1260
tgctccaaag tattttaatt gattatataa atattcttga accgctttcc ataatggtaa   1320
tgctttacta ggtactgcat ttattatcca tattaaatac attcctcttc cactatctat   1380
tacatagttt ggtataggaa tactttgatt aaaataattc ttttctaagt ccattaatac   1440
ctggtcttta gttttgccag ttttataata atccaagtct ataaacagtg tatttaactc   1500
ttttatattt tctaatcgcc tacacggctt ataaaaggta tttagagtta tatagatatt   1560
ttcatcactc atatctaaat cttttaattc agcgtattta tagtgccatt ggctatatcc   1620
tttttatctt ataacgctcc tggttatcca ccctttactt ctactatgaa tattatctat   1680
atagttcttt ttattcagct ttaatgcgtt tctcacttat tcacctcccc ttctgtaaaa   1740
ctaagaaaat tatatcatat tttcaataat tattaactat tcttaaactc ttaataaaaa   1800
atagagtaag tccccaattg aaacttaatc tattttttat gttttaattt attattttta   1860
ttaaaatatt ttaaactaaa ttaaatgatt ctttttaatt ttttactatt tcattccata   1920
atatattact ataattattt acaaataata tttcttcatt tgtaatattt agatgattta   1980
ctaattttag tttttatata ttaaataatt aatgtataat ttatataaaa aatcaaagga   2040
gcttataaat tatgattatt tccaaagata ctaaagattt aatttttttc aattttaaca   2100
atactttttg taatattatg tttaaattta attgtatttt tttcatataa taaagccgtt   2160
gaagtaaacc aatccatttt ccttatgatg ttattattaa atttaagttt tataataata   2220
tctttattat atttattgtt tttaaaaaaa ctagtgaaat ttctagtgaa atttccggct   2280
ttattaaact tatttttagg aattttattt tcattttcat ctttacagga tttgattata   2340
tctttaaata tgttttatca aatattatct ttttctaaat ttatatatat ttttattata   2400
tttattatta tatatatttt atttttaagt ttctttctaa cagctattaa aaagaaactt   2460
aaaaataaaa acacgtactc taaaccaata aataaaacta tttttattat tgctgccttg   2520
attggaatag tttttagtaa aattaatttc aatattccac aatattatat tataagctag   2580
cacgcctcga gatctccatg gacgcgtgac gtcgactcta gaggatcccc gggtaccgag   2640
ctcgaattcg taatcatggt catagctgtt tcctgtgtga aattgttatc cgctcacaat   2700
tccacacaac atacgagccg gaagcataaa gtgtaaagcc tggggtgcct aatgagtgag   2760
ctaactcaca ttaattgcgt tgcgctcact gcccgctttc cagtcgggaa acctgtcgtg   2820
ccagctgcat taatgaatcg gccaacgcgc ggggagaggc ggtttgcgta ttgggcgctc   2880
ttccgcttcc tcgctcactg actcgctgcg ctcggtcgtt cggctgcggc gagcggtatc   2940
agctcactca aaggcggtaa tacggttatc cacagaatca ggggataacg caggaaagaa   3000
catgtgagca aaaggccagc aaaaggccag gaaccgtaaa aaggccgcgt tgctggcgtt   3060
```

tttccatagg ctccgccccc ctgacgagca tcacaaaaat cgacgctcaa gtcagaggtg 3120
gcgaaacccg acaggactat aaagatacca ggcgtttccc cctggaagct ccctcgtgcg 3180
ctctcctgtt ccgaccctgc cgcttaccgg atacctgtcc gcctttctcc cttcgggaag 3240
cgtggcgctt tctcatagct cacgctgtag gtatctcagt tcggtgtagg tcgttcgctc 3300
caagctgggc tgtgtgcacg aaccccccgt tcagcccgac cgctgcgcct tatccggtaa 3360
ctatcgtctt gagtccaacc cggtaagaca cgacttatcg ccactggcag cagccactgg 3420
taacaggatt agcagagcga ggtatgtagg cggtgctaca gagttcttga agtggtggcc 3480
taactacggc tacactagaa gaacagtatt tggtatctgc gctctgctga agccagttac 3540
cttcggaaaa agagttggta gctcttgatc cggcaaacaa accaccgctg gtagcggtgg 3600
tttttttgtt tgcaagcagc agattacgcg cagaaaaaaa ggatctcaag aagatccttt 3660
gatcttttct acggggtctg acgctcagtg gaacgaaaac tcacgttaag ggattttggt 3720
catgagatta tcaaaaagga tcttcaccta gatcctttta aattaaaaat gaagttttaa 3780
atcaatctaa agtatatatg agtaaacttg gtctgacagt taccaaagct agcttaatac 3840
tagtatatac ttaatgtgat aagtgtctga cagctgaccg gtctaaagag gtccctagcg 3900
cctacgggga atttgtatcg ataaggggta caaattccca ctaagcgctc ggccggggat 3960
cgatccccgg gtacgtaccc ggcagttttt ctttttcggc aagtgttcaa gaagttatta 4020
agtcgggagt gcagtcgaag tgggcaagtt gaaaaattca caaaaatgtg gtataatatc 4080
tttgttcatt agagcgataa acttgaattt gagagggaac ttagatggta tttgaaaaaa 4140
ttgataaaaa tagttggaac agaaaagagt attttgacca ctactttgca agtgtacctt 4200
gtacctacag catgaccgtt aaagtggata tcacacaaat aaaggaaaag ggaatgaaac 4260
tatatcctgc aatgctttat tatattgcaa tgattgtaaa ccgccattca gagtttagga 4320
cggcaatcaa tcaagatggt gaattgggga tatatgatga gatgatacca agctatacaa 4380
tatttcacaa tgatactgaa acattttcca gcctttggac tgagtgtaag tctgacttta 4440
aatcattttt agcagattat gaaagtgata cgcaacggta tggaaacaat catagaatgg 4500
aaggaaagcc aaatgctccg gaaaacattt ttaatgtatc tatgataccg tggtcaacct 4560
tcgatggctt taatctgaat ttgcagaaag gatatgatta tttgattcct atttttacta 4620
tggggaaata ttataaagaa gataacaaaa ttatacttcc tttggcaatt caagttcatc 4680
acgcagtatg tgacggattt cacatttgcc gttttgtaaa cgaattgcag gaattgataa 4740
atagttaact tcaggtttgt ctgtaactaa aaactagtat ttaacctagg 4790

<210> SEQ ID NO 107
<211> LENGTH: 35
<212> TYPE: DNA
<213> ORGANISM: Artificial Sequence
<220> FEATURE:
<223> OTHER INFORMATION: Primer

<400> SEQUENCE: 107
acttgggtcg accacgataa aacaaggttt taagg 35

<210> SEQ ID NO 108
<211> LENGTH: 42
<212> TYPE: DNA
<213> ORGANISM: Artificial Sequence
<220> FEATURE:
<223> OTHER INFORMATION: Primer

<400> SEQUENCE: 108
taccagggat ccgtattaat gtaactatga tatcaattct tg 42

<210> SEQ ID NO 109
<211> LENGTH: 46
<212> TYPE: DNA
<213> ORGANISM: Artificial Sequence
<220> FEATURE:
<223> OTHER INFORMATION: Primer

<400> SEQUENCE: 109
atgcatggtc ccaatgaata ggtttacact tactttagtt ttatgg 46

<210> SEQ ID NO 110
<211> LENGTH: 39
<212> TYPE: DNA
<213> ORGANISM: Artificial Sequence
<220> FEATURE:
<223> OTHER INFORMATION: Primer

<400> SEQUENCE: 110
atgcgagtta acaacttcta aaatctgatt accaattag 39

<210> SEQ ID NO 111
<211> LENGTH: 47
<212> TYPE: DNA
<213> ORGANISM: Artificial Sequence
<220> FEATURE:
<223> OTHER INFORMATION: Primer

<400> SEQUENCE: 111
atgcatggat cccaatgaat aggtttacac ttactttagt tttatgg 47

<210> SEQ ID NO 112
<211> LENGTH: 39
<212> TYPE: DNA
<213> ORGANISM: Artificial Sequence
<220> FEATURE:
<223> OTHER INFORMATION: Primer

<400> SEQUENCE: 112
atgcgagagc tcaacttcta aaatctgatt accaattag 39

<210> SEQ ID NO 113
<211> LENGTH: 32
<212> TYPE: DNA
<213> ORGANISM: Artificial Sequence
<220> FEATURE:
<223> OTHER INFORMATION: Primer

<400> SEQUENCE: 113
atgcatggat ccgtctgaca gttaccaggt cc 32

<210> SEQ ID NO 114
<211> LENGTH: 39
<212> TYPE: DNA
<213> ORGANISM: Artificial Sequence
<220> FEATURE:
<223> OTHER INFORMATION: Primer

<400> SEQUENCE: 114
atgcgagagc tccaattgtt caaaaaaata atggcggag 39

<210> SEQ ID NO 115
<211> LENGTH: 32

<212> TYPE: DNA
<213> ORGANISM: Artificial Sequence
<220> FEATURE:
<223> OTHER INFORMATION: Primer

<400> SEQUENCE: 115
atgcatggat cccggcagtt tttctttttc gg 32

<210> SEQ ID NO 116
<211> LENGTH: 40
<212> TYPE: DNA
<213> ORGANISM: Artificial Sequence
<220> FEATURE:
<223> OTHER INFORMATION: Primer

<400> SEQUENCE: 116
atgcgagagc tcggttaaat actagttttt agttacagac 40

<210> SEQ ID NO 117
<211> LENGTH: 2686
<212> TYPE: DNA
<213> ORGANISM: Artificial Sequence
<220> FEATURE:
<223> OTHER INFORMATION: pUC19

<400> SEQUENCE: 117
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgc 240
atgcctgcag gtcgactcta gaggatcccc gggtaccgag ctcgaattca ctggccgtcg 300
ttttacaacg tcgtgactgg gaaaaccctg gcgttaccca acttaatcgc cttgcagcac 360 atccccctttt cgccagctgg cgtaatagcg aagaggcccg caccgatcgc ccttcccaac 420
agttgcgcag cctgaatggc gaatggcgcc tgatgcggta ttttctcctt acgcatctgt 480
gcggtatttc acaccgcata tggtgcactc tcagtacaat ctgctctgat gccgcatagt 540
taagccagcc ccgacacccg ccaacacccg ctgacgcgcc ctgacgggct tgtctgctcc 600
cggcatccgc ttacagacaa gctgtgaccg tctccgggag ctgcatgtgt cagaggtttt 660
caccgtcatc accgaaacgc gcgagacgaa agggcctcgt gatacgccta tttttatagg 720
ttaatgtcat gataataatg gtttcttaga cgtcaggtgg cacttttcgg ggaaatgtgc 780
gcggaacccc tatttgttta tttttctaaa tacattcaaa tatgtatccg ctcatgagac 840
aataaccctg ataaatgctt caataatatt gaaaaaggaa gagtatgagt attcaacatt 900
tccgtgtcgc ccttattccc ttttttgcgg cattttgcct tcctgttttt gctcacccag 960
aaacgctggt gaaagtaaaa gatgctgaag atcagttggg tgcacgagtg ggttacatcg 1020
aactggatct caacagcggt aagatccttg agagttttcg ccccgaagaa cgttttccaa 1080
tgatgagcac ttttaaagtt ctgctatgtg gcgcggtatt atcccgtatt gacgccgggc 1140
aagagcaact cggtcgccgc atacactatt ctcagaatga cttggttgag tactcaccag 1200
tcacagaaaa gcatcttacg gatggcatga cagtaagaga attatgcagt gctgccataa 1260
ccatgagtga taacactgcg gccaacttac ttctgacaac gatcggagga ccgaaggagc 1320
taaccgcttt tttgcacaac atgggggatc atgtaactcg ccttgatcgt tgggaaccgg 1380
agctgaatga agccatacca aacgacgagc gtgacaccac gatgcctgta gcaatggcaa 1440
caacgttgcg caaactatta actggcgaac tacttactct agcttcccgg caacaattaa 1500
tagactggat ggaggcggat aaagttgcag gaccacttct gcgctcggcc cttccggctg 1560
gctggtttat tgctgataaa tctggagccg gtgagcgtgg gtctcgcggt atcattgcag 1620
cactggggcc agatggtaag ccctcccgta tcgtagttat ctacacgacg gggagtcagg 1680
caactatgga tgaacgaaat agacagatcg ctgagatagg tgcctcactg attaagcatt 1740
ggtaactgtc agaccaagtt tactcatata tactttagat tgatttaaaa cttcattttt 1800
aatttaaaag gatctaggtg aagatccttt ttgataatct catgaccaaa atcccttaac 1860
gtgagttttc gttccactga gcgtcagacc ccgtagaaaa gatcaaagga tcttcttgag 1920
atcctttttt tctgcgcgta atctgctgct tgcaaacaaa aaaaccaccg ctaccagcgg 1980
tggtttgttt gccggatcaa gagctaccaa ctctttttcc gaaggtaact ggcttcagca 2040
gagcgcagat accaaatact gttcttctag tgtagccgta gttaggccac cacttcaaga 2100
actctgtagc accgcctaca tacctcgctc tgctaatcct gttaccagtg gctgctgcca 2160
gtggcgataa gtcgtgtctt accgggttgg actcaagacg atagttaccg gataaggcgc 2220
agcggtcggg ctgaacgggg ggttcgtgca cacagcccag cttggagcga acgacctaca 2280
ccgaactgag atacctacag cgtgagctat gagaaagcgc cacgcttccc gaagggagaa 2340
aggcggacag gtatccggta agcggcaggg tcggaacagg agagcgcacg agggagcttc 2400 caggggggaaa cgcctggtat ctttatagtc ctgtcgggtt tcgccacctc tgacttgagc 2460
gtcgattttt gtgatgctcg tcaggggggc ggagcctatg gaaaaacgcc agcaacgcgg 2520
cctttttacg gttcctggcc ttttgctggc cttttgctca catgttcttt cctgcgttat 2580
cccctgattc tgtggataac cgtattaccg cctttgagtg agctgatacc gctcgccgca 2640
gccgaacgac cgagcgcagc gagtcagtga gcgaggaagc ggaaga 2686

<210> SEQ ID NO 118
<211> LENGTH: 4282
<212> TYPE: DNA
<213> ORGANISM: Artificial Sequence
<220> FEATURE:
<223> OTHER INFORMATION: pNF2

<400> SEQUENCE: 118
ctggagagga ttgtccttat acttatcata agcatgaagg acttgttatt cctagataga 60
gaattaatta tgttaaagag atataataaa ctcattataa ttataatttt tagtataatt 120
attattgcaa ttttttcgta taaatatcta ataatgccaa aagagcatag aatagaaatt 180
tcaacattat caaacataga agtttttaaa tttaatagtt tttcaaagtt tagtaacgaa 240
aaaatgtata ctattaatga tagtgataag ttaataaaat tcaaaacact atttaataat 300
ttagataaat caaaagatat aaaaaagatt agtattccgg aaagtgaaaa tttaaatgca 360
tttaaatttt ctgcacatat aaaacttaac tttaactatg ttaataaaga tagccaaata 420
actgaaggtg cttttcttat gtatattttg gtagacaatt tagaagggaa gtcatatatg 480 actttttttag gacaagattc aagctatata ttagatagta atgaaactaa cattttaaga 540
gaaatattta tgaattcaga gattaattaa tttatgaatt cataaatatt atctaagcac 600
gataaaacaa ggttttaagg ataagaaaag tcatgagatt tatagtaaat cttgtgactt 660
tttttattga atagtagaga gagttcggaa gtataacacg ctatattctt gatattttta 720
gaatagcaag cattggattt gtcctgacac tttcccaaaa attaaggagt tattccttaa 780
accaaaaaga ttaatgtggg aacaaattta gtgtatccat ttttgaaggg cgcacttata 840

```
caccaccaaa atggtgtgtg cgaaatcttt aaaaaagatt tatcaaaaag cttttttaaa    900
gctgggacat ttagaaaatc aataatgttt tttgcccaat acgctagtct taaaatctgc    960
aaggttgata actatttagt cccaggtatt agaatggggc atatatatac aaagtatata   1020
tatgcgtaaa tatatgtggg actgtgggaa caaaattgcg tgctaaaatt gtattgaaaa   1080
ggtaatgaaa aggtcatgct ttggtattgc taacgtatag aaaaggtaat gaaaagctca   1140
tggttctata aaaaagatgt acccacgaaa ataataggct ttgcctattt ccccatgtaa   1200
tatgggggca gttttctctt atgctctttc ttaacatatt gaataaatac aaaatgcagc   1260
tttgtgggaa taaaaatatt tttgttttta ttcttatagt tagacaaaat tttaatcttt   1320
tttgtgctat aacaagatta aaatttgtgg gaacattaag aaatattgtt gtcacaaata   1380
aaaaggagag tgggaacaat tgctataaaa aacgcagaaa ttaagattag agttacaaaa   1440
gagcaaaaag aattatttaa gaaaattgca aaagctgaaa atatgagtat gagtgaattt   1500
attattgtga ccacagaata tttagccaga aaaaaagatg aaaatatgaa atcaaaagac   1560
atgatcgaga gaagagctgc gaagactgaa gaaaaaatta tgaagctaaa aaagaaacta   1620
aataaaaaca ggtaatatag attacagttt taagcttgtt ttccctatag actagagtaa   1680
atatataaat atacctgtca agggcttata agccccttta gggggtgcgt agcacccttg   1740
acaggtatat ttatatattt tagggtgcca ttaagggaaa caagctttaa aatgccttta   1800
aaggcatttt aaaataaata aaaaaaagat ggtttttacc atctttttta actcccgaaa   1860
gggagttctt tcttttcttg atactatacg taactatttc gatttgccct gaacctaatc   1920
aaagctagat aaattcagta ttagggcata aaaaaacttg ctttttcggg tggaaatctg   1980
tataatttaa attgcttaga taaaaattac caattccata cgaaaggagc aagttttaca   2040
taaggttaaa gccttatgtg aattctcatt taattacatg aataataata acacagaaag   2100
tgaagaatta aaagagcaaa gtcaactatt gcttgacaaa tgcacaaaaa agaaaaagaa   2160
aaatcctaaa tttagtagtt atatagaacc attagtaagc aagaaattat ctgaaagaat   2220
aaaggaatgt ggtgactttt tgcagatgtt atctgattta aaccttgaaa attcgaaact   2280
gcatagagca agtttttgtg gtaacagatt ttgtcctatg tgtagctggc gtattgcttg   2340
taaggatagt ttggaaatat ctattctcat ggagcattta cgcaaagagg aaagcaaaga   2400
atttatcttt ttgaccttaa caactccaaa tgtgaaaggt gcggaccttg ataattccat   2460
aaaagcatac aataaagcat ttaaaaagtt aatggaacgc aaagaggtca agagcatagt   2520
aaaaggctac ataagaaagc tagaagtaac ctataatttg gacaagagtt ccaaatcata   2580
taatacttat cacccacatt tccatgtggt actagcagtc aatagaagtt actttaaaaa   2640
gcaaaatcta tatataaacc atcatagatg gcttagtttg tggcaagagt caactggtga   2700
ttattcgata actcaagttg atgtaagaaa ggctaaaatt aacgattata aagaggttta   2760
tgagcttgct aagtattcgg ctaaggattc cgactattta atcaatagag aagtgtttac   2820
ggtattctac aaatctttaa agggtaaaca ggtacttgta tttagtggat tatttaaaga   2880
cgctcataaa atgtataaga atggagagct agatctgtat aagaagttgg atactatcga   2940
atatgcttat atggtaagtt ataactggct taaaaagaag tatgatactt caaatattag   3000
agaattaact gaggaagaaa agcagaaatt caataaaaat ttaatcgaag atgtggatat   3060
tgagtaggtg ggattatatc tcaccttttt tattgtcttt tcatgttgaa attttgacgc   3120
ttaatgcatg aagtattgac aagtttaaaa attacggttt ttaatcctta gttgattagc   3180
```

```
aggattatgg ccggaatgct ccgtccagtc ctgttaagga attaaaattc cctaaaaccc   3240
ttggctatga tttatagcga gaatcgtcaa ttaaaaattt aataggtgct atgaaagtcg   3300
attaataatt aattttaaaa tgcaatatga aacataatta caagaatttg acttttaata   3360
caagaattga tatcatagtt acattaatac atttattttg aagggggaaa atgttttatg   3420
aaaagactac ttaaactacc tattttatca ttattaggat tatttttaat tggatcaact   3480
ccaacattag ctttaactaa agataataat caaaatttag atactatgaa agtaaactta   3540
tatactgaaa cagtagatgt gtttgataaa gatgcattta aacaaacatt tactaataaa   3600
gatataaaat ttctagagga ttctttgaat gcaaaaataa attattcagg taaatctgtt   3660
acagtaacaa tgaaaaacaa aattaagcca tctactaaac aagggcttgt tttatatgta   3720
aatggaaaat cagttaatgt tgattcagat ggcagtataa aagtacctaa agatactaag   3780
aaaatttcta aattaaataa agataaatca atgatggatg gatcaatgat ggataaatca   3840
ttacatgatg agaattgtgt agtatcagat agtttttata atgctgatgt taataatata   3900
aattcaaaag aagcagaagc tgtatttaaa gtaagttctg gtgaattatt agctaaaatg   3960
gatgaaaaag aagatgatta catacaaaag aactcatcta aaattctagc agctgcttat   4020
cataagggat atggggacaa gtactatgaa ggagattggg ttcattgcaa taggtttaat   4080
ggtcaactta cagatgatgt tcactataat tggagaactg gaagtgtttc agaaaaagca   4140
gctgcaatga gaaattttta tggcagtgat tgtcatatag cattagttca agcaggtagt   4200
ggatgtacaa gtataggttc atgcgaatgc aatacagatc aaatagctgc gtattgttca   4260
ggtttcgtaa aagataaaaa ta                                            4282
```

```
<210> SEQ ID NO 119
<211> LENGTH: 5473
<212> TYPE: DNA
<213> ORGANISM: Artificial Sequence
<220> FEATURE:
<223> OTHER INFORMATION: pNF3

<400> SEQUENCE: 119
```

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg ccaagcttgc    240
atgcctgcag gtcgaccacg ataaaacaag gttttaagga taagaaaagt catgagattt    300
atagtaaatc ttgtgacttt ttttattgaa tagtagagag agttcggaag tataacacgc    360
tatattcttg atatttttag aatagcaagc attggatttg tcctgacact ttcccaaaaa    420
ttaaggagtt attccttaaa ccaaaaagat taatgtggga acaaatttag tgtatccatt    480
tttgaagggc gcacttatac accaccaaaa tggtgtgtgc gaaatcttta aaaaagattt    540
atcaaaaagc ttttttaaag ctgggacatt tagaaaatca ataatgtttt ttgcccaata    600
cgctagtctt aaaatctgca aggttgataa ctatttagtc ccaggtatta gaatggggca    660
tatatataca aagtatatat atgcgtaaat atatgtggga ctgtgggaac aaaattgcgt    720
gctaaaattg tattgaaaag gtaatgaaaa ggtcatgctt tggtattgct aacgtataga    780
aaaggtaatg aaaagctcat ggttctataa aaaagatgta cccacgaaaa taataggctt    840
tgcctatttc cccatgtaat atgggggcag ttttctctta tgctctttct taacatattg    900
aataaataca aaatgcagct ttgtgggaat aaaaatattt ttgtttttat tcttatagtt    960
```

```
agacaaaatt ttaatctttt ttgtgctata acaagattaa aatttgtggg aacattaaga   1020
aatattgttg tcacaaataa aaaggagagt gggaacaatt gctataaaaa acgcagaaat   1080
taagattaga gttacaaaag agcaaaaaga attatttaag aaaattgcaa aagctgaaaa   1140
tatgagtatg agtgaattta ttattgtgac cacagaatat ttagccagaa aaaaagatga   1200
aaatatgaaa tcaaaagaca tgatcgagag aagagctgcg aagactgaag aaaaaattat   1260
gaagctaaaa aagaaactaa ataaaaacag gtaatataga ttacagtttt aagcttgttt   1320
tccctataga ctagagtaaa tatataaata tacctgtcaa gggcttataa gcccctttag   1380
ggggtgcgta gcacccttga caggtatatt tatatatttt agggtgccat taagggaaac   1440
aagctttaaa atgcctttaa aggcatttta aaataaataa aaaaaagatg gtttttacca   1500
tctttttaa ctcccgaaag ggagttcttt cttttcttga tactatacgt aactatttcg   1560
atttgccctg aacctaatca aagctagata aattcagtat tagggcataa aaaaacttgc   1620
tttttcgggt ggaaatctgt ataatttaaa ttgcttagat aaaaattacc aattccatac   1680
gaaaggagca agttttacat aaggttaaag ccttatgtga attctcattt aattacatga   1740
ataataataa cacagaaagt gaagaattaa aagagcaaag tcaactattg cttgacaaat   1800
gcacaaaaaa gaaaaagaaa aatcctaaat ttagtagtta tatagaacca ttagtaagca   1860
agaaattatc tgaaagaata aaggaatgtg gtgacttttt gcagatgtta tctgatttaa   1920
accttgaaaa ttcgaaactg catagagcaa gtttttgtgg taacagattt tgtcctatgt   1980
gtagctggcg tattgcttgt aaggatagtt tggaaatatc tattctcatg gagcatttac   2040
gcaaagagga aagcaaagaa tttatctttt tgaccttaac aactccaaat gtgaaaggtg   2100
cggaccttga taattccata aaagcataca ataaagcatt taaaaagtta atggaacgca   2160
aagaggtcaa gagcatagta aaaggctaca taagaaagct agaagtaacc tataatttgg   2220
acaagagttc caaatcatat aatacttatc acccacattt ccatgtggta ctagcagtca   2280
atagaagtta ctttaaaaag caaaatctat atataaacca tcatagatgg cttagtttgt   2340
ggcaagagtc aactggtgat tattcgataa ctcaagttga tgtaagaaag gctaaaatta   2400
acgattataa agaggtttat gagcttgcta agtattcggc taaggattcc gactatttaa   2460
tcaatagaga agtgtttacg gtattctaca aatctttaaa gggtaaacag gtacttgtat   2520
ttagtggatt atttaaagac gctcataaaa tgtataagaa tggagagcta gatctgtata   2580
agaagttgga tactatcgaa tatgcttata tggtaagtta taactggctt aaaaagaagt   2640
atgatacttc aaatattaga gaattaactg aggaagaaaa gcagaaattc aataaaaatt   2700
taatcgaaga tgtggatatt gagtaggtgg gattatatct caccttttt attgtctttt   2760
catgttgaaa ttttgacgct taatgcatga agtattgaca agtttaaaaa ttacggtttt   2820
taatccttag ttgattagca ggattatggc cggaatgctc cgtccagtcc tgttaaggaa   2880
ttaaaattcc ctaaaaccct tggctatgat ttatagcgag aatcgtcaat taaaaattta   2940
ataggtgcta tgaaagtcga ttaataatta attttaaaat gcaatatgaa acataattac   3000
aagaatttga cttttaatac aagaattgat atcatagtta cattaatacg gatccccggg   3060
taccgagctc gaattcactg gccgtcgttt tacaacgtcg tgactgggaa aaccctggcg   3120
ttacccaact taatcgcctt gcagcacatc ccccttttcgc cagctggcgt aatagcgaag   3180
aggcccgcac cgatcgccct tcccaacagt tgcgcagcct gaatggcgaa tggcgcctga   3240
tgcggtattt tctccttacg catctgtgcg gtatttcaca ccgcatatgg tgcactctca   3300
```

```
gtacaatctg ctctgatgcc gcatagttaa gccagccccg acacccgcca acacccgctg   3360
acgcgccctg acgggcttgt ctgctcccgg catccgctta cagacaagct gtgaccgtct   3420
ccgggagctg catgtgtcag aggttttcac cgtcatcacc gaaacgcgcg agacgaaagg   3480
gcctcgtgat acgcctattt ttataggtta atgtcatgat aataatggtt tcttagacgt   3540
caggtggcac ttttcgggga aatgtgcgcg gaacccctat ttgtttattt ttctaaatac   3600
attcaaatat gtatccgctc atgagacaat aaccctgata aatgcttcaa taatattgaa   3660
aaaggaagag tatgagtatt caacatttcc gtgtcgccct tattcccttt tttgcggcat   3720
tttgccttcc tgtttttgct cacccagaaa cgctggtgaa agtaaaagat gctgaagatc   3780
agttgggtgc acgagtgggt tacatcgaac tggatctcaa cagcggtaag atccttgaga   3840
gttttcgccc cgaagaacgt tttccaatga tgagcacttt taaagttctg ctatgtggcg   3900
cggtattatc ccgtattgac gccgggcaag agcaactcgg tcgccgcata cactattctc   3960
agaatgactt ggttgagtac tcaccagtca cagaaaagca tcttacggat ggcatgacag   4020
taagagaatt atgcagtgct gccataacca tgagtgataa cactgcggcc aacttacttc   4080
tgacaacgat cggaggaccg aaggagctaa ccgctttttt gcacaacatg ggggatcatg   4140
taactcgcct tgatcgttgg gaaccggagc tgaatgaagc cataccaaac gacgagcgtg   4200
acaccacgat gcctgtagca atggcaacaa cgttgcgcaa actattaact ggcgaactac   4260
ttactctagc ttcccggcaa caattaatag actggatgga ggcggataaa gttgcaggac   4320
cacttctgcg ctcggccctt ccggctggct ggtttattgc tgataaatct ggagccggtg   4380
agcgtgggtc tcgcggtatc attgcagcac tggggccaga tggtaagccc tcccgtatcg   4440
tagttatcta cacgacgggg agtcaggcaa ctatggatga acgaaataga cagatcgctg   4500
agataggtgc ctcactgatt aagcattggt aactgtcaga ccaagtttac tcatatatac   4560
tttagattga tttaaaactt catttttaat ttaaaaggat ctaggtgaag atcctttttg   4620
ataatctcat gaccaaaatc ccttaacgtg agttttcgtt ccactgagcg tcagaccccg   4680
tagaaaagat caaaggatct tcttgagatc cttttttttct gcgcgtaatc tgctgcttgc   4740
aaacaaaaaa accaccgcta ccagcggtgg tttgtttgcc ggatcaagag ctaccaactc   4800
tttttccgaa ggtaactggc ttcagcagag cgcagatacc aaatactgtt cttctagtgt   4860
agccgtagtt aggccaccac ttcaagaact ctgtagcacc gcctacatac ctcgctctgc   4920
taatcctgtt accagtggct gctgccagtg gcgataagtc gtgtcttacc gggttggact   4980
caagacgata gttaccggat aaggcgcagc ggtcgggctg aacggggggt tcgtgcacac   5040
agcccagctt ggagcgaacg acctacaccg aactgagata cctacagcgt gagctatgag   5100
aaagcgccac gcttcccgaa gggagaaagg cggacaggta tccggtaagc ggcagggtcg   5160
gaacaggaga gcgcacgagg gagcttccag ggggaaacgc ctggtatctt tatagtcctg   5220
tcgggtttcg ccacctctga cttgagcgtc gatttttgtg atgctcgtca ggggggcgga   5280
gcctatggaa aaacgccagc aacgcggcct ttttacggtt cctggccttt tgctggcctt   5340
ttgctcacat gttctttcct gcgttatccc ctgattctgt ggataaccgt attaccgcct   5400
ttgagtgagc tgataccgct cgccgcagcc gaacgaccga gcgcagcgag tcagtgagcg   5460
aggaagcgga aga                                                      5473
```

<210> SEQ ID NO 120
<211> LENGTH: 9128
<212> TYPE: DNA
<213> ORGANISM: Artificial Sequence
<220> FEATURE:
<223> OTHER INFORMATION: pMTL007S-E1

<400> SEQUENCE: 120

```
gatcgggccc cctgcagggt gtagtagcct gtgaaataag taaggaaaaa aaagaagtaa     60
gtgttatata tgatgattat tttgtagatg tagataggat aatagaatcc atagaaaata    120
taggttatac agttatataa aaattacttt aaaaattaat aaaaacatgg taaaatataa    180
atcgtataaa gttgtgtaat ttttaagctt gagctcataa caatttcaca caggaaacag    240
ctatgaccat gattacggat tcactggccg tcgttttaca acgtcgtgac tgggaaaacc    300
ctggcgttac ccaacttaat cgccttgcag cacatccccc tttcgccagc tggcgtaata    360
gcgaagaggc ccgcaccgat cgcccttccc aacagttgcg cagcctgaat ggcgaatggc    420
gctaataaag atcttgtaca atctgtagga gaacctatgg gaacgaaacg aaagcgatgc    480
cgagaatctg aatttaccaa gacttaacac taactgggga taccctaaac aagaatgcct    540
aatagaaagg aggaaaaagg ctatagcact agagcttgaa aatcttgcaa gggtacggag    600
tactcgtagt agtctgagaa gggtaacgcc ctttacatgg caaaggggta cagttattgt    660
gtactaaaat taaaaattga ttagggagga aaacctcaaa atgaaaccaa caatggcaat    720
tttagaaaga atcagtaaaa attcacaaga aaatatagac gaagttttta caagacttta    780
tcgttatctt ttacgtccag atatttatta cgtggcgacg cgtgcgactc atagaattat    840
ttcctcccgt taaataatag ataactatta aaaatagaca atacttgctc ataagtaacg    900
gtacttaaat tgtttacttt ggcgtgtttc attgcttgat gaaactgatt tttagtaaac    960
agttgacgat attctcgatt gacccatttt gaaacaaagt acgtatatag cttccaatat   1020
ttatctggaa catctgtggt atggcgggta agttttatta agacactgtt tacttttggt   1080
ttaggatgaa agcattccgc tggcagctta agcaattgct gaatcgagac ttgagtgtgc   1140
aagagcaacc ctagtgttcg gtgaatatcc aaggtacgct tgtagaatcc ttcttcaaca   1200
atcagataga tgtcagacgc atggctttca aaaaccactt ttttaataat ttgtgtgctt   1260
aaatggtaag gaatactccc aacaatttta tacctctgtt tgttagggaa ttgaaactgt   1320
agaatatctt ggtgaattaa agtgacacga gtattcagtt ttaatttttc tgacgataag   1380
ttgaatagat gactgtctaa ttcaatagac gttacctgtt tacttatttt agccagtttc   1440
gtcgttaaat gccctttacc tgttccaatt tcgtaaacgg tatcggtttc ttttaaattc   1500
aattgtttta ttatttggtt gagtactttt tcactcgtta aaaagttttg agaatatttt   1560
atatttttgt tcataccagc accagaagca ccagcatctc ttgggttaat tgaggcctga   1620
gtataaggtg acttatactt gtaatctatc taaacgggga acctctctag tagacaatcc   1680
cgtgctaaat tgtaggactg ccctttaata aatacttcta tatttaaaga ggtatttatg   1740
aaaagcggaa tttatcagat taaaaatact ttctctagag aaaatttcgt ctggattagt   1800
tacttatcgt gtaaaatctg ataaatggaa ttggttctac ataaatgcct aacgactatc   1860
cctttgggga gtagggtcaa gtgactcgaa acgatagaca acttgcttta acaagttgga   1920
gatatagtct gctctgcatg gtgacatgca gctggatata attccggggt aagattaacg   1980
accttatctg aacataatgc catatgaatc cctcctaatt tatacgtttt ctctaacaac   2040
ttaattatac ccactattat tatttttatc aatataacgc gttgggaaat ggcaatgata   2100
gcgaaacaac gtaaaactct tgttgtatgc tttcattgtc atcgtcacgt gattcataaa   2160
cacaagtgaa tgtcgacagt gaatttttac gaacgaacaa taacagagcc gtatactccg   2220
```

-continued agaggggtac gtacggttcc cgaagagggt ggtgcaaacc agtcacagta atgtgaacaa 2280
ggcggtacct ccctacttca ccatatcatt ttctgcagcc ccctagaaat aattttgttt 2340
aactttaaga aggagatata catatatggc tagatcgtcc attccgacag catcgccagt 2400
cactatggcg tgctgctagc gctatatgcg ttgatgcaat ttctatgcac tcgtagtagt 2460
ctgagaaggg taacgccctt tacatggcaa aggggtacag ttattgtgta ctaaaattaa 2520
aaattgatta gggaggaaaa cctcaaaatg aaaccaacaa tggcaatttt agaaagaatc 2580
agtaaaaatt cacaagaaaa tatagacgaa gtttttacaa gactttatcg ttatctttta 2640
cgtccagata tttattacgt ggcgtatcaa aatttatatt ccaataaagg agcttccaca 2700
aaaggaatat tagatgatac agcggatggc tttagtgaag aaaaaataaa aaagattatt 2760
caatctttaa aagacggaac ttactatcct caacctgtac gaagaatgta tattgcaaaa 2820
aagaattcta aaaagatgag acctttagga attccaactt tcacagataa attgatccaa 2880
gaagctgtga gaataattct tgaatctatc tatgaaccgg tattcgaaga tgtgtctcac 2940
ggttttagac ctcaacgaag ctgtcacaca gctttgaaaa caatcaaaag agagtttggc 3000
ggcgcaagat ggtttgtgga gggagatata aaaggctgct tcgataatat agaccacgtt 3060
acactcattg gactcatcaa tcttaaaatc aaagatatga aatgagccca attgatttat 3120
aaatttctaa aagcaggtta tctggaaaac tggcagtatc acaaaactta cagcggaaca 3180
cctcaaggtg gaattctatc tcctcttttg gccaacatct atcttcatga attggataag 3240
tttgttttac aactcaaaat gaagtttgac cgagaaagtc cagaaagaat aacacctgaa 3300
tatcgggagc tccacaatga gataaaaaga atttctcacc gtctcaagaa gttggagggt 3360
gaagaaaaag ctaaagttct tttagaatat caagaaaaac gtaaaagatt acccacactc 3420
ccctgtacct cacagacaaa taaagtattg aaatacgtcc ggtatgcgga cgacttcatt 3480
atctctgtta aaggaagcaa agaggactgt caatggataa aagaacaatt aaaacttttt 3540
attcataaca agctaaaaat ggaattgagt gaagaaaaaa cactcatcac acatagcagt 3600
caacccgctc gttttctggg atatgatata cgagtaagga gatctggaac gataaaacga 3660
tctggtaaag tcaaaaagag aacactcaat gggagtgtag aactccttat tcctcttcaa 3720
gacaaaattc gtcaatttat ttttgacaag aaaatagcta tccaaaagaa agatagctca 3780
tggtttccag ttcacaggaa atatcttatt cgttcaacag acttagaaat catcacaatt 3840
tataattctg aactccgcgg gatttgtaat tactacggtc tagcaagtaa ttttaaccag 3900
ctcaattatt ttgcttatct tatggaatac agctgtctaa aaacgatagc ctccaaacat 3960
aagggaacac tttcaaaaac catttccatg tttaaagatg gaagtggttc gtgggggatc 4020
ccgtatgaga taaagcaagg taagcagcgc cgttattttg caaattttag tgaatgtaaa 4080
tccccttatc aatttacgga tgagataagt caagctcctg tattgtatgg ctatgcccgg 4140
aatactcttg aaaacaggtt aaaagctaaa tgttgtgaat tatgtgggac gtctgatgaa 4200
aatacttcct atgaaattca ccatgtcaat aaggtcaaaa atcttaaagg caaagaaaaa 4260
tgggaaatgg caatgatagc gaaacaacgt aaaactcttg ttgtatgctt tcattgtcat 4320
cgtcacgtga ttcataaaca caagtgaatg tcgagcaccc gttctcggag cactgtccga 4380
ccgctttggc cgccgcccag tcctgctcgc ttcgctactt ggagccacta tcgactacgc 4440
gatcatggcg accacacccg tcctgtggat cgccaagccg ccgatggtag tgtggggtct 4500
ccccatgcga gagtagggaa ctgccaggca tcaaataaaa cgaaaggctc agtcgaaaga 4560
ctgggccttt cgttttatct gttgtttgtc ggtgaacgct ctcctgagta ggacaaatcc 4620

```
gccgggagcg gatttgaacg ttgcgaagca acggcccgga gggtggcggg caggacgccc   4680
gccataaact gccaggcatc aaattaagca gaaggccatc ctgacggatg gcctttttgc   4740
gtttctacaa actcttcctg tcgtcatatc tacaagccat ccccccacag atacgggcgc   4800
gccgccatta tttttttgaa caattgacaa ttcatttctt atttttttatt aagtgatagt   4860
caaaaggcat aacagtgctg aatagaaaga aatttacaga aaagaaaatt atagaattta   4920
gtatgattaa ttatactcat ttatgaatgt ttaattgaat acaaaaaaaa atacttgtta   4980
tgtattcaat tacgggttaa aatatagaca agttgaaaaa tttaataaaa aaataagtcc   5040
tcagctctta tatattaagc taccaactta gtatataagc caaaacttaa atgtgctacc   5100
aacacatcaa gccgttagag aactctatct atagcaatat ttcaaatgta ccgacataca   5160
agagaaacat taactatata tattcaattt atgagattat cttaacagat ataaatgtaa   5220
attgcaataa gtaagattta gaagtttata gcctttgtgt attggaagca gtacgcaaag   5280
gctttttttat ttgataaaaa ttagaagtat atttattttt tcataattaa tttatgaaaa   5340
tgaaaggggg tgagcaaagt gacagaggaa agcagtatct tatcaaataa caaggtatta   5400
gcaatatcat tattgacttt agcagtaaac attatgactt ttatagtgct tgtagctaag   5460
tagtacgaaa gggggagctt taaaaagctc cttggaatac atagaattca taaattaatt   5520
tatgaaaaga agggcgtata tgaaaacttg taaaaattgc aaagagttta ttaaagatac   5580
tgaaatatgc aaaatacatt cgttgatgat tcatgataaa acagtagcaa cctattgcag   5640
taaatacaat gagtcaagat gtttacataa agggaaagtc caatgtatta attgttcaaa   5700
gatgaaccga tatggatggt gtgccataaa aatgagatgt tttacagagg aagaacagaa   5760
aaaagaacgt acatgcatta aatattatgc aaggagcttt aaaaaagctc atgtaaagaa   5820
gagtaaaaag aaaaaataat ttatttatta atttaatatt gagagtgccg acacagtatg   5880
cactaaaaaa tatatctgtg gtgtagtgag ccgatacaaa aggatagtca ctcgcatttt   5940
cataatacat cttatgttat gattatgtgt cggtgggact tcacgacgaa aacccacaat   6000
aaaaaaagag ttcggggtag ggttaagcat agttgaggca actaaacaat caagctagga   6060
tatgcagtag cagaccgtaa ggtcgttgtt taggtgtgtt gtaatacata cgctattaag   6120
atgtaaaaat acggatacca atgaagggaa aagtataatt tttggatgta gtttgtttgt   6180
tcatctatgg gcaaactacg tccaaagccg tttccaaatc tgctaaaaag tatatccttt   6240
ctaaaatcaa agtcaagtat gaaatcataa ataaagttta attttgaagt tattatgata   6300
ttatgttttt ctattaaaat aaattaagta tatagaatag tttaataata gtatatactt   6360
aatgtgataa gtgtctgaca gtgtcacaga aaggatgatt gttatggatt ataagcggcc   6420
ggcccaatga ataggtttac acttacttta gttttatgga aatgaaagat catatcatat   6480
ataatctaga ataaaattaa ctaaaataat tattatctag ataaaaaatt tagaagccaa   6540
tgaaatctat aaataaacta aattaagttt atttaattaa caactatgga tataaaatag   6600
gtactaatca aaatagtgag gaggatatat ttgaatacat acgaacaaat taataaagtg   6660
aaaaaaatac ttcggaaaca tttaaaaaat aaccttattg gtacttacat gtttggatca   6720
ggagttgaga gtggactaaa accaaatagt gatcttgact ttttagtcgt cgtatctgaa   6780
ccattgacag atcaaagtaa agaaatactt atacaaaaaa ttagacctat ttcaaagaaa   6840
ataggagata aaagcaactt acgatatatt gaattaacaa ttattattca gcaagaaatg   6900
gtaccgtgga atcatcctcc caaacaagaa tttatttatg gagaatggtt acaagagctt   6960
```

```
tatgaacaag gatacattcc tcagaaggaa ttaaattcag atttaaccat aatgctttac   7020
caagcaaaac gaaaaaataa aagaatatac ggaaattatg acttagagga attactacct   7080
gatattccat tttctgatgt gagaagagcc attatggatt cgtcagagga attaatagat   7140
aattatcagg atgatgaaac caactctata ttaactttat gccgtatgat tttaactatg   7200
gacacgggta aaatcatacc aaaagatatt gcgggaaatg cagtggctga atcttctcca   7260
ttagaacata gggagagaat tttgttagca gttcgtagtt atcttggaga gaatattgaa   7320
tggactaatg aaaatgtaaa tttaactata aactatttaa ataacagatt aaaaaaatta   7380
taaaaaaatt gaaaaaatgg tggaaacact tttttcaatt tttttgtttt attatttaat   7440
atttgggaaa tattcattct aattggtaat cagattttag aagtttaaac tcctttttga   7500
taatctcatg accaaaatcc cttaacgtga gttttcgttc cactgagcgt cagaccccgt   7560
agaaaagatc aaaggatctt cttgagatcc tttttttctg cgcgtaatct gctgcttgca   7620
aacaaaaaaa ccaccgctac cagcggtggt ttgtttgccg gatcaagagc taccaactct   7680
ttttccgaag gtaactggct tcagcagagc gcagatacca aatactgttc ttctagtgta   7740
gccgtagtta ggccaccact tcaagaactc tgtagcaccg cctacatacc tcgctctgct   7800
aatcctgtta ccagtggctg ctgccagtgg cgataagtcg tgtcttaccg ggttggactc   7860
aagacgatag ttaccggata aggcgcagcg gtcgggctga acggggggtt cgtgcacaca   7920
gcccagcttg gagcgaacga cctacaccga actgagatac ctacagcgtg agctatgaga   7980
aagcgccacg cttcccgaag ggagaaaggc ggacaggtat ccggtaagcg gcagggtcgg   8040
aacaggagag cgcacgaggg agcttccagg gggaaacgcc tggtatcttt atagtcctgt   8100
cgggtttcgc cacctctgac ttgagcgtcg atttttgtga tgctcgtcag gggggcggag   8160
cctatggaaa aacgccagca acgcggcctt tttacggttc ctggcctttt gctggccttt   8220
tgctcacatg ttctttcctg cgttatcccc tgattctgtg gataaccgta ttaccgcctt   8280
tgagtgagct gataccgctc gccgcagccg aacgaccgag cgcagcgagt cagtgagcga   8340
ggaagcggaa gagcgcccaa tacgcagggc cccctgcttc ggggtcatta tagcgatttt   8400
ttcggtatat ccatcctttt tcgcacgata tacaggattt tgccaaaggg ttcgtgtaga   8460
ctttccttgg tgtatccaac ggcgtcagcc gggcaggata ggtgaagtag gcccacccgc   8520
gagcgggtgt tccttcttca ctgtccctta ttcgcacctg gcggtgctca acgggaatcc   8580
tgctctgcga ggctggccgg ctaccgccgg cgtaacagat gagggcaagc ggatggctga   8640
tgaaaccaag ccaaccagga agggcagccc acctatcaag gtgtactgcc ttccagacga   8700
acgaagagcg attgaggaaa aggcggcggc ggccggcatg agcctgtcgg cctacctgct   8760
ggccgtcggc cagggctaca aaatcacggg cgtcgtggac tatgagcacg tccgcgagct   8820
ggcccgcatc aatggcgacc tgggccgcct gggcggcctg ctgaaactct ggctcaccga   8880
cgacccgcgc acggcgcggt tcggtgatgc cacgatcctc gccctgctgg cgaagatcga   8940
agagaagcag gacgagcttg gcaaggtcat gatgggcgtg gtccgcccga gggcagagcc   9000
atgacttttt tagccgctaa aacggccggg gggtgcgcgt gattgccaag cacgtcccca   9060
tgcgctccat caagaagagc gacttcgcgg agctggtgaa gtacatcacc gacgagcaag   9120
gcaagacc                                                            9128
```

<210> SEQ ID NO 121
<211> LENGTH: 5002
<212> TYPE: DNA
<213> ORGANISM: Artificial Sequence
<220> FEATURE:
<223> OTHER INFORMATION: pEC751S

<400> SEQUENCE: 121

```
atcaaaaaaa tttccaataa tcccactcta agccacaaac acgccctata aaatcccgct     60
ttaatcccac tttgagacac atgtaatatt actttacgcc ctagtatagt gataattttt    120
tacattcaat gccacgcaaa aaaataaagg ggcactataa taaaagttcc ttcggaacta    180
actaaagtaa aaaattatct ttacaacctc cccaaaaaaa agaacaggta caaagtaccc    240
tataatacaa gcgtaaaaaa aatgagggta aaaataaaaa aataaaaaaa taaaaaaata    300
aaaaaataaa aaaataaaaa aataaaaaaa tataaaaata aaaaaatata aaaataaaaa    360
aatataaaaa taaaaaaata aaaaaatata aaaataaaaa aataaaaaaa tataaaaata    420
tttttattt aaagtttgaa aaaaattttt ttatattata taatctttga agaaaagaat    480
ataaaaaatg agcctttata aaagcccatt ttttttcata tacgtaatat gacgttctaa    540
tgtttttatt ggtacttcta acattagagt aatttcttta tttttaaagc ctttttcttt    600
aagggctttt attttttttc ttaatacatt taattcctct tttttgttg cttttccttt    660
agcttttaat tgctcttgat aatttttttt acctctaata ttttctcttc tcttatattc    720
ctttttagaa attattattg tcatatattt ttgttcttct tctgtaattt ctaataactc    780
tataagagtt tcattcttat acttatattg cttattttta tctaaataac atctttcagc    840
acttctagtt gctcttataa cttctctttc acttaaatgt tgtctaaaca tactattaag    900
ttctaaaaca tcatttaatg ccttctcaat gtcttctgta aagctacaaa gataatatct    960
atataaaaat aatataagct ctctgtgtcc ttttaaatca tattctctta gttcacaaag   1020
ttttattatg tcttgtattc ttccataata taaacttctt tctctataaa tataatttat   1080
tttgcttggt ctacccttttt tcctttcata tggttttaat tcaggtaaaa atccattttg   1140
tatttctctt aagtcataaa tatattcgta ctcatctaat atattgacta ctgtttttga   1200
tttagagttt atacttcctg gaactcttaa tattctcgtt gcatctaagg cttgtctatc   1260
tgctccaaag tattttaatt gattatataa atattcttga accgctttcc ataatggtaa   1320
tgctttacta ggtactgcat ttattatcca tattaaatac attcctcttc cactatctat   1380
tacatagttt ggtataggaa tactttgatt aaaataattc ttttctaagt ccattaatac   1440
ctggtcttta gttttgccag ttttataata atccaagtct ataaacagtg tatttaactc   1500
ttttatattt tctaatcgcc tacacggctt ataaaaggta tttagagtta tatagatatt   1560
ttcatcactc atatctaaat cttttaattc agcgtattta tagtgccatt ggctatatcc   1620
ttttttatct ataacgctcc tggttatcca ccctttactt ctactatgaa tattatctat   1680
atagttcttt ttattcagct ttaatgcgtt tctcacttat tcacctcccc ttctgtaaaa   1740
ctaagaaaat tatatcatat tttcaataat tattaactat tcttaaactc ttaataaaaa   1800
atagagtaag tccccaattg aaacttaatc tattttttat gttttaattt attattttta   1860
ttaaaatatt ttaaactaaa ttaaatgatt ctttttaatt ttttactatt tcattccata   1920
atatattact ataattattt acaaataata tttcttcatt tgtaatattt agatgattta   1980
ctaattttag tttttatata ttaaataatt aatgtataat ttatataaaa aatcaaagga   2040
gcttataaat tatgattatt tccaaagata ctaaagattt aattttttttc aattttaaca   2100
atactttttg taatattatg tttaaattta attgtatttt tttcatataa taaagccgtt   2160
gaagtaaacc aatccatttt ccttatgatg ttattattaa atttaagttt tataataata   2220
```

```
tctttattat atttattgtt tttaaaaaaa ctagtgaaat ttctagtgaa atttccggct   2280
ttattaaact tatttttagg aattttattt tcattttcat ctttacagga tttgattata   2340
tctttaaata tgttttatca aatattatct ttttctaaat ttatatatat ttttattata   2400
tttattatta tatatatttt atttttaagt ttctttctaa cagctattaa aaagaaactt   2460
aaaaataaaa acacgtactc taaaccaata aataaaacta tttttattat tgctgccttg   2520
attggaatag tttttagtaa aattaatttc aatattccac aatattatat tataagctag   2580
cacgcctcga gatctccatg gacgcgtgac gtcgactcta gaggatcccc gggtaccgag   2640
ctcgaattcg taatcatggt catagctgtt tcctgtgtga aattgttatc cgctcacaat   2700
tccacacaac atacgagccg gaagcataaa gtgtaaagcc tggggtgcct aatgagtgag   2760
ctaactcaca ttaattgcgt tgcgctcact gcccgctttc cagtcgggaa acctgtcgtg   2820
ccagctgcat taatgaatcg gccaacgcgc ggggagaggc ggtttgcgta ttgggcgctc   2880
ttccgcttcc tcgctcactg actcgctgcg ctcggtcgtt cggctgcggc gagcggtatc   2940
agctcactca aaggcggtaa tacggttatc cacagaatca ggggataacg caggaaagaa   3000
catgtgagca aaaggccagc aaaaggccag gaaccgtaaa aaggccgcgt tgctggcgtt   3060
tttccatagg ctccgccccc ctgacgagca tcacaaaaat cgacgctcaa gtcagaggtg   3120
gcgaaacccg acaggactat aaagatacca ggcgtttccc cctggaagct ccctcgtgcg   3180
ctctcctgtt ccgaccctgc cgcttaccgg atacctgtcc gcctttctcc cttcgggaag   3240
cgtggcgctt tctcatagct cacgctgtag gtatctcagt tcggtgtagg tcgttcgctc   3300
caagctgggc tgtgtgcacg aaccccccgt tcagcccgac cgctgcgcct tatccggtaa   3360
ctatcgtctt gagtccaacc cggtaagaca cgacttatcg ccactggcag cagccactgg   3420
taacaggatt agcagagcga ggtatgtagg cggtgctaca gagttcttga agtggtggcc   3480
taactacggc tacactagaa gaacagtatt tggtatctgc gctctgctga agccagttac   3540
cttcggaaaa agagttggta gctcttgatc cggcaaacaa accaccgctg gtagcggtgg   3600
tttttttgtt tgcaagcagc agattacgcg cagaaaaaaa ggatctcaag aagatccttt   3660
gatcttttct acggggtctg acgctcagtg gaacgaaaac tcacgttaag ggattttggt   3720
catgagatta tcaaaaagga tcttcaccta gatcctttta aattaaaaat gaagttttaa   3780
atcaatctaa agtatatatg agtaaacttg gtctgacagt taccaaagct agcttaatac   3840
tagtatatac ttaatgtgat aagtgtctga cagctgaccg gtctaaagag gtcccaatga   3900
ataggtttac acttacttta gttttatgga aatgaaagat catatcatat ataatctaga   3960
ataaaattaa ctaaaataat tattatctag ataaaaaatt tagaagccaa tgaaatctat   4020
aaataaacta aattaagttt atttaattaa caactatgga tataaaatag gtactaatca   4080
aaatagtgag gaggatatat ttgaatacat acgaacaaat taataaagtg aaaaaaatac   4140
ttcggaaaca tttaaaaaat aaccttattg gtacttacat gtttggatca ggagttgaga   4200
gtggactaaa accaaatagt gatcttgact ttttagtcgt cgtatctgaa ccattgacag   4260
atcaaagtaa agaaatactt atacaaaaaa ttagacctat ttcaaagaaa ataggagata   4320
aaagcaactt acgatatatt gaattaacaa ttattattca gcaagaaatg gtaccgtgga   4380
atcatcctcc caaacaagaa tttatttatg gagaatggtt acaagagctt tatgaacaag   4440
gatacattcc tcagaaggaa ttaaattcag atttaaccat aatgctttac caagcaaaac   4500
gaaaaaataa aagaatatac ggaaattatg acttagagga attactacct gatattccat   4560
tttctgatgt gagaagagcc attatggatt cgtcagagga attaatagat aattatcagg   4620
```

atgatgaaac caactctata ttaactttat gccgtatgat tttaactatg gacacgggta 4680
aaatcatacc aaaagatatt gcgggaaatg cagtggctga atcttctcca ttagaacata 4740
gggagagaat tttgttagca gttcgtagtt atcttggaga gaatattgaa tggactaatg 4800
aaaatgtaaa tttaactata aactatttaa ataacagatt aaaaaaatta taaaaaaatt 4860
gaaaaaatgg tggaaacact tttttcaatt tttttgtttt attatttaat atttgggaaa 4920
tattcattct aattggtaat cagattttag aagttgttaa cttcaggttt gtctgtaact 4980
aaaaactagt atttaaccta gg 5002

<210> SEQ ID NO 122
<211> LENGTH: 3907
<212> TYPE: DNA
<213> ORGANISM: Artificial Sequence
<220> FEATURE:
<223> OTHER INFORMATION: pFW01

<400> SEQUENCE: 122
tcgagatctc catggacgcg tgacgtcgac tctagaggat ccccgggtac cgagctcgaa 60
ttcgtaatca tggtcatagc tgtttcctgt gtgaaattgt tatccgctca caattccaca 120
caacatacga gccggaagca taaagtgtaa agcctggggt gcctaatgag tgagctaact 180
cacattaatt gcgttgcgct cactgcccgc tttccagtcg ggaaacctgt cgtgccagct 240
gcattaatga atcggccaac gcgcggggag aggcggtttg cgtattgggc gctcttccgc 300
ttcctcgctc actgactcgc tgcgctcggt cgttcggctg cggcgagcgg tatcagctca 360
ctcaaaggcg gtaatacggt tatccacaga atcaggggat aacgcaggaa agaacatgtg 420
agcaaaaggc cagcaaaagg ccaggaaccg taaaaaggcc gcgttgctgg cgtttttcca 480
taggctccgc ccccctgacg agcatcacaa aaatcgacgc tcaagtcaga ggtggcgaaa 540
cccgacagga ctataaagat accaggcgtt tccccctgga agctccctcg tgcgctctcc 600
tgttccgacc ctgccgctta ccggatacct gtccgccttt ctcccttcgg gaagcgtggc 660
gctttctcat agctcacgct gtaggtatct cagttcggtg taggtcgttc gctccaagct 720
gggctgtgtg cacgaacccc ccgttcagcc cgaccgctgc gccttatccg gtaactatcg 780
tcttgagtcc aacccggtaa gacacgactt atcgccactg gcagcagcca ctggtaacag 840
gattagcaga gcgaggtatg taggcggtgc tacagagttc ttgaagtggt ggcctaacta 900
cggctacact agaaggacag tatttggtat ctgcgctctg ctgaagccag ttaccttcgg 960
aaaaagagtt ggtagctctt gatccggcaa acaaaccacc gctggtagcg gtggtttttt 1020
tgtttgcaag cagcagatta cgcgcagaaa aaaaggatct caagaagatc ctttgatctt 1080
ttctacgggg tctgacgctc agtggaacga aaactcacgt taagggattt tggtcatgag 1140
attatcaaaa aggatcttca cctagatcct tttaaattaa aaatgaagtt ttaaatcaat 1200
ctaaagtata tatgagtaaa cttggtctga cagttaccag gtccactgcc gggcctcttg 1260
cgggatcaaa agaaaaacga aatgatacac caatcagtgc aaaaaaagat ataatgggag 1320
ataagacggt tcgtgttcgt gctgacttgc accatatcat aaaaatcgaa acagcaaaga 1380
atggcggaaa cgtaaaagaa gttatggaaa taagacttag aagcaaactt aagagtgtgt 1440
tgatagtgca gtatcttaaa attttgtata ataggaattg aagttaaatt agatgctaaa 1500
aatttgtaat taagaaggag tgattacatg aacaaaaata taaaatattc tcaaaacttt 1560
ttaacgagtg aaaaagtact caaccaaata ataaaacaat tgaatttaaa agaaaccgat 1620

```
accgtttacg aaattggaac aggtaaaggg catttaacga cgaaactggc taaaataagt   1680
aaacaggtaa cgtctattga attagacagt catctattca acttatcgtc agaaaaatta   1740
aaactgaata ctcgtgtcac tttaattcac caagatattc tacagtttca attccctaac   1800
aaacagaggt ataaaattgt tgggagtatt ccttaccatt taagcacaca aattattaaa   1860
aaagtggttt ttgaaagcca tgcgtctgac atctatctga ttgttgaaga aggattctac   1920
aagcgtacct tggatattca ccgaacacta gggttgctct tgcacactca agtctcgatt   1980
cagcaattgc ttaagctgcc agcggaatgc tttcatccta aaccaaaagt aaacagtgtc   2040
ttaataaaac ttacccgcca taccacagat gttccagata aatattggaa gctatatacg   2100
tactttgttt caaaatgggt caatcgagaa tatcgtcaac tgtttactaa aaatcagttt   2160
catcaagcaa tgaaacacgc caaagtaaac aatttaagta ccgttactta tgagcaagta   2220
ttgtctattt ttaatagtta tctattattt aacgggagga aataattcta tgagtcccta   2280
ggcaggcctc cgccattatt tttttgaaca attgacaatt catttcttat tttttattaa   2340
gtgatagtca aaaggcataa cagtgctgaa tagaaagaaa tttacagaaa agaaaattat   2400
agaatttagt atgattaatt atactcattt atgaatgttt aattgaatac aaaaaaaaat   2460
acttgttatg tattcaatta cgggttaaaa tatagacaag ttgaaaaatt taataaaaaa   2520
ataagtcctc agctcttata tattaagcta ccaacttagt atataagcca aaacttaaat   2580
gtgctaccaa cacatcaagc cgttagagaa ctctatctat agcaatattt caaatgtacc   2640
gacatacaag agaaacatta actatatata ttcaatttat gagattatct taacagatat   2700
aaatgtaaat tgcaataagt aagatttaga agtttatagc ctttgtgtat tggaagcagt   2760
acgcaaaggc tttttttattt gataaaaatt agaagtatat ttattttttc ataattaatt   2820
tatgaaaatg aaagggggtg agcaaagtga cagaggaaag cagtatctta tcaaataaca   2880
aggtattagc aatatcatta ttgactttag cagtaaacat tatgactttt atagtgcttg   2940
tagctaagta gtacgaaagg gggagcttta aaaagctcct tggaatacat agaattcata   3000
aattaattta tgaaaagaag ggcgtatatg aaaacttgta aaaattgcaa agagtttatt   3060
aaagatactg aaatatgcaa aatacattcg ttgatgattc atgataaaac agtagcaacc   3120
tattgcagta aatacaatga gtcaagatgt ttacataaag ggaaagtcca atgtattaat   3180
tgttcaaaga tgaaccgata tggatggtgt gccataaaaa tgagatgttt tacagaggaa   3240
gaacagaaaa aagaacgtac atgcattaaa tattatgcaa ggagctttaa aaaagctcat   3300
gtaaagaaga gtaaaaagaa aaaataattt atttattaat ttaatattga gagtgccgac   3360
acagtatgca ctaaaaaata tatctgtggt gtagtgagcc gatacaaaag gatagtcact   3420
cgcattttca taatacatct tatgttatga ttatgtgtcg gtgggacttc acgacgaaaa   3480
cccacaataa aaaaagagtt cggggtaggg ttaagcatag ttgaggcaac taaacaatca   3540
agctaggata tgcagtagca gaccgtaagg tcgttgttta ggtgtgttgt aatacatacg   3600
ctattaagat gtaaaaatac ggataccaat gaagggaaaa gtataatttt tggatgtagt   3660
ttgtttgttc atctatgggc aaactacgtc caaagccgtt tccaaatctg ctaaaaagta   3720
tatcctttct aaaatcaaag tcaagtatga aatcataaat aaagtttaat tttgaagtta   3780
ttatgatatt atgtttttct attaaaataa attaagtata tagaatagtt taataatagt   3840
atatacttaa tgtgataagt gtctgacagt gtcacagaaa ggatgattgt tatggattat   3900
aagcggc                                                              3907
```

<210> SEQ ID NO 123
<211> LENGTH: 6525
<212> TYPE: DNA
<213> ORGANISM: Artificial Sequence
<220> FEATURE:
<223> OTHER INFORMATION: pNF3S

<400> SEQUENCE: 123
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgc 240
atgcctgcag gtcgaccacg ataaaacaag gttttaagga taagaaaagt catgagattt 300
atagtaaatc ttgtgacttt ttttattgaa tagtagagag agttcggaag tataacacgc 360
tatattcttg atatttttag aatagcaagc attggatttg tcctgacact ttcccaaaaa 420
ttaaggagtt attccttaaa ccaaaaagat taatgtggga acaaatttag tgtatccatt 480
tttgaagggc gcacttatac accaccaaaa tggtgtgtgc gaaatcttta aaaaagattt 540
atcaaaaagc ttttttaaag ctgggacatt tagaaaatca ataatgtttt ttgcccaata 600
cgctagtctt aaaatctgca aggttgataa ctatttagtc ccaggtatta gaatggggca 660
tatatataca aagtatatat atgcgtaaat atatgtggga ctgtgggaac aaaattgcgt 720
gctaaaattg tattgaaaag gtaatgaaaa ggtcatgctt tggtattgct aacgtataga 780
aaaggtaatg aaaagctcat ggttctataa aaaagatgta cccacgaaaa taataggctt 840
tgcctatttc cccatgtaat atgggggcag ttttctctta tgctctttct taacatattg 900
aataaataca aaatgcagct ttgtgggaat aaaaatattt ttgtttttat tcttatagtt 960
agacaaaatt ttaatctttt ttgtgctata acaagattaa aatttgtggg aacattaaga 1020
aatattgttg tcacaaataa aaaggagagt gggaacaatt gctataaaaa acgcagaaat 1080
taagattaga gttacaaaag agcaaaaaga attatttaag aaaattgcaa aagctgaaaa 1140
tatgagtatg agtgaattta ttattgtgac cacagaatat ttagccagaa aaaaagatga 1200
aaatatgaaa tcaaaagaca tgatcgagag aagagctgcg aagactgaag aaaaaattat 1260
gaagctaaaa aagaaactaa ataaaaacag gtaatataga ttacagtttt aagcttgttt 1320
tccctataga ctagagtaaa tatataaata tacctgtcaa gggcttataa gcccctttag 1380
ggggtgcgta gcacccttga caggtatatt tatatatttt agggtgccat taagggaaac 1440
aagctttaaa atgcctttaa aggcatttta aaataaataa aaaaaagatg gtttttacca 1500 tctttttaa ctcccgaaag ggagttcttt cttttcttga tactatacgt aactatttcg 1560
atttgccctg aacctaatca aagctagata aattcagtat tagggcataa aaaaacttgc 1620
tttttcgggt ggaaatctgt ataatttaaa ttgcttagat aaaaattacc aattccatac 1680
gaaaggagca agttttacat aaggttaaag ccttatgtga attctcattt aattacatga 1740
ataataataa cacagaaagt gaagaattaa aagagcaaag tcaactattg cttgacaaat 1800
gcacaaaaaa gaaaaagaaa aatcctaaat ttagtagtta tatagaacca ttagtaagca 1860
agaaattatc tgaaagaata aaggaatgtg gtgacttttt gcagatgtta tctgatttaa 1920
accttgaaaa ttcgaaactg catagagcaa gtttttgtgg taacagattt tgtcctatgt 1980
gtagctggcg tattgcttgt aaggatagtt tggaaatatc tattctcatg gagcatttac 2040
gcaaagagga aagcaaagaa tttatctttt tgaccttaac aactccaaat gtgaaaggtg 2100
cggaccttga taattccata aaagcataca ataaagcatt taaaaagtta atggaacgca 2160
aagaggtcaa gagcatagta aaaggctaca taagaaagct agaagtaacc tataatttgg 2220
acaagagttc caaatcatat aatacttatc acccacattt ccatgtggta ctagcagtca 2280
atagaagtta ctttaaaaag caaaatctat atataaacca tcatagatgg cttagtttgt 2340
ggcaagagtc aactggtgat tattcgataa ctcaagttga tgtaagaaag gctaaaatta 2400
acgattataa agaggtttat gagcttgcta agtattcggc taaggattcc gactatttaa 2460
tcaatagaga agtgtttacg gtattctaca aatctttaaa gggtaaacag gtacttgtat 2520
ttagtggatt atttaaagac gctcataaaa tgtataagaa tggagagcta gatctgtata 2580
agaagttgga tactatcgaa tatgcttata tggtaagtta taactggctt aaaaagaagt 2640
atgatacttc aaatattaga gaattaactg aggaagaaaa gcagaaattc aataaaaatt 2700
taatcgaaga tgtggatatt gagtaggtgg gattatatct caccttttt attgtctttt 2760
catgttgaaa ttttgacgct taatgcatga agtattgaca agtttaaaaa ttacggtttt 2820
taatccttag ttgattagca ggattatggc cggaatgctc cgtccagtcc tgttaaggaa 2880
ttaaaattcc ctaaaaccct tggctatgat ttatagcgag aatcgtcaat taaaaattta 2940
ataggtgcta tgaaagtcga ttaataatta attttaaaat gcaatatgaa acataattac 3000
aagaatttga cttttaatac aagaattgat atcatagtta cattaatacg gatcccaatg 3060
aataggttta cacttacttt agttttatgg aaatgaaaga tcatatcata tataatctag 3120
aataaaatta actaaaataa ttattatcta gataaaaaat ttagaagcca atgaaatcta 3180
taaataaact aaattaagtt tatttaatta acaactatgg atataaaata ggtactaatc 3240
aaaatagtga ggaggatata tttgaataca tacgaacaaa ttaataaagt gaaaaaaata 3300
cttcggaaac atttaaaaaa taaccttatt ggtacttaca tgtttggatc aggagttgag 3360
agtggactaa aaccaaatag tgatcttgac tttttagtcg tcgtatctga accattgaca 3420
gatcaaagta aagaaatact tatacaaaaa attagaccta tttcaaagaa aataggagat 3480
aaaagcaact tacgatatat tgaattaaca attattattc agcaagaaat ggtaccgtgg 3540
aatcatcctc ccaaacaaga atttatttat ggagaatggt tacaagagct ttatgaacaa 3600
ggatacattc ctcagaagga attaaattca gatttaacca taatgcttta ccaagcaaaa 3660
cgaaaaaata aaagaatata cggaaattat gacttagagg aattactacc tgatattcca 3720
ttttctgatg tgagaagagc cattatggat tcgtcagagg aattaataga taattatcag 3780
gatgatgaaa ccaactctat attaacttta tgccgtatga ttttaactat ggacacgggt 3840
aaaatcatac caaaagatat tgcgggaaat gcagtggctg aatcttctcc attagaacat 3900
agggagagaa ttttgttagc agttcgtagt tatcttggag agaatattga atggactaat 3960
gaaaatgtaa atttaactat aaactattta aataacagat taaaaaaatt ataaaaaaat 4020
tgaaaaaatg gtggaaacac ttttttcaat ttttttgttt tattatttaa tatttgggaa 4080
atattcattc taattggtaa tcagatttta gaagttgagc tcgaattcac tggccgtcgt 4140
tttacaacgt cgtgactggg aaaaccctgg cgttacccaa cttaatcgcc ttgcagcaca 4200
tccccctttc gccagctggc gtaatagcga agaggcccgc accgatcgcc cttcccaaca 4260
gttgcgcagc ctgaatggcg aatggcgcct gatgcggtat tttctcctta cgcatctgtg 4320
cggtatttca caccgcatat ggtgcactct cagtacaatc tgctctgatg ccgcatagtt 4380
aagccagccc cgacacccgc caacacccgc tgacgcgccc tgacgggctt gtctgctccc 4440
ggcatccgct tacagacaag ctgtgaccgt ctccgggagc tgcatgtgtc agaggttttc 4500

```
accgtcatca ccgaaacgcg cgagacgaaa gggcctcgtg atacgcctat ttttataggt   4560
taatgtcatg ataataatgg tttcttagac gtcaggtggc acttttcggg gaaatgtgcg   4620
cggaacccct atttgtttat ttttctaaat acattcaaat atgtatccgc tcatgagaca   4680
ataaccctga taaatgcttc aataatattg aaaaaggaag agtatgagta ttcaacattt   4740
ccgtgtcgcc cttattccct tttttgcggc attttgcctt cctgtttttg ctcacccaga   4800
aacgctggtg aaagtaaaag atgctgaaga tcagttgggt gcacgagtgg gttacatcga   4860
actggatctc aacagcggta agatccttga gagttttcgc cccgaagaac gttttccaat   4920
gatgagcact tttaaagttc tgctatgtgg cgcggtatta tcccgtattg acgccgggca   4980
agagcaactc ggtcgccgca tacactattc tcagaatgac ttggttgagt actcaccagt   5040
cacagaaaag catcttacgg atggcatgac agtaagagaa ttatgcagtg ctgccataac   5100
catgagtgat aacactgcgg ccaacttact tctgacaacg atcggaggac cgaaggagct   5160
aaccgctttt ttgcacaaca tgggggatca tgtaactcgc cttgatcgtt gggaaccgga   5220
gctgaatgaa gccataccaa acgacgagcg tgacaccacg atgcctgtag caatggcaac   5280
aacgttgcgc aaactattaa ctggcgaact acttactcta gcttcccggc aacaattaat   5340
agactggatg gaggcggata aagttgcagg accacttctg cgctcggccc ttccggctgg   5400
ctggtttatt gctgataaat ctggagccgg tgagcgtggg tctcgcggta tcattgcagc   5460
actggggcca gatggtaagc cctcccgtat cgtagttatc tacacgacgg ggagtcaggc   5520
aactatggat gaacgaaata gacagatcgc tgagataggt gcctcactga ttaagcattg   5580
gtaactgtca gaccaagttt actcatatat actttagatt gatttaaaac ttcattttta   5640
atttaaaagg atctaggtga agatcctttt tgataatctc atgaccaaaa tcccttaacg   5700
tgagttttcg ttccactgag cgtcagaccc cgtagaaaag atcaaaggat cttcttgaga   5760
tccttttttt ctgcgcgtaa tctgctgctt gcaaacaaaa aaaccaccgc taccagcggt   5820
ggtttgtttg ccggatcaag agctaccaac tctttttccg aaggtaactg gcttcagcag   5880
agcgcagata ccaaatactg ttcttctagt gtagccgtag ttaggccacc acttcaagaa   5940
ctctgtagca ccgcctacat acctcgctct gctaatcctg ttaccagtgg ctgctgccag   6000
tggcgataag tcgtgtctta ccgggttgga ctcaagacga tagttaccgg ataaggcgca   6060
gcggtcgggc tgaacggggg gttcgtgcac acagcccagc ttggagcgaa cgacctacac   6120
cgaactgaga tacctacagc gtgagctatg agaaagcgcc acgcttcccg aagggagaaa   6180
ggcggacagg tatccggtaa gcggcagggt cggaacagga gagcgcacga gggagcttcc   6240
agggggaaac gcctggtatc tttatagtcc tgtcgggttt cgccacctct gacttgagcg   6300
tcgatttttg tgatgctcgt caggggggcg gagcctatgg aaaaacgcca gcaacgcggc   6360
ctttttacgg ttcctggcct tttgctggcc ttttgctcac atgttctttc ctgcgttatc   6420
ccctgattct gtggataacc gtattaccgc ctttgagtga gctgataccg ctcgccgcag   6480
ccgaacgacc gagcgcagcg agtcagtgag cgaggaagcg gaaga                   6525
```

<210> SEQ ID NO 124
<211> LENGTH: 6554
<212> TYPE: DNA
<213> ORGANISM: Artificial Sequence
<220> FEATURE:
<223> OTHER INFORMATION: pNF3E

<400> SEQUENCE: 124

```
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg ccaagcttgc    240
atgcctgcag gtcgaccacg ataaaacaag gttttaagga taagaaaagt catgagattt    300
atagtaaatc ttgtgacttt ttttattgaa tagtagagag agttcggaag tataacacgc    360
tatattcttg atatttttag aatagcaagc attggatttg tcctgacact ttcccaaaaa    420
ttaaggagtt attccttaaa ccaaaaagat taatgtggga acaaatttag tgtatccatt    480
tttgaagggc gcacttatac accaccaaaa tggtgtgtgc gaaatcttta aaaaagattt    540
atcaaaaagc ttttttaaag ctgggacatt tagaaaatca ataatgtttt ttgcccaata    600
cgctagtctt aaaatctgca aggttgataa ctatttagtc ccaggtatta gaatggggca    660
tatatataca aagtatatat atgcgtaaat atatgtggga ctgtgggaac aaaattgcgt    720
gctaaaattg tattgaaaag gtaatgaaaa ggtcatgctt tggtattgct aacgtataga    780
aaaggtaatg aaaagctcat ggttctataa aaaagatgta cccacgaaaa taataggctt    840
tgcctatttc cccatgtaat atgggggcag ttttctctta tgctctttct taacatattg    900
aataaataca aaatgcagct ttgtgggaat aaaaatattt ttgtttttat tcttatagtt    960
agacaaaatt ttaatctttt ttgtgctata acaagattaa aatttgtggg aacattaaga   1020
aatattgttg tcacaaataa aaaggagagt gggaacaatt gctataaaaa acgcagaaat   1080
taagattaga gttacaaaag agcaaaaaga attatttaag aaaattgcaa aagctgaaaa   1140
tatgagtatg agtgaattta ttattgtgac cacagaatat ttagccagaa aaaaagatga   1200
aaatatgaaa tcaaaagaca tgatcgagag aagagctgcg aagactgaag aaaaaattat   1260
gaagctaaaa aagaaactaa ataaaaacag gtaatataga ttacagtttt aagcttgttt   1320
tccctataga ctagagtaaa tatataaata tacctgtcaa gggcttataa gcccctttag   1380
ggggtgcgta gcacccttga caggtatatt tatatatttt agggtgccat taagggaaac   1440
aagctttaaa atgcctttaa aggcatttta aaataaataa aaaaaagatg gtttttacca   1500
tctttttttaa ctcccgaaag ggagttcttt cttttcttga tactatacgt aactatttcg   1560
atttgccctg aacctaatca aagctagata aattcagtat tagggcataa aaaaacttgc   1620
tttttcgggt ggaaatctgt ataatttaaa ttgcttagat aaaaattacc aattccatac   1680
gaaaggagca agttttacat aaggttaaag ccttatgtga attctcattt aattacatga   1740
ataataataa cacagaaagt gaagaattaa aagagcaaag tcaactattg cttgacaaat   1800
gcacaaaaaa gaaaaagaaa aatcctaaat ttagtagtta tatagaacca ttagtaagca   1860
agaaattatc tgaaagaata aaggaatgtg gtgacttttt gcagatgtta tctgatttaa   1920
accttgaaaa ttcgaaactg catagagcaa gtttttgtgg taacagattt tgtcctatgt   1980
gtagctggcg tattgcttgt aaggatagtt tggaaatatc tattctcatg gagcatttac   2040
gcaaagagga aagcaaagaa tttatctttt tgaccttaac aactccaaat gtgaaaggtg   2100
cggaccttga taattccata aaagcataca ataaagcatt taaaaagtta atggaacgca   2160
aagaggtcaa gagcatagta aaaggctaca taagaaagct agaagtaacc tataatttgg   2220
acaagagttc caaatcatat aatacttatc acccacattt ccatgtggta ctagcagtca   2280
atagaagtta ctttaaaaag caaaatctat atataaacca tcatagatgg cttagtttgt   2340
ggcaagagtc aactggtgat tattcgataa ctcaagttga tgtaagaaag gctaaaatta   2400
```

acgattataa agaggtttat gagcttgcta agtattcggc taaggattcc gactatttaa 2460
tcaatagaga agtgtttacg gtattctaca aatctttaaa gggtaaacag gtacttgtat 2520
ttagtggatt atttaaagac gctcataaaa tgtataagaa tggagagcta gatctgtata 2580
agaagttgga tactatcgaa tatgcttata tggtaagtta taactggctt aaaaagaagt 2640
atgatacttc aaatattaga gaattaactg aggaagaaaa gcagaaattc aataaaaatt 2700
taatcgaaga tgtggatatt gagtaggtgg gattatatct caccttttt attgtctttt 2760
catgttgaaa ttttgacgct taatgcatga agtattgaca agtttaaaaa ttacggtttt 2820
taatccttag ttgattagca ggattatggc cggaatgctc cgtccagtcc tgttaaggaa 2880
ttaaaattcc ctaaaaccct tggctatgat ttatagcgag aatcgtcaat taaaaattta 2940
ataggtgcta tgaaagtcga ttaataatta attttaaaat gcaatatgaa acataattac 3000
aagaatttga cttttaatac aagaattgat atcatagtta cattaatacg gatccgtctg 3060
acagttacca ggtccactgc cgggcctctt gcgggatcaa aagaaaaacg aaatgataca 3120
ccaatcagtg caaaaaaaga tataatggga gataagacgg ttcgtgttcg tgctgacttg 3180
caccatatca taaaaatcga aacagcaaag aatggcggaa acgtaaaaga agttatggaa 3240
ataagactta gaagcaaact taagagtgtg ttgatagtgc agtatcttaa aatttgtat 3300
aataggaatt gaagttaaat tagatgctaa aaatttgtaa ttaagaagga gtgattacat 3360
gaacaaaaat ataaaatatt ctcaaaactt tttaacgagt gaaaaagtac tcaaccaaat 3420
aataaaacaa ttgaatttaa aagaaaccga taccgtttac gaaattggaa caggtaaagg 3480
gcatttaacg acgaaactgg ctaaaataag taaacaggta acgtctattg aattagacag 3540
tcatctattc aacttatcgt cagaaaaatt aaaactgaat actcgtgtca ctttaattca 3600
ccaagatatt ctacagtttc aattccctaa caaacagagg tataaaattg ttgggagtat 3660
tccttaccat ttaagcacac aaattattaa aaaagtggtt tttgaaagcc atgcgtctga 3720
catctatctg attgttgaag aaggattcta caagcgtacc ttggatattc accgaacact 3780
agggttgctc ttgcacactc aagtctcgat tcagcaattg cttaagctgc cagcggaatg 3840
ctttcatcct aaaccaaaag taaacagtgt cttaataaaa cttacccgcc ataccacaga 3900
tgttccagat aaatattgga agctatatac gtactttgtt tcaaaatggg tcaatcgaga 3960
atatcgtcaa ctgtttacta aaaatcagtt tcatcaagca atgaaacacg ccaaagtaaa 4020
caatttaagt accgttactt atgagcaagt attgtctatt tttaatagtt atctattatt 4080
taacgggagg aaataattct atgagtccct aggcaggcct ccgccattat ttttttgaac 4140
aattggagct cgaattcact ggccgtcgtt ttacaacgtc gtgactggga aaaccctggc 4200
gttacccaac ttaatcgcct tgcagcacat ccccctttcg ccagctggcg taatagcgaa 4260
gaggcccgca ccgatcgccc ttcccaacag ttgcgcagcc tgaatggcga atggcgcctg 4320
atgcggtatt ttctccttac gcatctgtgc ggtatttcac accgcatatg gtgcactctc 4380
agtacaatct gctctgatgc cgcatagtta agccagcccc gacacccgcc aacacccgct 4440
gacgcgccct gacgggcttg tctgctcccg gcatccgctt acagacaagc tgtgaccgtc 4500
tccgggagct gcatgtgtca gaggttttca ccgtcatcac cgaaacgcgc gagacgaaag 4560
ggcctcgtga tacgcctatt tttataggtt aatgtcatga taataatggt ttcttagacg 4620
tcaggtggca cttttcgggg aaatgtgcgc ggaaccccta tttgtttatt tttctaaata 4680
cattcaaata tgtatccgct catgagacaa taaccctgat aaatgcttca ataatattga 4740
aaaaggaaga gtatgagtat tcaacatttc cgtgtcgccc ttattccctt ttttgcggca 4800
ttttgccttc ctgtttttgc tcacccagaa acgctggtga aagtaaaaga tgctgaagat 4860
cagttgggtg cacgagtggg ttacatcgaa ctggatctca acagcggtaa gatccttgag 4920
agttttcgcc ccgaagaacg ttttccaatg atgagcactt ttaaagttct gctatgtggc 4980
gcggtattat cccgtattga cgccgggcaa gagcaactcg gtcgccgcat acactattct 5040
cagaatgact tggttgagta ctcaccagtc acagaaaagc atcttacgga tggcatgaca 5100
gtaagagaat tatgcagtgc tgccataacc atgagtgata acactgcggc caacttactt 5160
ctgacaacga tcggaggacc gaaggagcta accgcttttt tgcacaacat gggggatcat 5220
gtaactcgcc ttgatcgttg ggaaccggag ctgaatgaag ccataccaaa cgacgagcgt 5280
gacaccacga tgcctgtagc aatggcaaca acgttgcgca aactattaac tggcgaacta 5340
cttactctag cttcccggca acaattaata gactggatgg aggcggataa agttgcagga 5400
ccacttctgc gctcggccct tccggctggc tggtttattg ctgataaatc tggagccggt 5460
gagcgtgggt ctcgcggtat cattgcagca ctggggccag atggtaagcc ctcccgtatc 5520
gtagttatct acacgacggg gagtcaggca actatggatg aacgaaatag acagatcgct 5580
gagataggtg cctcactgat taagcattgg taactgtcag accaagttta ctcatatata 5640
ctttagattg atttaaaact tcatttttaa tttaaaagga tctaggtgaa gatccttttt 5700
gataatctca tgaccaaaat cccttaacgt gagttttcgt tccactgagc gtcagacccc 5760
gtagaaaaga tcaaaggatc ttcttgagat cctttttttc tgcgcgtaat ctgctgcttg 5820
caaacaaaaa aaccaccgct accagcggtg gtttgtttgc cggatcaaga gctaccaact 5880
ctttttccga aggtaactgg cttcagcaga gcgcagatac caaatactgt tcttctagtg 5940
tagccgtagt taggccacca cttcaagaac tctgtagcac cgcctacata cctcgctctg 6000
ctaatcctgt taccagtggc tgctgccagt ggcgataagt cgtgtcttac cgggttggac 6060
tcaagacgat agttaccgga taaggcgcag cggtcgggct gaacgggggg ttcgtgcaca 6120
cagcccagct tggagcgaac gacctacacc gaactgagat acctacagcg tgagctatga 6180
gaaagcgcca cgcttcccga agggagaaag gcggacaggt atccggtaag cggcagggtc 6240
ggaacaggag agcgcacgag ggagcttcca gggggaaacg cctggtatct ttatagtcct 6300
gtcgggtttc gccacctctg acttgagcgt cgatttttgt gatgctcgtc aggggggcgg 6360
agcctatgga aaaacgccag caacgcggcc tttttacggt tcctggcctt ttgctggcct 6420
tttgctcaca tgttctttcc tgcgttatcc cctgattctg tggataaccg tattaccgcc 6480
tttgagtgag ctgataccgc tcgccgcagc cgaacgaccg agcgcagcga gtcagtgagc 6540
gaggaagcgg aaga 6554

<210> SEQ ID NO 125
<211> LENGTH: 6271
<212> TYPE: DNA
<213> ORGANISM: Artificial Sequence
<220> FEATURE:
<223> OTHER INFORMATION: pNF3C

<400> SEQUENCE: 125
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgc 240

```
atgcctgcag gtcgaccacg ataaaacaag gttttaagga taagaaaagt catgagattt    300
atagtaaatc ttgtgacttt ttttattgaa tagtagagag agttcggaag tataacacgc    360
tatattcttg atatttttag aatagcaagc attggatttg tcctgacact ttcccaaaaa    420
ttaaggagtt attccttaaa ccaaaaagat taatgtggga acaaatttag tgtatccatt    480
tttgaagggc gcacttatac accaccaaaa tggtgtgtgc gaaatcttta aaaaagattt    540
atcaaaaagc ttttttaaag ctgggacatt tagaaaatca ataatgtttt ttgcccaata    600
cgctagtctt aaaatctgca aggttgataa ctatttagtc ccaggtatta gaatggggca    660
tatatataca aagtatatat atgcgtaaat atatgtggga ctgtgggaac aaaattgcgt    720
gctaaaattg tattgaaaag gtaatgaaaa ggtcatgctt tggtattgct aacgtataga    780
aaaggtaatg aaaagctcat ggttctataa aaaagatgta cccacgaaaa taataggctt    840
tgcctatttc cccatgtaat atgggggcag ttttctctta tgctctttct taacatattg    900
aataaataca aaatgcagct ttgtgggaat aaaaatattt ttgtttttat tcttatagtt    960
agacaaaatt ttaatctttt ttgtgctata acaagattaa aatttgtggg aacattaaga   1020
aatattgttg tcacaaataa aaaggagagt gggaacaatt gctataaaaa acgcagaaat   1080
taagattaga gttacaaaag agcaaaaaga attatttaag aaaattgcaa aagctgaaaa   1140
tatgagtatg agtgaattta ttattgtgac cacagaatat ttagccagaa aaaaagatga   1200
aaatatgaaa tcaaaagaca tgatcgagag aagagctgcg aagactgaag aaaaaattat   1260
gaagctaaaa aagaaactaa ataaaaacag gtaatataga ttacagtttt aagcttgttt   1320
tccctataga ctagagtaaa tatataaata tacctgtcaa gggcttataa gccccttttag  1380
ggggtgcgta gcacccttga caggtatatt tatatatttt agggtgccat taagggaaac   1440
aagctttaaa atgcctttaa aggcatttta aaataaataa aaaaaagatg gtttttacca   1500
tctttttttaa ctcccgaaag ggagttcttt cttttcttga tactatacgt aactatttcg  1560
atttgccctg aacctaatca aagctagata aattcagtat tagggcataa aaaaacttgc   1620
tttttcgggt ggaaatctgt ataatttaaa ttgcttagat aaaaattacc aattccatac   1680
gaaaggagca agttttacat aaggttaaag ccttatgtga attctcattt aattacatga   1740
ataataataa cacagaaagt gaagaattaa aagagcaaag tcaactattg cttgacaaat   1800
gcacaaaaaa gaaaaagaaa aatcctaaat ttagtagtta tatagaacca ttagtaagca   1860
agaaattatc tgaaagaata aaggaatgtg gtgacttttt gcagatgtta tctgatttaa   1920
accttgaaaa ttcgaaactg catagagcaa gtttttgtgg taacagattt tgtcctatgt   1980
gtagctggcg tattgcttgt aaggatagtt tggaaatatc tattctcatg gagcatttac   2040
gcaaagagga aagcaaagaa tttatctttt tgaccttaac aactccaaat gtgaaaggtg   2100
cggaccttga taattccata aaagcataca ataaagcatt taaaaagtta atggaacgca   2160
aagaggtcaa gagcatagta aaaggctaca taagaaagct agaagtaacc tataatttgg   2220
acaagagttc caaatcatat aatacttatc acccacattt ccatgtggta ctagcagtca   2280
atagaagtta ctttaaaaag caaaatctat atataaacca tcatagatgg cttagtttgt   2340
ggcaagagtc aactggtgat tattcgataa ctcaagttga tgtaagaaag gctaaaatta   2400
acgattataa agaggtttat gagcttgcta agtattcggc taaggattcc gactatttaa   2460
tcaatagaga agtgtttacg gtattctaca aatctttaaa gggtaaacag gtacttgtat   2520
ttagtggatt atttaaagac gctcataaaa tgtataagaa tggagagcta gatctgtata   2580
```

agaagttgga tactatcgaa tatgcttata tggtaagtta taactggctt aaaaagaagt 2640
atgatacttc aaatattaga gaattaactg aggaagaaaa gcagaaattc aataaaaatt 2700
taatcgaaga tgtggatatt gagtaggtgg gattatatct caccttttt attgtctttt 2760 catgttgaaa ttttgacgct taatgcatga agtattgaca agtttaaaaa ttacggtttt 2820
taatccttag ttgattagca ggattatggc cggaatgctc cgtccagtcc tgttaaggaa 2880
ttaaaattcc ctaaaaccct tggctatgat ttatagcgag aatcgtcaat taaaaattta 2940
ataggtgcta tgaaagtcga ttaataatta attttaaaat gcaatatgaa acataattac 3000
aagaatttga cttttaatac aagaattgat atcatagtta cattaatacg gatcccggca 3060
gtttttcttt ttcggcaagt gttcaagaag ttattaagtc gggagtgcag tcgaagtggg 3120
caagttgaaa aattcacaaa aatgtggtat aatatctttg ttcattagag cgataaactt 3180
gaatttgaga gggaacttag atggtatttg aaaaaattga taaaaatagt tggaacagaa 3240
aagagtattt tgaccactac tttgcaagtg taccttgtac ctacagcatg accgttaaag 3300
tggatatcac acaaataaag gaaaagggaa tgaaactata tcctgcaatg ctttattata 3360
ttgcaatgat tgtaaaccgc cattcagagt ttaggacggc aatcaatcaa gatggtgaat 3420
tggggatata tgatgagatg ataccaagct atacaatatt tcacaatgat actgaaacat 3480
tttccagcct ttggactgag tgtaagtctg actttaaatc atttttagca gattatgaaa 3540
gtgatacgca acggtatgga aacaatcata gaatggaagg aaagccaaat gctccggaaa 3600
acatttttaa tgtatctatg ataccgtggt caaccttcga tggctttaat ctgaatttgc 3660
agaaaggata tgattatttg attcctattt ttactatggg gaaatattat aaagaagata 3720
acaaaattat acttcctttg gcaattcaag ttcatcacgc agtatgtgac ggatttcaca 3780
tttgccgttt tgtaaacgaa ttgcaggaat tgataaatag ttaacttcag gtttgtctgt 3840
aactaaaaac tagtatttaa ccgagctcga attcactggc cgtcgtttta caacgtcgtg 3900
actgggaaaa ccctggcgtt acccaactta atcgccttgc agcacatccc cctttcgcca 3960
gctggcgtaa tagcgaagag gcccgcaccg atcgcccttc ccaacagttg cgcagcctga 4020
atggcgaatg gcgcctgatg cggtattttc tccttacgca tctgtgcggt atttcacacc 4080
gcatatggtg cactctcagt acaatctgct ctgatgccgc atagttaagc cagccccgac 4140
acccgccaac acccgctgac gcgccctgac gggcttgtct gctcccggca tccgcttaca 4200
gacaagctgt gaccgtctcc gggagctgca tgtgtcagag gttttcaccg tcatcaccga 4260
aacgcgcgag acgaaagggc ctcgtgatac gcctattttt ataggttaat gtcatgataa 4320
taatggtttc ttagacgtca ggtggcactt ttcggggaaa tgtgcgcgga acccctattt 4380
gtttattttt ctaaatacat tcaaatatgt atccgctcat gagacaataa ccctgataaa 4440
tgcttcaata atattgaaaa aggaagagta tgagtattca acatttccgt gtcgccctta 4500
ttcccttttt tgcggcattt tgccttcctg tttttgctca cccagaaacg ctggtgaaag 4560
taaaagatgc tgaagatcag ttgggtgcac gagtgggtta catcgaactg gatctcaaca 4620
gcggtaagat ccttgagagt tttcgccccg aagaacgttt tccaatgatg agcactttta 4680
aagttctgct atgtggcgcg gtattatccc gtattgacgc cgggcaagag caactcggtc 4740
gccgcataca ctattctcag aatgacttgg ttgagtactc accagtcaca gaaaagcatc 4800
ttacggatgg catgacagta agagaattat gcagtgctgc cataaccatg agtgataaca 4860
ctgcggccaa cttacttctg acaacgatcg gaggaccgaa ggagctaacc gcttttttgc 4920
acaacatggg ggatcatgta actcgccttg atcgttggga accggagctg aatgaagcca 4980

```
taccaaacga cgagcgtgac accacgatgc ctgtagcaat ggcaacaacg ttgcgcaaac   5040
tattaactgg cgaactactt actctagctt cccggcaaca attaatagac tggatggagg   5100
cggataaagt tgcaggacca cttctgcgct cggcccttcc ggctggctgg tttattgctg   5160
ataaatctgg agccggtgag cgtgggtctc gcggtatcat tgcagcactg gggccagatg   5220
gtaagccctc ccgtatcgta gttatctaca cgacggggag tcaggcaact atggatgaac   5280
gaaatagaca gatcgctgag ataggtgcct cactgattaa gcattggtaa ctgtcagacc   5340
aagtttactc atatatactt tagattgatt taaaacttca tttttaattt aaaaggatct   5400
aggtgaagat cctttttgat aatctcatga ccaaaatccc ttaacgtgag ttttcgttcc   5460
actgagcgtc agaccccgta gaaaagatca aaggatcttc ttgagatcct ttttttctgc   5520
gcgtaatctg ctgcttgcaa acaaaaaaac caccgctacc agcggtggtt tgtttgccgg   5580
atcaagagct accaactctt tttccgaagg taactggctt cagcagagcg cagataccaa   5640
atactgttct tctagtgtag ccgtagttag gccaccactt caagaactct gtagcaccgc   5700
ctacatacct cgctctgcta atcctgttac cagtggctgc tgccagtggc gataagtcgt   5760
gtcttaccgg gttggactca agacgatagt taccggataa ggcgcagcgg tcgggctgaa   5820
cggggggttc gtgcacacag cccagcttgg agcgaacgac ctacaccgaa ctgagatacc   5880
tacagcgtga gctatgagaa agcgccacgc ttcccgaagg gagaaaggcg gacaggtatc   5940
cggtaagcgg cagggtcgga acaggagagc gcacgaggga gcttccaggg ggaaacgcct   6000
ggtatcttta tagtcctgtc gggtttcgcc acctctgact tgagcgtcga tttttgtgat   6060
gctcgtcagg ggggcggagc ctatggaaaa acgccagcaa cgcggccttt ttacggttcc   6120
tggccttttg ctggcctttt gctcacatgt tctttcctgc gttatcccct gattctgtgg   6180
ataaccgtat taccgccttt gagtgagctg ataccgctcg ccgcagccga acgaccgagc   6240
gcagcgagtc agtgagcgag gaagcggaag a                                  6271
```

<210> SEQ ID NO 126
<211> LENGTH: 2793
<212> TYPE: DNA
<213> ORGANISM: Artificial Sequence
<220> FEATURE:
<223> OTHER INFORMATION: OREP

<400> SEQUENCE: 126

```
cacgataaaa caaggtttta aggataagaa aagtcatgag atttatagta aatcttgtga     60
ctttttttat tgaatagtag agagagttcg gaagtataac acgctatatt cttgatattt    120
ttagaatagc aagcattgga tttgtcctga cactttccca aaaattaagg agttattcct    180
taaaccaaaa agattaatgt gggaacaaat ttagtgtatc catttttgaa gggcgcactt    240
atacaccacc aaaatggtgt gtgcgaaatc tttaaaaaag atttatcaaa aagctttttt    300
aaagctggga catttagaaa atcaataatg ttttttgccc aatacgctag tcttaaaatc    360
tgcaaggttg ataactattt agtcccaggt attagaatgg ggcatatata tacaaagtat    420
atatatgcgt aaatatatgt gggactgtgg gaacaaaatt gcgtgctaaa attgtattga    480
aaaggtaatg aaaaggtcat gctttggtat tgctaacgta tagaaaaggt aatgaaaagc    540
tcatggttct ataaaaaaga tgtacccacg aaaataatag gctttgccta tttccccatg    600
taatatgggg gcagttttct cttatgctct ttcttaacat attgaataaa tacaaaatgc    660
agctttgtgg gaataaaaat atttttgttt ttattcttat agttagacaa aattttaatc    720
```

```
tttttgtgc tataacaaga ttaaaatttg tgggaacatt aagaaatatt gttgtcacaa    780
ataaaaagga gagtgggaac aattgctata aaaaacgcag aaattaagat tagagttaca    840
aaagagcaaa aagaattatt taagaaaatt gcaaaagctg aaaatatgag tatgagtgaa    900
tttattattg tgaccacaga atatttagcc agaaaaaaag atgaaaatat gaaatcaaaa    960
gacatgatcg agagaagagc tgcgaagact gaagaaaaaa ttatgaagct aaaaaagaaa   1020
ctaaataaaa acaggtaata tagattacag ttttaagctt gttttcccta tagactagag   1080
taaatatata aatatacctg tcaagggctt ataagcccct ttagggggtg cgtagcaccc   1140
ttgacaggta tatttatata ttttagggtg ccattaaggg aaacaagctt taaaatgcct   1200
ttaaaggcat tttaaaataa ataaaaaaaa gatggttttt accatctttt ttaactcccg   1260
aaagggagtt ctttcttttc ttgatactat acgtaactat ttcgatttgc cctgaaccta   1320
atcaaagcta gataaattca gtattagggc ataaaaaaac ttgctttttc gggtggaaat   1380
ctgtataatt taaattgctt agataaaaat taccaattcc atacgaaagg agcaagtttt   1440
acataaggtt aaagccttat gtgaattctc atttaattac atgaataata ataacacaga   1500
aagtgaagaa ttaaaagagc aaagtcaact attgcttgac aaatgcacaa aaaagaaaaa   1560
gaaaaatcct aaatttagta gttatataga accattagta agcaagaaat tatctgaaag   1620
aataaaggaa tgtggtgact ttttgcagat gttatctgat ttaaaccttg aaaattcgaa   1680
actgcataga gcaagttttt gtggtaacag attttgtcct atgtgtagct ggcgtattgc   1740
ttgtaaggat agtttggaaa tatctattct catggagcat ttacgcaaag aggaaagcaa   1800
agaatttatc tttttgacct taacaactcc aaatgtgaaa ggtgcggacc ttgataattc   1860
cataaaagca tacaataaag catttaaaaa gttaatggaa cgcaaagagg tcaagagcat   1920
agtaaaaggc tacataagaa agctagaagt aacctataat ttggacaaga gttccaaatc   1980
atataatact tatcacccac atttccatgt ggtactagca gtcaatagaa gttactttaa   2040
aaagcaaaat ctatatataa accatcatag atggcttagt ttgtggcaag agtcaactgg   2100
tgattattcg ataactcaag ttgatgtaag aaaggctaaa attaacgatt ataaagaggt   2160
ttatgagctt gctaagtatt cggctaagga ttccgactat ttaatcaata gagaagtgtt   2220
tacggtattc tacaaatctt taaagggtaa acaggtactt gtatttagtg gattatttaa   2280
agacgctcat aaaatgtata agaatggaga gctagatctg tataagaagt tggatactat   2340
cgaatatgct tatatggtaa gttataactg gcttaaaaag aagtatgata cttcaaatat   2400
tagagaatta actgaggaag aaaagcagaa attcaataaa aatttaatcg aagatgtgga   2460
tattgagtag gtgggattat atctcacctt ttttattgtc ttttcatgtt gaaattttga   2520
cgcttaatgc atgaagtatt gacaagttta aaaattacgg tttttaatcc ttagttgatt   2580
agcaggatta tggccggaat gctccgtcca gtcctgttaa ggaattaaaa ttccctaaaa   2640
cccttggcta tgatttatag cgagaatcgt caattaaaaa tttaataggt gctatgaaag   2700
tcgattaata attaatttta aaatgcaata tgaaacataa ttacaagaat ttgactttta   2760
atacaagaat tgatatcata gttacattaa tac                                2793
```

<210> SEQ ID NO 127
<211> LENGTH: 2793
<212> TYPE: DNA
<213> ORGANISM: Clostridium beijerinckii

<400> SEQUENCE: 127

```
cacgataaaa caaggtttta aggataagaa aagtcatgag atttatagta aatcttgtga     60
```

```
cttttttat tgaatagtag agagagttcg gaagtataac acgctatatt cttgatattt    120
ttagaatagc aagcattgga tttgtcctga cactttccca aaaattaagg agttattcct    180
taaaccaaaa agattaatgt gggaacaaat ttagtgtatc catttttgaa gggcgcactt    240
atacaccacc aaaatggtgt gtgcgaaatc tttaaaaaag atttatcaaa aagctttttt    300
aaagctggga catttagaaa atcaataatg ttttttgccc aatacgctag tcttaaaatc    360
tgcaaggttg ataactattt agtcccaggt attagaatgg ggcatatata tacaaagtat    420
atatatgcgt aaatatatgt gggactgtgg gaacaaaatt gcgtgctaaa attgtattga    480
aaaggtaatg aaaaggtcat gctttggtat tgctaacgta tagaaaaggt aatgaaaagc    540
tcatggttct ataaaaaaga tgtacccacg aaaataatag gctttgccta tttccccatg    600
taatatgggg gcagttttct cttatgctct ttcttaacat attgaataaa tacaaaatgc    660
agctttgtgg gaataaaaat atttttgttt ttattcttat agttagacaa aattttaatc    720
ttttttgtgc tataacaaga ttaaaatttg tgggaacatt aagaaatatt gttgtcacaa    780
ataaaaagga gagtgggaac aattgctata aaaaacgcag aaattaagat tagagttaca    840
aaagagcaaa aagaattatt taagaaaatt gcaaaagctg aaaatatgag tatgagtgaa    900
tttattattg tgaccacaga atatttagcc agaaaaaaag atgaaaatat gaaatcaaaa    960
gacatgatcg agagaagagc tgcgaagact gaagaaaaaa ttatgaagct aaaaaagaaa   1020
ctaaataaaa acaggtaata tagattacag ttttaagctt gttttcccta tagactagag   1080
taaatatata aatatacctg tcaagggctt ataagcccct ttagggggtg cgtagcaccc   1140
ttgacaggta tatttatata ttttagggtg ccattaaggg aaacaagctt taaaatgcct   1200
ttaaaggcat tttaaaataa ataaaaaaaa gatggttttt accatctttt ttaactcccg   1260
aaagggagtt ctttcttttc ttgatactat acgtaactat ttcgatttgc cctgaaccta   1320
atcaaagcta gataaattca gtattagggc ataaaaaaac ttgctttttc gggtggaaat   1380
ctgtataatt taaattgctt agataaaaat taccaattcc atacgaaagg agcaagtttt   1440
acataaggtt aaagccttat gtgaattctc atttaattac atgaataata ataacacaga   1500
aagtgaagaa ttaaaagagc aaagtcaact attgcttgac aaatgcacaa aaaagaaaaa   1560
gaaaaatcct aaatttagta gttatataga accattagta agcaagaaat tatctgaaag   1620
aataaaggaa tgtggtgact ttttgcagat gttatctgat ttaaaccttg aaaattcgaa   1680
actgcataga gcaagttttt gtggtaacag attttgtcct atgtgtagct ggcgtattgc   1740
ttgtaaggat agtttggaaa tatctattct catggagcat ttacgcaaag aggaaagcaa   1800
agaatttatc tttttgacct taacaactcc aaatgtgaaa ggtgcggacc ttgataattc   1860
cataaaagca tacaataaag catttaaaaa gttaatggaa cgcaaagagg tcaagagcat   1920
agtaaaaggc tacataagaa agctagaagt aacctataat ttggacaaga gttccaaatc   1980
atataatact tatcacccac atttccatgt ggtactagca gtcaatagaa gttactttaa   2040
aaagcaaaat ctatatataa accatcatag atggcttagt ttgtggcaag agtcaactgg   2100
tgattattcg ataactcaag ttgatgtaag aaaggctaaa attaacgatt ataaagaggt   2160
ttatgagctt gctaagtatt cggctaagga ttccgactat ttaatcaata gagaagtgtt   2220
tacggtattc tacaaatctt taaagggtaa acaggtactt gtatttagtg gattatttaa   2280
agacgctcat aaaatgtata agaatggaga gctagatctg tataagaagt tggatactat   2340
cgaatatgct tatatggtaa gttataactg gcttaaaaag aagtatgata cttcaaatat   2400
```

```
tagagaatta actgaggaag aaaagcagaa attcaataaa aatttaatcg aagatgtgga   2460

tattgagtag gtgggattat atctcacctt ttttattgtc ttttcatgtt gaaattttga   2520

cgcttaatgc atgaagtatt gacaagttta aaaattacgg tttttaatcc ttagttgatt   2580

agcaggatta tggccggaat gctccgtcca gtcctgttaa ggaattaaaa ttccctaaaa   2640

cccttggcta tgatttatag cgagaatcgt caattaaaaa tttaataggt gctatgaaag   2700

tcgattaata attaatttta aaatgcaata tgaaacataa ttacaagaat ttgactttta   2760

atacaagaat tgatatcata gttacattaa tac                                2793
```

```
<210> SEQ ID NO 128
<211> LENGTH: 329
<212> TYPE: PRT
<213> ORGANISM: Clostridium beijerinckii

<400> SEQUENCE: 128

Met Asn Asn Asn Asn Thr Glu Ser Glu Glu Leu Lys Glu Gln Ser Gln
1               5                   10                  15

Leu Leu Leu Asp Lys Cys Thr Lys Lys Lys Lys Lys Asn Pro Lys Phe
            20                  25                  30

Ser Ser Tyr Ile Glu Pro Leu Val Ser Lys Lys Leu Ser Glu Arg Ile
        35                  40                  45

Lys Glu Cys Gly Asp Phe Leu Gln Met Leu Ser Asp Leu Asn Leu Glu
    50                  55                  60

Asn Ser Lys Leu His Arg Ala Ser Phe Cys Gly Asn Arg Phe Cys Pro
65                  70                  75                  80

Met Cys Ser Trp Arg Ile Ala Cys Lys Asp Ser Leu Glu Ile Ser Ile
                85                  90                  95

Leu Met Glu His Leu Arg Lys Glu Glu Ser Lys Glu Phe Ile Phe Leu
            100                 105                 110

Thr Leu Thr Thr Pro Asn Val Lys Gly Ala Asp Leu Asp Asn Ser Ile
        115                 120                 125

Lys Ala Tyr Asn Lys Ala Phe Lys Lys Leu Met Glu Arg Lys Glu Val
    130                 135                 140

Lys Ser Ile Val Lys Gly Tyr Ile Arg Lys Leu Glu Val Thr Tyr Asn
145                 150                 155                 160

Leu Asp Lys Ser Ser Lys Ser Tyr Asn Thr Tyr His Pro His Phe His
                165                 170                 175

Val Val Leu Ala Val Asn Arg Ser Tyr Phe Lys Lys Gln Asn Leu Tyr
            180                 185                 190

Ile Asn His His Arg Trp Leu Ser Leu Trp Gln Glu Ser Thr Gly Asp
        195                 200                 205

Tyr Ser Ile Thr Gln Val Asp Val Arg Lys Ala Lys Ile Asn Asp Tyr
    210                 215                 220

Lys Glu Val Tyr Glu Leu Ala Lys Tyr Ser Ala Lys Asp Ser Asp Tyr
225                 230                 235                 240

Leu Ile Asn Arg Glu Val Phe Thr Val Phe Tyr Lys Ser Leu Lys Gly
                245                 250                 255

Lys Gln Val Leu Val Phe Ser Gly Leu Phe Lys Asp Ala His Lys Met
            260                 265                 270

Tyr Lys Asn Gly Glu Leu Asp Leu Tyr Lys Lys Leu Asp Thr Ile Glu
        275                 280                 285

Tyr Ala Tyr Met Val Ser Tyr Asn Trp Leu Lys Lys Lys Tyr Asp Thr
    290                 295                 300
```

```
Ser Asn Ile Arg Glu Leu Thr Glu Glu Glu Lys Gln Lys Phe Asn Lys
305                 310                 315                 320

Asn Leu Ile Glu Asp Val Asp Ile Glu
                325


<210> SEQ ID NO 129
<211> LENGTH: 256
<212> TYPE: PRT
<213> ORGANISM: Artificial Sequence
<220> FEATURE:
<223> OTHER INFORMATION: Consensus COG5655

<400> SEQUENCE: 129

Met Cys Gln Lys Arg Ser Asp Tyr Ser Asp Glu Lys Ala Trp Leu Lys
1               5                   10                  15

Asp Lys Ser Lys Asp Gly Lys Val Glu Pro Trp Arg Glu Lys Lys Glu
            20                  25                  30

Ala Asn Val Lys Tyr Phe Glu Leu Leu Lys Ile Leu Met Phe Lys Lys
        35                  40                  45

Ala Glu Arg Val Tyr Arg Cys Asn Glu Leu Leu Glu Leu Gln Lys Val
    50                  55                  60

Asn Glu Thr Gly Glu Asn Lys Leu Cys Pro Asn Trp Phe Cys Lys Ser
65                  70                  75                  80

Leu Leu Cys Pro Met Cys Asn Trp Arg Lys Pro Met Lys Ser Asp Leu
                85                  90                  95

Gln Asp Gly Leu Tyr Val Lys Arg Val Ile Ser Tyr Gly Pro Leu Leu
            100                 105                 110

Lys Trp Lys His Leu Lys Leu Asn Leu Lys Asn Val Glu Asp Gly Asp
        115                 120                 125

Leu Leu Asn Lys Ser Leu Asp Glu Met Ala Leu Gly Phe Lys Arg Thr
    130                 135                 140

Met Gly Phe Lys Lys Ile Ala Lys Asn Phe Val Gly Phe Met Lys Ser
145                 150                 155                 160

Thr Glu Ile Thr Tyr Asn Glu Lys Asp Asn Ser Tyr Asn Gln His Met
                165                 170                 175

His Val Leu Phe Cys Ser Glu Gln Thr Tyr Phe Lys Asn Phe Ile Asn
            180                 185                 190

Asn Thr Pro Gln Glu Phe Trp Asn Lys Arg Trp Ser Lys Ala Met Lys
        195                 200                 205

Leu Asp Tyr Asp Pro Gln Val Met Lys Leu Trp Thr Met Tyr Lys Lys
    210                 215                 220

Glu Ile Lys Asn Tyr Ile Gln Thr Ala Leu Gln Glu Thr Ala Lys Tyr
225                 230                 235                 240

Asp Val Lys Asp Met Asp Ser Ala Thr Ile Asp Asp Glu Lys Ser Leu
                245                 250                 255


<210> SEQ ID NO 130
<211> LENGTH: 768
<212> TYPE: DNA
<213> ORGANISM: Enterococcus faecalis

<400> SEQUENCE: 130

gtgaggagga tatatttgaa tacatacgaa caaattaata aagtgaaaaa aatacttcgg      60

aaacatttaa aaaataacct tattggtact tacatgtttg gatcaggagt tgagagtgga     120

ctaaaaccaa atagtgatct tgacttttta gtcgtcgtat ctgaaccatt gacagatcaa     180

agtaaagaaa tacttataca aaaaattaga cctatttcaa agaaaatagg agataaaagc     240
```

aacttacgat atattgaatt aacaattatt attcagcaag aaatggtacc gtggaatcat 300
cctcccaaac aagaatttat ttatggagaa tggttacaag agctttatga acaaggatac 360
attcctcaga aggaattaaa ttcagattta accataatgc tttaccaagc aaaacgaaaa 420
aataaaagaa tatacggaaa ttatgactta gaggaattac tacctgatat tccattttct 480
gatgtgagaa gagccattat ggattcgtca gaggaattaa tagataatta tcaggatgat 540
gaaaccaact ctatattaac tttatgccgt atgattttaa ctatggacac gggtaaaatc 600
ataccaaaag atattgcggg aaatgcagtg gctgaatctt ctccattaga acatagggag 660
agaattttgt tagcagttcg tagttatctt ggagagaata ttgaatggac taatgaaaat 720
gtaaatttaa ctataaacta tttaaataac agattaaaaa aattataa 768

<210> SEQ ID NO 131
<211> LENGTH: 738
<212> TYPE: DNA
<213> ORGANISM: Clostridium difficile

<400> SEQUENCE: 131
atgaacaaaa atataaaata ttctcaaaac tttttaacga gtgaaaaagt actcaaccaa 60
ataataaaac aattgaattt aaaagaaacc gataccgttt acgaaattgg aacaggtaaa 120
gggcatttaa cgacgaaact ggctaaaata agtaaacagg taacgtctat tgaattagac 180
agtcatctat tcaacttatc gtcagaaaaa ttaaaactga atactcgtgt cactttaatt 240
caccaagata ttctacagtt tcaattccct aacaaacaga ggtataaaat tgttgggagt 300
attccttacc atttaagcac acaaattatt aaaaaagtgg tttttgaaag ccatgcgtct 360
gacatctatc tgattgttga agaaggattc tacaagcgta ccttggatat tcaccgaaca 420
ctagggttgc tcttgcacac tcaagtctcg attcagcaat tgcttaagct gccagcggaa 480
tgctttcatc ctaaaccaaa agtaaacagt gtcttaataa aacttacccg ccataccaca 540
gatgttccag ataaatattg gaagctatat acgtactttg tttcaaaatg ggtcaatcga 600
gaatatcgtc aactgtttac taaaaatcag tttcatcaag caatgaaaca cgccaaagta 660
aacaatttaa gtaccgttac ttatgagcaa gtattgtcta tttttaatag ttatctatta 720
tttaacggga ggaaataa 738

<210> SEQ ID NO 132
<211> LENGTH: 3792
<212> TYPE: DNA
<213> ORGANISM: Artificial Sequence
<220> FEATURE:
<223> OTHER INFORMATION: Optimized Mad7 CDS for B. subtilis

<400> SEQUENCE: 132
atgaacaacg gcacaaataa ttttcagaac tttattggca tttcatcatt gcagaaaacg 60
ttaagaaatg ctttaattcc gacggaaaca acgcaacagt ttattgttaa aaacggaatt 120
attaaagaag atgaattaag aggcgaaaac agacagattt taaaagatat tatggatgac 180
tactacagag gatttatttc tgaaacatta tcatctattg atgacattga ttggacaagc 240
ttatttgaaa aaatggaaat tcagttaaaa aatggtgata ataaagatac attaattaaa 300
gaacagacag aatatagaaa agcaattcat aaaaaatttg cgaacgacga tagatttaaa 360
aacatgttta gcgccaaatt aatttcagac attttacctg aatttgttat tcataacaat 420
aattattcag catcagaaaa agaagaaaaa acacaggtga ttaaattgtt ttcaagattt 480

```
gcgacaagct ttaaagatta ctttaaaaac agagcaaatt gcttttcagc ggacgatatt    540
tcatcaagca gctgccatag aattgttaac gacaatgcag aaattttttt ttcaaatgcg    600
ttagtttaca gaagaattgt aaaatcatta agcaatgacg atattaacaa aatttcaggc    660
gatatgaaag attcattaaa agaaatgtca ttagaagaaa tttattctta cgaaaaatat    720
ggcgaattta ttacacagga aggcattagc ttttataatg atatttgtgg caaagtgaat    780
tcttttatga acttatattg tcagaaaaat aaagaaaaca aaaatttata caaacttcag    840
aaacttcata aacagattct gtgcattgcg gacacaagct atgaagttcc gtataaattt    900
gaatcagacg aagaagtgta ccaatcagtt aacggctttc ttgataacat tagcagcaaa    960
catattgttg aaagattaag aaaaattggc gataactata acggctacaa cttagataaa   1020
atttatattg tgtccaaatt ttacgaaagc gttagccaaa aaacatacag agactgggaa   1080
acaattaata cagccttaga aattcattac aataatattt tgccgggtaa cggtaaatca   1140
aaagccgaca aagtaaaaaa agcggttaaa aatgatttac agaaatccat tacagaaatt   1200
aatgaactgg tgtcaaacta taaattatgc tcagacgaca acattaaagc ggaaacatat   1260
attcatgaaa ttagccatat tttgaataac tttgaagcac aggaattgaa atacaatccg   1320
gaaattcatc tggttgaatc cgaattaaaa gcgtcagaac ttaaaaacgt gttagacgtg   1380
attatgaatg cgtttcattg gtgttcagtt tttatgacag aagaacttgt tgataaagac   1440
aacaattttt atgcggaatt agaagaaatt tacgatgaaa tttatccggt aatttcatta   1500
tacaacttag ttagaaacta cgttacacag aaaccgtaca gcacgaaaaa aattaaattg   1560
aactttggaa ttccgacgtt agcagacggt tggtcaaaat ccaaagaata ttctaataac   1620
gctattattt taatgagaga caatttatat tatttaggca tttttaatgc gaaaaataaa   1680
ccggacaaaa aaattattga aggtaatacg tcagaaaata aaggtgacta caaaaaaatg   1740
atttataatt tgttaccggg tccgaacaaa atgattccga aagttttttt gagcagcaaa   1800
acgggcgtgg aaacgtataa accgagcgcc tatattctgg aaggctataa acagaataaa   1860
catattaaat cttcaaaaga ctttgatatt acattttgtc atgatttaat tgactacttt   1920
aaaaactgta ttgcaattca tccggaatgg aaaaactttg gttttgattt tagcgacaca   1980
tcaacatatg aagacatttc cggcttttat agagaagtag aattacaagg ttacaaaatt   2040
gattggacat acattagcga aaaagacatt gatttattac aggaaaaagg tcaattatat   2100
ttatttcaga tttataacaa agatttttca aaaaaatcaa caggcaatga caaccttcat   2160
acaatgtact taaaaaatct tttttcagaa gaaaatctta aagatattgt tttaaaactt   2220
aacggcgaag cggaaatttt ttttagaaaa agcagcatta aaaacccgat tattcataaa   2280
aaaggctcaa ttttagttaa cagaacatac gaagcagaag aaaaagacca gtttggcaac   2340
attcaaattg tgagaaaaaa tattccggaa aacatttatc aggaattata caaatacttt   2400
aacgataaaa gcgacaaaga attatctgat gaagcagcca aattaaaaaa tgtagtggga   2460
catcatgaag cagcgacgaa tattgttaaa gactatagat acacgtatga taaatacttt   2520
cttcatatgc ctattacgat taattttaaa gccaataaaa cgggttttat taatgataga   2580
attttacagt atattgctaa agaaaaagac ttacatgtga ttggcattga tagaggcgaa   2640
agaaacttaa tttacgtgtc cgtgattgat acatgtggta atattgttga acagaaaagc   2700
tttaacattg taaacggcta cgactatcag attaaattaa aacaacagga aggcgctaga   2760
cagattgcga gaaaagaatg gaaagaaatt ggtaaaatta aagaaattaa agaaggctac   2820
ttaagcttag taattcatga aatttctaaa atggtaatta aatacaatgc aattattgcg   2880
```

```
atggaagatt tgtcttatgg ttttaaaaaa ggcagattta aagttgaaag acaagtttac   2940

cagaaatttg aaacaatgtt aattaataaa ttaaactatt tagtatttaa agatatttca   3000

attacagaaa atggcggttt attaaaaggt tatcagttaa catacattcc tgataaactt   3060

aaaaacgtgg gtcatcagtg cggctgcatt ttttatgtgc ctgctgcata cacgagcaaa   3120

attgatccga caacaggctt tgtgaatatt tttaaattta aagacttaac agtggacgca   3180

aaaagagaat ttattaaaaa atttgactca attagatatg actcagaaaa aaatttattt   3240

tgctttacat ttgactacaa taactttatt acgcaaaaca cggttatgag caaatcatca   3300

tggtcagtgt atacatacgg cgtgagaatt aaaagaagat ttgtgaacgg cagattttca   3360

aacgaatcag atacaattga cattacaaaa gatatggaaa aaacgttgga aatgacggac   3420

attaactgga gagatggcca tgatcttaga caagacatta ttgattatga aattgttcag   3480

catatttttg aaatttttag attaacagtg caaatgagaa actccttgtc tgaattagaa   3540

gacagagatt acgatagatt aatttcacct gtattaaacg aaaataacat tttttatgac   3600

agcgcgaaag cgggcgatgc acttcctaaa gatgccgatg caaatggtgc gtattgtatt   3660

gcattaaaag gcttatatga aattaaacaa attacagaaa attggaaaga agatggtaaa   3720

ttttcaagag ataaattaaa aattagcaat aaagattggt ttgactttat tcagaataaa   3780

agatatttat aa                                                       3792
```

```
<210> SEQ ID NO 133
<211> LENGTH: 10469
<212> TYPE: DNA
<213> ORGANISM: Artificial Sequence
<220> FEATURE:
<223> OTHER INFORMATION: pCas9cond

<400> SEQUENCE: 133

catggataaa aagtacagta ttggtctaga cataggaact aactctgttg ggtgggctgt     60

tataacagat gaatataaag ttccatcaaa aaaatttaaa gtattaggaa acactgatag    120

acattcaata aaaaaaaact tgataggtgc tttattattc gattcaggag agactgctga    180

agctacacgt ttaaaaagaa cagctagacg tagatataca agaagaaaaa ataggatatg    240

ttatcttcaa gaaattttta gtaatgaaat ggcaaaagtt gatgattcat tctttcacag    300

actagaagaa agtttcttag ttgaagaaga taagaagcat gaaagacacc ctatttttgg    360

taatatcgta gatgaagtag catatcatga gaagtatcca actatctatc atttaagaaa    420

gaaattagtt gattctacag ataaagctga tctgagatta atatatttag ctttagctca    480

tatgattaaa tttagaggac atttttttaat agaaggtgat ttaaacccag acaacagcga    540

tgtagataaa ttatttatcc aattagttca aacttataat caattattcg aagagaatcc    600

aattaatgca agtggtgtag acgctaaggc tatattatca gctagattat caaaatctag    660

aagattagaa aatctaatag ctcaacttcc tggagaaaag aaaaatggac tttttgggaa    720

cctaatagct ctctcactcg gactaacacc aaattttaaa agcaattttg atcttgctga    780

agacgcaaag ttacaactat caaaggatac atacgatgat gatttagata atttgttagc    840

tcaaataggt gatcaatatg ctgatttgtt tcttgcagca aaaaacttaa gtgatgcaat    900

tttactatca gatatactta gagtaaatac agaaataaca aaggctcctt tatcagcaag    960

tatgattaaa cgatatgatg agcatcatca agatttaaca ttattaaagg cacttgtaag   1020

acaacaatta ccagaaaaat ataaagaaat tttctttgat caatctaaaa atggatatgc   1080
```

```
tggatatata gacggtggag caagtcaaga agagttttat aaatttataa agcctatttt   1140
agaaaaaatg gatggaactg aagaattact tgttaaactt aacagagaag atttacttag   1200
aaaacaaaga acttttgata atggttcaat tcctcaccaa attcatttag gagaattaca   1260
tgctatacta agaagacaag aagattttta tccatttctt aaagataata gagaaaaaat   1320
tgaaaaaatt ttaactttta gaataccata ttatgtagga ccacttgcaa ggggaaattc   1380
aagatttgca tggatgacta gaaaatcaga agaaactata accccgtgga attttgaaga   1440
agtagtagat aaaggagcta gtgctcaatc atttatagaa agaatgacaa attttgataa   1500
gaatcttcct aacgaaaagg ttttgccaaa gcatagcctt ctttatgagt attttacagt   1560
ttataatgag cttactaaag taaaatacgt tacagaagga atgagaaaac cagcattttt   1620
gtctggtgaa caaaagaaag caatagtaga cctattattt aaaacaaata ggaaggttac   1680
cgtaaagcaa cttaaagaag attacttcaa aaaaattgaa tgctttgata gtgttgaaat   1740
atcaggagtt gaagatagat ttaatgcttc acttggtaca tatcacgatc tcttaaaaat   1800
tataaaagat aaggattttt tagataatga agaaaatgaa gatattcttg aagatatagt   1860
attaacattg acacttttg aagatagaga aatgatagaa gaaagattaa aaacatatgc   1920
acatcttttt gatgataagg ttatgaagca acttaaaaga agaagatata caggttgggg   1980
acgtttgtca agaaagctaa ttaatggtat tagagataaa caatcaggaa agactattct   2040
cgattttctt aaatcagatg gatttgctaa tagaaacttt atgcaattaa ttcatgatga   2100
ttctcttact ttcaaagagg atattcaaaa ggctcaagtt tctggacaag gcgatagctt   2160
acacgaacac attgctaacc ttgcagggag ccccgctatc aaaaaaggaa ttttacaaac   2220
agttaaagtt gtagatgaac ttgttaaagt tatgggaaga cacaaacctg agaatatagt   2280
tatagaaatg gccagagaaa atcaaacaac acaaaaagga caaaaaaatt ctagagagag   2340
aatgaagaga attgaagaag gaataaaaga gctaggatca caaatattaa aagaacatcc   2400
agttgaaaat actcaattgc aaaatgaaaa gttatatttg tattacttac aaaatggaag   2460
agatatgtat gttgatcaag aactcgatat taatagatta agtgactatg atgttgatca   2520
tattgttcct caatcatttt taaaagatga ttcaatcgat aacaaagtat taactagatc   2580
agataaaaat agaggaaagt cagataatgt accatctgaa gaagttgtta aaaaaatgaa   2640
gaactattgg agacaacttt taaatgcaaa gctaattaca caaagaaaat ttgacaattt   2700
aacaaaagca gaaagaggag gattaagcga attagacaaa gctggattta taaaaagaca   2760
acttgttgag acaagacaaa taactaagca tgttgctcaa atacttgatt caagaatgaa   2820
tacaaaatat gatgaaaatg ataaattaat cagagaagta aaagtaataa cattaaagtc   2880
aaaattagta tcagatttca gaaaggattt tcaattttac aaagttcgtg aaataaataa   2940
ctatcatcat gctcatgatg catacttaaa tgctgttgta ggaactgctc ttattaagaa   3000
atatcctaaa ctagaaagcg aatttgttta tggagattat aaagtttatg atgtgcgcaa   3060
aatgatcgcg aaatccgaac aagaaatcgg taaggctaca gcaaaatatt tcttttatag   3120
taatataatg aattttttta agacagaaat aactttggct aatggtgaaa tcagaaaaag   3180
accacttatc gaaacaaatg gagagacagg agaaatagta tgggataaag gaagagattt   3240
tgctactgtt agaaaagtac taagtatgcc acaagtaaat atcgtaaaga aaactgaagt   3300
tcaaactgga ggtttctcta aggaatcaat tttacctaag agaaattcag ataagttaat   3360
tgcaaggaaa aaagattggg acccaaaaaa atacggtggt tttgatagtc caacagttgc   3420
ctatagtgtt cttgtagtag cgaaagttga gaaaggtaag tcaaaaaagt tgaaaagcgt   3480
```

```
aaaagaactt cttggtatca caattatgga aagatcttca tttgaaaaaa atccaattga   3540
ctttttagaa gctaagggtt ataaagaagt taaaaaggat ttaatcataa aactaccaaa   3600
gtatagtcta tttgaactcg aaaacggaag aaaacgaatg ctcgctagcg caggagaact   3660
tcaaaaagga aatgaacttg cgctgccatc aaagtatgta aatttcttat atttagcttc   3720
tcattatgag aaattaaaag gatcaccaga ggataatgaa caaaagcaac tatttgtaga   3780
acaacacaaa cattatttag atgaaataat agaacaaata tctgaatttt ctaaaagagt   3840
tatacttgcc gacgcaaatc tagataaggt gctttcagcg tataataaac acagagataa   3900
accaataaga gaacaagcag aaaacattat ccatcttttt acattaacta atcttggtgc   3960
accagctgca tttaagtact ttgatacaac aatagataga aaaagataca catctactaa   4020
agaagtatta gacgcaactt taatacatca atctattaca gggctttatg aaacaagaat   4080
tgatttaagt caactaggcg gagattaagt cgacaaagta ttgttaaaaa taactctgta   4140
gaattataaa ttagttctac agagttattt tttgacccgg gtaccgagct cgaattcgta   4200
atcatggtca tagctgtttc ctgtgtgaaa ttgttatccg ctcacaattc cacacaacat   4260
acgagccgga agcataaagt gtaaagcctg gggtgcctaa tgagtgagct aactcacatt   4320
aattgcgttg cgctcactgc ccgctttcca gtcgggaaac ctgtcgtgcc agctgcatta   4380
atgaatcggc caacgcgcgg ggagaggcgg tttgcgtatt gggcgctctt ccgcttcctc   4440
gctcactgac tcgctgcgct cggtcgttcg gctgcggcga gcggtatcag ctcactcaaa   4500
ggcggtaata cggttatcca cagaatcagg ggataacgca ggaaagaaca tgtgagcaaa   4560
aggccagcaa aaggccagga accgtaaaaa ggccgcgttg ctggcgtttt tccataggct   4620
ccgcccccct gacgagcatc acaaaaatcg acgctcaagt cagaggtggc gaaacccgac   4680
aggactataa agataccagg cgtttccccc tggaagctcc ctcgtgcgct ctcctgttcc   4740
gaccctgccg cttaccggat acctgtccgc ctttctccct tcgggaagcg tggcgctttc   4800
tcatagctca cgctgtaggt atctcagttc ggtgtaggtc gttcgctcca agctgggctg   4860
tgtgcacgaa ccccccgttc agcccgaccg ctgcgcctta tccggtaact atcgtcttga   4920
gtccaacccg gtaagacacg acttatcgcc actggcagca gccactggta acaggattag   4980
cagagcgagg tatgtaggcg gtgctacaga gttcttgaag tggtggccta actacggcta   5040
cactagaagg acagtatttg gtatctgcgc tctgctgaag ccagttacct tcggaaaaag   5100
agttggtagc tcttgatccg gcaaacaaac caccgctggt agcggtggtt tttttgtttg   5160
caagcagcag attacgcgca gaaaaaaagg atctcaagaa gatcctttga tcttttctac   5220
ggggtctgac gctcagtgga acgaaaactc acgttaaggg attttggtca tgagattatc   5280
aaaaaggatc ttcacctaga tccttttaaa ttaaaaatga agttttaaat caatctaaag   5340
tatatatgag taaacttggt ctgacagtta ccaatgctta atcagtgagg cacctatctc   5400
agcgatctgt ctatttcgtt catccatagt tgcctgactc cccgtcgtgt agataactac   5460
gatacgggag ggcttaccat ctggccccag tgctgcaatg ataccgcgag acccacgctc   5520
accggctcca gatttatcag caataaacca gccagccgga agggccgagc gcagaagtgg   5580
tcctgcaact ttatccgcct ccatccagtc tattaattgt tgccgggaag ctagagtaag   5640
tagttcgcca gttaatagtt tgcgcaacgt tgttgccatt gctacaggca tcgtggtgtc   5700
acgctcgtcg tttggtatgg cttcattcag ctccggttcc caacgatcaa ggcgagttac   5760
atgatccccc atgttgtgca aaaaagcggt tagctccttc ggtcctccga tcgttgtcag   5820
```

aagtaagttg gccgcagtgt tatcactcat ggttatggca gcactgcata attctcttac 5880
tgtcatgcca tccgtaagat gcttttctgt gactggtgag tactcaacca agtcattctg 5940
agaatagtgt atgcggcgac cgagttgctc ttgcccggcg tcaatacggg ataataccgc 6000
gccacatagc agaactttaa aagtgctcat cattggaaaa cgttcttcgg ggcgaaaact 6060
ctcaaggatc ttaccgctgt tgagatccag ttcgatgtaa cccactcgtg cacccaactg 6120
atcttcagca tcttttactt tcaccagcgt ttctgggtga gcaaaaacag gaaggcaaaa 6180
tgccgcaaaa aagggaataa gggcgacacg gaaatgttga atactcatac tcttcctttt 6240
tcaatattat tgaagcattt atcagggtta ttgtctcatg agcggataca tatttgaatg 6300
tatttagaaa aataaacaaa taggggttcc gcgcacattt ccccgaaaag tgccacctga 6360
ctgccgggcc tcttgcggga tcaaaagaaa aacgaaatga tacaccaatc agtgcaaaaa 6420
aagatataat gggagataag acggttcgtg ttcgtgctga cttgcaccat atcataaaaa 6480
tcgaaacagc aaagaatggc ggaaacgtaa aagaagttat ggaaataaga cttagaagca 6540
aacttaagag tgtgttgata gtgcagtatc ttaaaatttt gtataatagg aattgaagtt 6600
aaattagatg ctaaaaattt gtaattaaga aggagtgatt acatgaacaa aaatataaaa 6660
tattctcaaa actttttaac gagtgaaaaa gtactcaacc aaataataaa acaattgaat 6720
ttaaaagaaa ccgataccgt ttacgaaatt ggaacaggta aagggcattt aacgacgaaa 6780
ctggctaaaa taagtaaaca ggtaacgtct attgaattag acagtcatct attcaactta 6840
tcgtcagaaa aattaaaact gaatactcgt gtcactttaa ttcaccaaga tattctacag 6900
tttcaattcc ctaacaaaca gaggtataaa attgttggga gtattcctta ccatttaagc 6960
acacaaatta ttaaaaaagt ggtttttgaa agccatgcgt ctgacatcta tctgattgtt 7020
gaagaaggat tctacaagcg taccttggat attcaccgaa cactagggtt gctcttgcac 7080
actcaagtct cgattcagca attgcttaag ctgccagcgg aatgctttca tcctaaacca 7140
aaagtaaaca gtgtcttaat aaaacttacc cgccatacca cagatgttcc agataaatat 7200
tggaagctat atacgtactt tgtttcaaaa tgggtcaatc gagaatatcg tcaactgttt 7260
actaaaaatc agtttcatca agcaatgaaa cacgccaaag taaacaattt aagtaccgtt 7320
acttatgagc aagtattgtc tatttttaat agttatctat tatttaacgg gaggaaataa 7380
ttctatgagt ccctaggccc aactaactca acgctagtag tggatttaat cccaaatgag 7440
ccaacagaac cagaaccaga aacagaatca gaacaagtaa cattggattt agaaatggaa 7500
gaagaaaaaa gcaatgactt cgtgtgaata atgcacgaaa tcgttgctta ttttttttta 7560
aaagcggtat actagatata acgaaacaac gaactgaata gaaacgaaaa aagagccatg 7620
acacatttat aaaatgtttg acgacatttt ataaatgcat agcccgataa gattgccaaa 7680
ccaacgctta tcagttagtc agatgaactc ttccctcgta agaagttatt taattaactt 7740
tgtttgaaga cggtatataa ccgtactatc attatatagg gaaatcagag agttttcaag 7800
tatctaagct actgaattta agaattgtta agcaatcaat cggaaatcgt ttgattgctt 7860
tttttgtatt catttataga aggtggagtt tgtatgaatc atgatgaatg taaaacttat 7920
ataaaaaata gtttattgga gataagaaaa ttagcaaata tctatacact agaaacgttt 7980
aagaaagagt tagaaaagag aaatatctac ttagaaacaa aatcagataa gtatttttct 8040
tcggaggggg aagattatat atataagtta atagaaaata acaaaataat ttattcgatt 8100
agtggaaaaa aattgactta taaaggaaaa aaatcttttt caaaacatgc aatattgaaa 8160
cagttgaatg aaaaagcaaa ccaagttaat taaacaacct attttatagg atttatagga 8220

```
aaggagaaca gctgaatgaa tatccctttt gttgtagaaa ctgtgcttca tgacggcttg   8280
ttaaagtaca aatttaaaaa tagtaaaatt cgctcaatca ctaccaagcc aggtaaaagc   8340
aaaggggcta tttttgcgta tcgctcaaaa tcaagcatga ttggcggtcg tggtgttgtt   8400
ctgacttccg aggaagcgat tcaagaaaat caagatacat ttacacattg gacacccaac   8460
gtttatcgtt atggaacgta tgcagacgaa aaccgttcat acacgaaagg acattctgaa   8520
aacaatttaa gacaaatcaa taccttcttt attgattttg atattcacac ggcaaaagaa   8580
actatttcag caagcgatat tttaacaacc gctattgatt taggttttat gcctactatg   8640
attatcaaat ctgataaagg ttatcaagca tattttgttt tagaaacgcc agtctatgtg   8700
acttcaaaat cagaatttaa atctgtcaaa gcagccaaaa taatttcgca aaatatccga   8760
gaatattttg gaaagtcttt gccagttgat ctaacgtgta atcattttgg tattgctcgc   8820
ataccaagaa cggacaatgt agaatttttt gatcctaatt accgttattc tttcaaagaa   8880
tggcaagatt ggtctttcaa acaaacagat aataagggct ttactcgttc aagtctaacg   8940
gttttaagcg gtacagaagg caaaaaacaa gtagatgaac cctggtttaa tctcttattg   9000
cacgaaacga aattttcagg agaaaagggt ttaatagggc gtaataacgt catgtttacc   9060
ctctctttag cctactttag ttcaggctat tcaatcgaaa cgtgcgaata taatatgttt   9120
gagtttaata atcgattaga tcaaccctta gaagaaaaag aagtaatcaa aattgttaga   9180
agtgcctatt cagaaaacta tcaaggggct aatagggaat acattaccat tctttgcaaa   9240
gcttgggtat caagtgattt aaccagtaaa gatttatttg tccgtcaagg gtggtttaaa   9300
ttcaagaaaa aaagaagcga acgtcaacgt gttcatttgt cagaatggaa agaagattta   9360
atggcttata ttagcgaaaa aagcgatgta tacaagcctt atttagtgac gaccaaaaaa   9420
gagattagag aagtgctagg cattcctgaa cggacattag ataaattgct gaaggtactg   9480
aaggcgaatc aggaaatttt ctttaagatt aaaccaggaa gaaatggtgg cattcaactt   9540
gctagtgtta aatcattgtt gctatcgatc attaaagtaa aaaaagaaga aaaagaaagc   9600
tatataaagg cgctgacaaa ttcttttgac ttagagcata cattcattca agagacttta   9660
aacaagctag cagaacgccc taaaacggac acacaactcg atttgtttag ctatgataca   9720
ggctgaaaat aaaacccgca ctatgccatt acatttatat ctatgatacg tgtttgtttt   9780
ttctttgctg tttagcgaat gattagcaga aatatacaga gtaagatttt aattaattat   9840
tagggggaga aggagagagt agcccgaaaa cttttagttg gcttggactg aacgaagtga   9900
gggaaaggct actaaaacgt cgaggggcag tgagagcgaa gcgaacactt gatttttttaa   9960
ttttctatct tttataggtc attagagtat acttatttgt cctataaact atttagcagc  10020
ataatagatt tattgaatag gtcatttaag ttgagcatat tagaggagga aaatcttgga  10080
gaaatatttg aagaacccga ttacatggat tggattagtt cttgtggtta cgtggttttt  10140
aactaaaagt agtgaatttt tgatttttgg tgtgtgtgtc ttgttgttag tatttgctag  10200
tcaaagtgat taaatagaat tctagcgcca ttcgccattc aggctgcgca actgttggga  10260
agggcgatcg gtgcgggcct cttcgctatt acgccagctg gcgaaagggg gatgtgctgc  10320
aaggcgatta agttgggtaa cgccagggtt ttcccagtca cgacgttgta aaacgacggc  10380
cagtgccaag cttgcatgcc tgcaggcctc gagtatattg ataaaaataa taatagtggg  10440
tataattaag ttgttaggag gttagttac                                    10469
```

<210> SEQ ID NO 134

<211> LENGTH: 8559
<212> TYPE: DNA
<213> ORGANISM: Artificial Sequence
<220> FEATURE:
<223> OTHER INFORMATION: pMAD7

<400> SEQUENCE: 134
tcgagtccct atcagtgata gattgaaact ctatcattga tagagtataa tatctttgtt 60
cattagagcg ataaacttga atttgagagg gaacttagat gaacaacggc acaaataatt 120
ttcagaactt catagggata tcaagtttgc agaaaacgtt aagaaatgct ttaataccca 180
cggaaaccac gcaacagttc atagttaaga acggaataat taaagaagat gagttaagag 240
gcgagaacag acagatttta aaagatataa tggatgacta ctacagagga ttcatatctg 300
agactttaag ttctattgat gacatagatt ggactagctt attcgaaaaa atggaaattc 360
agttaaaaaa tggtgataat aaagatacct taattaagga acagacagag tatagaaaag 420
caatacataa aaaatttgcg aacgacgata gatttaagaa catgtttagc gccaaattaa 480
ttagtgacat attacctgaa tttgttatac acaacaataa ttattcggca tcagagaaag 540
aggaaaaaac ccaggtgata aaattgtttt cgagatttgc gactagcttt aaagattact 600
tcaagaacag agcaaattgc ttttcagcgg acgatatttc atcaagcagc tgccatagaa 660
tagttaacga caatgcagag atattctttt caaatgcgtt agtttacaga agaatagtaa 720
aatcgttaag caatgacgat ataaacaaaa tttcgggcga tatgaaagat tcattaaaag 780
aaatgagttt agaagaaata tattcttacg agaagtatgg ggaatttatt acccaggaag 840
gcattagctt ctataatgat atatgtggga aagtgaattc ttttatgaac ttatattgtc 900
agaaaaataa agaaaacaaa aatttataca aacttcagaa acttcacaaa cagattctat 960
gcattgcgga cactagctat gaggttccgt ataaatttga aagtgacgag gaagtgtacc 1020
aatcagttaa cggcttcctt gataacatta gcagcaaaca tatagttgaa agattaagaa 1080
aaataggcga taactataac ggctacaact tagataaaat ttatatagtg tccaaatttt 1140
acgagagcgt tagccaaaaa acctacagag actgggaaac aattaatacc gccttagaaa 1200
ttcattacaa taatatattg ccgggtaacg gtaaaagtaa agccgacaaa gtaaaaaaag 1260
cggttaagaa tgatttacag aaatccataa ccgaaataaa tgaactagtg tcaaactata 1320
agttatgcag tgacgacaac ataaaagcgg agacttatat acatgagatt agccatatat 1380
tgaataactt tgaagcacag gaattgaaat acaatccgga aattcaccta gttgaatccg 1440
agttaaaagc gagtgagctt aaaaacgtgt tagacgtgat aatgaatgcg tttcattggt 1500
gttcggtttt tatgactgag gaacttgttg ataaagacaa caatttttat gcggaattag 1560
aggagattta cgatgaaatt tatccagtaa ttagtttata caacttagtt agaaactacg 1620
ttacccagaa accgtacagc acgaaaaaga ttaaattgaa ctttggaata ccgacgttag 1680
cagacggttg gtcaaagtcc aaagagtatt ctaataacgc tataatatta atgagagaca 1740
atttatatta tttaggcata tttaatgcga agaataaacc ggacaagaag attatagagg 1800
gtaatacgtc agaaaataag ggtgactaca aaaagatgat ttataatttg ttaccgggtc 1860
ccaacaaaat gataccgaaa gttttcttga gcagcaagac gggggtggaa acgtataaac 1920
cgagcgccta tatactagag gggtataaac agaataaaca tataaagtct tcaaaagact 1980
ttgatataac tttctgtcat gatttaatag actacttcaa aaactgtatt gcaattcatc 2040
ccgagtggaa aaacttcggt tttgatttta gcgacaccag tacttatgaa gacatttccg 2100
ggttttatag agaggtagag ttacaaggtt acaagattga ttggacatac attagcgaaa 2160

```
aagacattga tttattacag gaaaaaggtc aattatattt attccagata tataacaaag   2220
atttttcgaa aaaatcaacc gggaatgaca accttcacac catgtactta aaaaatcttt   2280
tctcagaaga aaatcttaag gatatagttt taaaacttaa cggcgaagcg gaaatattct   2340
tcaggaagag cagcataaag aacccaataa ttcataaaaa aggctcgatt ttagttaaca   2400
gaacctacga agcagaagaa aaagaccagt ttggcaacat tcaaattgtg agaaaaaata   2460
ttccggaaaa catttatcag gagttataca aatacttcaa cgataaaagc gacaaagagt   2520
tatctgatga agcagccaaa ttaaagaatg tagtgggaca ccacgaggca gcgacgaata   2580
tagttaagga ctatagatac acgtatgata aatacttcct tcatatgcct attacgataa   2640
atttcaaagc caataaaacg ggttttatta atgataggat attacagtat atagctaaag   2700
aaaaagactt acatgtgata ggcattgata gaggcgagag aaacttaata tacgtgtccg   2760
tgattgatac ttgtggtaat atagttgaac agaaaagctt taacattgta aacggctacg   2820
actatcagat aaaattaaaa caacaggagg gcgctagaca gattgcgaga aaagaatgga   2880
aagaaattgg taaaattaaa gagataaaag agggctactt aagcttagta atacacgaga   2940
tatctaaaat ggtaataaaa tacaatgcaa ttatagcgat ggaggatttg tcttatggtt   3000
ttaaaaaagg gagatttaag gttgaaagac aagtttacca gaaatttgaa accatgttaa   3060
taaataaatt aaactattta gtatttaaag atatttcgat taccgagaat ggcggtttat   3120
taaaaggtta tcagttaaca tacattcctg ataaacttaa aaacgtgggt catcagtgcg   3180
gctgcatttt ttatgtgcct gctgcataca cgagcaaaat tgatccgacc accggctttg   3240
tgaatatatt taaatttaaa gacttaacag tggacgcaaa aagagaattc attaaaaaat   3300
ttgactcaat tagatatgac agtgaaaaaa atttattctg ctttacattt gactacaata   3360
actttattac gcaaaacacg gttatgagca aatcatcgtg gagtgtgtat acatacggcg   3420
tgagaataaa aagaagattt gtgaacggca gattctcaaa cgaaagtgat accattgaca   3480
taaccaaaga tatggagaaa acgttggaaa tgacggacat taactggaga gatggccacg   3540
atcttagaca agacattata gattatgaaa ttgttcagca catattcgaa attttcagat   3600
taacagtgca aatgagaaac tccttgtctg aattagagga cagagattac gatagattaa   3660
tttcacctgt attaaacgaa aataacattt tttatgacag cgcgaaagcg gggatgcac    3720
ttcctaagga tgccgatgca aatggtgcgt attgtattgc attaaaaggg ttatatgaaa   3780
ttaaacaaat taccgaaaat tggaaagaag atggtaaatt ttcgagagat aaattaaaaa   3840
taagcaataa agattggttc gactttatac agaataagag atatttataa gtcgacaaag   3900
tattgttaaa aataactctg tagaattata aattagttct acagagttat tttttgaccc   3960
gggtatattg ataaaaataa taatagtggg tataattaag ttgttaggag gttagttaga   4020
atgatgtcaa gattagataa aagtaaagtg attaacagcg cattagagct gcttaatgag   4080
gtcggaatcg aaggtttaac aacccgtaaa ctcgcccaga agctaggtgt agagcagcct   4140
acattgtatt ggcatgtaaa aaataagcgg gctttgctcg acgccttagc cattgagatg   4200
ttagataggc accatactca cttttgccct ttagaagggg aaagctggca agatttttta   4260
cgtaataacg ctaaaagttt tagatgtgct ttactaagtc atcgcgatgg agcaaaagta   4320
catttaggta cacggcctac agaaaaacag tatgaaactc tcgaaaatca attagccttt   4380
ttatgccaac aaggtttttc actagagaat gcattatatg cactcagcgc tgtggggcat   4440
tttactttag gttgcgtatt ggaagatcaa gagcatcaag tcgctaaaga agaaagggaa   4500
```

```
acacctacta ctgatagtat gccgccatta ttacgacaag ctatcgaatt atttgatcac   4560
caaggtgcag agccagcctt cttattcggc cttgaattga tcatatgcgg attagaaaaa   4620
caacttaaat gtgaaagtgg gtcttaaaag cagcataacc tttttccgtg atggtaactt   4680
cacggtaacc aagatgtcga gttgagctcg aattcgtaat catggtcata gctgtttcct   4740
gtgtgaaatt gttatccgct cacaattcca cacaacatac gagccggaag cataaagtgt   4800
aaagcctggg gtgcctaatg agtgagctaa ctcacattaa ttgcgttgcg ctcactgccc   4860
gctttccagt cgggaaacct gtcgtgccag ctgcattaat gaatcggcca acgcgcgggg   4920
agaggcggtt tgcgtattgg gcgctcttcc gcttcctcgc tcactgactc gctgcgctcg   4980
gtcgttcggc tgcggcgagc ggtatcagct cactcaaagg cggtaatacg gttatccaca   5040
gaatcagggg ataacgcagg aaagaacatg tgagcaaaag gccagcaaaa ggccaggaac   5100
cgtaaaaagg ccgcgttgct ggcgtttttc cataggctcc gcccccctga cgagcatcac   5160
aaaaatcgac gctcaagtca gaggtggcga aacccgacag gactataaag ataccaggcg   5220
tttccccctg gaagctccct cgtgcgctct cctgttccga ccctgccgct taccggatac   5280
ctgtccgcct ttctcccttc gggaagcgtg gcgctttctc atagctcacg ctgtaggtat   5340
ctcagttcgg tgtaggtcgt tcgctccaag ctgggctgtg tgcacgaacc ccccgttcag   5400
cccgaccgct gcgccttatc cggtaactat cgtcttgagt ccaacccggt aagacacgac   5460
ttatcgccac tggcagcagc cactggtaac aggattagca gagcgaggta tgtaggcggt   5520
gctacagagt tcttgaagtg gtggcctaac tacggctaca ctagaaggac agtatttggt   5580
atctgcgctc tgctgaagcc agttaccttc ggaaaaagag ttggtagctc ttgatccggc   5640
aaacaaacca ccgctggtag cggtggtttt tttgtttgca agcagcagat tacgcgcaga   5700
aaaaaaggat ctcaagaaga tcctttgatc ttttctacgg ggtctgacgc tcagtggaac   5760
gaaaactcac gttaagggat tttggtcatg agattatcaa aaaggatctt cacctagatc   5820
cttttaaatt aaaaatgaag ttttaaatca atctaaagta tatatgagta aacttggtct   5880
gacagttacc aggtccactg ccgggcctct tgcgggatca aagaaaaaac gaaatgatac   5940
accaatcagt gcaaaaaaag atataatggg agataagacg gttcgtgttc gtgctgactt   6000
gcaccatatc ataaaaatcg aaacagcaaa gaatggcgga aacgtaaaag aagttatgga   6060
aataagactt agaagcaaac ttaagagtgt gttgatagtg cagtatctta aaattttgta   6120
taataggaat tgaagttaaa ttagatgcta aaaatttgta attaagaagg agtgattaca   6180
tgaacaaaaa tataaaatat tctcaaaact ttttaacgag tgaaaaagta ctcaaccaaa   6240
taataaaaca attgaattta aaagaaaccg ataccgttta cgaaattgga acaggtaaag   6300
ggcatttaac gacgaaactg gctaaaataa gtaaacaggt aacgtctatt gaattagaca   6360
gtcatctatt caacttatcg tcagaaaaat taaaactgaa tactcgtgtc actttaattc   6420
accaagatat tctacagttt caattcccta acaaacagag gtataaaatt gttgggagta   6480
ttccttacca tttaagcaca caaattatta aaaaagtggt ttttgaaagc catgcgtctg   6540
acatctatct gattgttgaa gaaggattct acaagcgtac cttggatatt caccgaacac   6600
tagggttgct cttgcacact caagtctcga ttcagcaatt gcttaagctg ccagcggaat   6660
gctttcatcc taaaccaaaa gtaaacagtg tcttaataaa acttacccgc cataccacag   6720
atgttccaga taaatattgg aagctatata cgtactttgt ttcaaaatgg gtcaatcgag   6780
aatatcgtca actgtttact aaaaatcagt ttcatcaagc aatgaaacac gccaaagtaa   6840
acaatttaag taccgttact tatgagcaag tattgtctat ttttaatagt tatctattat   6900
```

-continued

```
ttaacgggag gaaataattc tatgagtccc taggcaggcc tccgccatta tttttttgaa   6960
caattgacaa ttcatttctt attttttatt aagtgatagt caaaaggcat aacagtgctg   7020
aatagaaaga aatttacaga aaagaaaatt atagaattta gtatgattaa ttatactcat   7080
ttatgaatgt ttaattgaat acaaaaaaaa atacttgtta tgtattcaat tacgggttaa   7140
aatatagaca agttgaaaaa tttaataaaa aaataagtcc tcagctctta tatattaagc   7200
taccaactta gtatataagc caaaacttaa atgtgctacc aacacatcaa gccgttagag   7260
aactctatct atagcaatat ttcaaatgta ccgacataca agagaaacat taactatata   7320
tattcaattt atgagattat cttaacagat ataaatgtaa attgcaataa gtaagattta   7380
gaagtttata gcctttgtgt attggaagca gtacgcaaag gctttttat ttgataaaaa   7440
ttagaagtat atttattttt tcataattaa tttatgaaaa tgaaaggggg tgagcaaagt   7500
gacagaggaa agcagtatct tatcaaataa caaggtatta gcaatatcat tattgacttt   7560
agcagtaaac attatgactt ttatagtgct tgtagctaag tagtacgaaa gggggagctt   7620
taaaaagctc cttggaatac atagaattca taaattaatt tatgaaaaga agggcgtata   7680
tgaaaacttg taaaaattgc aaagagttta ttaaagatac tgaaatatgc aaaatacatt   7740
cgttgatgat tcatgataaa acagtagcaa cctattgcag taaatacaat gagtcaagat   7800
gtttacataa agggaaagtc caatgtatta attgttcaaa gatgaaccga tatggatggt   7860
gtgccataaa aatgagatgt tttacagagg aagaacagaa aaaagaacgt acatgcatta   7920
aatattatgc aaggagcttt aaaaaagctc atgtaaagaa gagtaaaaag aaaaaataat   7980
ttatttatta atttaatatt gagagtgccg acacagtatg cactaaaaaa tatatctgtg   8040
gtgtagtgag ccgatacaaa aggatagtca ctcgcatttt cataatacat cttatgttat   8100
gattatgtgt cggtgggact tcacgacgaa aacccacaat aaaaaaagag ttcggggtag   8160
ggttaagcat agttgaggca actaaacaat caagctagga tatgcagtag cagaccgtaa   8220
ggtcgttgtt taggtgtgtt gtaatacata cgctattaag atgtaaaaat acggatacca   8280
atgaagggaa aagtataatt tttggatgta gtttgtttgt tcatctatgg gcaaactacg   8340
tccaaagccg tttccaaatc tgctaaaaag tatatccttt ctaaaatcaa agtcaagtat   8400
gaaatcataa ataaagttta attttgaagt tattatgata ttatgttttt ctattaaaat   8460
aaattaagta tatagaatag tttaataata gtatatactt aatgtgataa gtgtctgaca   8520
gtgtcacaga aaggatgatt gttatggatt ataagcggc                          8559
```

OPTIMIZED GENETIC TOOL FOR MODIFYING BACTERIA

CROSS-REFERENCE TO RELATED APPLICATION

This application is the U.S. national stage application of International Patent Application No. PCT/FR2020/050853, filed May 22, 2020.

REFERENCE TO SEQUENCE LISTING

The Sequence Listing for this application is labeled "Seq-List.txt" which was created on Oct. 29, 2021 and is 358 KB. The entire content of the sequence listing is incorporated herein by reference in its entirety.

The present invention relates to the transformation and genetic modification of bacteria, in particular belonging to the phylum Firmicutes, typically of solventogenic bacteria, for example of the genus *Clostridium*, preferably of bacteria possessing in the wild state both a bacterial chromosome and at least one DNA molecule (or natural plasmid) different from the chromosomal DNA. It thus relates to methods, tools and kits allowing such genetic modification, involving in particular a nucleic acid sequence used to facilitate transformation of the bacterium, said sequence comprising i) all or part of the sequence SEQ ID NO: 126 and ii) a sequence allowing the modification of the genetic material of a bacterium and/or expression within said bacterium of a DNA sequence partially or totally absent from the genetic material present within the wild-type version of said bacterium. The description also relates to the genetically modified bacteria obtained and uses thereof, in particular for producing a solvent, preferably on an industrial scale.

TECHNOLOGICAL BACKGROUND

The genus *Clostridium* contains Gram-positive, strictly anaerobic and spore-forming bacteria, belonging to the phylum Firmicutes. The Clostridia are an important group for the scientific community for several reasons. The first is that a certain number of serious diseases (e.g. tetanus, botulism) are due to infections with pathogenic members of this family (John & Wood, 1986; Gonzales et al., 2014). The second is the possibility of using so-called acidogenic or solventogenic strains in biotechnology (Moon et al., 2016). These non-pathogenic Clostridia possess naturally the capacity to convert a wide variety of sugars to produce chemical species of interest, and more particularly acetone, butanol, and ethanol (John & Wood, 1986) in a process called ABE fermentation. Similarly, IBE fermentation is possible in certain particular species, during which acetone is reduced in a variable proportion to isopropanol (Chen et al., 1986, George et al., 1983) owing to the presence, in the genome of these strains, of genes encoding secondary alcohol dehydrogenases (s-ADH; Ismael et al., 1993, Hiu et al., 1987).

The solventogenic species of Clostridia have important phenotypic similarities, which made them difficult to classify before the emergence of modern sequencing techniques (Rogers et al., 2006). With the possibility of sequencing the complete genomes of these bacteria, it is now possible to classify this bacterial genus in 4 major species: *C. acetobutylicum, C. saccharoperbutylacetonicum, C. saccharobutylicum* and *C. beijerinckii*. A recent publication proposes, after comparative analysis of the complete genomes of 30 strains, classifying these solventogenic Clostridia in 4 main clades (FIG. 1).

In particular, these groups separate the species *C. acetobutylicum* and *C. beijerinckii* with as respective references *C. acetobutylicum* ATCC 824 (also designated DSM 792 or LMG 5710) and *C. beijerinckii* NCIMB 8052. The latter are model strains for investigating ABE fermentation.

The strains *Clostridium* naturally capable of effecting an IBE fermentation are few in number and mainly belong to the species *Clostridium beijerinckii* (cf. Zhang et al., 2018, Table 1). These strains are typically selected from the strains *C. butylicum* LMD 27.6, *C. aurantibutylicum* NCIB 10659, *C. beijerinckii* LMD 27.6, *C. beijerinckii* VPI2968, *C. beijerinckii* NRRL B-593, *C. beijerinckii* ATCC 6014, *C. beijerinckii* McClung 3081, *C. isopropylicum* IAM 19239, *C. beijerinckii* DSM 6423, C. sp. A1424, *C. beijerinckii optinoii*, and *C. beijerinckii* BGS1.

Although they have been used in industry for more than a century, knowledge about the bacteria, in particular belonging to the genus *Clostridium*, has for a long time been limited by the difficulties encountered in modifying them genetically. Various genetic tools have been developed in recent years for optimizing the strains of this genus, the latest generation being based on the use of CRISPR (Clustered Regularly Interspaced Short Palindromic Repeats)/Cas (CRISPR-associated protein) technology. This method is based on the use of an enzyme called nuclease (typically a nuclease of the Cas type in the case of the CRISPR/Cas genetic tool, such as the protein Cas9 of *Streptococcus pyogenes*), which, guided by a molecule of RNA, will perform a double-strand break within a DNA molecule (target sequence of interest). The sequence of the guide RNA (gRNA) will determine the cutting site of the nuclease, thus endowing it with very high specificity (FIG. 1).

Since a double-strand break within an essential DNA molecule is lethal for an organism, the survival of the latter will depend on its ability for repairing it (cf. for example Cui & Bikard, 2016). In the bacteria of the genus *Clostridium*, repair of a double-strand break depends on a homologous recombination mechanism requiring an intact copy of the cleaved sequence. By supplying the bacterium with a DNA fragment allowing this repair to be effected while modifying the original sequence, it is possible to force the microorganism to integrate the desired changes in its genome. The modification carried out should no longer allow targeting of the genomic DNA by the Cas9-gRNA ribonucleoprotein complex, via the modification of the target sequence or of the PAM site (FIG. 2).

Various approaches have been described for trying to make this genetic tool functional in bacteria of the genus *Clostridium*. These microorganisms are indeed known to be difficult to modify genetically because of their low frequencies of transformation and of homologous recombination. Some approaches are based on the use of Cas9, expressed constitutively in *C. beijerinckii* and *C. ljungdahlii* (Wang et al., 2015; Huang et al., 2016) or under the control of an inducible promoter in *C. beijerinckii, C. saccharoperbutylacetonicum* and *C. authoethanogenum* (Wang et al., 2016; Nagaraju et al., 2016; Wang et al., 2017). Other authors have described the use of a modified version of the nuclease, Cas9n, which performs single-strand breaks, instead of double-strand breaks, within the genome (Xu et al., 2015; Li et al., 2016). This choice is due to the observations according to which the toxicity of Cas9 is too high for it to be used in bacteria of the genus *Clostridium* under the experimental conditions tested. Most of the tools described above are based on the use of a single plasmid. Finally, it is also possible to use endogenous CRISPR/Cas systems when they have been identified in the genome of the microorganism, as for example in *C. pasteurianum* (Pyne et al., 2016).

Unless they use (as in the last case described above) the endogenous machinery of the strain to be modified, the tools based on CRISPR technology have the major drawback of significantly limiting the size of the nucleic acid of interest (and therefore the number of coding sequences or genes) able to be inserted in the bacterial genome (about 1.8 kb at best according to Xu et al., 2015).

The inventors have developed and described a more powerful genetic tool for modifying bacteria, suitable for the bacteria of the genus *Clostridium*, based on the use of two different nucleic acids, typically of two plasmids (WO2017064439, Wasels et al., 2017 and FIG. 3), which solves this problem in particular. In a particular embodiment, the first nucleic acid of this tool allows expression of cas9 and a second nucleic acid, specific to the modification to be effected, contains one or more gRNA expression cassettes as well as a repair matrix allowing replacement of a portion of the bacterial DNA targeted by Cas9 with a sequence of interest. The toxicity of the system is limited by placing cas9 and/or the gRNA expression cassette(s) under the control of inducible promoters. The inventors have recently improved this tool, giving a very significant increase in transformation efficiency and therefore obtaining, in useful number and quantity (in particular in a context of selection of robust strains for production on an industrial scale), genetically modified bacteria of interest (cf. FR 18/548356). In this improved tool at least one nucleic acid comprises a sequence encoding an anti-CRISPR protein ("acr"), placed under the control of an inducible promoter. This anti-CRISPR protein makes it possible to repress the activity of the DNA endonuclease/guide RNA complex. The expression of the protein is regulated to allow its expression only during the step of transformation of the bacterium.

The inventors have also very recently succeeded in genetically modifying bacteria comprising, in the wild state, a gene endowing the bacterium with resistance to one or more antibiotics in order to make them sensitive to said antibiotic(s), making it easier to use their genetic tool based on the use of at least two nucleic acids. They have thus succeeded in genetically modifying the strain *C. beijerinckii* DSM 6423, which produces isopropanol naturally. They have in particular succeeded in removing, from this strain, a natural plasmid that is not essential for the strain, identified in the present description as "pNF2" (cf. FR18/73492).

The inventors then discovered, and disclose for the first time in the context of the present invention, that removal of this plasmid pNF2 makes it possible to obtain a bacterium *C. beijerinckii* DSM 6423 for which the efficiency of introduction of genetic material (i.e. of transformation) is increased by a factor between about $10^1$ and $5\times10^3$. As explained below, the inventors have also succeeded in improving, again very significantly, the genetic tool based on the use of at least two nucleic acids, by using a part of the plasmid pNF2 in order to design particular nucleic acids bearing a sequence making it possible to modify the genetic material of a bacterium and/or express, in a bacterium, a DNA sequence that is absent from the genetic material present in the wild-type version of said bacterium. These nucleic acids and new tools spectacularly improve the transformation efficiency of the bacteria, in particular the transformation efficiency of bacteria previously depleted of the natural plasmid or plasmids they contain in the wild state. The present invention thus facilitates very advantageously the transformation efficiency and therefore the exploitation of the bacteria, in particular on an industrial scale.

SUMMARY OF THE INVENTION

The inventors describe, in the context of the present invention and for the first time, a nucleic acid (also identified as nucleic acid "OPT" in the present text) facilitating the transformation of bacteria (by improving the maintenance, within said bacteria, of all of the genetic material introduced). The nucleic acid OPT comprises i) all or part of the sequence SEQ ID NO: 126 and ii) a sequence allowing modification of the genetic material of a bacterium and/or expression, in said bacterium, of a DNA sequence partially or totally absent from the genetic material present in the wild-type version of said bacterium. The sequence SEQ ID NO: 126 is also identified in the present text as nucleic acid "OREP".

The inventors have succeeded in improving the frequencies of transformation of a nucleic acid within the bacterium *C. beijerinckii* DSM 6423 in particular by suppressing the sequence OREP within said bacterium and advantageously using all or part of this sequence OREP for constructing nucleic acids and/or genetic tools allowing modification of the genetic material of a bacterium and/or expression, in said bacterium, of a DNA sequence partially or totally absent from the genetic material present in the wild-type version of said bacterium.

The sequence OREP comprises a nucleotide sequence (SEQ ID NO: 127) encoding a protein involved in the replication of a nucleic acid OPT of interest. This protein involved in the replication is also identified in the present text as protein "REP" (SEQ ID NO: 128—"MNNNNTE-SEELKEQSQLLLDKCTKKKKNPKFSSYIEPLVSKKL-SERIKECGDFLQMLSDLNLE NSK-LHRASFCGNRFCPMCSWRIACKDSLEISILMEHLRKE ESKEFIFLTLTTPNVKGADLDNSIKA YNKAFKKLMERKEVK-SIVKGYIRKLEVTYNLDKSSKSYNTYHPHFHVV-LAVNRSYFKKQNLYIN HHRWLSLWQESTGDYSITQVDVRKAKINDYKEV-YELAKYSAKDSDYLINREVFTVFYKSLKGK QVLVFSGLFKDAHKMYKNGELD-LYKKLDTIEYAYMVSYNWLKKKYDTSNIRE-LTEEEKQKFNK NLIEDVDIE"). The protein REP has a conserved domain in the Firmicutes, called "COG 5655" (Plasmid rolling circle replication initiator protein REP), of sequence SEQ ID NO: 129.

A genetic tool is also described allowing optimized transformation and then modification by homologous recombination, of the genetic material of a bacterium and/or expression, in said bacterium, of a DNA sequence partially or totally absent from the material of a bacterium belonging to the phylum Firmicutes, for example of a bacterium of the genus *Clostridium*, of the genus *Bacillus* or of the genus *Lactobacillus* (Hidalgo-Cantabrana, C. et al.; Yadav, R. et al).

In a particular embodiment, the tool for modification by homologous recombination is typically characterized i) in that it comprises at least:

- a "first" nucleic acid encoding at least one DNA endonuclease, for example the enzyme Cas9, wherein the sequence encoding the DNA endonuclease is placed under the control of a promoter, and
- at least one "second" nucleic acid containing a repair matrix allowing, by a mechanism of homologous recombination, the replacement of a portion of the bacterial DNA targeted by the endonuclease with a sequence of interest, wherein ii) at least one of said nucleic acids further encodes one or more guide RNAs (gRNA) or wherein the genetic tool further comprises one or more guide RNAs, each guide RNA comprising an RNA structure for fixation to the DNA endonuclease and a complementary sequence of the targeted portion of the bacterial DNA, and preferably iii) wherein at least one of said nucleic acids further comprises a sequence encoding an anti-CRISPR protein placed under the control of an inducible promoter, or wherein the genetic tool further comprises a third nucleic acid encoding an anti-CRISPR protein placed under the control of an inducible promoter.

In particular, a genetic tool of this kind is described comprising at least:

- a "first" nucleic acid encoding at least one DNA endonuclease, wherein the sequence encoding the DNA endonuclease is placed under the control of a promoter, and
- "another" nucleic acid comprising, or consisting of, a sequence of "nucleic acid OREP", i.e. comprising, or consisting of, i) all or part of the sequence SEQ ID NO: 126 and ii) a sequence allowing modification of the genetic material of a bacterium and/or expression, in said bacterium, of a DNA sequence partially or totally absent from the genetic material present in the wild-type version of said bacterium.

In a particular embodiment the "second nucleic acid containing a repair matrix" as described above comprises this "other nucleic acid".

The inventors also describe a method for transforming, and preferably for modifying genetically, for example by homologous recombination, a bacterium belonging to the phylum Firmicutes, for example a bacterium of the genus *Clostridium*, of the genus *Bacillus* or of the genus *Lactobacillus*, typically a solventogenic bacterium, as well as the bacterium or bacteria obtained (transformed and typically modified genetically) using said method. This method advantageously comprises a step of transformation of the bacterium by introducing, into said bacterium, all or part of a genetic tool as described in the present text, in particular a nucleic acid ("nucleic acid OREP") comprising, or consisting of, i) all or part of the sequence SEQ ID NO: 126 and ii) a sequence allowing modification of the genetic material of a bacterium and/or expression, in said bacterium, of a DNA sequence partially or totally absent from the genetic material present in the wild-type version of said bacterium.

In a particular embodiment, this method advantageously comprises the following steps:

a) introducing, into the bacterium, a genetic tool as described in the present text, preferably in the presence of an agent for inducing expression of the anti-CRISPR protein, and b) culturing the transformed bacterium obtained at the end of step a) on a medium not containing the agent for inducing expression of the anti-CRISPR protein, and typically allowing expression of the DNA endonuclease/gRNA ribonucleoprotein complex, for example Cas9/gRNA.

The inventors also describe a kit for transforming, and preferably genetically modifying, a bacterium belonging to the phylum Firmicutes, for example a bacterium of the genus *Clostridium*, of the genus *Bacillus* or of the genus *Lactobacillus*, or for producing at least one solvent, for example a mixture of solvents, using such a bacterium. This kit preferably comprises a nucleic acid as described in the present text and an inducer suitable for the inducible promoter of the expression of the selected anti-CRISPR protein used in the genetic tool as described in the present text. In a particular embodiment, the kit comprises all or part of the elements of a genetic tool as described in the present text.

The use is also described of a nucleic acid or of a genetic tool, disclosed for the first time in the present text, for transforming and optionally genetically modifying a bacterium belonging to the phylum Firmicutes, for example a bacterium of the genus *Clostridium*, of the genus *Bacillus* or of the genus *Lactobacillus*, preferably a bacterium possessing, in the wild state, both a bacterial chromosome and at least one DNA molecule different from the chromosomal DNA (typically a natural plasmid).

There is also described for the first time in the present text, the use of a nucleic acid, of a genetic tool, of a method for transforming and preferably genetically modifying such a bacterium, the bacterium obtained by a method of this kind and/or a kit, to allow production, preferably on an industrial scale, of a solvent or of a mixture of solvents, preferably acetone, butanol, ethanol, isopropanol or a mixture thereof, typically an isopropanol/butanol, butanol/ethanol or isopropanol/ethanol mixture.

DETAILED DESCRIPTION OF THE INVENTION

Although used in industry for more than a century, knowledge about the solventogenic bacteria, in particular belonging to the genus *Clostridium*, is limited by the difficulties encountered in modifying them genetically. For example, the bacteria of the genus *Clostridium* that produce isopropanol naturally, typically possessing in their genome a gene adh encoding a primary/secondary alcohol dehydrogenase, which allows reduction of acetone to isopropanol, differ both genetically and functionally from the bacteria capable of ABE fermentation in the natural state.

The inventors succeeded, advantageously, in the context of the present invention, in transforming and genetically modifying a bacterium of the genus *Clostridium* that produces isopropanol naturally, the bacterium *C. beijerinckii* DSM 6423, as well as the reference strain *C. acetobutylicum* DSM 792.

Some of the work described in the experimental section was carried out in a strain capable of IBE fermentation, i.e. the strain *C. beijerinckii* DSM 6423, whose genome and an analysis of the transcriptome were described recently by the inventors (Mate de Gerando et al., 2018).

During assembly of the genome of this strain, the inventors discovered in particular, in addition to the chromosome, the presence of mobile genetic elements (accession number PRJEB11626—https://www.ebi.ac.uk/ena/data/view/PRJEB11626): two natural plasmids (pNF1 and pNF2) and a linear bacteriophage (Φ6423).

The strain *C. beijerinckii* DSM 6423 is naturally sensitive to erythromycin but resistant to thiamphenicol. Patent application No. FR18/73492 describes a particular strain, the strain *C. beijerinckii* DSM 6423 ΔcatB (also identified in the present text as *C. beijerinckii* IFP962 ΔcatB), made sensitive to thiamphenicol. In a particular embodiment of the invention, the inventors succeeded in removing, from the strain *C. beijerinckii* DSM 6423, its natural plasmid pNF2, and obtained a strain *C. beijerinckii* DSM6423 ΔcatB ΔpNF2 (also identified in the present text as *C. beijerinckii* IFP963 ΔcatB ΔpNF2). This strain is characterized for the first time in the context of the present application. It was registered on 20 Feb. 2019 under the deposition number LMG P-31277 with the BCCM-LMG collection. This strain lacks the gene catB of sequence SEQ ID NO: 18 and the plasmid pNF2 (wild-type). The description also relates to any derived bacterium, clone, mutant or genetically modified version of the latter, typically also lacking the gene catB of sequence SEQ ID NO: 18 and the plasmid pNF2 (wild-type). It also relates more generally to any bacterium possessing, in the wild state, both a bacterial chromosome and at least one DNA molecule different from the chromosomal DNA (identified in the present text as "non-chromosomal (bacterial) DNA" or "natural (bacterial) plasmid"), modified genetically using a nucleic acid and/or genetic tool described in the context of the present invention so that it no longer comprises at least one of its non-chromosomal DNA molecules, typically several of its non-chromosomal DNA molecules (for example two, three or four non-chromosomal DNA molecules), preferably all of its non-chromosomal DNA molecules.

The inventors thus describe, in the present application, a solventogenic bacterium belonging to the phylum Firmicutes, for example a bacterium of the genus *Clostridium*, of the genus *Bacillus* or of the genus *Lactobacillus*, more particularly a bacterium of the genus *Clostridium*, naturally capable (i.e. capable in the wild state) of producing isopropanol, in particular naturally capable of effecting an IBE fermentation, which has been modified genetically and has, owing to this genetic modification, in particular lost at least one natural plasmid (i.e. a plasmid naturally present in the wild-type version of said bacterium), preferably all of its natural plasmids, as well as the tools, in particular the genetic tools, that allowed it to be obtained.

These tools offer the advantage of greatly facilitating the transformation and genetic modification of bacteria. The experiments carried out by the inventors demonstrated the possible use of the tools and more generally of the technology described in the present text for genetically modifying a bacterium, particularly bacteria belonging to the phylum Firmicutes, for example bacteria of the genus *Clostridium*, of the genus *Bacillus* or of the genus *Lactobacillus*, in particular of the bacteria of the genus *Clostridium* capable, in the wild state, of producing isopropanol, in particular of effecting IBE fermentation, in particular those bearing a gene encoding an enzyme responsible for resistance to an antibiotic, in particular a gene encoding an amphenicol-O-acetyltransferase, for example a chloramphenicol-O-acetyltransferase or a thiamphenicol-O-acetyltransferase.

In a particular embodiment, the inventors have thus succeeded in rendering a bacterium sensitive to antibiotics belonging to the class of the amphenicols, said bacterium bearing naturally (bearing in the wild state) a gene encoding an enzyme responsible for resistance to these antibiotics.

Other preferred bacteria contain, in the wild state, both a bacterial chromosome and at least one DNA molecule different from the chromosomal DNA.

Bacteria that are also preferred contain, in the wild state, both a bacterial chromosome and at least one DNA molecule different from the chromosomal DNA, as well as a gene conferring resistance to an antibiotic. In a particular embodiment, this gene encodes an amphenicol-O-acetyltransferase, for example a chloramphenicol-O-acetyltransferase or a thiamphenicol-O-acetyltransferase.

A first object described by the inventors relates to a nucleic acid (identified in the present text as nucleic acid "OPT"), advantageously usable for facilitating the transformation of the bacteria by improving maintenance of all of the genetic material introduced within said bacteria. This nucleic acid OPT comprises i) all or part of the sequence SEQ ID NO: 126 (sequence "OREP") or of a functional variant of the latter and ii) a sequence (also identified in the present text as "sequence of interest") allowing modification of the genetic material of a bacterium and/or expression, in said bacterium, of a DNA sequence partially or totally absent from the genetic material present in the wild-type version of said bacterium.

The sequence OREP (SEQ ID NO: 126) comprises a nucleotide sequence of sequence SEQ ID NO: 127. The sequence SEQ ID NO: 127 preferably comprises a sequence encoding a protein involved in replication of the nucleic acid OPT. A protein considered to be involved in the replication is also identified in the present text as protein "REP" (SEQ ID NO: 128). The protein REP has a conserved domain in Firmicutes, called "COG 5655", of sequence SEQ ID NO: 129.

In a particular embodiment, the nucleic acid OPT comprises a part of the sequence OREP (SEQ ID NO: 126), typically one or more fragments of the sequence OREP, preferably at least the protein encoding the sequence REP (SEQ ID NO: 128) or a variant or functional fragment of the latter (i.e. the fragment involved in replication), typically the sequence SEQ ID NO: 127 or a variant or fragment of the latter encoding the fragment involved, within the protein REP, in the replication of a nucleic acid OPT. The functional fragment of the sequence OREP encoding the fragment, present within the protein REP, involved in the replication of a nucleic acid OPT, comprises the domain of sequence SEQ ID NO: 129. Examples of such fragments of nucleic acid encoding a functional fragment of the protein REP, and variants of the latter, can easily be prepared by a person skilled in the art. A typical example of a variant has a sequence homology with the sequence SEQ ID NO: 127 between 70% and 100%, preferably between 85 and 99%, even more preferably between 95 and 99%, for example 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In a preferred embodiment, the fragment or functional variant of the sequence OREP encodes a protein involved in the replication of the nucleic acid OPT.

In a preferred embodiment of the invention, the fragment or functional variant of the sequence OREP comprises, in addition to the sequence encoding a protein (for example the protein REP) involved in the replication of the nucleic acid OPT (for example a genetic construct of the plasmid type) or of a variant or functional fragment of the latter, a site with 1 to 150 bases, preferably 1 to 15 bases, for example a sequence rich in bases A and T (Rajewska et al), preferably a site present within the plasmid pNF2 of sequence SEQ ID NO: 118, allowing fixation of a protein allowing replication of the nucleic acid OPT.

The sequence of interest allowing modification of the genetic material of the bacterium is typically a modification matrix allowing, for example by a mechanism of homologous recombination, for example according to one of the methods described in the present text, the replacement of a portion of the genetic material of the bacterium with a sequence of interest. The sequence of interest allowing modification of the genetic material of the bacterium may also be a sequence recognizing (binding at least partly), and preferably targeting, i.e. recognizing and allowing cutting, in the genome of a bacterium of interest, of at least one strand i) of a target sequence, ii) of a sequence controlling the transcription of a target sequence, or iii) of a sequence flanking a target sequence.

The sequence of interest allowing expression, within said bacterium, of a DNA sequence partially or totally absent from the genetic material present in the wild-type version of said bacterium, typically allows the bacterium to express one or more proteins that it is incapable of expressing, or expressing in sufficient quantity, in the wild state.

According to a particular aspect, the "nucleic acid OPT" further comprises iii) a sequence encoding a DNA endonuclease, for example Cas9, and/or iv) one or more guide RNAs (gRNA), each gRNA comprising an RNA structure for fixation to the DNA endonuclease and a complementary sequence of the targeted portion of the genetic material of the bacterium.

According to another particular aspect, the "nucleic acid OPT" does not display methylation at the level of the units recognized by the methyltransferases of type Dam and Dcm.

Preferably, the "nucleic acid OPT" is selected from an expression cassette and a vector, and is preferably a plasmid, for example a plasmid having a sequence selected from SEQ ID NO: 119, SEQ ID NO: 123, SEQ ID NO: 124 and SEQ ID NO: 125.

Another object described by the inventors relates to a genetic tool usable for transforming and/or genetically modifying a bacterium of interest, typically a bacterium as described in the present text belonging to the phylum Firmicutes, for example a bacterium of the genus *Clostridium*, of the genus *Bacillus* or of the genus *Lactobacillus*, preferably a bacterium of the genus *Clostridium* naturally capable (i.e. capable in the wild state) of producing isopropanol, in particular naturally capable of effecting an IBE fermentation, preferably a bacterium naturally resistant to one or more antibiotics, such as a bacterium *C. beijerinckii*. A preferred bacterium has, in the wild state, both a bacterial chromosome and at least one DNA molecule different from the chromosomal DNA.

"Bacterium belonging to the phylum Firmicutes" means, in the context of the present description, the bacteria belonging to the class of the Clostridia, Mollicutes, Bacilli or Togobacteria, preferably to the class of the Clostridia or Bacilli.

Particular bacteria belonging to the phylum Firmicutes comprise for example the bacteria of the genus *Clostridium*, the bacteria of the genus *Bacillus* or the bacteria of the genus *Lactobacillus*.

"Bacterium of the genus *Clostridium*" means in particular the species of *Clostridium* said to be of industrial interest, typically the solventogenic or acetogenic bacteria of the genus *Clostridium*. The expression "bacterium of the genus *Clostridium*" includes the wild-type bacteria as well as the strains derived from the latter, modified genetically with the aim of improving their performance (for example overexpressing the genes ctfA, ctfB and adc) without being exposed to the CRISPR system.

"Species of *Clostridium* of industrial interest" means species capable of producing, by fermentation, solvents and acids such as butyric acid or acetic acid, from sugars or monosaccharides, typically starting from sugars comprising 5 carbon atoms such as xylose, arabinose or fructose, from sugars comprising 6 carbon atoms such as glucose or mannose, from polysaccharides such as cellulose or the hemicelluloses and/or from any other carbon source assimilable and usable by bacteria of the genus *Clostridium* (CO, $CO_2$, and methanol for example). Examples of solventogenic bacteria of interest are the bacteria of the genus *Clostridium* that produce acetone, butanol, ethanol and/or isopropanol, such as the strains identified in the literature as "ABE strains" [strains effecting fermentations allowing the production of acetone, butanol and ethanol] and "IBE strains" [strains effecting fermentations allowing the production of isopropanol (by reduction of acetone), butanol and ethanol]. Solventogenic bacteria of the genus *Clostridium* may be selected for example from *C. acetobutylicum, C. cellulolyticum, C. phytofermentans, C. beijerinckii, C. saccharobutylicum, C. saccharoperbutylacetonicum, C. sporogenes, C. butyricum, C. aurantibutyricum* and *C. tyrobutyricum*, preferably from *C. acetobutylicum, C. beijerinckii, C. butyricum, C. tyrobutyricum* and *C. cellulolyticum*, and even more preferably from *C. acetobutylicum* and *C. beijerinckii.*

A bacterium capable of producing isopropanol in the wild state, in particular capable of effecting an IBE fermentation in the wild state, may be for example a bacterium selected from a bacterium *C. beijerinckii*, a bacterium *C. diolis*, a bacterium *C. puniceum*, a bacterium *C. butyricum*, a bacterium *C. saccharoperbutylacetonicum*, a bacterium *C. botulinum*, a bacterium *C. drakei*, a bacterium *C. scatologenes*, a bacterium *C. perfringens*, and a bacterium *C. tunisiense*, preferably a bacterium selected from a bacterium *C. beijerinckii*, a bacterium *C. diolis*, a bacterium *C. puniceum* and a bacterium *C. saccharoperbutylacetonicum*. A particularly preferred bacterium naturally capable of producing isopropanol, in particular capable of effecting an IBE fermentation in the wild state, is a bacterium *C. beijerinckii.*

The acetogenic bacteria of interest are bacteria that produce acids and/or solvents starting from $CO_2$ and $H_2$. Acetogenic bacteria of the genus *Clostridium* may be selected for example from *C. aceticum, C. thermoaceticum, C. ljungdahlii, C. autoethanogenum, C. difficile, C. scatologenes* and *C. carboxydivorans.*

In a particular embodiment, the bacterium of the genus *Clostridium* in question is an "ABE strain", preferably the strain DSM 792 (also designated strain ATCC 824 or else LMG 5710) of *C. acetobutylicum*, or the strain NCIMB 8052 of *C. beijerinckii.*

In another particular embodiment, the bacterium of the genus *Clostridium* in question is an "IBE strain", preferably a subclade of *C. beijerinckii* selected from DSM 6423, LMG 7814, LMG 7815, NRRL B-593, NCCB 27006, or a bacterium *C. aurantibutyricum* DSZM 793 (Georges et al., 1983), and a subclade of said bacterium *C. beijerinckii* or *C. aurantibutyricum* having at least 90%, 95%, 96%, 97%, 98% or 99% identity with the strain DSM 6423. A particularly preferred bacterium *C. beijerinckii*, or a particularly preferred subclade of bacterium *C. beijerinckii*, lacks the plasmid pNF2.

The respective genomes of the subclades LMG 7814, LMG 7815, NRRL B-593 and NCCB 27006 on the one hand, and DSZM 793 on the other hand, have percentage sequence identity of at least 97% with the genome of the subclade DSM 6423.

The inventors have carried out fermentation tests, confirming that the bacteria *C. beijerinckii* of subclade DSM 6423, LMG 7815 and NCCB 27006 are capable of producing isopropanol in the wild state (cf. Table 1).

TABLE 1

| | Concentration (g/L) | | | | | | | | Glucose | |
|---|---|---|---|---|---|---|---|---|---|---|
| | Glucose | Acetic acid | Butyric acid | Ethanol | Acetone | Isopropanol | Butanol | Solvents | consumed (g/L) | Yield |
| Control | 56.19 | 2.1406 | 0 | — | — | — | — | 0.00 | | |
| DSM 6423_A | 31.70 | 0 | 0 | 0.16 | 0.24 | 3.72 | 6.16 | 10.11 | 24.50 | 0.41 |
| DSM 6423_B | 29.08 | 0 | 0 | 0.18 | 0.23 | 4.33 | 6.94 | 11.50 | 27.12 | 0.42 |
| LMG_7815_A | 27.65 | 0.93 | 0.73 | 0.16 | 0.35 | 3.93 | 7.28 | 11.56 | 28.55 | 0.40 |
| LMG_7815_B | 27.50 | 0.63 | 0.73 | 0.18 | 0.29 | 4.30 | 7.63 | 12.22 | 28.70 | 0.43 |
| NCCB 27006_A | 36.28 | 0.98 | 2.59 | 0.13 | 0.15 | 2.83 | 5.22 | 8.19 | 19.91 | 0.41 |
| NCCB 27006_B | 36.10 | 1.08 | 2.27 | 0.13 | 0.15 | 2.70 | 5.17 | 8.02 | 20.10 | 0.40 |

Balance of the fermentation tests of glucose using the strains that produce isopropanol naturally *C. beijerinckii* DSM 6423, LMG 7815 and NCCB 27006. In a particularly preferred embodiment of the invention, the bacterium *C. beijerinckii* is the bacterium of subclade DSM 6423.

In yet another preferred embodiment of the invention, the bacterium *C. beijerinckii* is a strain *C. beijerinckii* IFP963 ΔcatB ΔpNF2 (registered on 20 Feb. 2019 under the deposition number LMG P-31277 with the collection BCCM-LMG, and also identified in the present text as *C. beijerinckii* DSM 6423 ΔcatB ΔpNF2), or a genetically modified version of the latter. The bacterium *C. beijerinckii* IFP963 ΔcatB ΔpNF2, or said genetically modified version of the latter, lacks the gene catB of sequence SEQ ID NO: 18 and the plasmid pNF2.

"Bacterium of the genus *Bacillus*" means in particular *B. amyloliquefaciens, B. thurigiensis, B. coagulans, B. cereus, B. anthracia* or else *B. subtilis.*

During recent experiments, the inventors observed that removal of the natural plasmid pNF2 has a significant advantage for the introduction and maintenance of additional genetic elements, natural or synthetic (for example expression cassette(s) or plasmid expression vector(s)). The strain IFP963 ΔcatB ΔpNF2 can thus be transformed with an efficiency 10 to $5\times10^3$ times higher than its wild-type homologue or the strain DSM 6423 ΔcatB (also identified in the present text as IFP962 ΔcatB).

The bacterium intended to be transformed, and preferably genetically modified, is preferably a bacterium that has been exposed to a first step of transformation and to a first step of genetic modification using a nucleic acid or genetic tool according to the invention that has made it possible to remove at least one molecule of extrachromosomal DNA (typically at least one plasmid) present naturally in said bacterium in the wild state.

A particular genetic tool described by the inventors is characterized i) in that it comprises:

- at least one "first" nucleic acid encoding at least one DNA endonuclease, for example the enzyme Cas9, wherein the sequence encoding the DNA endonuclease is placed under the control of a promoter, and
- at least one "second" nucleic acid containing a repair matrix allowing, by a mechanism of homologous recombination, replacement of a portion of the bacterial DNA targeted by the endonuclease with a sequence of interest, wherein ii) at least one of said nucleic acids further encodes one or more guide RNAs (gRNA) or in that the genetic tool further comprises one or more guide RNAs, each guide RNA comprising an RNA structure for fixation to the DNA endonuclease and a complementary sequence of the targeted portion of the bacterial DNA.

An example of a genetic tool described by the inventors contains, just like the CRISPR/Cas system, two distinct essential elements, i.e. i) an endonuclease, in the present case the nuclease associated with the CRISPR system (Cas or "CRISPR associated protein"), Cas, and ii) a guide RNA. The guide RNA is in the form of a chimeric RNA that consists of a combination of a bacterial CRISPR RNA (crRNA) and a tracrRNA (trans-activating CRISPR RNA) (Jinek et al., Science 2012). The gRNA combines the targeting specificity of the crRNA corresponding to the "spacer sequences" which serve as guides for the Cas proteins, and the conformational properties of the tracrRNA in a single transcript. When the gRNA and the Cas protein are expressed simultaneously in the cell, the target genomic sequence is typically, advantageously modified permanently owing to a repair matrix that is supplied.

The genetic tool according to the invention is preferably characterized iii) in that at least one of said ("first" and "second") nucleic acids further comprises a sequence encoding an anti-CRISPR protein placed under the control of an inducible promoter, or wherein the genetic tool further comprises a third nucleic acid encoding an anti-CRISPR protein placed under the control of an inducible promoter.

In particular, a genetic tool is described comprising at least:

- a first nucleic acid encoding at least one DNA endonuclease, wherein the sequence encoding the DNA endonuclease is placed under the control of a promoter, and
- another nucleic acid (or an "n-th nucleic acid") comprising, or consisting of, a nucleic acid sequence "OPT", i.e. a sequence comprising i) all or part of the sequence SEQ ID NO: 126 ("OREP") and ii) a sequence allowing modification of the genetic material of a bacterium and/or expression, in said bacterium, of a DNA sequence partially or totally absent from the genetic material present in the wild-type version of said bacterium, at least one of said nucleic acids of this particular genetic tool preferably further comprising a sequence encoding an anti-CRISPR protein placed under the control of an inducible promoter, or said particular genetic tool preferably further comprising a third nucleic acid encoding an anti-CRISPR protein placed under the control of an inducible promoter.

In a particular embodiment the "second" or "n-th nucleic acid containing a repair matrix" as described above comprises, or consists of, this "other nucleic acid".

In another particular embodiment the "first nucleic acid" further encodes one or more guide RNAs (gRNA).

"Nucleic acid" means, in the sense of the invention, any natural, synthetic, semisynthetic, or recombinant DNA or RNA molecule, optionally modified chemically (i.e. comprising non-natural bases, modified nucleotides comprising for example a modified linkage, modified bases and/or modified sugars), or optimized so that the codons of the transcripts synthesized from the coding sequences are the codons most often found in a bacterium of the genus *Clostridium* with a view to use thereof in the latter. In the case of the genus *Clostridium*, the optimized codons are typically codons rich in adenine bases ("A") and thymine bases ("T").

In the peptide sequences described in this document, the amino acids are represented by their single-letter codes according to the following nomenclature: C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan and Y: tyrosine.

A genetic tool described in the context of the present invention comprises a first nucleic acid encoding at least one DNA endonuclease (also identified in the present text as "nuclease"), typically a nuclease of the Cas type, for example Cas9 or MAD7.

"Cas9" means the Cas9 protein (also called CRISPR-associated protein 9, Csn1 or Csx12) or a functional protein, peptide, or polypeptide fragment of the latter, i.e. capable of interacting with the guide RNA or guide RNAs and of exerting the enzymatic (nuclease) activity that allows it to perform double-strand break of the DNA of the target genome. "Cas9" may thus denote a protein that has been modified, for example truncated, in order to remove the domains of the protein that are not essential to the predefined functions of the protein, in particular the domains not necessary for interaction with the gRNA or gRNAs. The nuclease MAD7 (whose amino acid sequence corresponds to the sequence SEQ ID NO: 72), also identified as "Cas12" or "Cpf1", may otherwise be used advantageously in the context of the present invention by combining it with one or more of the gRNAs known by a person skilled in the art to be capable of binding to a nuclease of this kind (cf. Garcia-Doval et al., 2017 and Stella S. et al., 2017).

According to a particular aspect, the sequence encoding the nuclease MAD7 is a sequence optimized for being easily expressed in strains of *Clostridium*, preferably the sequence SEQ ID NO: 71.

According to another particular aspect, the sequence encoding the nuclease MAD7 is a sequence optimized for being easily expressed in strains of *Bacillus*, preferably the sequence SEQ ID NO: 132.

The sequence encoding Cas9 (the entire protein or a fragment thereof) such as is usable in one of the possible embodiment examples of the invention may be obtained starting from any known Cas9 protein (Makarova et al., 2011). Examples of Cas9 proteins usable in the present invention include, but are not limited to, the Cas9 proteins of *S. pyogenes* (cf. SEQ ID NO: 1 of application WO2017/064439 and NCBI accession number: WP_010922251.1), *Streptococcus thermophilus, Streptococcus mutans, Campylobacter jejuni, Pasteurella multocida, Francisella novicida, Neisseria meningitidis, Neisseria* lactamica and *Legionella pneumophila* (cf. Fonfara et al., 2013; Makarova et al., 2015).

In a particular embodiment, the Cas9 protein, or a functional protein, peptide, or polypeptide fragment thereof, encoded by one of the nucleic acids of the genetic tool according to the invention comprises, or consists of, the amino acid sequence SEQ ID NO: 75, or any other amino acid sequence having at least 50%, preferably at least 60%, identity with the latter, and containing as a minimum the two aspartic acids ("D") occupying positions 10 ("D10") and 840 ("D840") of the amino acid sequence SEQ ID NO: 75. In a preferred embodiment, Cas9 comprises, or consists of, the Cas9 protein (NCBI accession number: WP_010922251.1, SEQ ID NO: 75), encoded by the cas9 gene of the strain of *S. pyogenes* M1 GAS (NCBI accession number: NC_002737.2 SPy_1046, SEQ ID NO: 76) or a version of the latter that has undergone optimization ("optimized version") at the origin of a transcript containing the codons used preferentially by the bacteria of the genus *Clostridium*, typically the codons rich in adenine ("A") and thymine ("T") bases, allowing facilitated expression of the Cas9 protein in this bacterial genus. These optimized codons respect the way of using codons, well known by a person skilled in the art, specific to each bacterial strain.

According to a particular embodiment, the Cas9 domain consists of an entire Cas9 protein, preferably the Cas9 protein of *S. pyogenes* or of an optimized version thereof.

Each of the nucleic acids of a genetic tool described in the present text, typically the "first" nucleic acid and the "second" or "n-th" nucleic acid of said genetic tool, consists of a distinct entity and is typically in the form of an expression cassette (or "construct") such as for example a nucleic acid comprising at least one transcriptional promoter linked operationally (in the sense as understood by a person skilled in the art) to one or more (coding) sequences of interest, for example to an operon comprising several coding sequences of interest whose expression products contribute to the performance of a function of interest within the bacterium, or a nucleic acid further comprising a transcription activating and/or terminating sequence; or in the form of a circular or linear, single or double stranded vector, for example a plasmid, a phage, a cosmid, an artificial or synthetic chromosome, comprising one or more expression cassettes as defined above. Preferably, the vector is a plasmid.

The nucleic acids of interest, typically the cassettes or expression vectors, may be constructed by conventional techniques that are familiar to a person skilled in the art and may comprise one or more promoters, bacterial replication origins (ORI sequences), termination sequences, selector genes, for example antibiotic resistance genes, and sequences ("flanked regions") allowing targeted insertion of the cassette or vector. Moreover, these expression cassettes and vectors may be integrated within the bacterial genome by techniques that are familiar to a person skilled in the art.

ORI sequences of interest may be selected from pIP404, pAMβ1, repH (replication origin in *C. acetobutylicum*), ColE1 or rep (replication origin in *E. coli*), or any other replication origin allowing the vector, typically the plasmid, to be maintained within a bacterial cell, for example a cell of *Clostridium* or of *Bacillus*.

In the context of the present invention, a preferred ORI sequence is that present within the sequence OREP (SEQ ID NO: 126) of the plasmid pNF2 (SEQ ID NO: 118).

Termination sequences of interest may be selected from those of the genes adc, thl, of the operon bcs, or of any other terminator, familiar to a person skilled in the art, allowing transcription to be stopped within a bacterial cell, for example a cell of *Clostridium* or of *Bacillus*.

Selector genes (resistance genes) of interest may be selected from ermB, catP, bla, tetA, tetM, and/or any other gene for resistance to ampicillin, erythromycin, chloramphenicol, thiamphenicol, spectinomycin, tetracycline or any other antibiotic usable for selecting bacteria, for example of the genus *Clostridium* or *Bacillus*, familiar to a person skilled in the art.

The sequence encoding the DNA endonuclease, for example Cas9, optionally present within one of the nucleic acids of a genetic tool according to the invention, may be placed under the control of a promoter. This promoter may be a constitutive promoter or an inducible promoter. In a preferred embodiment, the promoter controlling expression of the nuclease is an inducible promoter.

Examples of constitutive promoters usable in the context of the present invention may be selected from the promoter of the gene thl, of the gene ptb, of the gene adc, of the operon BCS, or a derivative thereof, preferably a functional derivative but shorter (truncated) such as the "miniPthl" derivative of the promoter of the gene thl of *C. acetobutylicum* (Dong et al., 2012), or any other promoter, familiar to a person skilled in the art, allowing expression of a protein within a bacterium of interest, for example a bacterium of the genus *Clostridium.*

Examples of inducible promoters usable in the context of the present invention may be selected for example from a promoter whose expression is controlled by the transcriptional repressor TetR, for example the promoter of the gene tetA (tetracycline resistance gene originally present on the transposon Tn10 of *E. coli*); a promoter whose expression is controlled by L-arabinose, for example the promoter of the gene ptk (Zhang et al., 2015), preferably in combination with the araR cassette regulating expression in *C. acetobutylicum* so as to construct a system ARAi (Zhang et al., 2015); a promoter whose expression is controlled by laminaribiose (dimer of glucose β-1,3), for example the promoter of the gene celC, preferably followed immediately by the repressor gene glyR3 and the gene of interest (Mearls et al. 2015) or the promoter of the gene celC (Newcomb et al., 2011); a promoter whose expression is controlled by lactose, for example the promoter of the gene bgaL (Banerjee et al., 2014); a promoter whose expression is controlled by xylose, for example the promoter of the gene xylB (Nariya et al., 2011); and a promoter whose expression is controlled by exposure to UV, for example the promoter of the gene bcn (Dupuy et al., 2005).

A promoter derived from one of the promoters described above, preferably a shorter (truncated) functional derivative, may also used be in the context of the invention.

Other inducible promoters usable in the context of the present invention are also described for example in the articles by Ransom et al. (2015), Currie et al. (2013) and Hartman et al. (2011).

A preferred inducible promoter is a promoter derived from tetA, inducible with anhydrotetracycline (aTc; less toxic than tetracycline and capable of removing the inhibition of the transcriptional repressor TetR at lower concentration), selected from Pcm-2tetO1 and Pcm-2tetO2/1 (Dong et al., 2012).

Another preferred inducible promoter is a promoter inducible by lactose, for example the promoter of the gene bgaL (Banerjee et al., 2014).

A nucleic acid of particular interest, typically an expression cassette or vector, comprises one or more expression cassettes, each cassette encoding a gRNA.

The term "guide RNA" or "gRNA" denotes, in the sense of the invention, an RNA molecule capable of interacting with a DNA endonuclease in order to guide it to a target region of the bacterial chromosome. The cutting specificity is determined by the gRNA. As explained above, each gRNA comprises two regions:

- a first region (commonly called "SDS" region), at the 5' end of the gRNA, which is complementary to the target chromosomal region and which imitates the crRNA of the endogenous CRISPR system, and
- a second region (commonly called "handle" region), at the 3' end of the gRNA, which mimics the base pairing interactions between tracrRNA ("trans-activating crRNA") and the crRNA of the endogenous CRISPR system and has a double-stranded stem-loop structure ending at 3' with an essentially single-stranded sequence. This second region is essential for binding the gRNA to the DNA endonuclease.

The first region of the gRNA ("SDS" region) varies according to the chromosomal sequence targeted.

The "SDS" region of the gRNA that is complementary to the target chromosomal region comprises at least 1 nucleotide, preferably at least 1, 2, 3, 4, 5, 10, 15, 20, 25, 30, 35 or 40 nucleotides, typically between 1 and 40 nucleotides. Preferably, this region has a length of 20, 21, 22, 23, 24, 25, 26, 27, 28, 29 or 30 nucleotides.

The second region of the gRNA ("handle" region) has a stem-loop structure (or hairpin structure). The "handle" regions of the various gRNAs do not depend on the chromosomal target selected.

According to a particular embodiment, the "handle" region comprises, or consists of, a sequence of at least 1 nucleotide, preferably at least 1, 50, 100, 200, 500 and 1000 nucleotides, typically between 1 and 1000 nucleotides. Preferably, this region has a length from 40 to 120 nucleotides.

The total length of a gRNA is generally from 50 to 1000 nucleotides, preferably from 80 to 200 nucleotides, and more particularly preferably from 90 to 120 nucleotides. According to a particular embodiment, a gRNA as used in the present invention has a length between 95 and 110 nucleotides, for example a length of about 100 or of about 110 nucleotides.

A person skilled in the art can easily define the sequence and the structure of the gRNAs depending on the chromosomal region to be targeted using techniques that are well known (see for example the article by DiCarlo et al., 2013).

The DNA region/portion/sequence targeted within the bacterial genome, for example of the bacterial chromosome, may correspond to a non-coding portion of DNA or to a coding portion of DNA.

In a particular embodiment consisting of modifying a given sequence, the targeted portion of the bacterial DNA is essential to the bacterium's survival. It corresponds for example to any region of the bacterial chromosome or to any region located on the non-chromosomal DNA, for example on a mobile genetic element indispensable to the survival of the microorganism in particular growth conditions, for example a plasmid containing a marker of resistance to an antibiotic when the growth conditions envisaged require culturing the bacterium in the presence of said antibiotic.

In another particular embodiment with the aim of removing a genetic element that is not indispensable in the particular growth conditions associated with culture of the microorganism, the targeted portion of the bacterial DNA may correspond to any region of said non-chromosomal bacterial DNA.

Particular examples of DNA portion targeted within a bacterium of the genus *Clostridium* are the sequences used in example 1 of the experimental section. They are for example sequences encoding the genes bdhA (SEQ ID NO: 77) and bdhB (SEQ ID NO: 78). The DNA region/portion/sequence targeted is followed by a sequence "PAM" ("protospacer adjacent motif") which is involved in binding to the DNA endonuclease.

The "SDS" region of a given gRNA is identical (to 100%) or identical to at least 80%, preferably at least 85%, 90%, 95%, 96%, 97%, 98% or 99% to the DNA region/portion/ sequence targeted within the bacterial genome, for example the bacterial chromosome, and is capable of hybridizing to all or part of the complementary sequence of said region/portion/sequence, typically to a sequence comprising at least 1 nucleotide, preferably at least 1, 2, 3, 4, 5, 10, 15, 20, 25, 30, 35 or 40 nucleotides, typically between 1 and 40 nucleotides, preferably to a sequence comprising 14, 15, 16, 17, 18, 19, 20, 21, 22, 23, 24, 25, 26, 27, 28, 29 or 30 nucleotides.

In the context of the invention, the nucleic acid of interest may comprise one or more guide RNAs (gRNA) targeting a sequence ("target sequence", "targeted sequence" or "sequence recognized"). These various gRNAs may target chromosomal regions, or regions belonging to non-chromosomal bacterial DNA (for example to the mobile genetic elements) optionally present within the microorganism, identical or different.

The gRNAs may be introduced into the bacterial cell in the form of molecules of gRNA (mature or precursors), in the form of precursors or in the form of one or more nucleic acids encoding said gRNAs. The gRNAs are preferably introduced into the bacterial cell in the form of one or more nucleic acids encoding said gRNA.

When the gRNA or gRNAs are introduced into the cell directly in the form of RNA molecules, these gRNAs (mature or precursors) may contain modified nucleotides or chemical modifications allowing them, for example, to increase their resistance to nucleases and thus increase their lifetime in the cell. They may in particular comprise at least one modified or non-natural nucleotide such as, for example, a nucleotide comprising a modified base, such as inosine, methyl-5-deoxycytidine, dimethylamino-5-deoxyuridine, deoxyuridine, diamino-2,6-purine, bromo-5-deoxyuridine or any other modified base allowing hybridization. The gRNAs used according to the invention may also be modified at the level of the internucleotide linkage, for example such as phosphorothioates, H-phosphonates or alkyl-phosphonates, or at the level of the skeleton for example such as alpha-oligonucleotides, 2'-O-alkyl riboses or PNAs (Peptide Nucleic Acids) (Egholm et al., 1992).

The gRNAs may be natural RNAs, synthetic RNAs or RNAs produced by recombination techniques. These gRNAs may be prepared by all methods known by a person skilled in the art such as, for example, chemical synthesis, in vivo transcription or amplification techniques.

When the gRNAs are introduced into the bacterial cell in the form of one or more nucleic acids, the sequence or sequences encoding the gRNA or gRNAs are placed under the control of an expression promoter. This promoter may be constitutive or inducible.

When several gRNAs are used, the expression of each gRNA may be controlled by a different promoter. Preferably, the promoter used is the same for all the gRNAs. In a particular embodiment, one and the same promoter may be used for allowing the expression of several, for example of just some, or in other words some or all, of the gRNAs intended to be expressed.

In a preferred embodiment, the promoter or promoters controlling expression of the gRNA/gRNAs is/are inducible promoters.

Examples of constitutive promoters usable in the context of the present invention may be selected from the promoter of the gene thl, of the gene ptb or of the operon BCS, or a derivative thereof, preferably miniPthl, or any other promoter, familiar to a person skilled in the art, allowing synthesis of a (coding or non-coding) RNA within the bacterium of interest.

Examples of inducible promoters usable in the context of the present invention may be selected from the promoter of the gene tetA, of the gene xylA, of the gene lad, or of the gene bgaL, or a derivative thereof, preferably 2tetO1 or tetO2/1. A preferred inducible promoter is 2tetO1.

The promoters controlling expression of the DNA endonuclease and of the gRNA/gRNAs may be identical or different and constitutive or inducible. In a particular preferred embodiment, the promoters controlling respectively expression of the DNA endonuclease or of the gRNA or gRNAs are different promoters but are inducible by the same inducer.

The inducible promoters as described above make it possible to control advantageously the action of the DNA endonuclease/gRNA ribonucleoprotein complex, for example Cas9/gRNA, and facilitate selection of transformants that have undergone the desired genetic modifications.

The genetic tool according to the invention may further comprise advantageously a sequence encoding at least one anti-CRISPR protein, i.e. a protein capable of inhibiting or of preventing/neutralizing the action of Cas, and/or a protein capable of inhibiting or of preventing/neutralizing the action of a CRISPR/Cas system, for example of a CRISPR/Cas system of type II when the nuclease is a nuclease of the Cas9 type. This sequence is typically placed under the control of an inducible promoter different from the promoters controlling expression of the DNA endonuclease and/or of the gRNA or gRNAs, and is inducible by another inducer. In a preferred embodiment, the sequence encoding the anti-CRISPR protein is moreover typically localized on one of the at least two nucleic acids present within the genetic tool. In a particular embodiment, the sequence encoding the anti-CRISPR protein is localized on a nucleic acid different from the first two (typically a "third nucleic acid"). In yet another particular embodiment, both the sequence encoding the anti-CRISPR protein and the sequence encoding the transcriptional repressor of said anti-CRISPR protein are integrated in the bacterial chromosome.

In a preferred embodiment, the sequence encoding an anti-CRISPR protein is placed, within the genetic tool, on the nucleic acid encoding the DNA endonuclease (also identified in the present text as "first nucleic acid"). In another embodiment, the sequence encoding an anti-CRISPR protein is placed, within the genetic tool, on a nucleic acid different from that encoding the DNA endonuclease, for example on the nucleic acid identified in the present text as "second nucleic acid" or else on an "n-th" (typically a "third") nucleic acid optionally comprised in the genetic tool.

The anti-CRISPR protein is typically an "anti-Cas9" protein or an "anti-MAD7" protein, i.e. a protein capable of inhibiting or of preventing/neutralizing the action of Cas9 or of CAST.

The anti-CRISPR protein is advantageously an "anti-Cas9" protein, for example selected from AcrIIA1, AcrIIA2, AcrIIA3, AcrIIA4, AcrIIA5, AcrIIC1, AcrIIC2 and AcrIIC3 (Pawluk et al., 2018). Preferably the "anti-Cas9" protein is AcrIIA2 or AcrIIA4. Even more preferably the "anti-Cas9" protein is AcrIIA4. Said protein is typically capable of limiting very significantly, ideally of preventing, the action of Cas9, for example by binding to the enzyme Cas9 (Dong et al., 2017; Rauch et al., 2017).

Another anti-CRISPR protein advantageously usable is an "anti-MAD7" protein, for example the protein AcrVA1 (Marino et al., 2018).

In a preferred embodiment, the anti-CRISPR protein is capable of inhibiting, preferably neutralizing, the action of the DNA endonuclease, preferably during the step of introducing the nucleic acid sequences of the genetic tool into the bacterial strain of interest.

The promoter controlling expression of the sequence encoding the anti-CRISPR protein is preferably an inducible promoter. The inducible promoter is associated with a gene expressed constitutively, typically responsible for the expression of a protein allowing transcriptional repression starting from said inducible promoter. This promoter may for example be selected from the promoter of the gene tetA, of the gene xylA, of the gene lad, or of the gene bgaL, or a derivative thereof.

An example of inducible promoter usable in the context of the invention is the promoter Pbgal (inducible with lactose) present, within the genetic tool and on the same nucleic acid, alongside the gene bgaR expressed constitutively and whose expression product allows transcriptional repression starting from Pbgal. In the presence of the inducer, lactose, transcriptional repression of the promoter Pbgal is removed, allowing transcription of the gene placed downstream of the latter. Preferably, the gene placed downstream corresponds, in the context of the present invention, to the gene encoding the anti-CRISPR protein, for example acrIIA4.

The promoter controlling expression of the anti-CRISPR protein makes it possible to control advantageously the action of the DNA endonuclease, for example of the enzyme Cas9, and thus facilitate transformation of bacteria, for example bacteria of the genus *Clostridium, Bacillus* or *Lactobacillus*, and the production of transformants that have undergone the desired genetic modifications.

In a particular embodiment, the invention relates to a genetic tool comprising a plasmid vector whose sequence is that of SEQ ID NO: 23 as “first” nucleic acid.

In yet another particular embodiment, the invention relates to a genetic tool comprising a plasmid vector whose sequence is selected from one of the sequences SEQ ID NO: 79, SEQ ID NO: 80, SEQ ID NO: 119, SEQ ID NO: 123, SEQ ID NO: 124 and SEQ ID NO: 125 as “second” or “n-th” nucleic acid.

In yet another particular embodiment, the invention relates to a genetic tool comprising a plasmid vector whose sequence is selected from one of the sequences SEQ ID NO: 119, SEQ ID NO: 123, SEQ ID NO: 124 and SEQ ID NO: 125 as “nucleic acid OPT”. In another particular embodiment, the genetic tool comprises several (for example at least two or three) sequences among SEQ ID NO: 23, 79, 80, 119, 123, 124 and 125, said sequences being different from one another.

The inventors describe examples of nucleic acid of interest, typically DNA sequences of interest, allowing expression, within a bacterium, of a DNA sequence partially or totally absent from the genetic material present in the wild-type version of said bacterium.

In a particular embodiment, expression of the DNA sequence of interest allows the bacterium, for example the bacterium of the genus *Clostridium*, to ferment (typically simultaneously) several different sugars, for example at least two different sugars, typically at least two different sugars among the sugars comprising 5 carbon atoms (such as glucose or mannose) and/or among the sugars comprising 6 carbon atoms (such as xylose, arabinose or fructose), preferably at least three different sugars, selected for example from glucose, xylose and mannose; glucose, arabinose and mannose; and glucose, xylose and arabinose.

In another particular embodiment, the DNA sequence of interest encodes at least one product of interest, preferably a product promoting production of solvent by the bacterium, for example by the bacterium of the genus *Clostridium, Bacillus* or *Lactobacillus*, typically at least one protein of interest, for example an enzyme; a membrane protein such as a transporter; a protein for maturation of other proteins (chaperone protein); a transcription factor; or a combination thereof.

In a preferred embodiment, the DNA sequence of interest promotes the production of solvent and is typically selected from a sequence encoding i) an enzyme, for example an enzyme involved in the conversion of aldehydes to alcohol, for example selected from a sequence encoding an alcohol dehydrogenase (for example a sequence selected from adh, adhE, adhE1, adhE2, bdhA, bdhB and bdhC), a sequence encoding a transferase (for example a sequence selected from ctfA, ctfB, atoA and atoB), a sequence encoding a decarboxylase (for example adc), a sequence encoding a hydrogenase (for example a sequence selected from etfA, etfB and hydA), and a combination thereof, ii) a membrane protein, for example a sequence encoding a phosphotransferase (for example a sequence selected from glcG, bglC, cbe4532, cbe4533, cbe4982, cbe4983, cbe0751), iii) a transcription factor (for example a sequence selected from sigL, sigE, sigF, sigG, sigH, sigK) and iv) a combination thereof.

Furthermore, the inventors describe examples of nucleic acid of interest recognizing (binding at least partly), and preferably targeting, i.e. recognizing and allowing cutting, in the genome of a bacterium of interest, of at least one strand i) of a target sequence, ii) of a sequence controlling the transcription of a target sequence, or iii) of a sequence flanking a target sequence.

The sequence recognized is also identified in the present text as “target sequence” or “targeted sequence”. A genetic tool comprising, or consisting of, said nucleic acid of interest is also described. In this case, the nucleic acid of interest is typically present within the “second” or “n-th” nucleic acid of a genetic tool as described in the present text.

The nucleic acid of interest is typically used in the context of the present description for suppressing the recognized sequence of the genome of the bacterium or for modifying its expression, for example for modulating/regulating its expression, in particular inhibiting it, preferably for modifying it so as to make said bacterium incapable of expressing a protein, in particular a functional protein, starting from said sequence.

When the target sequence is a sequence encoding an enzyme allowing the bacterium of interest to grow in a culture medium containing an antibiotic with respect to which it endows it with resistance, a sequence controlling the transcription of such a sequence or a sequence flanking such a sequence, the antibiotic is typically an antibiotic belonging to the class of amphenicols. Examples of amphenicols of interest in the context of the present description are chloramphenicol, thiamphenicol, azidamfenicol and florfenicol (Schwarz S. et al., 2004), in particular chloramphenicol and thiamphenicol.

In a particular embodiment, the nucleic acid of interest comprises at least one complementary region of the target sequence 100% identical or 80% identical at least, preferably 85%, 90%, 95%, 96%, 97%, 98% or 99% identical at least to the DNA region/portion/sequence targeted within the bacterial genome and is capable of hybridizing to all or part of the complementary sequence of said region/portion/sequence, typically to a sequence comprising at least 1 nucleotide, preferably at least 1, 2, 3, 4, 5, 10, 14, 15, 20, 25, 30, 35 or 40 nucleotides, typically between 1, 10 or 20 and 1000 nucleotides, for example between 1, 10 or 20 and 900, 800, 700, 600, 500, 400, 300 or 200 nucleotides, between 1, 10 or 20 and 100 nucleotides, between 1, 10 or 20 and 50 nucleotides, or between 1, 10 or 20 and 40 nucleotides, for example between 10 and 40 nucleotides, between 10 and 30 nucleotides, between 10 and 20 nucleotides, between 20 and 30 nucleotides, between 15 and 40 nucleotides, between 15 and 30 nucleotides or between 15 and 20 nucleotides, preferably to a sequence comprising 14, 15, 16, 17, 18, 19, 20, 21, 22, 23, 24, 25, 26, 27, 28, 29 or 30 nucleotides. The complementary region of the target sequence present within the nucleic acid of interest may correspond to the "SDS" region of a guide RNA (gRNA) used in a CRISPR tool as described in the present text.

In another particular embodiment described, the nucleic acid of interest comprises at least two regions each complementary of a target sequence, 100% identical or at least 80% identical, preferably a least 85%, 90%, 95%, 96%, 97%, 98% or 99% identical to said DNA region/portion/sequence targeted within the bacterial genome. These regions are capable of hybridizing to all or part of the complementary sequence of said region/portion/sequence, typically to a sequence as described above comprising at least 1 nucleotide, preferably at least 100 nucleotides, typically between 100 and 1000 nucleotides. The complementary regions of the target sequence present within the nucleic acid of interest may recognize, preferably target, the flanking regions at 5' and at 3' of the targeted sequence in a tool for genetic modification as described in the present text, for example the genetic tool ClosTron®, the genetic tool Targetron® or an allelic exchange tool of the ACE® type.

According to a particular aspect, the target sequence is a sequence encoding an amphenicol-O-acetyltransferase, for example a chloramphenicol-O-acetyltransferase or a thiamphenicol-O-acetyltransferase, controlling the transcription of such a sequence or flanking such a sequence, within the genome of a bacterium of interest, for example of the genus *Clostridium*, capable of growing in a culture medium containing one or more antibiotics belonging to the class of amphenicols, for example chloramphenicol and/or thiamphenicol.

The sequence recognized is for example the sequence SEQ ID NO: 18 corresponding to the gene catB (CIBE_3859) encoding a chloramphenicol-O-acetyltransferase of *C. beijerinckii* DSM 6423 or an amino acid sequence at least 70%, 75%, 80%, 85%, 90% or 95% identical to said chloramphenicol-O-acetyltransferase, or a sequence comprising all or at least 70%, 75%, 80%, 85%, 90%, 95%, 96%, 97%, 98% or 99% of the sequence SEQ ID NO: 18. In other words, the sequence recognized may be a sequence comprising at least 1 nucleotide, preferably at least 1, 2, 3, 4, 5, 10, 15, 20, 25, 30, 35 or 40 nucleotides, typically between 1 and 40 nucleotides, preferably a sequence comprising 14, 15, 16, 17, 18, 19, 20, 21, 22, 23, 24, 25, 26, 27, 28, 29 or 30 nucleotides of the sequence SEQ ID NO: 18.

Examples of amino acid sequences at least 70% identical to chloramphenicol-O-acetyltransferase encoded by the sequence SEQ ID NO: 18 correspond to the sequences identified in the NCBI database under the following references: WP_077843937.1, SEQ ID NO: 44 (WP_063843219.1), SEQ ID NO: 45 (WP_078116092.1), SEQ ID NO: 46 (WP_077840383.1), SEQ ID NO: 47 (WP_077307770.1), SEQ ID NO: 48 (WP_103699368.1), SEQ ID NO: 49 (WP_087701812.1), SEQ ID NO: 50 (WP_017210112.1), SEQ ID NO: 51 (WP_077831818.1), SEQ ID NO: 52 (WP_012059398.1), SEQ ID NO: 53 (WP_077363893.1), SEQ ID NO: 54 (WP_015393553.1), SEQ ID NO: 55 (WP_023973814.1), SEQ ID NO: 56 (WP_026887895.1), SEQ ID NO 57 (AWK51568.1), SEQ ID NO: 58 (WP_003359882.1), SEQ ID NO: 59 (WP_091687918.1), SEQ ID NO: 60 (WP_055668544.1), SEQ ID NO: 61 (KGK90159.1), SEQ ID NO: 62 (WP_032079033.1), SEQ ID NO: 63 (WP_029163167.1), SEQ ID NO: 64 (WP_017414356.1), SEQ ID NO: 65 (WP_073285202.1), SEQ ID NO: 66 (WP_063843220.1), and SEQ ID NO: 67 (WP_021281995.1).

Examples of amino acid sequences at least 75% identical to chloramphenicol-O-acetyltransferase encoded by the sequence SEQ ID NO: 18 correspond to the sequences WP_077843937.1, WP_063843219.1, WP_078116092.1, WP_077840383.1, WP_077307770.1, WP_103699368.1, WP_087701812.1, WP_017210112.1, WP_077831818.1, WP_012059398.1, WP_077363893.1, WP_015393553.1, WP_023973814.1, WP_026887895.1 AWK51568.1, WP_003359882.1, WP_091687918.1, WP_055668544.1 and KGK90159.1.

Examples of amino acid sequences at least 90% identical to chloramphenicol-O-acetyltransferase encoded by the sequence SEQ ID NO: 18, are the sequences WP_077843937.1, WP_063843219.1, WP_078116092.1, WP_077840383.1, WP_077307770.1, WP_103699368.1, WP_087701812.1, WP_017210112.1, WP_077831818.1, WP_012059398.1, WP_077363893.1, WP_015393553.1, WP_023973814.1, WP_026887895.1 and AWK51568.1.

Examples of amino acid sequences at least 95% identical to chloramphenicol-O-acetyltransferase encoded by the sequence SEQ ID NO: 18 correspond to the sequences WP_077843937.1, WP_063843219.1, WP_078116092.1, WP_077840383.1, WP_077307770.1, WP_103699368.1, WP_087701812.1, WP_017210112.1, WP_077831818.1, WP_012059398.1, WP_077363893.1, WP_015393553.1, WP_023973814.1, and WP_026887895.1.

Preferred amino acid sequences, at least 99% identical to chloramphenicol-O-acetyltransferase encoded by the sequence SEQ ID NO: 18, are the sequences WP_077843937.1, SEQ ID NO: 44 (WP_063843219.1) and SEQ ID NO: 45 (WP_078116092.1).

A particular sequence identical to the sequence SEQ ID NO: 18 is the sequence identified in the NCBI database under the reference WP_077843937.1.

According to a particular example, the target sequence is the sequence SEQ ID NO: 68 corresponding to the gene catQ encoding a chloramphenicol-O-acetyltransferase of *C. perfringens* whose amino acid sequence corresponds to SEQ ID NO: 66 (WP_063843220.1), or a sequence at least 70%, 75%, 80%, 85%, 90% or 95% identical to said chloramphenicol-O-acetyltransferase, or a sequence comprising all or at least 70%, 75%, 80%, 85%, 90%, 95%, 96%, 97%, 98% or 99% of the sequence SEQ ID NO: 68.

In other words, the recognized sequence may be a sequence comprising at least 1 nucleotide, preferably at least 1, 2, 3, 4, 5, 10, 15, 20, 25, 30, 35 or 40 nucleotides, typically between 1 and 40 nucleotides, preferably a sequence comprising 14, 15, 16, 17, 18, 19, 20, 21, 22, 23, 24, 25, 26, 27, 28, 29 or 30 nucleotides of the sequence SEQ ID NO: 68.

In yet another particular example, the recognized sequence is selected from a nucleic acid sequence catB (SEQ ID NO: 18), catQ (SEQ ID NO 68), catD (SEQ ID NO: 69, Schwarz S. et al., 2004) or catP (SEQ ID NO: 70, Schwarz S. et al., 2004) known by a person skilled in the art, present naturally within a bacterium or introduced artificially into said bacterium.

As stated above, according to another particular example, the target sequence may also be a sequence controlling the transcription of a coding sequence as described above (encoding an enzyme allowing the bacterium of interest of grow in a culture medium containing an antibiotic against which it endows it with resistance), typically a promoter sequence, for example the promoter sequence (SEQ ID NO: 73) of the gene catB or that (SEQ ID NO: 74) of the gene catQ.

The nucleic acid of interest then recognizes, and is therefore typically capable of binding to a sequence controlling the transcription of a coding sequence as described above.

According to another particular example, the target sequence may be a sequence flanking a coding sequence as described above, for example a sequence flanking the gene catB of sequence SEQ ID NO: 18 or a sequence at least 70% identical to the latter. Said flanking sequence typically comprises 1, 10 or 20 and 1000 nucleotides, for example between 1, 10 or 20 and 900, 800, 700, 600, 500, 400, 300 or 200 nucleotides, between 1, 10 or 20 and 100 nucleotides, between 1, 10 or 20 and 50 nucleotides, or between 1, 10 or 20 and 40 nucleotides, for example between 10 and 40 nucleotides, between 10 and 30 nucleotides, between 10 and 20 nucleotides, between 20 and 30 nucleotides, between 15 and 40 nucleotides, between 15 and 30 nucleotides or between 15 and 20 nucleotides.

According to a particular aspect, the target sequence corresponds to the pair of sequences flanking said coding sequence, each flanking sequence typically comprising at least 20 nucleotides, typically between 100 and 1000 nucleotides, preferably between 200 and 800 nucleotides.

In the context of the present description, a particular example of nucleic acid of interest, used for transforming and/or genetically modifying a bacterium of interest, is a DNA fragment i) recognizing a coding sequence, ii) controlling the transcription of a coding sequence, or iii) flanking a coding sequence, an enzyme of interest, preferably an amphenicol-O-acetyltransferase, for example a chloramphenicol-O-acetyltransferase or a thiamphenicol-O-acetyltransferase, within the genome of a bacterium, for example of a bacterium of the genus *Clostridium* as described above.

As stated above, an example of nucleic acid of interest according to the invention is capable of suppressing the recognized sequence ("target sequence") of the genome of the bacterium or of modifying its expression, for example modulating it, in particular inhibiting it, preferably of modifying it so as to make said bacterium incapable of expressing a protein, for example an amphenicol-O-acetyltransferase, in particular a functional protein, starting from said sequence.

In a particular embodiment in which the recognized sequence encoding an enzyme is a sequence endowing the bacterium with resistance to chloramphenicol and/or to thiamphenicol, the selection gene used is not a gene of resistance to chloramphenicol and/or to thiamphenicol, and preferably is not one of the genes catB, catQ, catD or catP.

In a particular embodiment, the nucleic acid of interest comprises one or more guide RNAs (gRNA) targeting a coding sequence, controlling the transcription of a coding sequence, or flanking a coding sequence, an enzyme of interest, in particular an amphenicol-O-acetyltransferase, and/or a modification matrix (also identified in the present text as "editing matrix"), for example a matrix making it possible to remove or modify all or part of the target sequence, preferably with the aim of inhibiting or suppressing expression of the target sequence, typically a matrix comprising homologous sequences (corresponding) to the sequences located upstream and downstream of the target sequence as described above, typically sequences (homologous to said sequences located upstream and downstream of the target sequence) each comprising between 10 or 20 base pairs and 1000, 1500 or 2000 base pairs, for example between 100, 200, 300, 400 or 500 base pairs and 1000, 1200, 1300, 1400 or 1500 base pairs, preferably between 100 and 1500 or between 100 and 1000 base pairs, and even more preferably between 500 and 1000 base pairs or between 200 and 800 base pairs.

In a particular embodiment, the nucleic acid of interest used for transforming and/or genetically modifying a bacterium of interest is a nucleic acid that does not have a methylation at the level of the motifs recognized by methyltransferases of the Dam and Dcm type (prepared from an *Escherichia coli* bacterium having the dam− dcm− genotype).

When the bacterium of interest to be transformed and/or modified genetically is a bacterium *C. beijerinckii*, in particular belonging to one of the subclades DSM 6423, LMG 7814, LMG 7815, NRRL B-593 and NCCB 27006, the nucleic acid of interest used as a genetic tool, for example the plasmid, is a nucleic acid that does not have a methylation at the level of the motifs recognized by methyltransferases of the Dam and Dcm type, typically a nucleic acid whose adenosine ("A") of the GATC motif and/or the second cytosine "C" of the CCWGG motif (W may correspond to an adenosine ("A") or to a thymine ("T")) are demethylated.

A nucleic acid that does not have a methylation at the level of the motifs recognized by methyltransferases of the Dam and Dcm type may typically be prepared from an *Escherichia coli* bacterium having the $dam^-$ $dcm^-$ genotype (for example *Escherichia coli* INV 110, Invitrogen). This same nucleic acid may comprise other methylations performed for example by methyltransferases of the ecoKI type, the latter targeting the adenines ("A") of the motifs AAC(N6)GTGC and GCAC(N6)GTT (N may correspond to any base).

In a particular embodiment, the targeted sequence corresponds to a gene encoding an amphenicol-O-acetyltransferase for example a chloramphenicol-O-acetyltransferase such as the gene catB, to a sequence controlling the transcription of this gene, or to a sequence flanking this gene.

A nucleic acid of particular interest described by the inventors is for example a vector, preferably a plasmid, for example the plasmid pCas9ind-ΔcatB of sequence SEQ ID NO: 21 or the plasmid pCas9ind-gRNA_catB of sequence SEQ ID NO: 38 described in the experimental section of the present description (cf. example 2), in particular a version of said sequence that does not have a methylation at the level of the motifs recognized by methyltransferases of the Dam and Dcm type.

The present description also relates to the use of a nucleic acid of interest for transforming and/or genetically modifying a bacterium of interest as described in the present text.

Another aspect described by the inventors relates to a method for transforming, and preferably in addition genetically modifying, a bacterium belonging to the phylum Firmicutes, for example a bacterium of the genus *Clostridium*, of the genus *Bacillus* or of the genus *Lactobacillus*, typically a solventogenic bacterium, in particular a solventogenic bacterium of the genus *Clostridium*, using a genetic tool according to the invention, typically using a nucleic acid of interest according to the invention as described above. This method advantageously comprises a step of transformation of the bacterium by introducing, into said bacterium, all or part of a genetic tool as described in the present text, in particular a nucleic acid of interest described in the present text, preferably a "nucleic acid OPT" comprising, or consisting of, i) all or part of the sequence SEQ ID NO: 126 (OREP) and ii) a sequence allowing modification of the genetic material of a bacterium and/or expression, in said bacterium, of a DNA sequence partially or totally absent from the genetic material present in the wild-type version of said bacterium. The method may further comprise a step of obtaining, of recovering, of selecting or of isolating the transformed bacterium, i.e. the bacterium having the required recombination or recombinations/modification or modifications/optimization or optimizations.

In a particular embodiment, the method for transforming, and preferably genetically modifying, a bacterium as described in the present text, involves a tool for genetic modification, for example a tool for genetic modification selected from a CRISPR tool, a tool based on the use of type II introns (for example the Targetron® tool or the ClosTron® tool) and an allelic exchange tool (for example the ACE® tool), and comprises a step of transforming the bacterium by introducing, into said bacterium, a nucleic acid of interest according to the invention as described above.

The present invention is typically advantageously employed if the genetic modification tool selected for transforming, and preferably genetically modifying, a bacterium belonging to the phylum Firmicutes, for example a bacterium of the genus *Clostridium*, is intended to be used on a bacterium, such as *C. beijerinckii*, bearing in the wild state a gene encoding an enzyme responsible for resistance to one or more antibiotics and/or bearing in the wild state at least one extrachromosomal DNA sequence, and the application of said genetic tool comprises a step of transforming said bacterium using a nucleic acid allowing expression of a marker of resistance to an antibiotic to which this bacterium is resistant in the wild state and/or a step of selecting the transformed and/or genetically modified bacteria using said antibiotic (to which the bacterium is resistant in the wild state), preferably for selecting, among said bacteria, bacteria that have lost said extrachromosomal DNA sequence.

A modification advantageously performable owing to the present invention, for example using a tool for genetic modification selected from a CRISPR tool, a tool based on the use of type II introns and an allelic exchange tool, consists of suppressing an undesirable sequence, for example a sequence encoding an enzyme endowing the bacterium with resistance to one or more antibiotics, or to make this undesirable sequence non-functional. Another modification advantageously performable owing to the present invention consists of genetically modifying a bacterium in order to improve its performance, for example its performance in the production of a solvent or of a mixture of solvents of interest, said bacterium having already been modified beforehand by means of the invention to make it sensitive to an antibiotic to which it was resistant in the wild state, and/or to remove an extrachromosomal DNA sequence that is present in the wild form of said bacterium.

In a preferred embodiment, the method according to the invention is based on the use of (employs) the CRISPR (Clustered Regularly Interspaced Short Palindromic Repeats) technology/genetic tool, in particular the CRISPR/Cas (CRISPR-associated protein) genetic tool.

The present invention may be implemented using a conventional CRISPR/Cas genetic tool using a single plasmid comprising a nuclease, a gRNA and a repair matrix such as described by Wang et al. (2015).

A person skilled in the art can easily define the sequence and the structure of the gRNAs according to the chromosomal region or the mobile genetic element to be targeted using well known techniques (see for example the article by DiCarlo et al., 2013).

The inventors have developed and described a genetic tool for modifying bacteria, suitable for the bacteria of the genus *Clostridium*, also usable in the context of the present invention, based on the use of two plasmids (cf. WO2017/064439, Wasels et al., 2017, and FIG. 15 appended to the present description). In a particular embodiment, the "first" plasmid of this tool allows expression of the nuclease Cas and a "second" plasmid, specific to the modification to be effected, contains one or more gRNA expression cassettes (typically targeting different regions of the bacterial DNA) as well as a repair matrix allowing, by a mechanism of homologous recombination, replacement of a portion of the bacterial DNA targeted by Cas with a sequence of interest. The gene cas and/or the gRNA expression cassette(s) are placed under the control of constitutive or inducible, preferably inducible, expression promoters known by a person skilled in the art (described for example in application WO2017/064439 and incorporated in the present description by reference), and preferably different, but inducible by the same inducer.

The gRNAs that are usable correspond to the gRNAs as described above in the present text.

A particular method involving CRISPR technology, usable in the context of the present invention for transforming, and typically for genetically modifying by homologous recombination, a bacterium as described in the present text, comprises the following steps:

a) introducing, into the bacterium, a nucleic acid or genetic tool described by the inventors in the presence of an agent for inducing the expression of an anti-CRISPR protein, and b) culturing the transformed bacterium obtained at the end of step a) on a medium not containing (or in conditions not involving) the inducer of expression of the anti-CRISPR protein, typically allowing expression of the DNA endonuclease/gRNA ribonucleoprotein complex, typically Cas/gRNA (in order to stop production of said anti-CRISPR protein and allow the action of the endonuclease).

The inducer of expression of the anti-CRISPR protein is present in sufficient quantity to induce said expression. In the case of the promoter Pbgal, the inducer, lactose, makes it possible to remove the inhibition of expression (transcriptional repression) of the anti-CRISPR protein linked to expression of the protein BgaR.

The inducer of expression of the anti-CRISPR protein is preferably used at a concentration between about 1 mM and about 1M, preferably between about 10 mM and about 100 mM, for example about 40 mM.

In a preferred embodiment, the anti-CRISPR protein is capable of inhibiting, preferably neutralizing, the action of the nuclease, preferably during the step of introducing the nucleic acid sequences of the genetic tool into the bacterial strain of interest.

In a particular embodiment, the method further comprises, during or after step b), a step of induction of expression of the inducible promoter or promoters controlling expression of the nuclease and/or of the guide RNA or guide RNAs when said promoter(s) are present in the genetic tool, in order to allow the genetic modification of interest of the bacterium once said genetic tool has been introduced into said bacterium. Induction is carried out using a substance making it possible to remove the inhibition of expression linked to the inducible promoter selected.

The induction step, when present, may thus be carried out by any method of culture on a medium allowing expression of the endonuclease/gRNA ribonucleoprotein complex known by a person skilled in the art after introducing the genetic tool according to the invention into the target bacterium. It is for example carried out by contacting the bacterium with a suitable substance, present in sufficient quantity, or by exposure to UV light. This substance makes it possible to remove the inhibition of expression linked to the inducible promoter selected. When the promoter selected is a promoter inducible with anhydrotetracycline (aTc), selected from Pcm-2tetO1 and Pcm-tetO2/1, the aTc is preferably used at a concentration between about 1 ng/ml and about 5000 ng/ml, preferably between about 10 ng/ml and 1000 ng/ml, 10 ng/ml and 800 ng/ml, 10 ng/ml and 500 ng/ml, 100 ng/ml or 200 ng/ml and about 800 ng/ml or 1000 ng/ml, or between about 100 ng/ml or 200 ng/ml and about 500 ng/ml, 600 ng/ml or 700 ng/ml, for example about 50 ng/ml, 100 ng/ml, 150 ng/ml, 200 ng/ml, 250 ng/ml, 300 ng/ml, 350 ng/ml, 400 ng/ml, 450 ng/ml, 500 ng/ml, 550 ng/ml, 600 ng/ml, 650 ng/ml, 700 ng/ml, 750 ng/ml or 800 ng/ml.

In another particular embodiment, the method comprises an additional step c) of removing the nucleic acid containing the repair matrix (the bacterial cell then being regarded as "stripped" of said nucleic acid) and/or of removing the guide RNA or guide RNAs or sequences encoding the guide RNA or guide RNAs introduced with the genetic tool in step a).

In yet another particular embodiment, the method comprises one or more additional steps, subsequent to step b) or to step c), of introducing an n-th, for example third, fourth, fifth, etc., nucleic acid containing a repair matrix different from that or those already introduced, and one or more expression cassettes of guide RNAs allowing integration of the sequence of interest contained in said distinct repair matrix in a targeted zone of the genome of the bacterium, in the presence of an agent for inducing expression of the anti-CRISPR protein, each additional step being followed by a step of culturing the bacterium thus transformed on a medium not containing the agent for inducing expression of the anti-CRISPR protein, typically allowing expression of the Cas/gRNA ribonucleoprotein complex.

In a particular embodiment of the method according to the invention, the bacterium is transformed using a nucleic acid or a genetic tool such as those described above, using (for example coding) an enzyme responsible for the cutting of at least one strand of the target sequence of interest, in which, in a particular embodiment, the enzyme is a nuclease, preferably a nuclease of the Cas type, preferably selected from a Cas9 enzyme and a MAD7 enzyme. In one embodiment example, the target sequence of interest is a sequence, for example the gene catB, encoding an enzyme endowing the bacterium with resistance to one or more antibiotics, preferably to one or more antibiotics belonging to the class of amphenicols, typically an amphenicol-O-acetyltransferase such as a chloramphenicol-O-acetyltransferase, a sequence controlling transcription of the coding sequence or a sequence flanking said coding sequence.

When it is used, the anti-CRISPR protein is typically an "anti-Cas" protein as described above. The anti-CRISPR protein is advantageously an "anti-Cas9" protein or an "anti-MAD7" protein.

Just like the portion of DNA targeted ("sequence recognized"), the editing/repair matrix may itself comprise one or more nucleic acid sequences or portions of nucleic acid sequence corresponding to natural and/or synthetic, coding and/or non-coding sequences. The matrix may also comprise one or more "foreign" sequences, i.e. naturally absent from the genome of the bacteria belonging to the phylum Firmicutes, in particular to the genus *Clostridium*, the genus *Bacillus* or the genus *Lactobacillus*, or the genome of particular species of said genus. The matrix may also comprise a combination of sequences.

The genetic used tool in the context of the present invention allows the repair matrix to guide incorporation, within the bacterial genome, of a nucleic acid of interest, typically of a sequence or portion of DNA sequence comprising at least 1 base pair (bp), preferably at least 1, 2, 3, 4, 5, 10, 15, 20, 50, 100, 1 000, 10 000, 100 000 or 1 000 000 bp, typically between 1 bp and 20 kb, for example 2, 3, 4, 5, 6, 7, 8, 9, 10, 11, 12 or 13 kb, or between 1 bp and 10 kb, preferably between 10 bp and 10 kb or between 1 kb and 10 kb, for example between 1 bp and 5 kb, between 2 kb and 5 kb, or else between 2.5 or 3 kb and 5 kb.

In a particular embodiment, expression of the DNA sequence of interest allows the bacterium belonging to the phylum Firmicutes, in particular of the genus *Clostridium*, of the genus *Bacillus* or of the genus *Lactobacillus*, to ferment (typically simultaneously) several different sugars, for example at least two different sugars, typically at least two different sugars among the sugars comprising 5 carbon atoms (such as glucose or mannose) and/or among the sugars comprising 6 carbon atoms (such as xylose, arabinose or fructose), preferably at least three different sugars, selected for example from glucose, xylose and mannose; glucose, arabinose and mannose; and glucose, xylose and arabinose.

In another particular embodiment, the DNA sequence of interest encodes at least one product of interest, preferably a product promoting production of solvent by the modified bacterium, typically at least one protein of interest, for example an enzyme; a membrane protein such as a transporter; a protein for maturation of other proteins (chaperone protein); a transcription factor; or a combination thereof.

The elements (nucleic acids or gRNA) of the genetic tool are introduced into the bacterium by any method, direct or indirect, known by a person skilled in the art, for example by transformation, conjugation, microinjection, transfection, electroporation, etc., preferably by electroporation (Mermelstein et al., 1993).

In another embodiment, the method according to the invention is based on the use of type II introns, and for example employs the ClosTron® technology/genetic tool or the Targetron® genetic tool.

The Targetron® technology is based on the use of a reprogrammable intron of group II (based on the intron Ll.ltrB of *Lactococcus lactis*), capable of integrating the bacterial genome rapidly to a desired locus (Chen et al., 2005, Wang et al., 2013), typically with the aim of inactivating a targeted gene. The mechanisms of recognition of the edited zone as well as insertion in the genome by retrosplicing are based on homology between the intron and said zone on the one hand, and on the activity of a protein (ltrA) on the other hand.

The ClosTron® technology is based on a similar approach, supplemented with addition of a selection marker in the sequence of the intron (Heap et al., 2007). This marker makes it possible to select integration of the intron in the genome, and therefore facilitates production of the desired mutants. This genetic system also makes use of type I introns. In fact, the selection marker (called RAM, for retrotransposition-activated marker) is interrupted by a genetic element of this kind, which prevents its expression from the plasmid (a more precise description of the system:

Zhong et al.). Splicing of this genetic element takes place before integration in the genome, which allows production of a chromosome having an active form of the resistance gene. An optimized version of the system comprises FLP/FRT sites upstream and downstream of this gene, which makes it possible to use the recombinase FRT to remove the resistance gene (Heap et al., 2010).

In another embodiment, the method according to the invention is based on the use of an allelic exchange tool, and for example employs the ACE® technology/genetic tool.

The ACE® technology is based on the use of an auxotrophic mutant (for uracil in *C. acetobutylicum* ATCC 824 by deletion of the gene pyrE, which also gives rise to resistance to 5-fluoroorotic acid (5-FOA); Heap et al., 2012). The system uses the allelic exchange mechanism, well known by a person skilled in the art. Following transformation with a pseudo-suicide vector (with very weak copies), integration of the latter in the bacterial chromosome by a first allelic exchange event can be verified owing to the resistance gene present on the plasmid initially. The integration step may be carried out in two different ways, either within the locus pyrE or within another locus:

In the case of integration at the locus pyrE, the gene pyrE is also placed on the plasmid, but without being expressed (no functional promoter). The second recombination restores a functional gene pyrE and can then be selected by auxotrophy (minimum medium, not containing uracil). As the non-functional gene pyrE also has a selectable character (sensitivity to 5-FOA), other integrations are then conceivable on the same model, by successively alternating the state of pyrE between functional and non-functional.

In the case of integration at another locus, a genomic zone allowing expression of the counter-selection marker after recombination is targeted (typically, to operon after another gene, preferably a strongly expressed gene). This second recombination is then selected by auxotrophy (minimum medium not containing uracil).

In the embodiments described based on the use of type II introns, and for example employing the ClosTron® technology/genetic tool or the Targetron® genetic tool, or based on the use of an allelic exchange tool, and for example employing the ACE® technology/genetic tool, the sequence targeted is typically one of the sequences described in the present text.

Particularly advantageously, the nucleic acids and the genetic tools according to the invention allow the introduction of both small and large sequences of interest into the bacterium, in one step, i.e. using a single nucleic acid (typically the "nucleic acid OPT" or the "second" or "n-th" nucleic acid of a tool as described in the present text) or in several steps, i.e. using several nucleic acids (typically the "second" or the "n-th" nucleic acids as described in the present text), preferably in one step.

In a particular embodiment of the invention, the nucleic acids and the genetic tools according to the invention make it possible to suppress a targeted portion of the bacterial DNA or replace it with a shorter sequence (for example with a sequence that has lost at least one base pair) and/or non-functional. In a preferred particular embodiment of the invention, the nucleic acids and the genetic tools according to the invention advantageously make it possible to introduce, into the bacterium, for example into the bacterial genome, a nucleic acid of interest comprising at least one base pair, and up to 2, 3, 4, 5, 6, 7, 8, 9, 10, 11, 12, 13, 14, or 15 kb.

The invention further relates to a transformed and/or genetically modified bacterium, typically a bacterium belonging to the phylum Firmicutes, and belonging for example to the genus *Clostridium*, the genus *Bacillus* or the genus *Lactobacillus*, typically a solventogenic bacterium, preferably a bacterium belonging to a species a corresponding to one of the subclades described by the inventors in the present text or obtained using a method as described by the inventors in the present text, as well as any derived bacterium, clone, mutant or genetically modified version thereof, and uses thereof.

An example of a bacterium thus transformed and/or genetically modified in accordance with the invention is a bacterium no longer expressing an enzyme endowing it with resistance to one or more antibiotics, in particular a bacterium no longer expressing an amphenicol-O-acetyltransferase, for example a bacterium expressing the gene catB in the wild state, and lacking said gene catB or incapable of expressing said gene catB once transformed and/or genetically modified in accordance with the invention. The bacterium thus transformed and/or genetically modified in accordance with the invention is made sensitive to an amphenicol, for example to an amphenicol as described in the present text, in particular to chloramphenicol or thiamphenicol.

A particular example of a genetically modified bacterium preferred according to the invention is the bacterium identified in the present description as *C. beijerinckii* IFP962 ΔcatB as registered under the deposition number LMG P-31151 with the Belgian Co-ordinated Collections of Microorganisms ("BCCM", K. L. Ledeganckstraat 35, B-9000 Ghent—Belgium) on 6 Dec. 2018.

Another particular example of a genetically modified bacterium preferred according to the invention is the bacterium identified in the present description as *C. beijerinckii* is a strain *C. beijerinckii* IFP963 ΔcatB ΔpNF2 as registered under the deposition number LMG P-31277 with the collection BCCM-LMG on 20 Feb. 2019.

The description also relates to any derived bacterium, clone, mutant or genetically modified version of one of said bacteria, for example any derived bacterium, clone, mutant, or genetically modified version remaining sensitive to an amphenicol such as thiamphenicol and/or chloramphenicol, typically a bacterium lacking the gene catB of sequence SEQ ID NO: 18 and the plasmid pNF2.

According to a particular embodiment, the transformed and/or genetically modified bacterium according to the invention, for example the bacterium *C. beijerinckii* IFP962 ΔcatB or the bacterium *C. beijerinckii* IFP963 ΔcatB ΔpNF2, is still able to be transformed, and preferably modified genetically. This may be carried out using a nucleic acid, for example a plasmid as described in the present description, for example in the experimental section. An example of nucleic acid usable advantageously is the plasmid pCas$9_{acr}$ of sequence SEQ ID NO: 23 (described in the experimental section of the present description) or else a plasmid selected from pCas$9_{ind}$ (SEQ ID NO: 22), pCas$9_{cond}$ (SEQ ID NO: 133) and pMAD7 (SEQ ID NO: 134).

A particular aspect of the invention relates in fact to the use of a genetically modified bacterium described in the present text, preferably the bacterium *C. beijerinckii* IFP962 ΔcatB (also identified in the present text as *C. beijerinckii* DSM 6423 ΔcatB) deposited under number LMG P-31151, even more preferably the bacterium *C. beijerinckii* IFP963 ΔcatB ΔpNF2 deposited under number LMG P-31277, or a genetically modified version of one of the latter, for example using one of the nucleic acids, genetic tools or methods described in the present text, to produce, owing to expression of the nucleic acid or nucleic acids of interest introduced deliberately into its genome, one or more solvents, preferably at least isopropanol, preferably on an industrial scale.

The invention also relates to a kit comprising (i) a nucleic acid as described in the present text, for example "a nucleic acid OPT" or a DNA fragment recognizing a target sequence in a bacterium belonging to the phylum Firmicutes as described in the present text, and (ii) at least one tool, preferably several tools, selected from the elements of a tool for genetic modification as described in the present text making it possible to transform, and typically modify genetically, a bacterium of this kind, with a view to producing an improved variant of said bacterium; a nucleic acid as gRNA; a nucleic acid as repair matrix; a "nucleic acid OPT"; at least one primer pair, for example a primer pair as described in the context of the present invention; and an inducer allowing expression of a protein encoded by said tool, for example a nuclease of the Cas9 or MAD7 type.

The tool for genetic modification for transforming, and typically genetically modifying a bacterium belonging to the phylum Firmicutes as described in the present text, may for example be selected from a "nucleic acid OPT", a CRISPR tool, a tool based on the use of type II introns and an allelic exchange tool, as explained above.

In a particular embodiment, the kit comprises some or all of the elements of a genetic tool as described in the present text.

A particular kit for transforming, and preferably genetically modifying, a bacterium belonging to the phylum Firmicutes as described in the present text, or for producing at least one solvent, for example a mixture of solvents, using a bacterium of this kind, comprises a nucleic acid comprising, or consisting of, i) all or part of the sequence SEQ ID NO: 126 and ii) a sequence allowing modification of the genetic material of a bacterium and/or expression, in said bacterium, of a DNA sequence partially or totally absent from the genetic material present in the wild-type version of said bacterium; as well as at least one inducer suitable for the inducible promoter of expression of the anti-CRISPR protein selected, used in a genetic tool described in the present text.

The kit may further comprise one or more inducers suitable for the selected inducible promoter(s) optionally used in the genetic tool for controlling expression of the nuclease used and/or of one or more guide RNAs.

A particular kit according to the invention allows expression of a nuclease comprising a label (or "tag").

The kits according to the invention may further comprise one or more consumables such as a culture medium, at least one competent bacterium belonging to the phylum Firmicutes as described in the present text, for example a bacterium of the genus *Clostridium, Bacillus* or *Lactobacillus* (i.e. conditioned with a view to transformation), at least one gRNA, a nuclease, one or more selection molecules, or also an explanatory leaflet.

The description also relates to the use of a kit according to the invention, or of one or more of the elements of this kit, for carrying out a method described in the present text, of transformation, and ideally of genetic modification, of a bacterium belonging to the phylum Firmicutes as described in the present text, for example a bacterium of the genus *Clostridium, Bacillus* or *Lactobacillus* (for example the bacterium *C. beijerinckii* IFP962 ΔcatB deposited under number LMG P-31151), preferably a bacterium possessing, in the wild state, both a bacterial chromosome and at least one DNA molecule different from the chromosomal DNA (typically a natural plasmid), most preferably the bacterium *C. beijerinckii* IFP963 ΔcatB ΔpNF2 deposited under number LMG P-31277, and/or for producing solvent(s) or biofuel(s), or mixtures thereof, preferably on an industrial scale, using said bacterium.

Solvents that may be produced are typically acetone, butanol, ethanol, isopropanol or a mixture thereof, typically an ethanol/isopropanol, butanol/isopropanol, or ethanol/butanol mixture, preferably an isopropanol/butanol mixture.

The use of bacteria transformed according to the invention typically allows annual production on an industrial scale of at least 100 tons of acetone, at least 100 tons of ethanol, at least 1000 tons of isopropanol, at least 1800 tons of butanol, or at least 40 000 tons of a mixture thereof.

The examples and figures given hereunder are for the purpose of illustrating the invention more fully, without limiting its scope.

FIGURES

FIG. 1 shows the CRISPR/Cas9 system used for editing the genome as a genetic tool making it possible to create, using the nuclease Cas9, one or more double-strand breaks in the genomic DNA guided by gRNA. gRNA, guide RNA; PAM, Protospacer Adjacent Motif. Figure adapted from Jinek et al., 2012.

Figure 1:
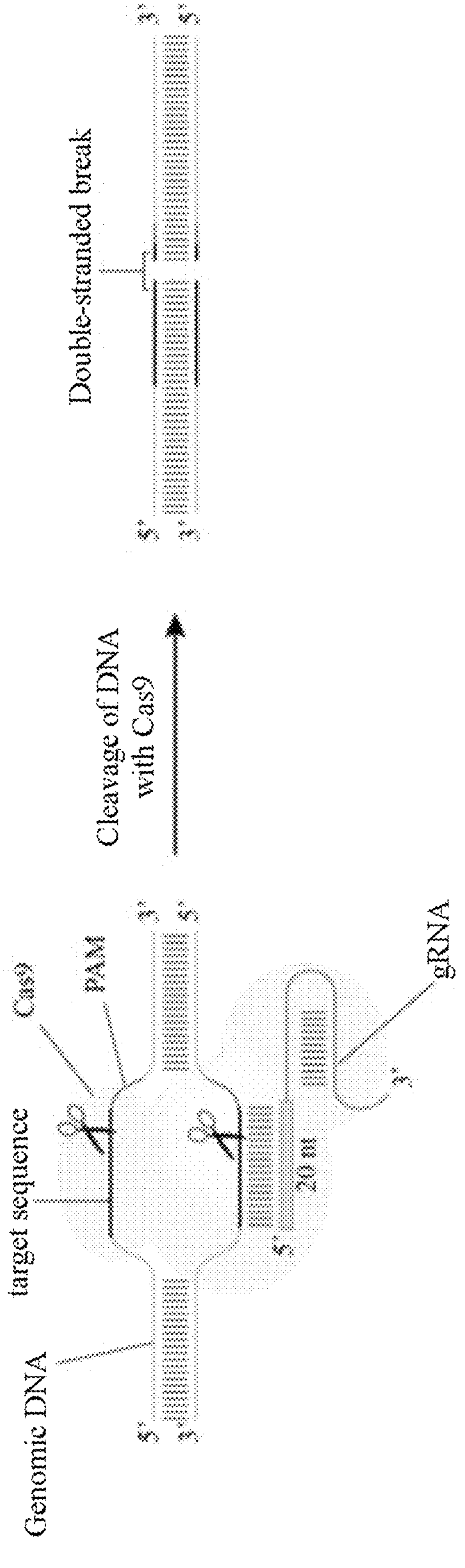
Figure 2:
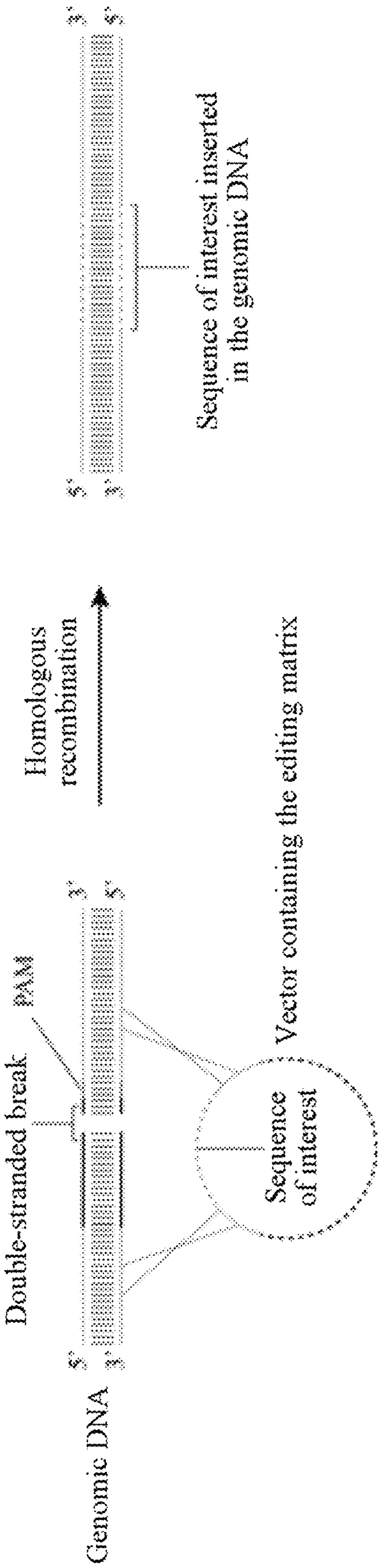
FIG. 2 shows repair by homologous recombination of a double-strand break induced by Cas9. PAM, Protospacer Adjacent Motif.
Figure 3:
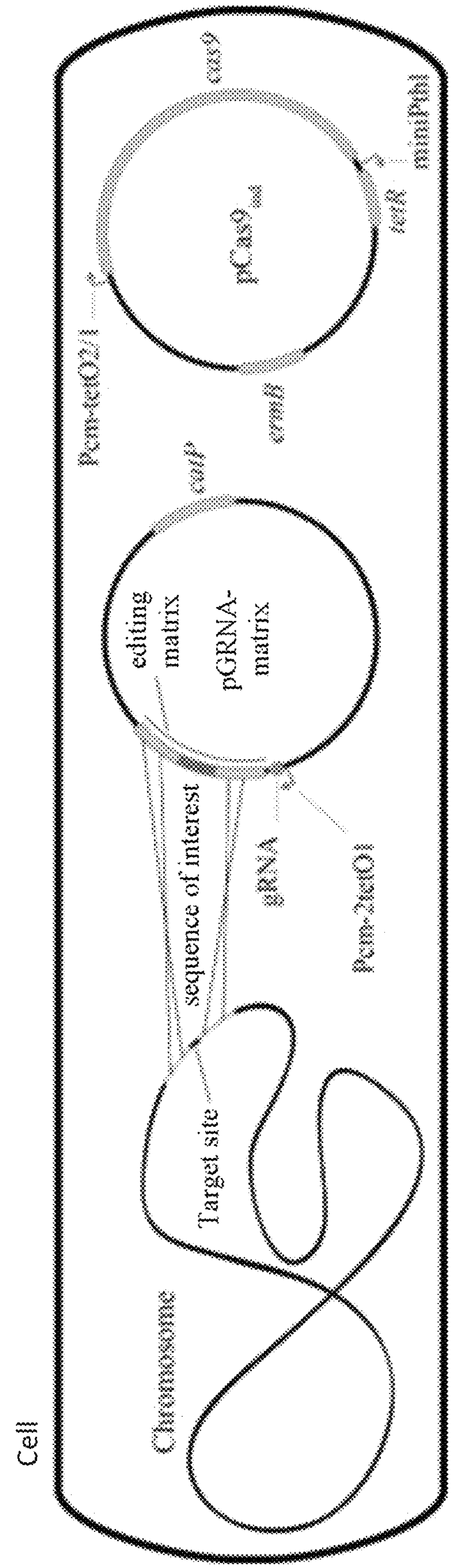
FIG. 3 shows the use of CRISPR/Cas9 in *Clostridium*. ermB, erythromycin resistance gene; catP (SEQ ID NO: 70), thiamphenicol/chloramphenicol resistance gene; tetR, gene whose expression product represses transcription starting from Pcm-tetO2/1; Pcm-2tetO1 and Pcm-tetO2/1, anhydrotetracycline inducible promoters, "aTc" (Dong et al., 2012); miniPthl, constitutive promoter (Dong et al., 2012).
Figure 4:
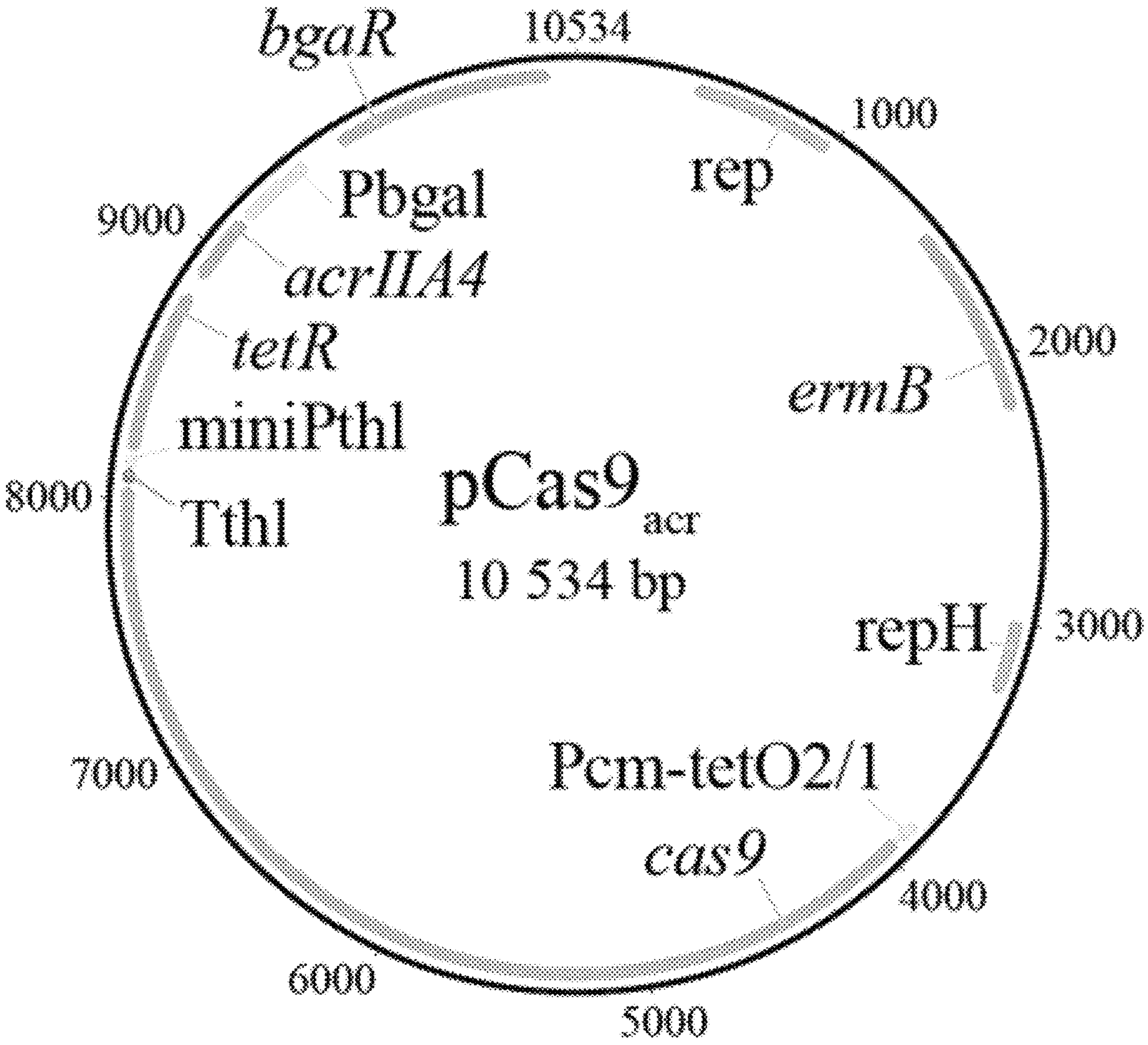

FIG. 4 shows the pCas9$_{acr}$ plasmid map (SEQ ID NO: 23). ermB, erythromycin resistance gene; rep, replication origin in *E. coli*; repH, replication origin in *C. acetobutylicum*; Tthl, thiolase terminator; miniPthl, constitutive promoter (Dong et al., 2012); Pcm-tetO2/1, promoter repressed by the product of tetR and inducible by anhydrotetracycline, "aTc" (Dong et al., 2012); Pbgal, promoter repressed by the product of lacR and inducible by lactose (Hartman et al., 2011); acrIIA4, gene encoding the anti-CRISPR protein AcrII14; bgaR, gene whose expression product represses transcription starting from Pbgal.

Figure 5:
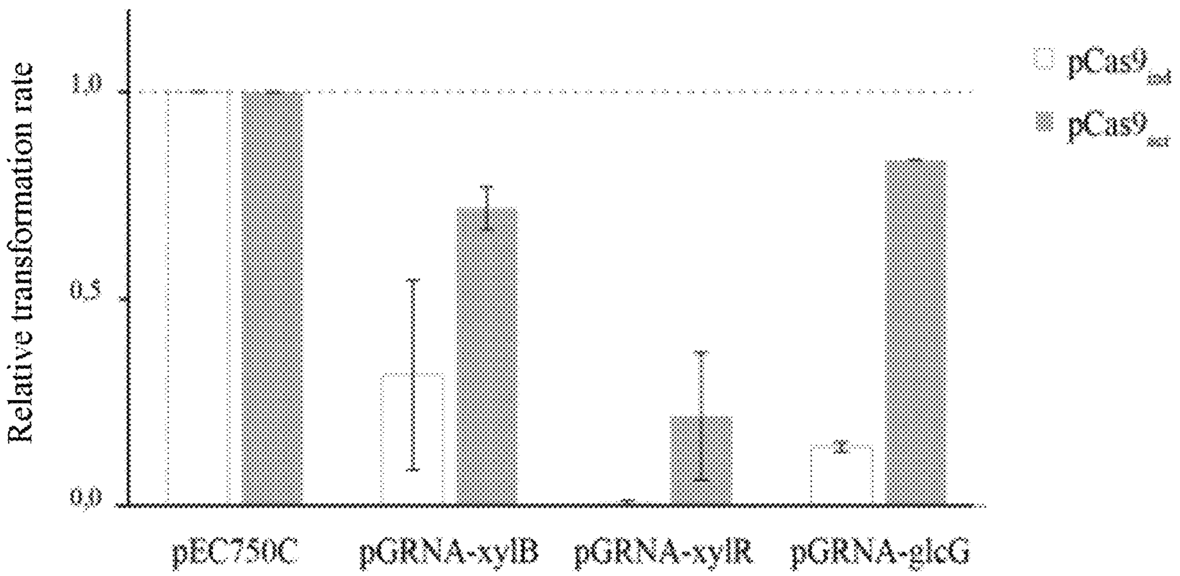

FIG. 5 shows the relative rate of transformation of *C. acetobutylicum* DSM 792 containing pCas9$_{ind}$ (SEQ ID NO: 22) or pCas9$_{acr}$ (SEQ ID NO: 23). The frequencies are expressed as number of transformants obtained per μg of DNA used in the transformation, relative to the frequencies of transformation of pEC750C (SEQ ID NO: 106), and represent the mean values of at least two independent experiments.

Figure 6:
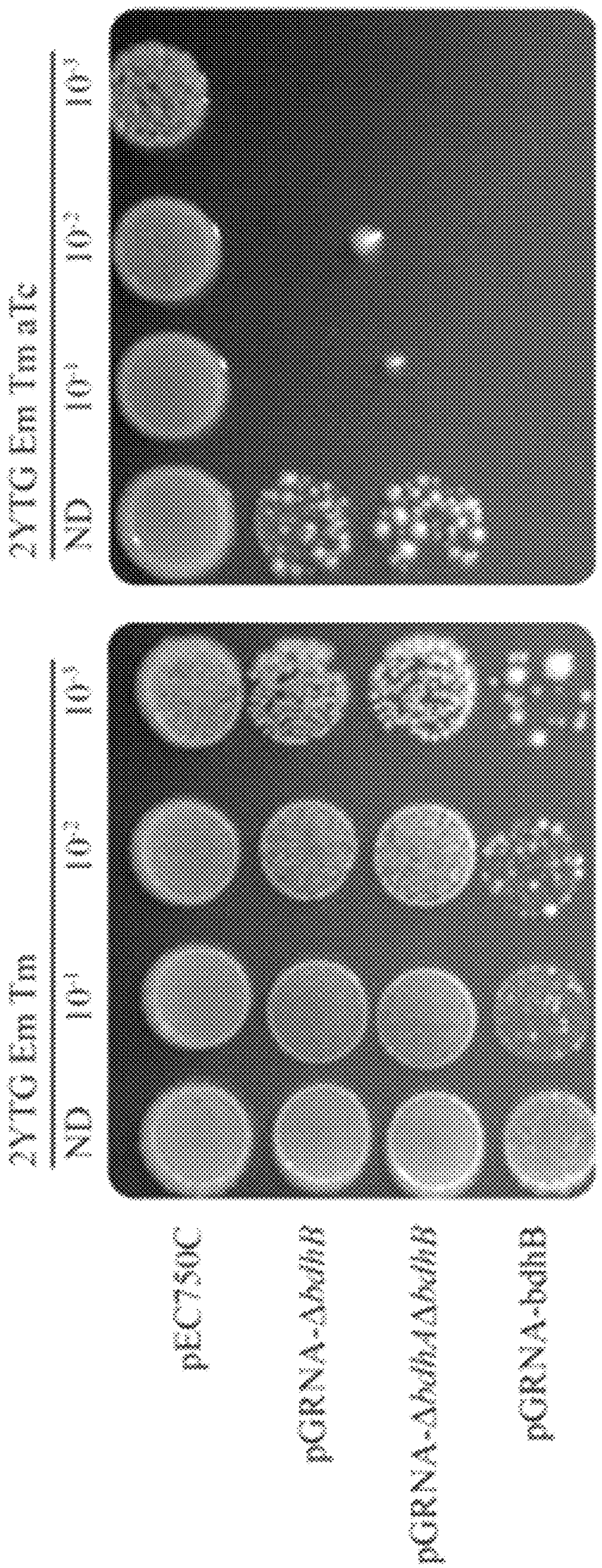

FIG. 6 shows the induction of the CRISPR/Cas9 system in transformants of the strain DSM 792 containing pCas9$_{acr}$ and an expression plasmid of the gRNA targeting bdhB, with (SEQ ID NO: 79 and SEQ ID NO: 80) or without (SEQ ID NO: 105) a repair matrix. Em, erythromycin; Tm, thiamphenicol; aTc, anhydrotetracycline; ND, not diluted.

Figure 7A:
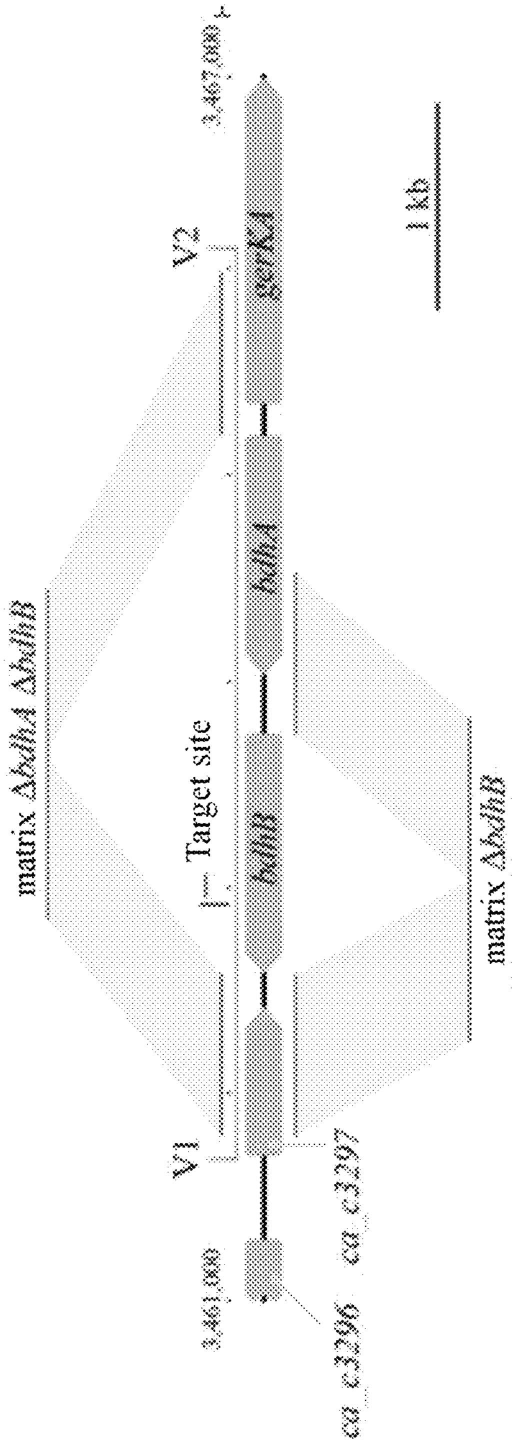

FIG. 7A shows modification of the locus bdh of *C. acetobutylicum* DSM792 by means of the CRISPR/Cas9 system. FIG. 7A shows the genetic organization of the locus bdh. The homologies between repair matrix and genomic DNA are highlighted with light grey parallelograms. The hybridization sites of the primers V1 and V2 are also shown.

Figure 7B:
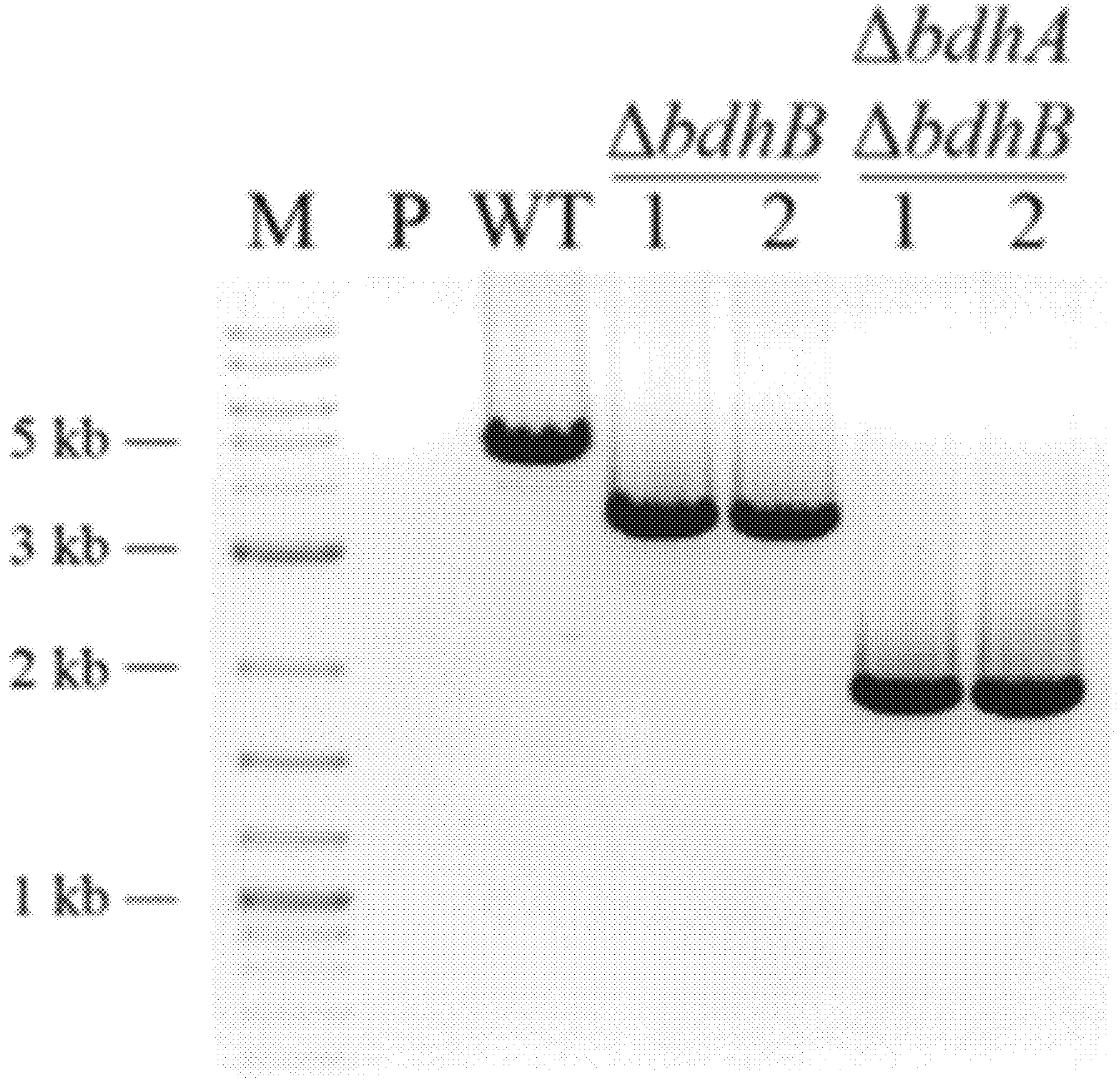

FIG. 7B shows modification of the locus bdh of *C. acetobutylicum* DSM792 by means of the CRISPR/Cas9 system. FIG. 7B shows amplification of the locus bdh using the primers V1 and V2. M, marker of size 2-log (NEB); P, plasmid pGRNA-ΔbdhAΔbdhB; WT, wild-type strain.

Figure 8:
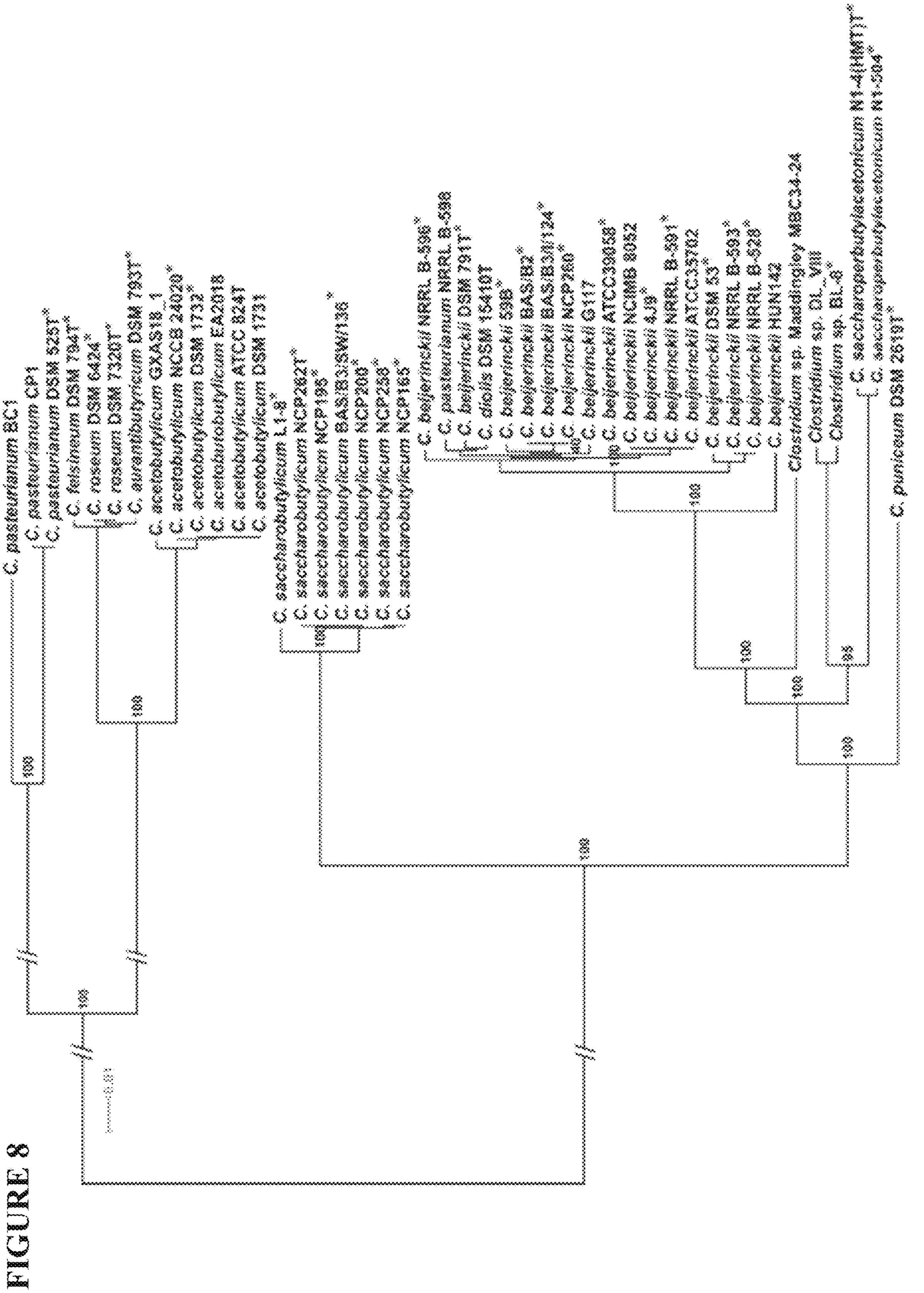

FIG. 8 shows classification of 30 solventogenic strains of *Clostridium*, according to Poehlein et al., 2017. Note that the subclade *C. beijerinckii* NRRL B-593 is also identified in the literature as *C. beijerinckii* DSM 6423.

Figure 9:
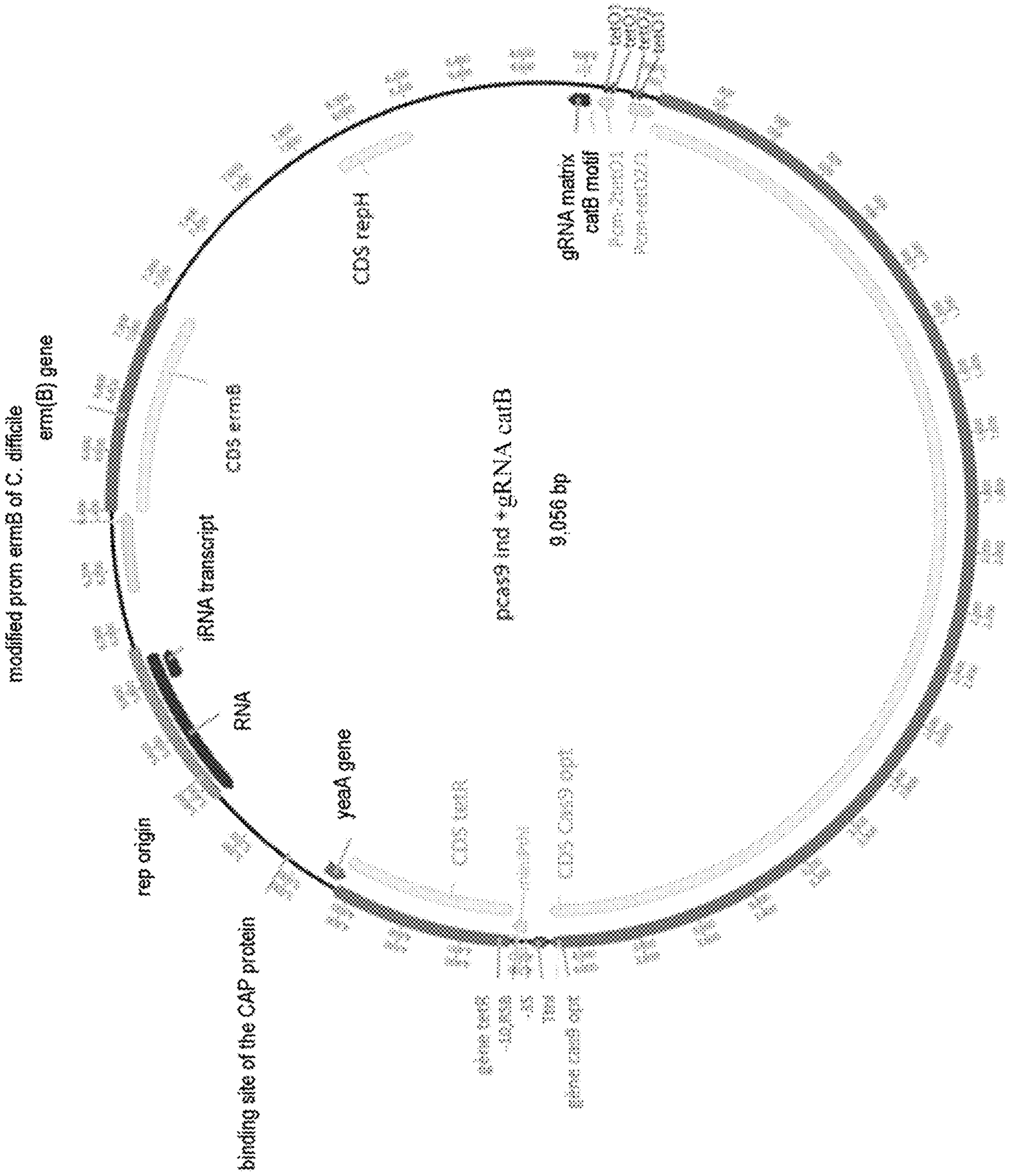

FIG. 9 shows the pCas9ind-ΔcatB plasmid map.

Figure 10:
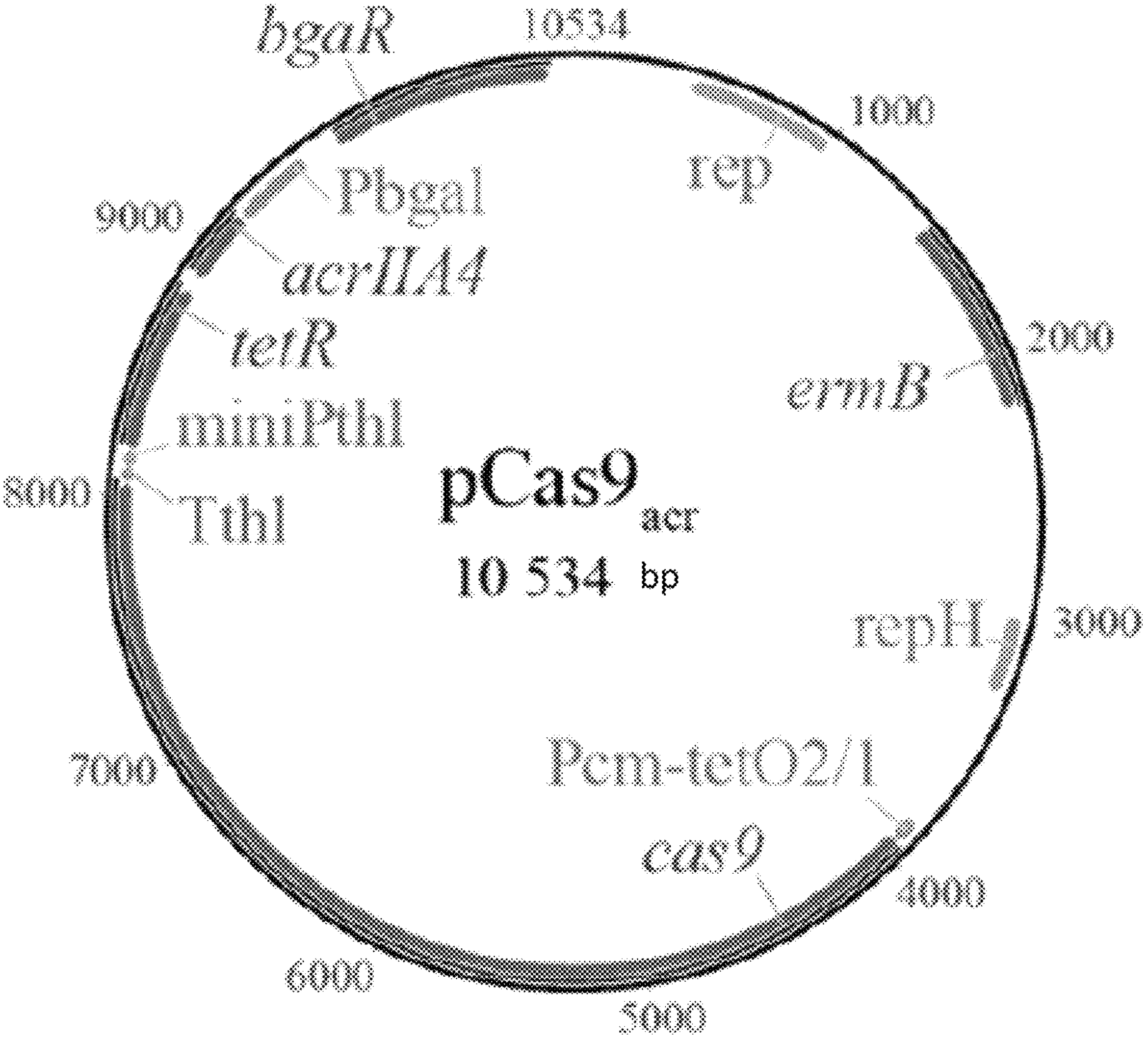

FIG. 10 shows the pCas9acr plasmid map.

Figure 11:
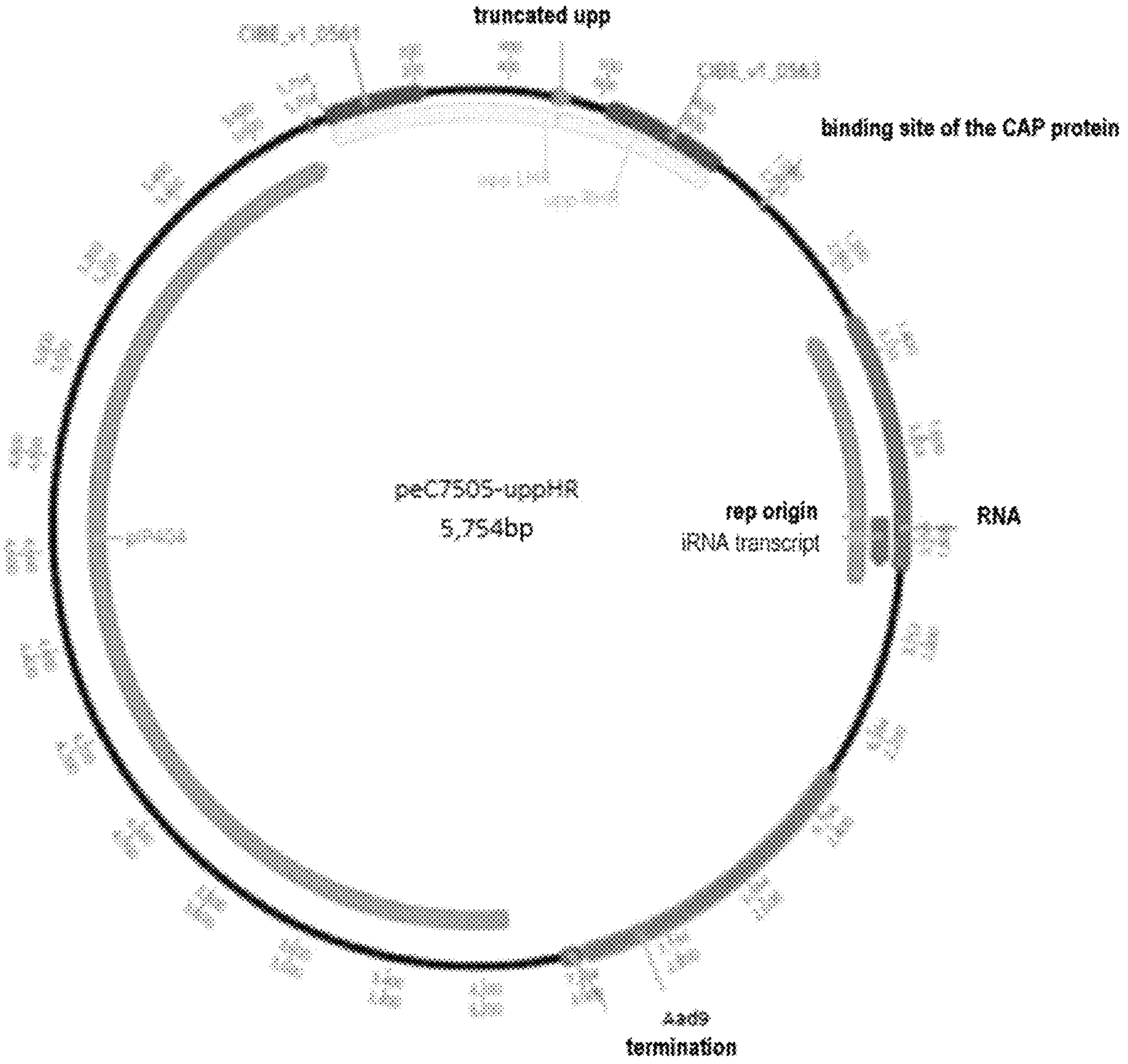

FIG. 11 shows the pEC750S-uppHR plasmid map.

Figure 12:
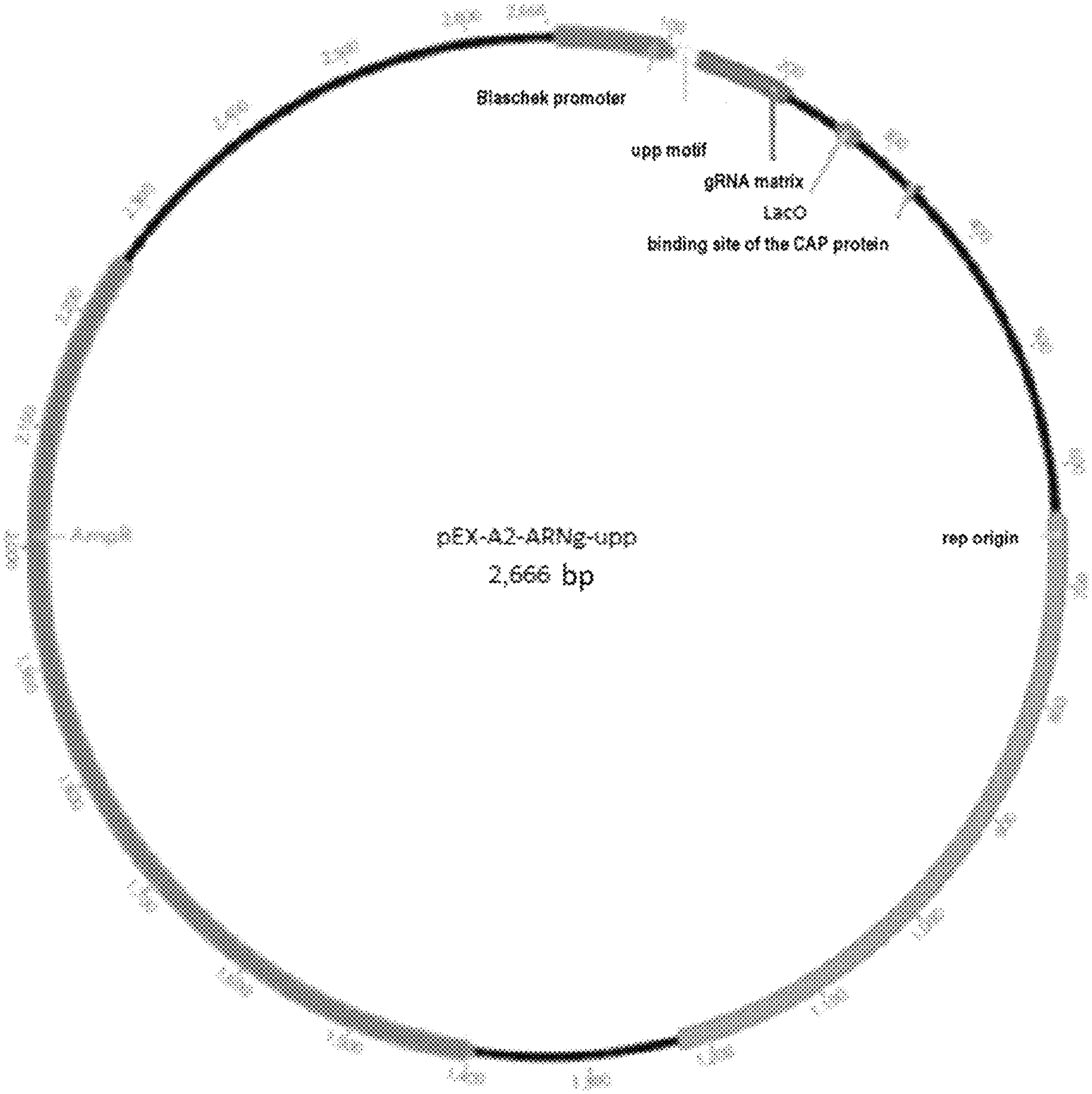

FIG. 12 shows the pEX-A2-gRNA-upp plasmid map.

Figure 13:
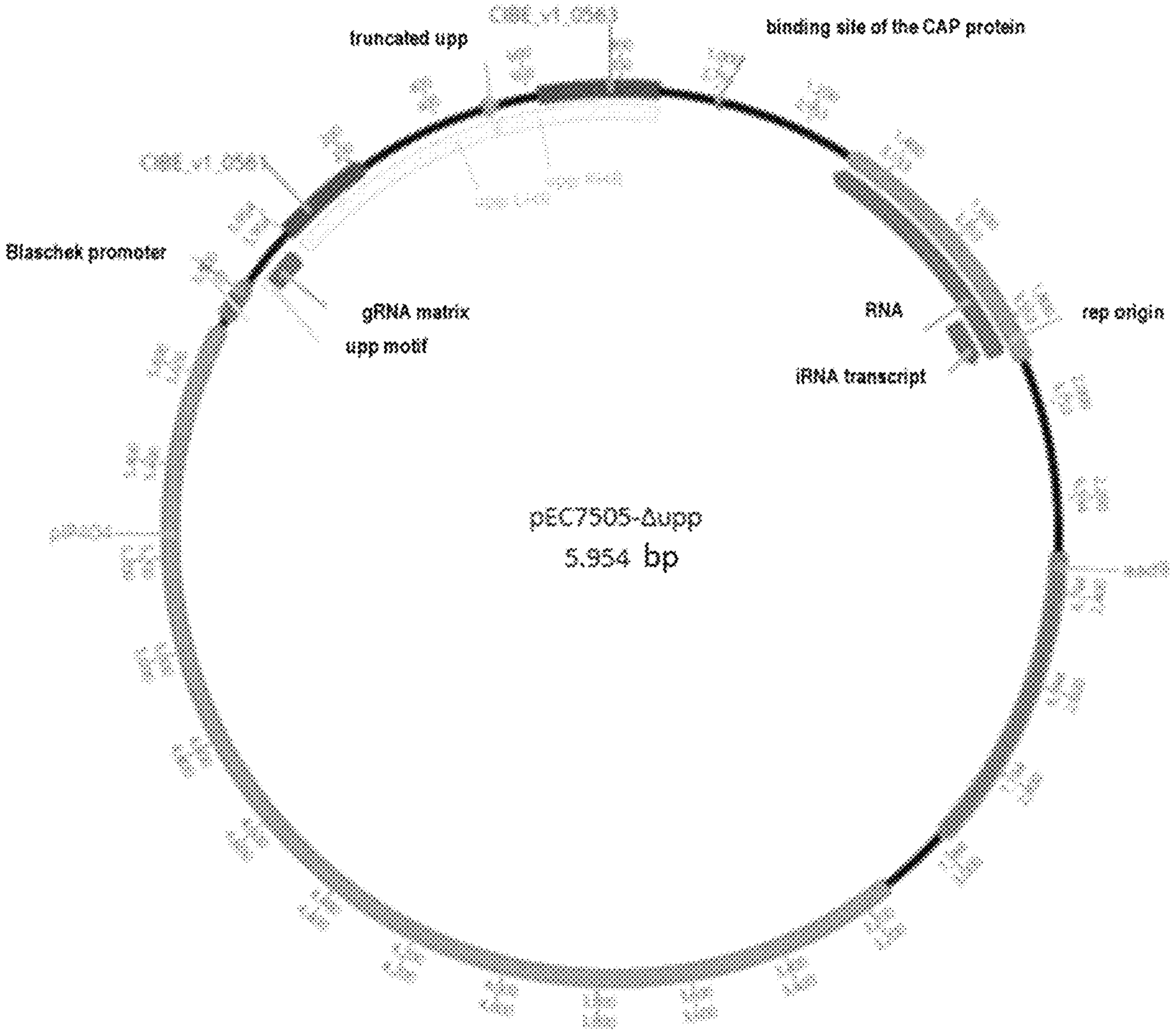

FIG. 13 shows the pEC750S-Δupp plasmid map.

Figure 14:
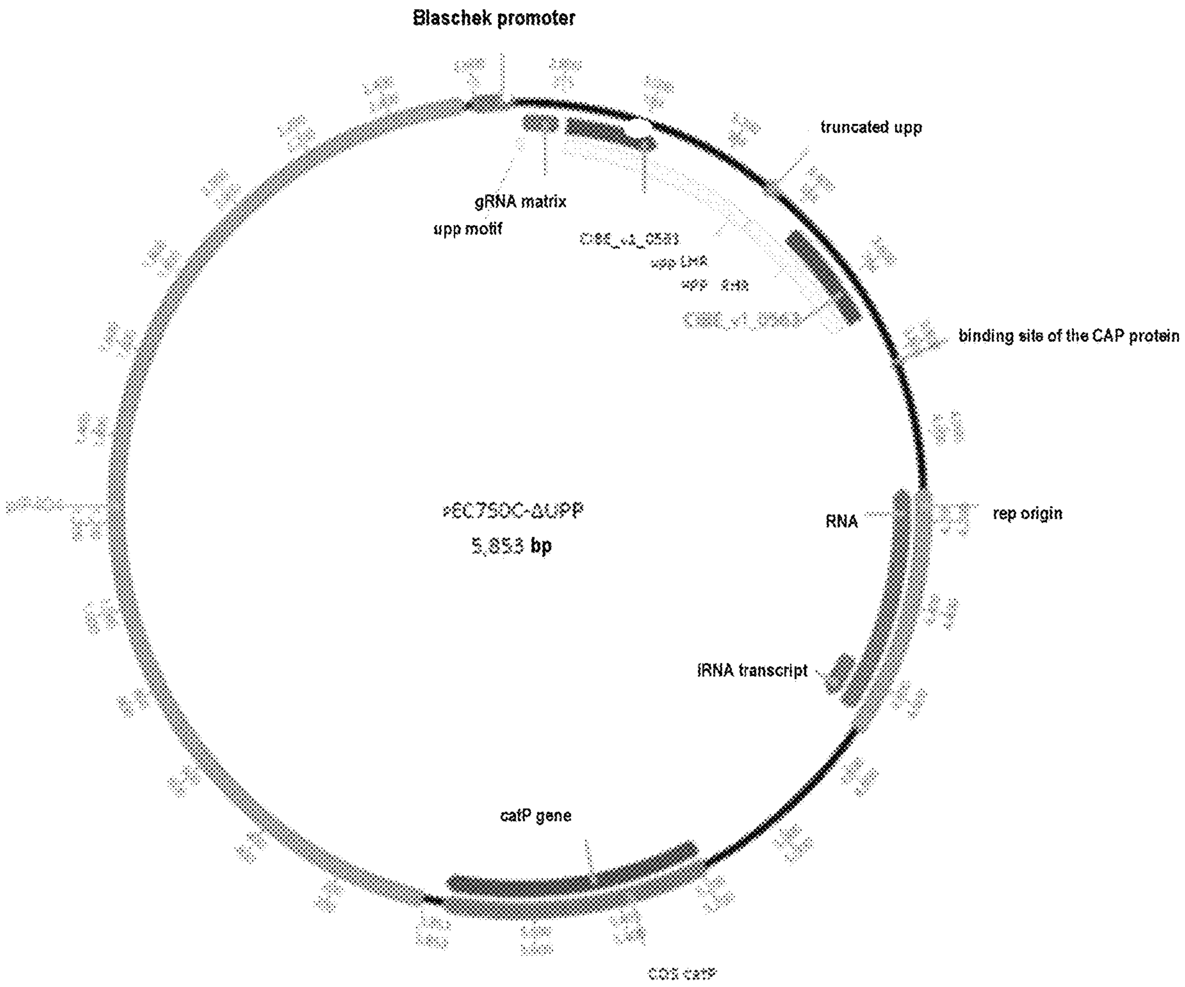

FIG. 14 shows the pEC750C-Δupp plasmid map.

Figure 15:
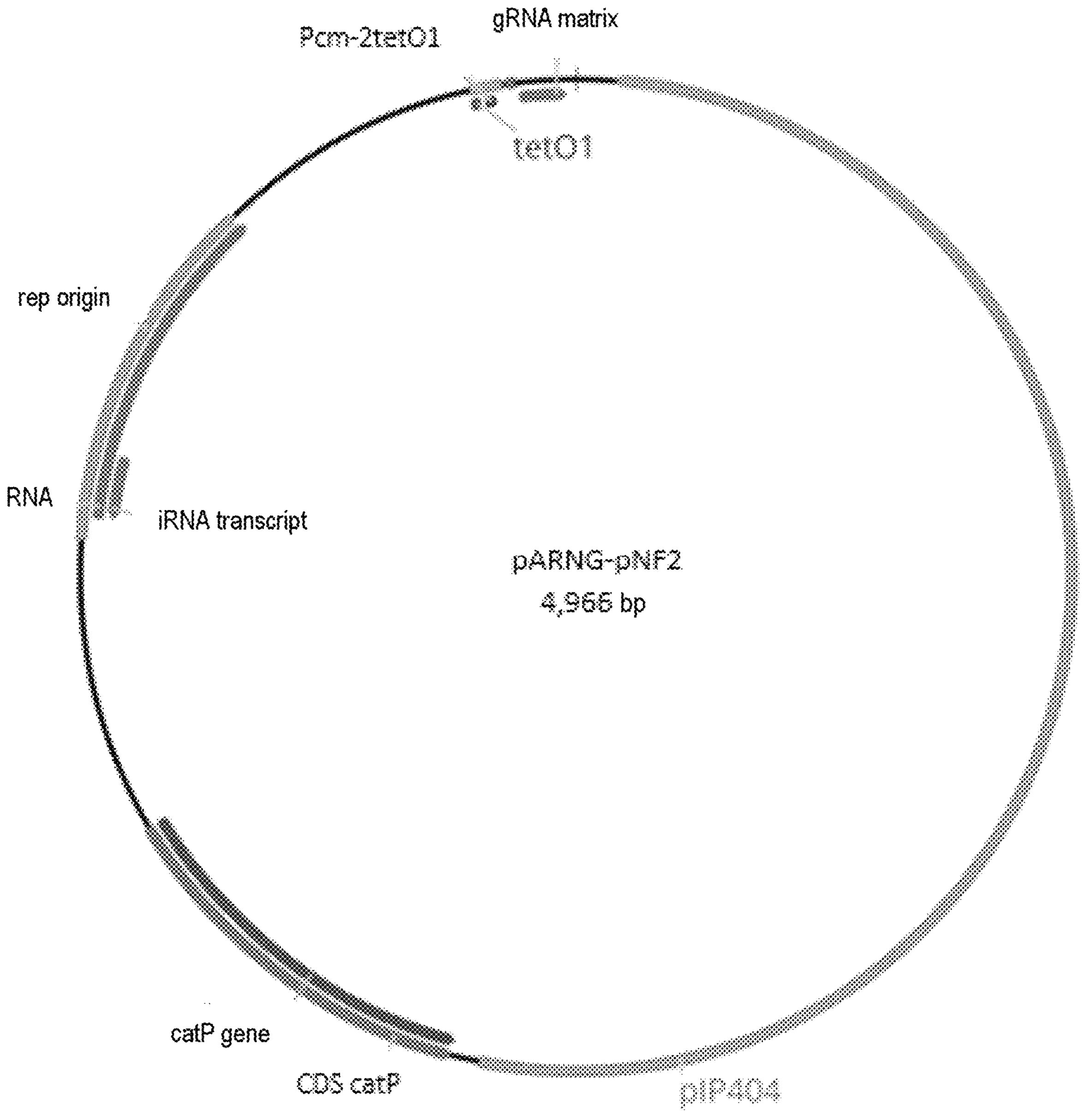

FIG. 15 shows the pGRNA-pNF2map.

Figure 16:
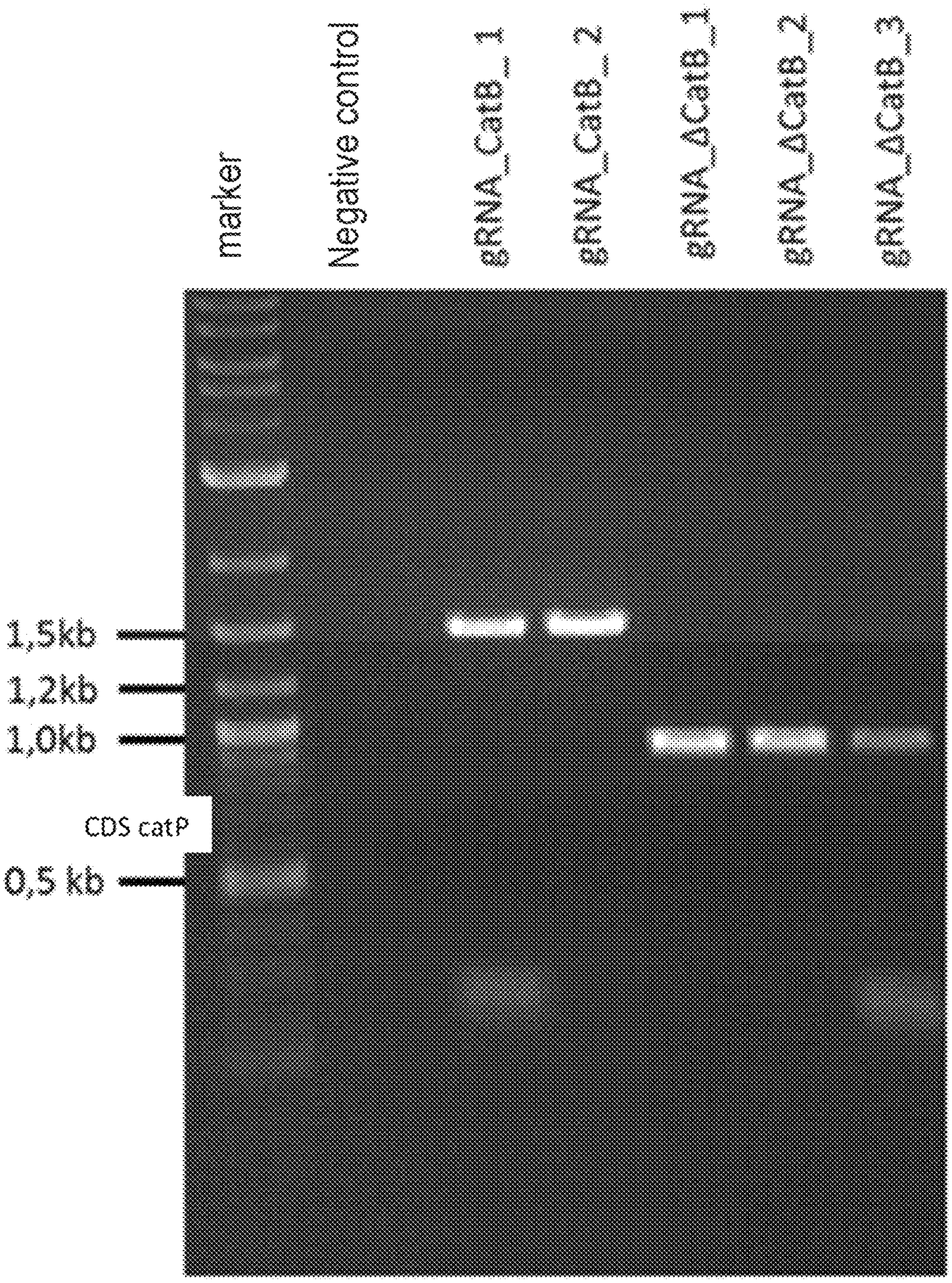

FIG. 16 shows PCR amplification of the gene catB in the clones resulting from bacterial transformation of the strain *C. beijerinckii* DSM 6423.

Amplification of about 1.5 kb if the strain still possesses the gene catB, or of about 900 bp if this gene has been deleted.

Figure 17:
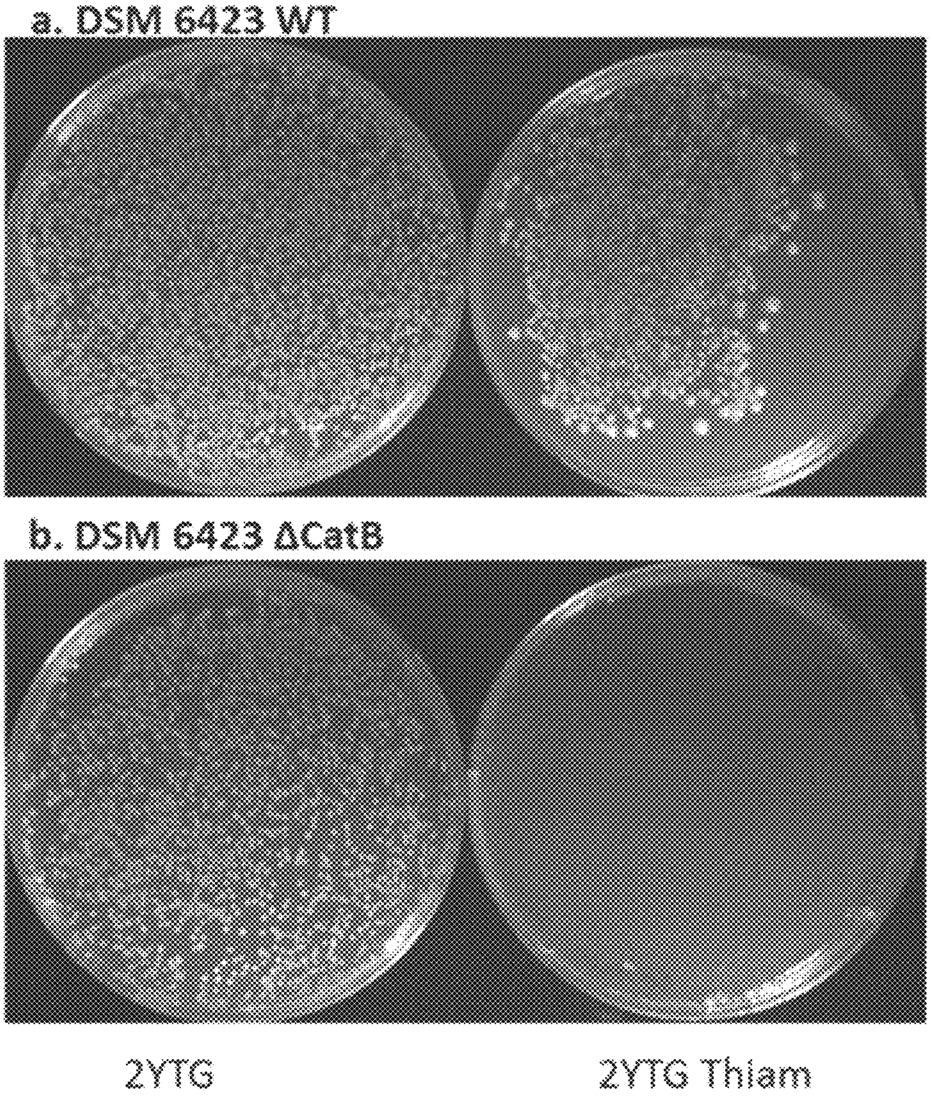

FIG. 17 shows the growth of the strains *C. beijerinckii* DSM 6423 WT and ΔcatB on 2YTG medium and 2YTG thiamphenicol selective medium.

Figure 18:
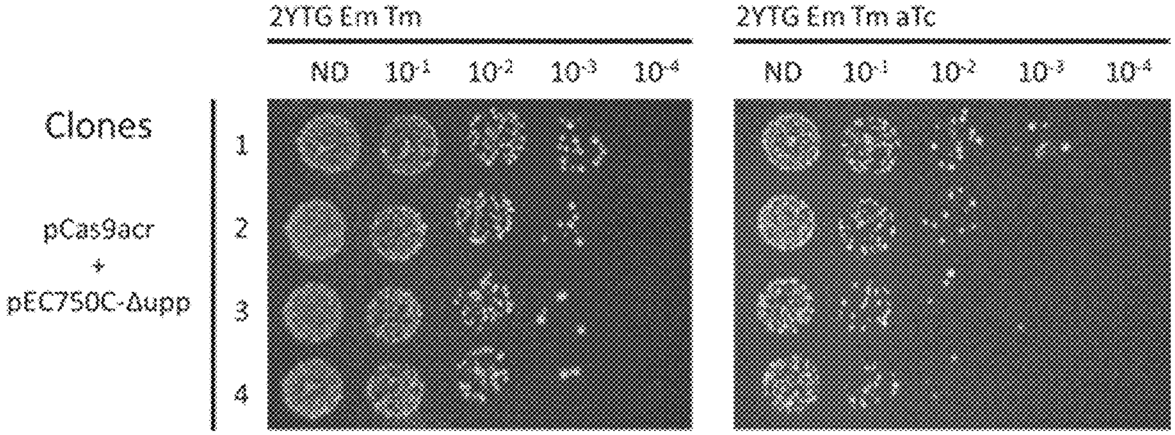

FIG. 18 shows induction of the CRISPR/Cas9acr system in transformants of the strain *C. beijerinckii* DSM 6423 containing pCas9$_{acr}$ and an expression plasmid of the gRNA targeting upp, with or without a repair matrix. Legend: Em, erythromycin; Tm, thiamphenicol; aTc, anhydrotetracycline; ND, not diluted.

FIG. 19A shows modification of the locus upp of *C. beijerinckii* DSM 6423 by means of the CRISPR/Cas9 system. FIG. 19A shows the genetic organization of the locus upp: genes, target site of the gRNA and repair matrices, associated with the corresponding homology regions on the genomic DNA. The hybridization sites of the primers for verification by PCR (RH010 and RH011) are also indicated.

FIG. 19B shows modification of the locus upp of *C. beijerinckii* DSM 6423 by means of the CRISPR/Cas9 system. FIG. 19B shows amplification of the locus upp using the primers RH010 and RH011. An amplification of 1680 bp is expected in the case of a wild-type gene, against 1090 bp for a modified gene upp. M, 100 bp-3 kb size marker (Lonza); WT, wild-type strain.

Figure 20:
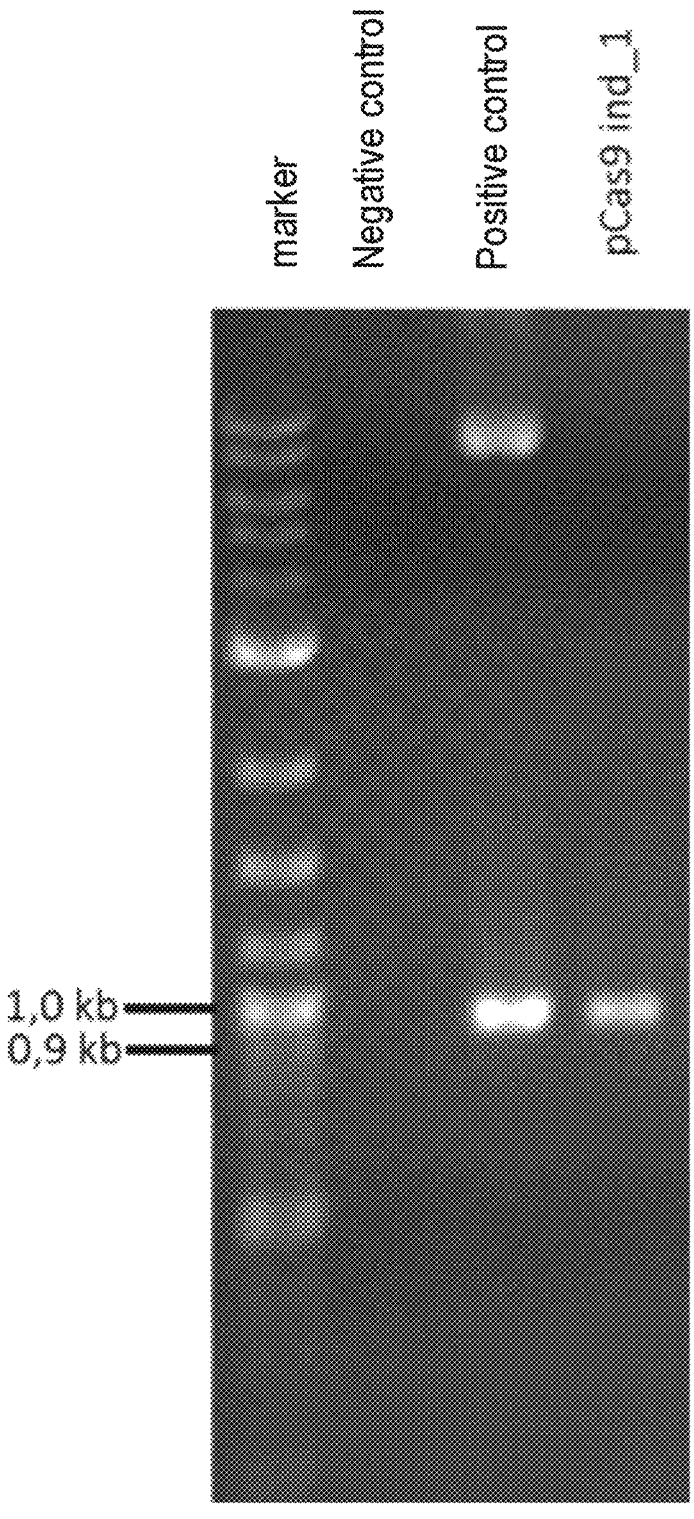

FIG. 20 shows PCR amplification verifying the presence of the plasmid pCas9$_{ind.}$ in the strain *C. beijerinckii* 6423 ΔcatB.

Figure 21:
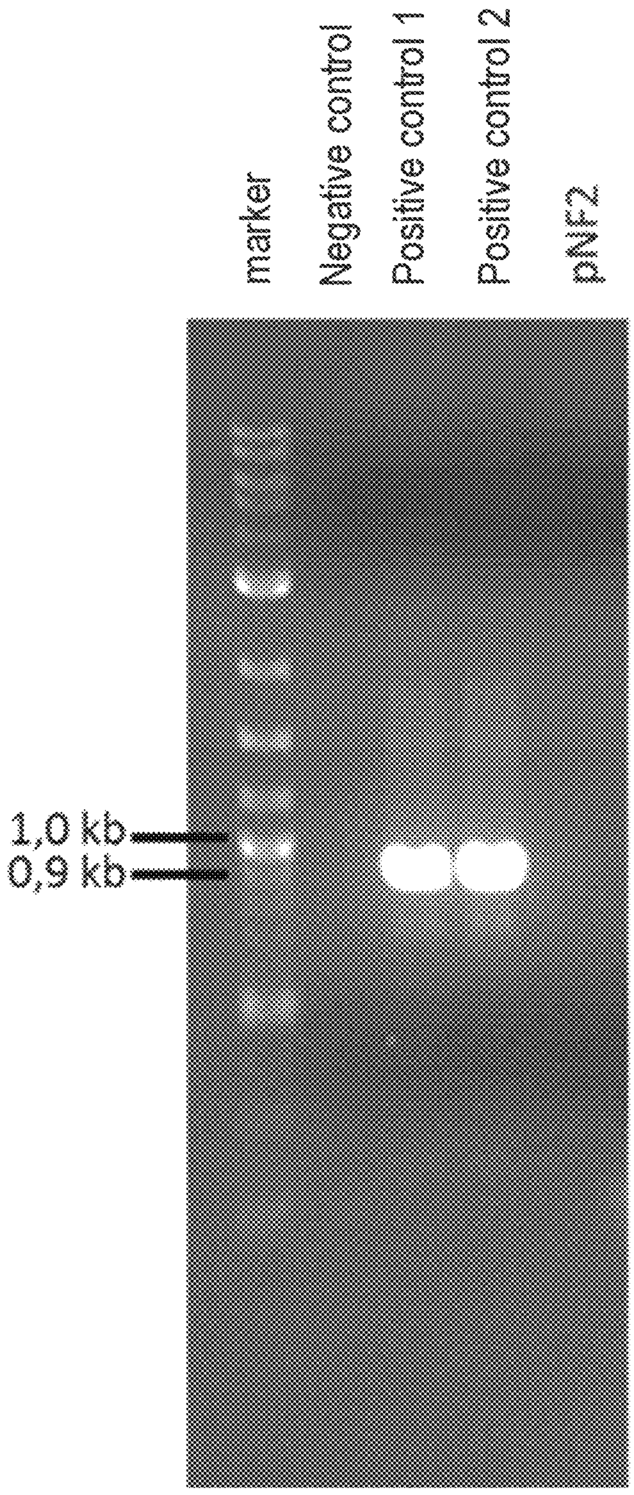

FIG. 21 shows PCR amplification (≈900 bp) verifying the presence or absence of the natural plasmid pNF2 before induction (positive control 1 and 2) and then after induction on medium containing aTc of the CRISPR-Cas9 system.

Figure 22:
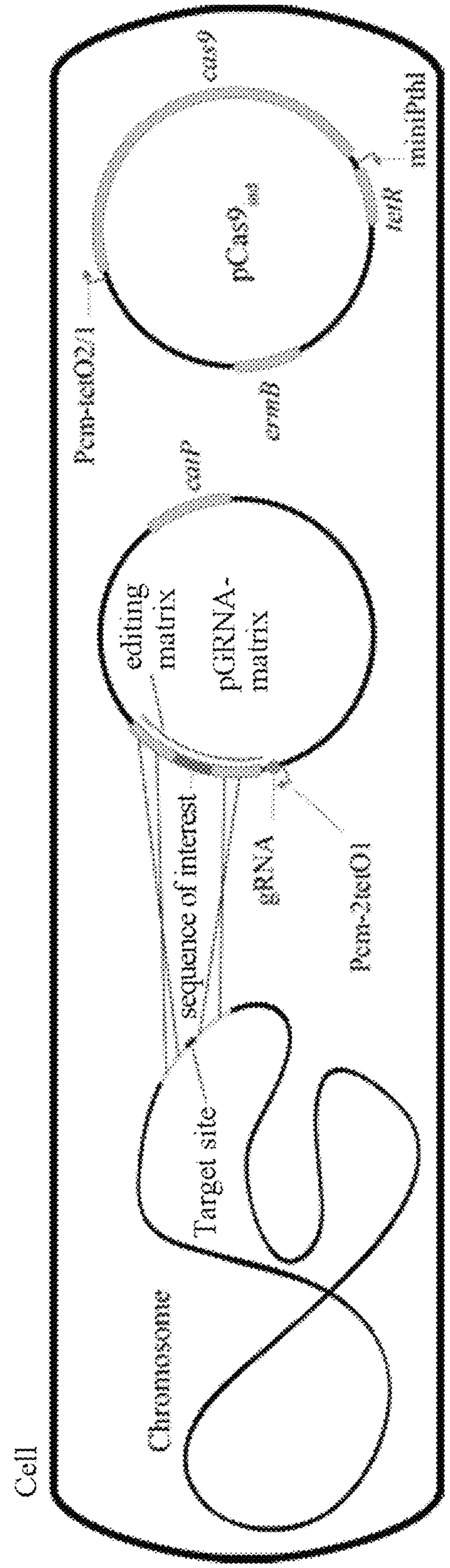

FIG. 22 shows the genetic tool for modification of bacteria, suitable for the bacteria of the genus *Clostridium*, based on the use of two plasmids (cf. WO2017/064439, Wasels et al., 2017).

Figure 23:
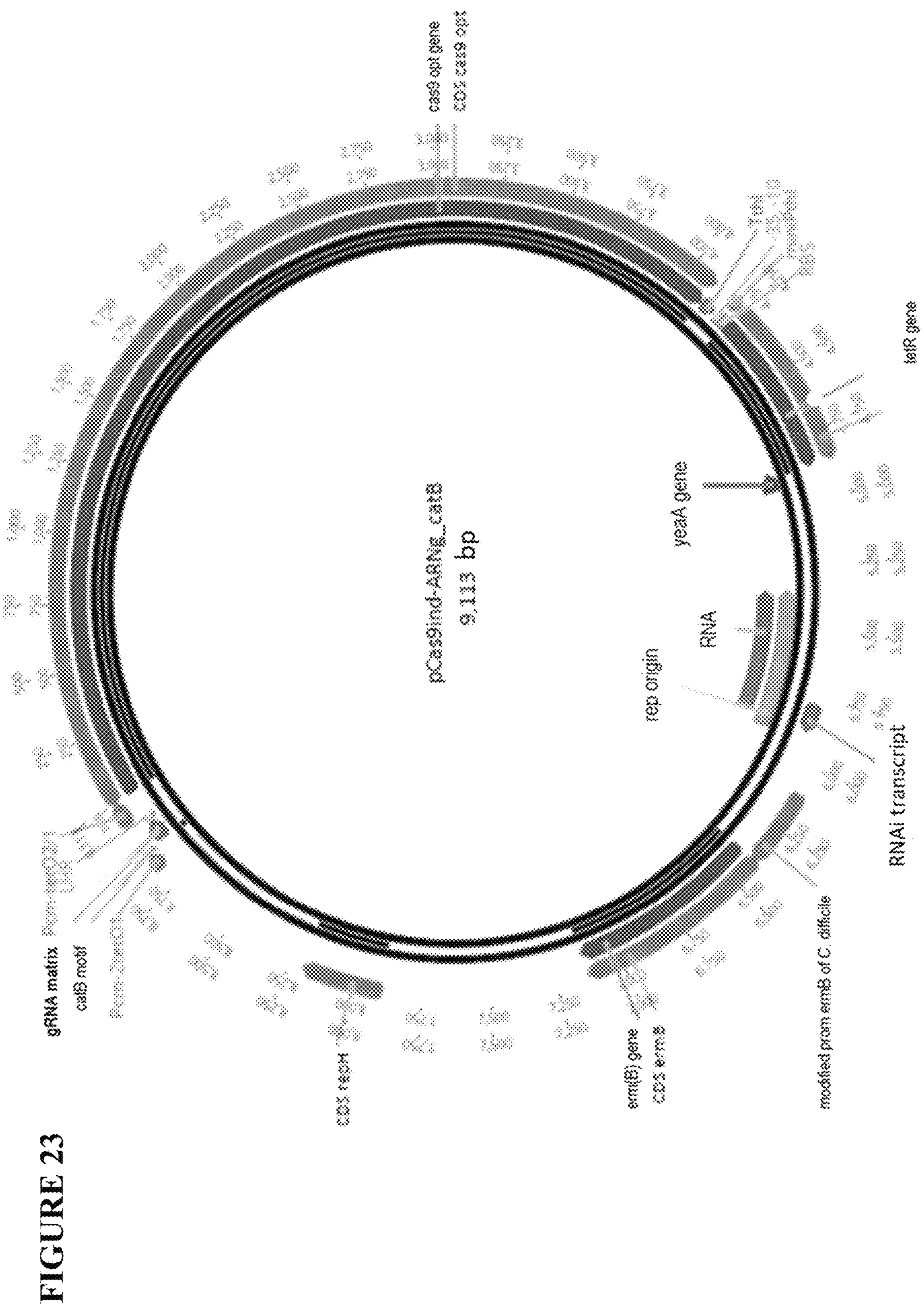

FIG. 23 shows the pCas9ind-gRNA_catB plasmid map.

Figure 24:
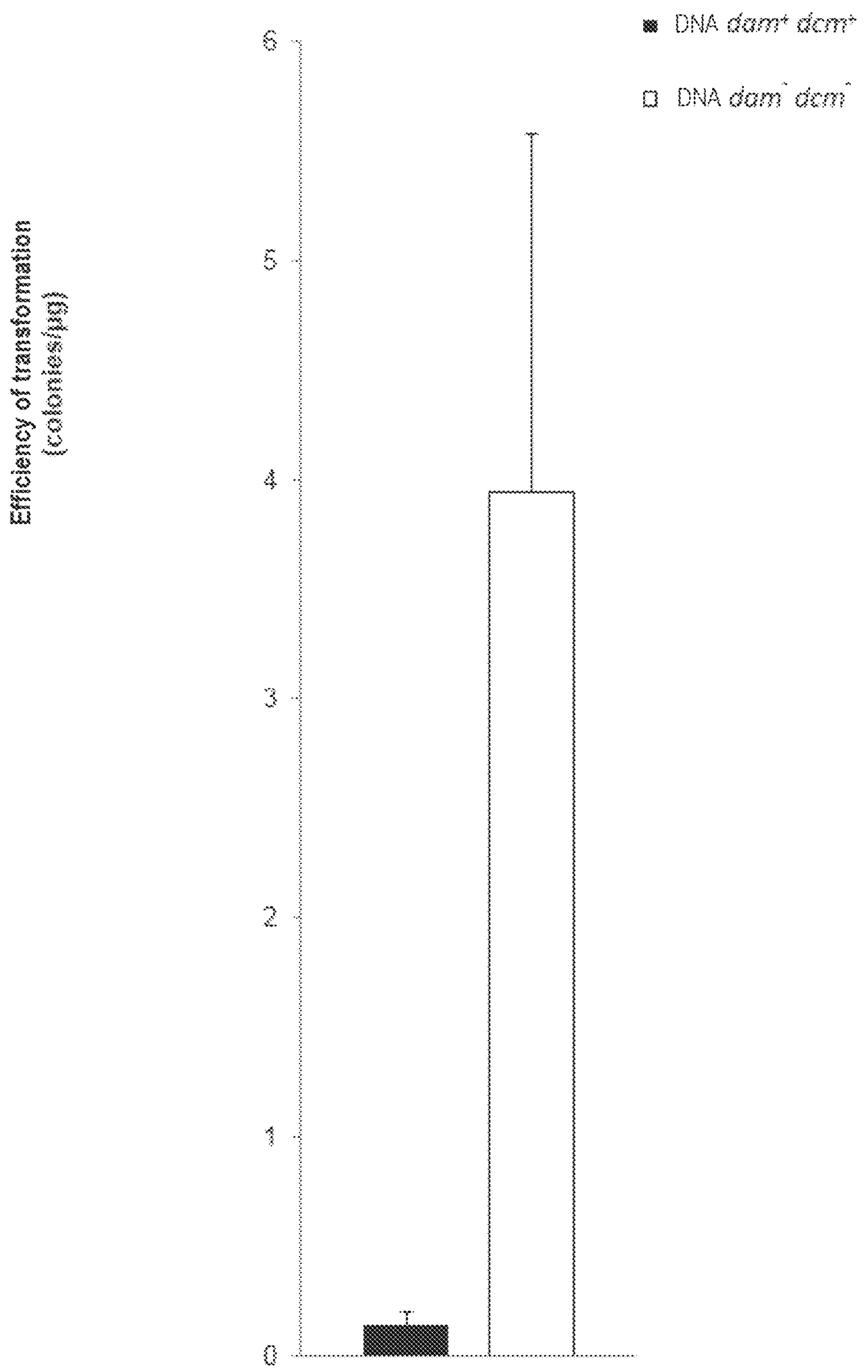

FIG. 24 shows the transformation efficiency (in colonies observed per μg of DNA transformed) for 20 μg of plasmid pCas9$_{ind}$ in the strain *C. beijerinckii* DSM6423. The error bars represent the standard error of the mean for a biological triplicate.

Figure 25:
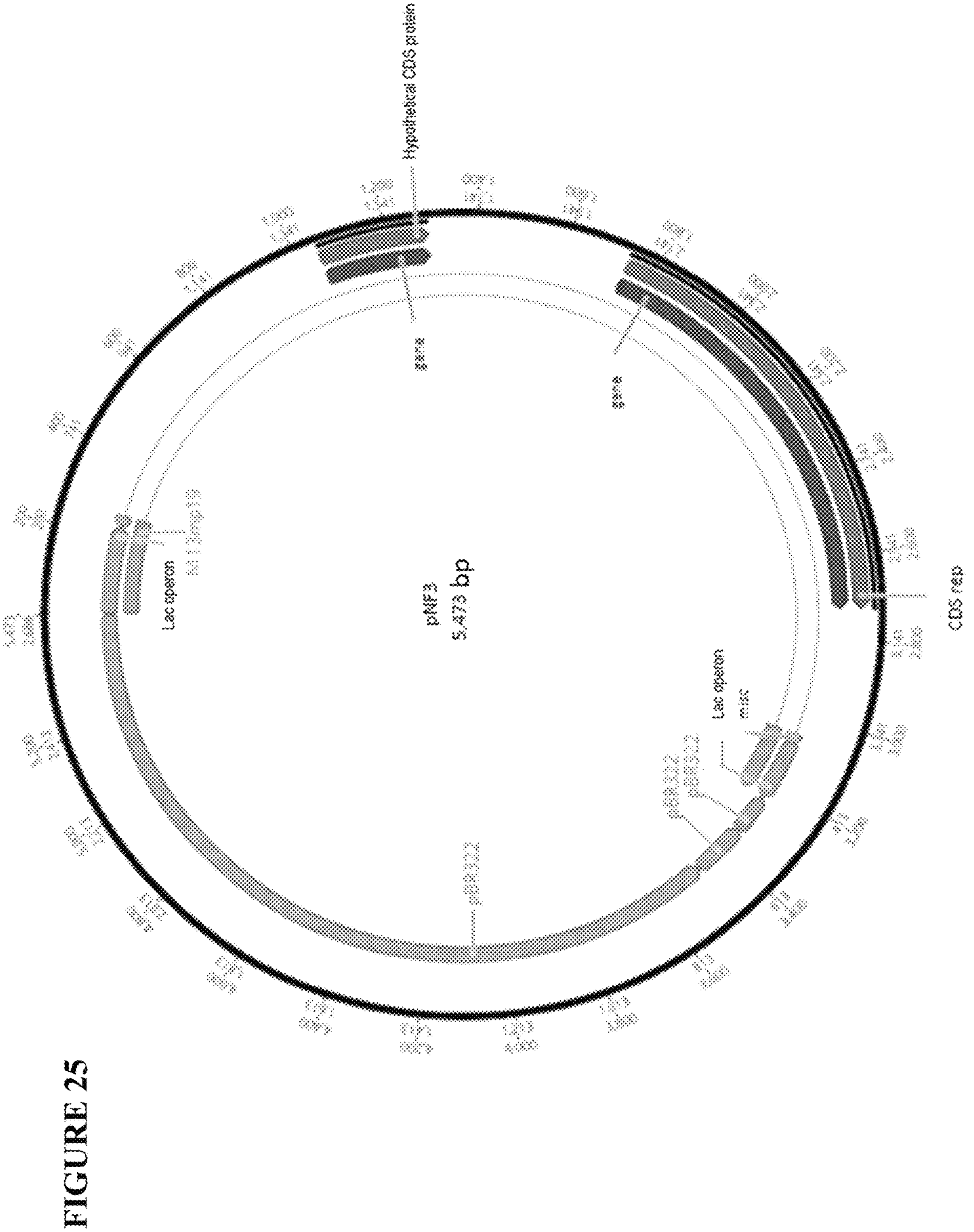

FIG. 25 shows the pNF3plasmid map.

Figure 26:
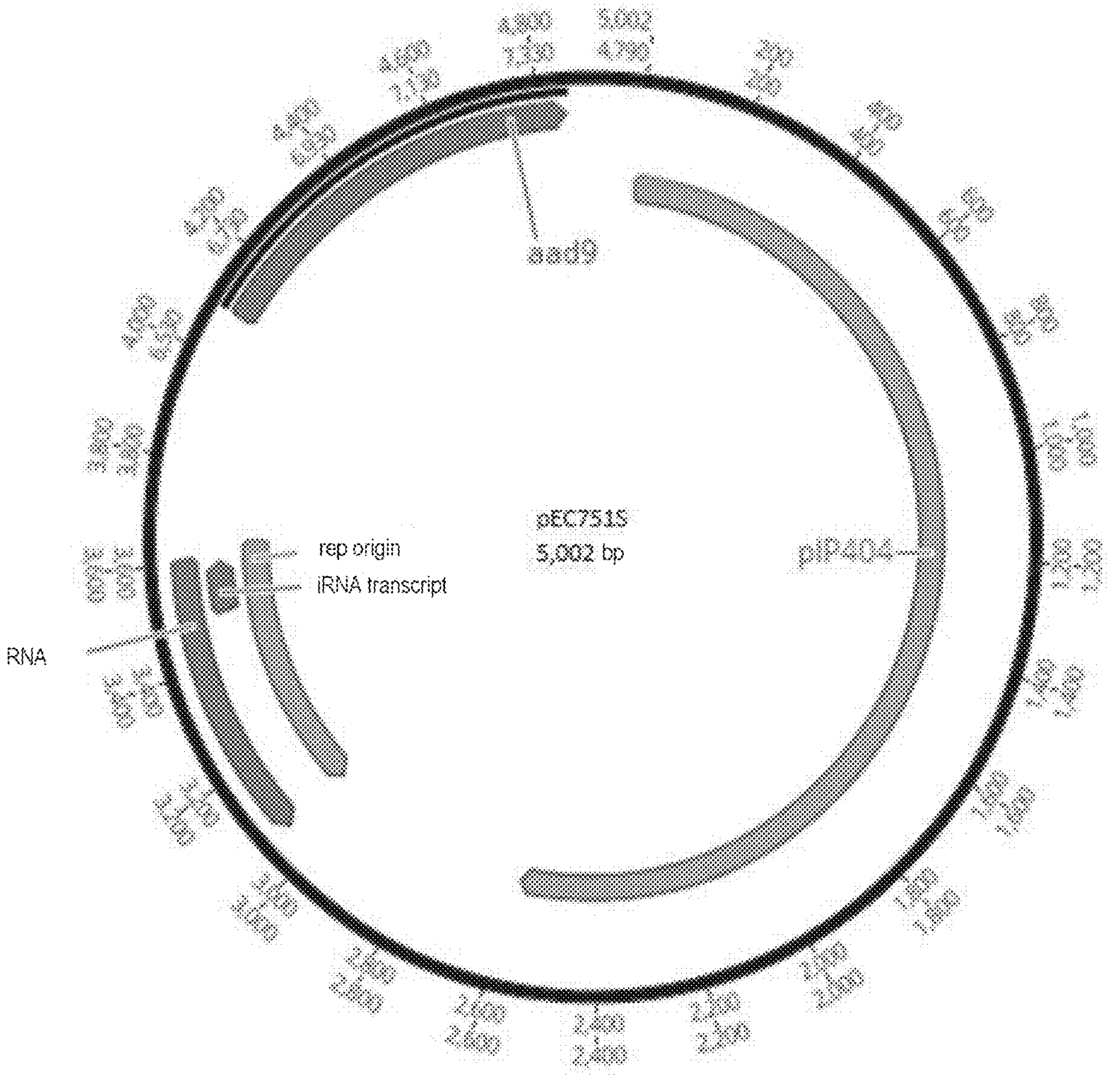

FIG. 26 shows the pEC751S plasmid map.

Figure 27:
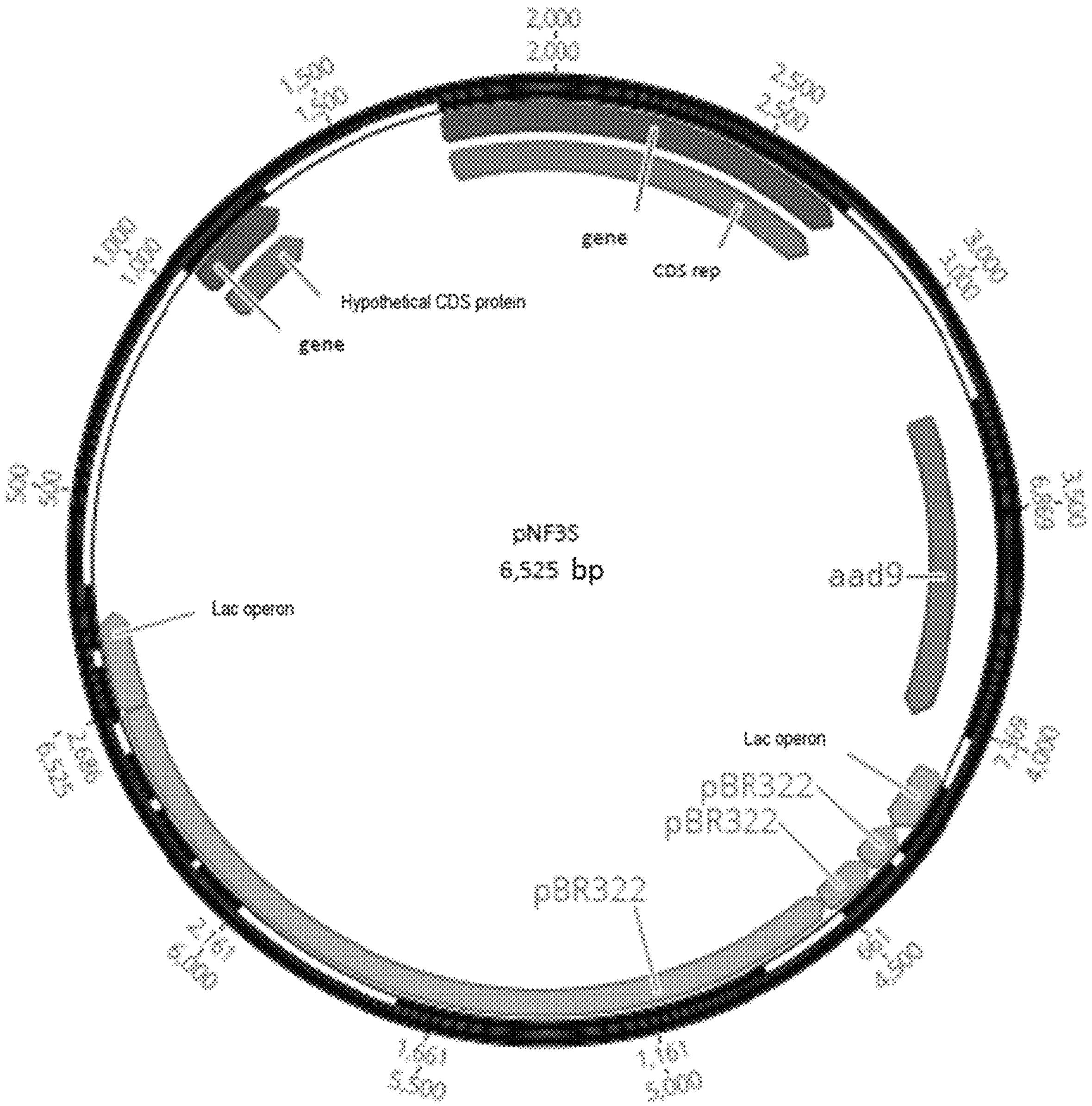

FIG. 27 shows the pNF3S plasmid map.

Figure 28:
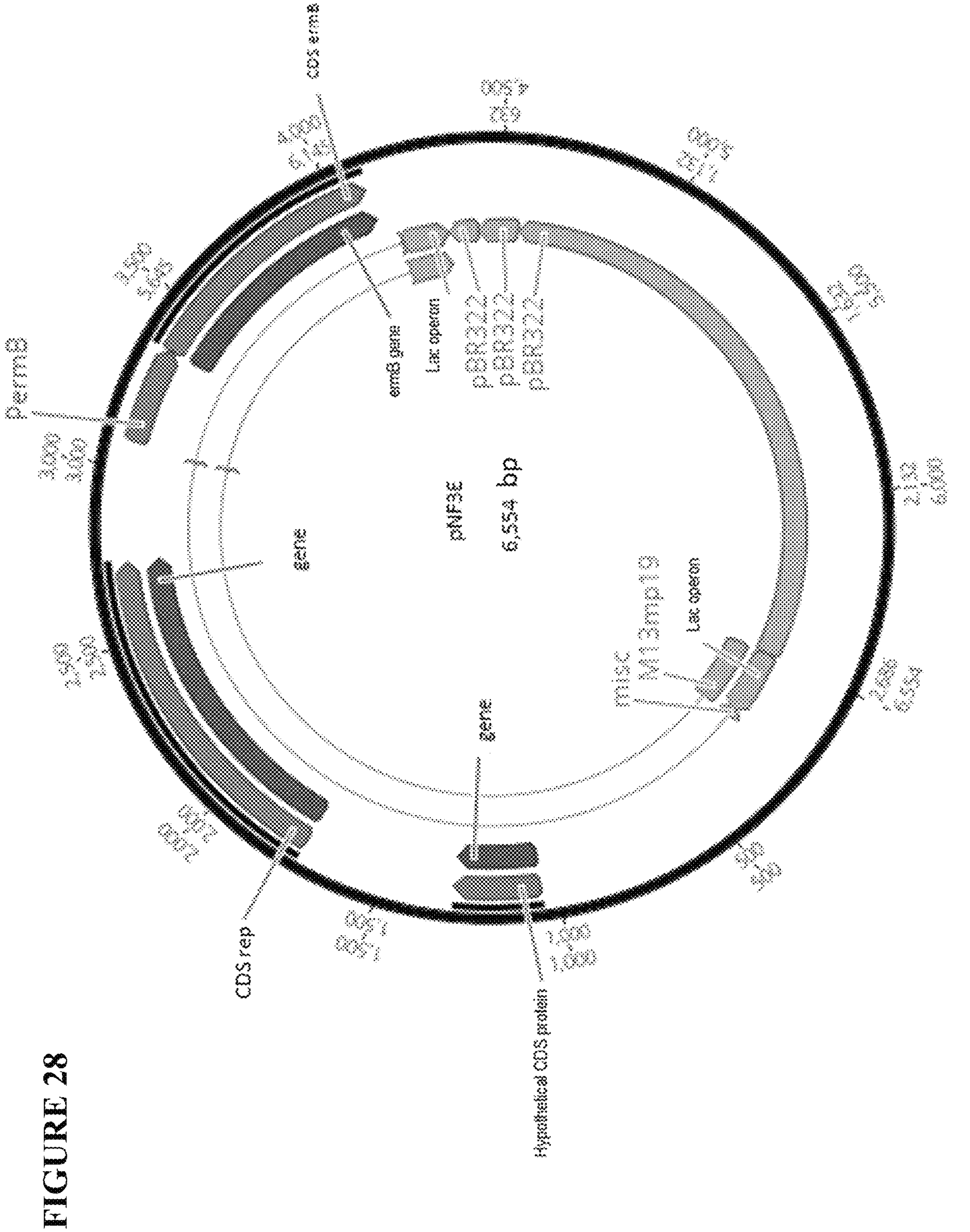

FIG. 28 shows the pNF3E plasmid map.

Figure 29:
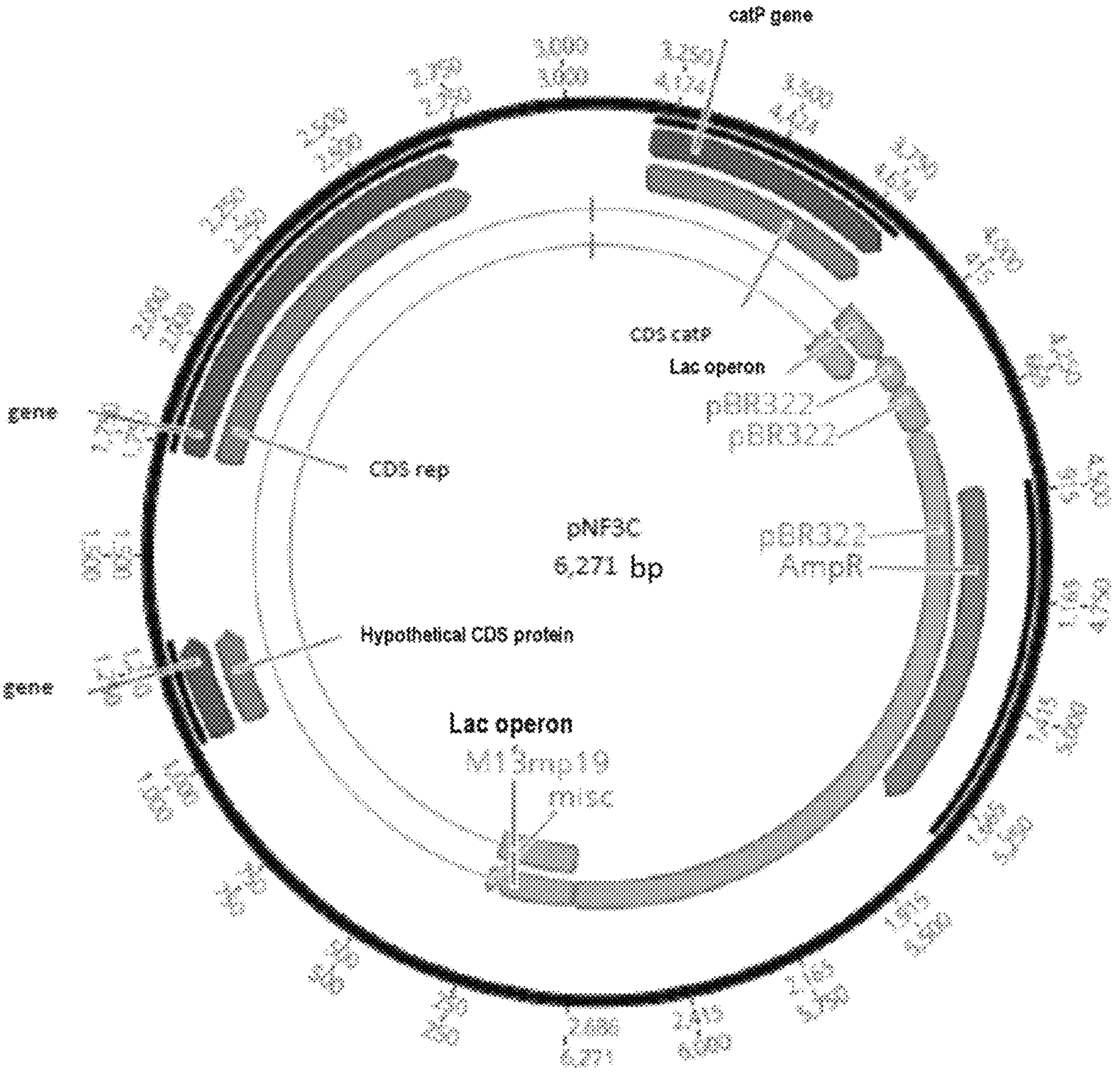

FIG. 29 shows the pNF3C plasmid map.

Figure 30:
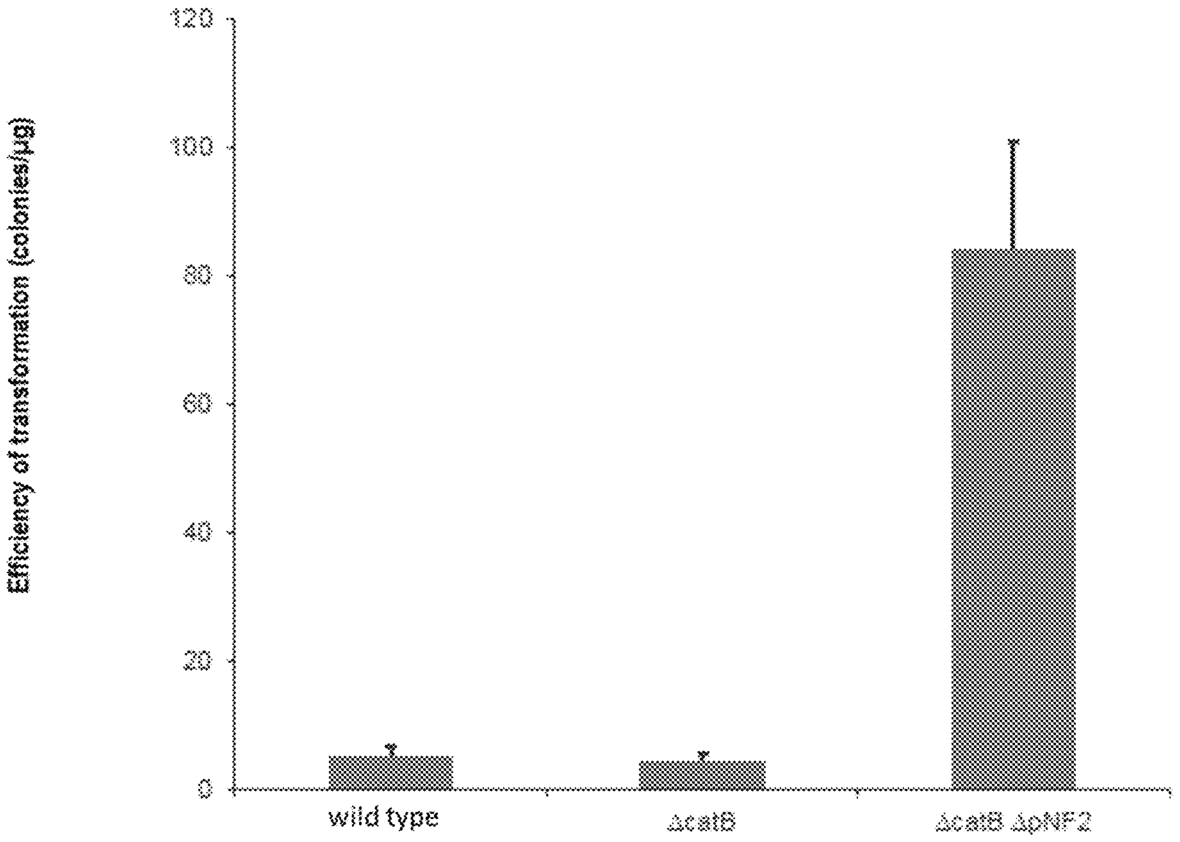

FIG. 30 shows the transformation efficiency (in colonies observed per μg of DNA transformed) of the plasmid pCas9$_{ind}$ in three strains of *C. beijerinckii* DSM 6423. The error bars correspond to the standard deviation of the mean for a biological duplicate.

Figure 31:
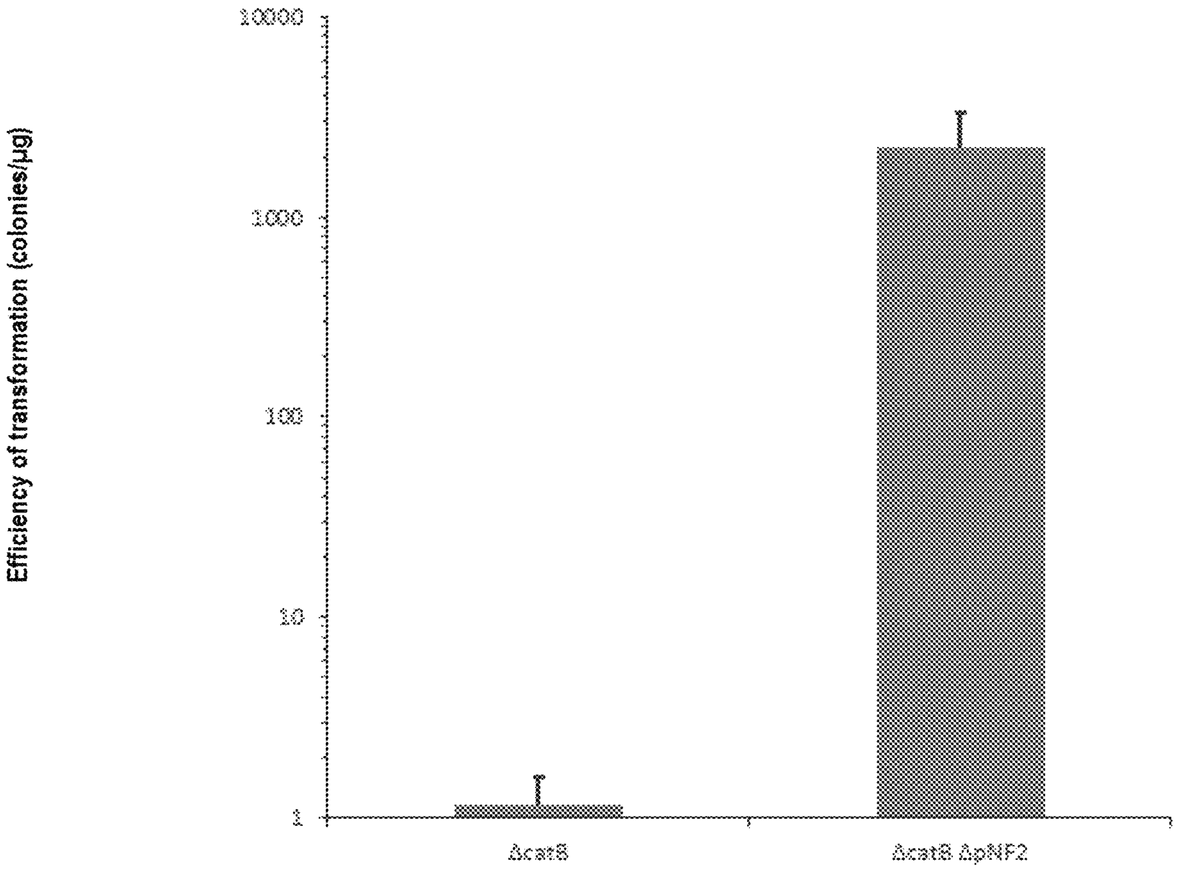

FIG. 31 shows the transformation efficiency (in colonies observed per μg of DNA transformed) of the plasmid pEC750C in two strains derived from *C. beijerinckii* DSM 6423. The error bars correspond to the standard deviation of the mean for a biological duplicate.

Figure 32:
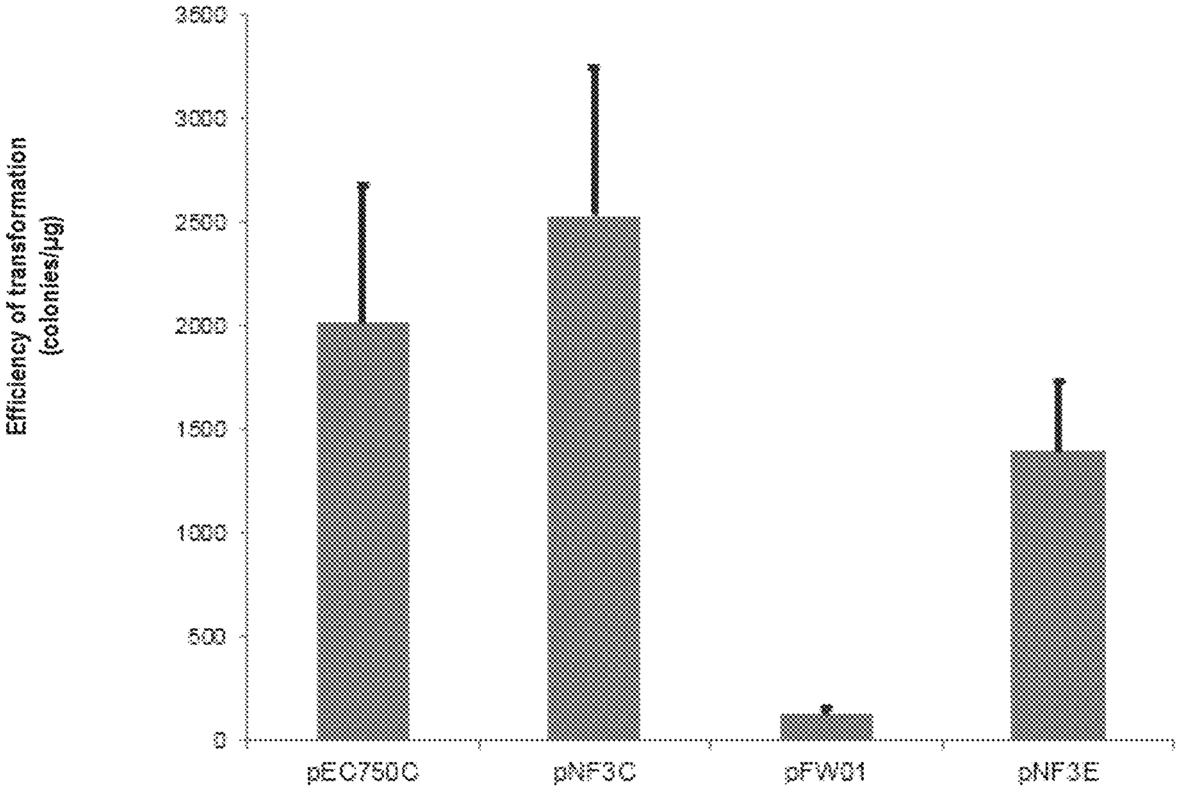

FIG. 32 shows the transformation efficiency (in colonies observed per μg of DNA transformed) of the plasmids pEC750C, pNF3C, pFW01 and pNF3E in the strain *C. beijerinckii* IFP963 ΔcatB ΔpNF2. The error bars correspond to the standard deviation of the mean for a biological triplicate.

Figure 33:
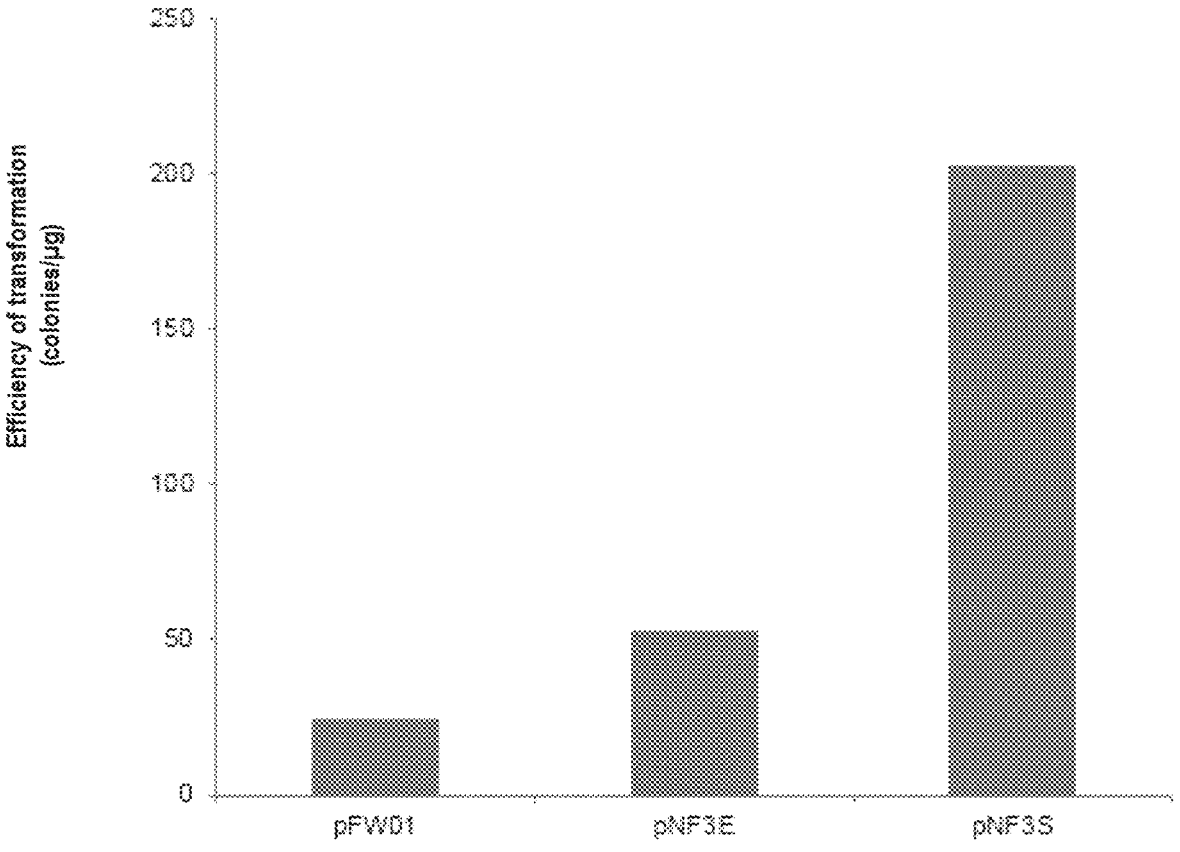

FIG. 33 shows the transformation efficiency (in colonies observed per μg of DNA transformed) of the plasmids pFW01, pNF3E and pNF3S in the strain *C. beijerinckii* NCIMB 8052.

EXAMPLES

Example No. 1

Material and Methods

Culture Conditions

*C. acetobutylicum* DSM 792 was cultured in 2YTG medium (Tryptone 16 g·l$^{-1}$, yeast extract 10 g·l$^{-1}$, glucose 5 g·l$^{-1}$, NaCl 4 g·l$^{-1}$). *E. coli* NEB10B was cultured in LB medium (Tryptone 10 g·l$^{-1}$, yeast extract 5 g·l$^{-1}$, NaCl 5 g·l$^{-1}$). The solid media were prepared by adding 15 g·l$^{-1}$ of agarose to the liquid media. Erythromycin (at concentrations of 40 or 500 mg·l$^{-1}$ respectively in 2YTG or LB medium), chloramphenicol (25 or 12.5 mg·l$^{-1}$ respectively in solid or liquid LB) and thiamphenicol (15 mg·l$^{-1}$ in 2YTG medium) were used when necessary.

Handling of the Nucleic Acids

All the enzymes and kits used were used following the suppliers' recommendations.

Construction of the Plasmids

The plasmid pCas9$_{acr}$ (SEQ ID NO: 23), shown in FIG. 4, was constructed by cloning the fragment (SEQ ID NO: 81) containing bgaR and acrIIA4 under the control of the promoter Pbgal synthesized by Eurofins Genomics at the level of the SacI site of the vector pCas9$_{ind}$ (Wasels et al., 2017).

The plasmid pGRNA$_{ind}$ (SEQ ID NO: 82) was constructed by cloning an expression cassette (SEQ ID NO: 83) of a gRNA under the control of the promoter Pcm-2tetO1 (Dong et al., 2012) synthesized by Eurofins Genomics in the SacI site of the vector pEC750C (SEQ ID NO: 106) (Wasels et al., 2017).

The plasmids pGRNA-xylB (SEQ ID NO: 102), pGRNA-xylR (SEQ ID NO: 103), pGRNA-glcG (SEQ ID NO: 104) and pGRNA-bdhB (SEQ ID NO: 105) were constructed by cloning the respective primer pairs 5'-TCATGATTTCTCCATATTAGCTAG-3' and 5'-AAACCTAGCTAATATGGAGAAATC-3', 5'-TCATGTTACACTTGGAACAGGCGT-3' and 5'-AAACACGCCTGTTCCAAGTGTAAC-3 5'-TCATTTCCGGCAGTAGGATCCCCA-3' and 5'-AAACTGGGGATCCTACTGCCGGAA-3', 5'-TCATGCTTATTACGACATAACACA-3' and 5'-AAACTGTGTTATGTCGTAATAAGC-3' within the plasmid pGRNA$_{ind}$ (SEQ ID NO: 82) digested with BsaI.

The plasmid pGRNA-ΔbdhB (SEQ ID NO: 79) was constructed by cloning the DNA fragment obtained by assembly by overlapping PCR of the PCR products obtained with the primers 5'-ATGCATGGATCCAAACGAACC-CAAAAAGAAAGTTTC-3' and 5'-GGTTGATTT-CAAATCTGTGTAAACCTACCG-3' on the one hand, 5'-ACACAGATTTGAAATCAACCACTTTAACCC-3' and 5'-ATGCATGTCGACTCTTAAGAA-CATGTATAAAGTATGG-3' on the other hand, in the vector pGRNA-bdhB digested with BamHI and SacI.

The plasmid pGRNA-ΔbdhAΔbdhB (SEQ ID NO: 80) was constructed by cloning the DNA fragment obtained by assembly by overlapping PCR of the PCR products obtained with the primers 5'-ATGCATGGATCCAAACGAACC-CAAAAAGAAAGTTTC-3' and 5'-GCTAAGTTT-TAAATCTGTGTAAACCTACCG-3' on the one hand, 5'-ACACAGATTTAAAACTTAGCATACTTCTTACC-3' and 5'-ATGCATGTCGACCTTCTAATCTCCTCTACTAT-TTTAG-3' on the other hand, in the vector pGRNA-bdhB digested with BamHI and SacI.

Transformation

*C. acetobutylicum* DSM 792 was transformed according to the protocol described by Mermelstein et al., 1993. Selection of transformants of *C. acetobutylicum* DSM 792 already containing an expression plasmid of Cas9 (pCas9$_{ind}$ or pCas9$_{acr}$) transformed with a plasmid containing an expression cassette of a gRNA was carried out on 2YTG solid medium containing erythromycin (40 mg·l$^{-1}$), thiamphenicol (15 mg·l$^{-1}$) and lactose (40 nM).

Induction of Expression of Cas9

Induction of expression of cas9 was carried out by growing the transformants obtained on a 2YTG solid medium containing erythromycin (40 mg·l$^{-1}$), thiamphenicol (15 mg·l$^{-1}$) and the inducer of expression of cas9 and gRNA, aTc (1 mg·l$^{-1}$).

Amplification of the Locus bdh

Control of the editing of the genome of *C. acetobutylicum* DSM 792 at the level of the locus of the genes bdhA and bdhB was effected by PCR using the enzyme Q5® High-Fidelity DNA Polymerase (NEB) with V1 (5'-ACACATT-GAAGGGAGCTTTT-3') and V2 (5'-GGCAACAA-CATCAGGCCTTT-3') primers.

Results

Transformation Efficiency

In order to evaluate the effect of insertion of the gene acrIIA4 on the transformation frequency of the expression plasmid of cas9, various gRNA expression plasmids were transformed into the DSM 792 strain containing pCas9$_{ind}$ (SEQ ID NO: 22) or pCas9$_{acr}$ (SEQ ID NO: 23), and the transformants were selected on a medium supplemented with lactose. The obtained transformation frequencies are presented in FIG. 5.

Generation of ΔbdhB and ΔbdhAΔbdhB Mutants

The targeting plasmid containing the gRNA expression cassette targeting bdhB (pGRNA-bdhB—SEQ ID NO: 105) as well as two derived plasmids containing repair matrices allowing deletion of the bdhB gene alone (pGRNA-ΔbdhB—SEQ ID NO: 79) or of the bdhA and bdhB genes (pGRNA-ΔbdhAΔbdhB—SEQ ID NO: 80) were transformed into the DSM 792 strain containing pCas9$_{ind}$ (SEQ ID NO: 22) or pCas9$_{acr}$ (SEQ ID NO: 23). The obtained transformation frequencies are presented in Table 2:

TABLE 2

| | DSM 792 | |
|---|---|---|
| | pCas9$_{ind}$ | pCas9$_{acr}$ |
| pEC750C | 32.6 ± 27.1 CFU · μg$^{-1}$ | 24.9 ± 27.8 CFU · μg$^{-1}$ |
| pGRNA-bdhB | 0 CFU · μg$^{-1}$ | 17.0 ± 10.7 CFU · μg$^{-1}$ |
| pGRNA-ΔbdhB | 0 CFU · μg$^{-1}$ | 13.3 ± 4.8 CFU · μg$^{-1}$ |
| pGRNA-ΔbdhAΔbdhB | 0 CFU · μg$^{-1}$ | 33.1 ± 13.4 CFU · μg$^{-1}$ |

Transformation frequencies of the DSM 792 strain containing pCas9$_{ind}$ or pCas9$_{acr}$ with plasmids targeting bdhB. The frequencies are expressed as number of transformants obtained per μg of DNA used in the transformation, and represent the mean values of at least two independent experiments.

The transformants obtained underwent a step of induction of the expression of the CRISPR/Cas9 system by passage on a medium supplemented with anhydrotetracycline, aTc (FIG. 6).

The desired modifications were confirmed by PCR on the genomic DNA of two aTc-resistant colonies (FIG. 7).

Conclusions

The genetic tool based on CRISPR/Cas9 described in Wasels et al. (2017) uses two plasmids:

- the first plasmid, pCas9$_{ind}$, contains cas9 under the control of a promoter inducible with aTc, and
- the second plasmid, derived from pEC750C, contains the expression cassette of a gRNA (placed under the control of a second promoter inducible with aTc) as well as an editing matrix allowing repair of the double-strand break induced by the system.

However, the inventors observed that certain gRNAs still seemed to be too toxic, despite control of their expression as well as of that of Cas9 by means of aTc-inducible promoters, consequently limiting the transformation efficiency of the bacteria by the genetic tool and therefore modification of the chromosome.

In order to improve this genetic tool, the cas9 expression plasmid was modified, by inserting an anti-CRISPR gene, acrIIA4, under the control of a lactose-inducible promoter. The transformation efficiencies of different gRNA expression plasmids could thus be improved very significantly, allowing transformants for all the plasmids tested to be obtained.

It has also been possible to perform editing of the locus bdhB within the genome of *C. acetobutylicum* DSM 792, using plasmids that could not be introduced into the DSM 792 strain containing pCas9$_{ind}$. The frequencies of modification observed are the same as those observed previously (Wasels et al., 2017), with 100% of the tested colonies modified.

In conclusion, modification of the cas9 expression plasmid allows better control of the Cas9-gRNA ribonucleoprotein complex, advantageously facilitating the production of transformants in which the action of Cas9 can be triggered in order to obtain mutants of interest.

Example No. 2

Material and Methods

Culture Conditions

*C. beijerinckii* DSM 6423 was cultured in 2YTG medium (Tryptone 16 g L$^{-1}$, yeast extract 10 g L$^{-1}$, glucose 5 g L$^{-1}$, NaCl 4 g L$^{-1}$). *E. coli* NEB 10-beta and INV110 were cultured in LB medium (Tryptone 10 g L$^{-1}$, yeast extract 5 g $L^{-1}$, NaCl 5 g $L^{-1}$). The solid media were prepared by adding 15 g $L^{-1}$ of agarose to the liquid media. Erythromycin (at concentrations of 20 or 500 mg $L^{-1}$ respectively in 2YTG or LB medium), chloramphenicol (25 or 12.5 mg $L^{-1}$ respectively in solid or liquid LB), thiamphenicol (15 mg $L^{-1}$ in 2YTG medium) or spectinomycin (at concentrations of 100 or 650 mg $L^{-1}$ respectively in LB or 2YTG medium) were used if necessary.

Nucleic Acids and Plasmid Vectors

All the enzymes and kits used were used following the suppliers' recommendations.

The PCR assays on colonies observed the following protocol:

An isolated colony of *C. beijerinckii* DSM 6423 is resuspended in 100 μL of Tris 10 mM pH 7.5 EDTA 5 mM. This solution is heated at 98° C. for 10 min without stirring. 0.5 μL of this bacterial lysate can then be used as PCR matrix in reactions of 10 μL with Phire (Thermo Scientific), Phusion (Thermo Scientific), Q5 (NEB) or KAPA2G Robust (Sigma-Aldrich) polymerase.

The list of the primers used for all of the constructions (name/DNA sequence) is detailed below:

| | |
|---|---|
| ΔcatB_fwd: | TGTTATGGATTATAAGCGGCTCGAGGACGTCAAACCATGTTAATCATTGC |
| ΔcatB_rev: | AATCTATCACTGATAGGGACTCGAGCAATTTCACCAAAGAATTCGCTAGC |
| ΔcatB_gRNA_rev: | AATCTATCACTGATAGGGACTCGAGGGGCAAAAGTGTAAAGACAAGCTTC |
| RH076: | CATATAATAAAAGGAAACCTCTTGATCG |
| RH077: | ATTGCCAGCCTAACACTTGG |
| RH001: | ATCTCCATGGACGCGTGACGTCGACATAAGGTACAGGAATTAGAGCAGC |
| RH002: | TCTATCTCCAGCTCTAGACCATTATTATTCCTCCA-AGTTTGCT |
| RH003: | ATAATGGTCTAGAGCTGGAGATAGATTATTTGGTACTAAG |
| RH004: | TATGACCATGATTACGAATTCGAGCTCGAAGCGCTTATTATTGCATTAGC |
| pEX-fwd: | CAGATTGTACTGAGAGTGCACC |
| pEX-rev: | GTGAGCGGATAACAATTTCACAC |
| pEC750C-fwd: | CAATATTCCACAATATTATATTATAAGCTAGC |
| M13-rev: | CAGGAAACAGCTATGAC |
| RH010: | CGGATATTGCATTACCAGTAGC |
| RH011: | TTATCAATCTCTTACACATGGAGC |
| RH025: | TAGTATGCCGCCATTATTACGACA |
| RH134: | GTCGACGTGGAATTGTGAGC |
| pNF2_fwd: | GGGCGCACTTATACACCACC |
| pNF2_rev: | TGCTACGCACCCCCTAAAGG |
| RH021: | ACTTGGGTCGACCACGATAAAACAAGGTTTTAAGG |
| RH022: | TACCAGGGATCCGTATTAATGTAACTATGATATCAATTCTTG |
| aad9-fwd2: | ATGCATGGTCCCAATGAATAGGTTTACACTTACTTTAGTTTTATGG |

-continued

| | |
|---|---|
| aad9-rev: | ATGCGAGTTAACAACTTCTAAAATCTGATTACCAATTAG |
| RH031: | ATGCATGGATCCCAATGAATAGGTTTACACTTACTTTAGTTTTATGG |
| RH032: | ATGCGAGAGCTCAACTTCTAAAATCTGATTACCAATTAG |
| RH138: | ATGCATGGATCCGTCTGACAGTTACCAGGTCC |
| RH139: | ATGCGAGAGCTCCAATTGTTCAAAAAAATAATGGCGGAG |
| RH140: | ATGCATGGATCCCGGCAGTTTTTCTTTTTCGG |
| RH141: | ATGCGAGAGCTCGGTTAAATACTAGTTTTTAGTTACAGAC |

The following plasmid vectors were prepared:

Plasmid No. 1: pEX-A258-ΔcatB (SEQ ID NO: 17)

It contains the synthesized DNA fragment ΔcatB cloned in the plasmid pEX-A258. This fragment ΔcatB comprises i) an expression cassette of a guide RNA targeting the gene catB (chloramphenicol resistance gene encoding a chloramphenicol-O-acetyltransferase—SEQ ID NO: 18) of *C. beijerinckii* DSM6423 under the control of an anhydrotetracycline-inducible promoter (expression cassette: SEQ ID NO: 19), and ii) an editing matrix (SEQ ID NO: 20) comprising 400 bp homologues located upstream and downstream of the gene catB.

Plasmid No. 2: pCas9ind-ΔcatB (cf. FIG. 9 and SEQ ID NO: 21)

It contains the fragment ΔcatB amplified by PCR (primers ΔcatB_fwd and ΔcatB_rev) and cloned in pCas9ind (described in patent application WO2017/064439—SEQ ID NO: 22) after digestion of the various DNAs with the XhoI restriction enzyme.

Plasmid No. 3: pCas9acr (cf. FIG. 10 and SEQ ID NO: 23)

Plasmid No. 4: pEC750S-uppHR (cf. FIG. 11 and SEQ ID NO: 24)

It contains a repair matrix (SEQ ID NO: 25) used for deleting the gene upp and consisting of two homologous DNA fragments upstream and downstream of the gene upp (respective sizes: 500 (SEQ ID NO: 26) and 377 (SEQ ID NO: 27) base pairs). The assembly was obtained using the Gibson cloning system (New England Biolabs, Gibson assembly Master Mix 2×). For this purpose, the parts upstream and downstream were amplified by PCR starting from the genomic DNA of the strain DSM 6423 (cf. Maté Gerando et al., 2018 and accession number PRJEB11626 (https://www.ebi.ac.uk/ena/data/view/PRJEB11626)) using the respective primers RH001/RH002 and RH003/RH004. These two fragments were then assembled in pEC750S linearized beforehand by enzymatic restriction (SalI and SacI restriction enzymes).

Plasmid No. 5: pEX-A2-gRNA-upp (cf. FIG. 12 and SEQ ID NO: 28)

This plasmid comprises the DNA fragment gRNA-upp corresponding to an expression cassette (SEQ ID NO: 29) of a guide RNA targeting the gene upp (protospacer targeting upp (SEQ ID NO: 31)) under the control of a constitutive promoter (non-coding RNA of sequence SEQ ID NO: 30), inserted in a replication plasmid designated pEX-A2.

Plasmid No. 6: pEC750S-Δupp (cf. FIG. 13 and SEQ ID NO: 32)

It has the plasmid pEC750S-uppHR (SEQ ID NO: 24) as base and in addition contains the DNA fragment comprising an expression cassette of a guide RNA targeting the gene upp under the control of a constitutive promoter.

This fragment was inserted in a pEX-A2, called pEX-A2-gRNA-upp. The insert was then amplified by PCR with the primers pEX-fwd and pEX-rev, and then digested with the restriction enzymes XhoI and NcoI. Finally, this fragment was cloned by ligation in pEC750S-uppHR digested beforehand with the same restriction enzymes to obtain pEC750S-Δupp.

Plasmid No. 7: pEC750C-Δupp (cf. FIG. 14 and SEQ ID NO: 33)

The cassette comprising the guide RNA as well as the repair matrix were then amplified with the primers pEC750C-fwd and M13-rev. The amplicon was digested with enzymatic restriction with the enzymes XhoI and SacI, and then cloned by enzymatic ligation in pEC750C to obtain pEC750C-Δupp.

Plasmid No. 8: pGRNA-pNF2 (cf. FIG. 15 and SEQ ID NO: 34)

This plasmid has pEC750C as base and contains an expression cassette of a guide RNA targeting the plasmid pNF2 (SEQ ID NO: 118).

Plasmid No. 9: pCas9ind-gRNΔcatB (cf. FIG. 23 and SEQ ID NO: 38).

It contains the sequence encoding the guide RNA targeting the locus catB amplified by PCR (primers ΔcatB_fwd and ΔcatBgRNA_rev) and cloned in pCas9ind (described in patent application WO2017/064439) after digestion of the various DNAs with the restriction enzyme XhoI and ligation.

Plasmid No. 10: pNF3 (cf. FIG. 25 and SEQ ID NO: 119)

It contains a part of the pNF2, in particular comprising the replication origin and a gene encoding a plasmid replication protein (CIBE_p20001), amplified with the primers RH021 and RH022. This PCR product was then cloned at the level of the restriction sites SalI and BamHI in the plasmid pUC19 (SEQ ID NO: 117).

Plasmid No. 11: pEC751S (cf. FIG. 26 and SEQ ID NO: 121)

It contains all the elements of pEC750C (SEQ ID NO: 106), except the chloramphenicol resistance gene catP (SEQ ID NO: 70). The latter was replaced with the gene aad9 of *Enterococcus faecalis* (SEQ ID NO: 130), which confers spectinomycin resistance. This element was amplified with the primers aad9-fwd2 and aad9-rev starting from the plasmid pMTL007S-E1 (SEQ ID NO: 120) and cloned in the sites AvaII and HpaI of pEC750C, in place of the gene catP (SEQ ID NO: 70).

Plasmid No. 12: pNF3S (cf. FIG. 27 and SEQ ID NO: 123)

It contains all the elements of pNF3, with an insertion of the gene aad9 (amplified with the primers RH031 and RH032 starting from pEC751S) between the sites BamHI and SacI.

Plasmid No. 13: pNF3E (cf. FIG. 28 and SEQ ID NO: 124)

It contains all the elements of pNF3, with an insertion of the gene ermB of *Clostridium difficile* (SEQ ID NO: 131) under the control of the promoter miniPthl. This element was amplified starting from pFW01 with the primers RH138 and RH139 and cloned between the sites BamHI and SacI of pNF3E.

Plasmid No. 14: pNF3C (cf. FIG. 29 and SEQ ID NO: 125)

It contains all the elements of pNF3, with an insertion of the gene catP of *Clostridium perfringens* (SEQ ID NO: 70). This element was amplified starting from pEC750C with the primers RH140 and RH141 and cloned between the sites BamHI and SacI of pNF3E.

Results No. 1

Transformation of the Strain *C. beijerinckii* DSM 6423

The plasmids were introduced and replicated in a strain of *E. coli* dam⁻ dcm⁻ (INV110, Invitrogen). This makes it possible to remove the methylations of the Dam and Dcm type on the plasmid pCas9ind-ΔcatB before introducing it by transformation in the DSM 6423 strain according to the protocol described by Mermelstein et al. (1993), with the following modifications: the strain is transformed with a larger amount of plasmid (20 μg), at an $OD_{600}$ of 0.8, and with the following electroporation parameters: 100Ω, 25 μF, 1400 V. Spreading on a Petri dish containing erythromycin (20 μg/mL) thus made it possible to obtain transformants of *C. beijerinckii* DSM 6423 containing the plasmid pCas9ind-ΔcatB.

Induction of Expression of Cas9 and Production of the Strain *C. beijerinckii* DSM 6423 ΔcatB (*C. beijerinckii* IFP962 ΔcatB)

Several erythromycin-resistant colonies were then taken up in 100 μL of culture medium (2YTG) and then diluted in series up to a dilution factor of $10^4$ in culture medium. For each colony, eight μL of each dilution was deposited on a Petri dish containing erythromycin and anhydrotetracycline (200 ng/mL), making it possible to induce expression of the gene encoding the nuclease Cas9.

After extraction of genomic DNA, deletion of the gene catB within the clones that had grown on this dish was verified by PCR, using the primers RH076 and RH077 (cf. FIG. 16).

Verification of the Sensitivity of the Strain *C. beijerinckii* DSM 6423 ΔcatB to Thiamphenicol To ensure that deletion of the gene catB does indeed confer new thiamphenicol sensitivity, comparative analyses were carried out on agar medium. Precultures of *C. beijerinckii* DSM 6423 and *C. beijerinckii* DSM 6423 ΔcatB were carried out on 2YTG medium and then 100 μL of these precultures was spread on 2YTG agar media supplemented or not with thiamphenicol at a concentration of 15 mg/L. It can be seen from FIG. 17 that only the initial strain *C. beijerinckii* DSM 6423 is capable of growing on a medium supplemented with thiamphenicol.

Deletion of the Gene Upp by the CRISPR-Cas9 Tool in the Strain *C. beijerinckii* DSM 6423 ΔcatB A clone of the strain *C. beijerinckii* DSM 6423 ΔcatB was transformed beforehand with the vector $pCas9_{acr}$ that does not have a methylation at the level of the motifs recognized by methyltransferases of the dam and dcm type (prepared from a bacterium *Escherichia coli* having the dam⁻ dcm⁻ genotype). Presence of the plasmid $pCas9_{acr}$ maintained in the strain *C. beijerinckii* DSM 6423 was verified by PCR on a colony with the primers RH025 and RH134.

An erythromycin-resistant clone was then transformed with pEC750C-Δupp demethylated beforehand. The colonies thus obtained were selected on medium containing erythromycin (20 μg/mL), thiamphenicol (15 μg/mL) and lactose (40 mM).

Several of these clones were then resuspended in 100 μL of culture medium (2YTG) and then diluted in series in culture medium (up to a dilution factor of $10^4$). Five μL of each dilution was deposited on a Petri dish containing erythromycin, thiamphenicol and anhydrotetracycline (200 ng/mL) (cf. FIG. 18).

Figure 19:
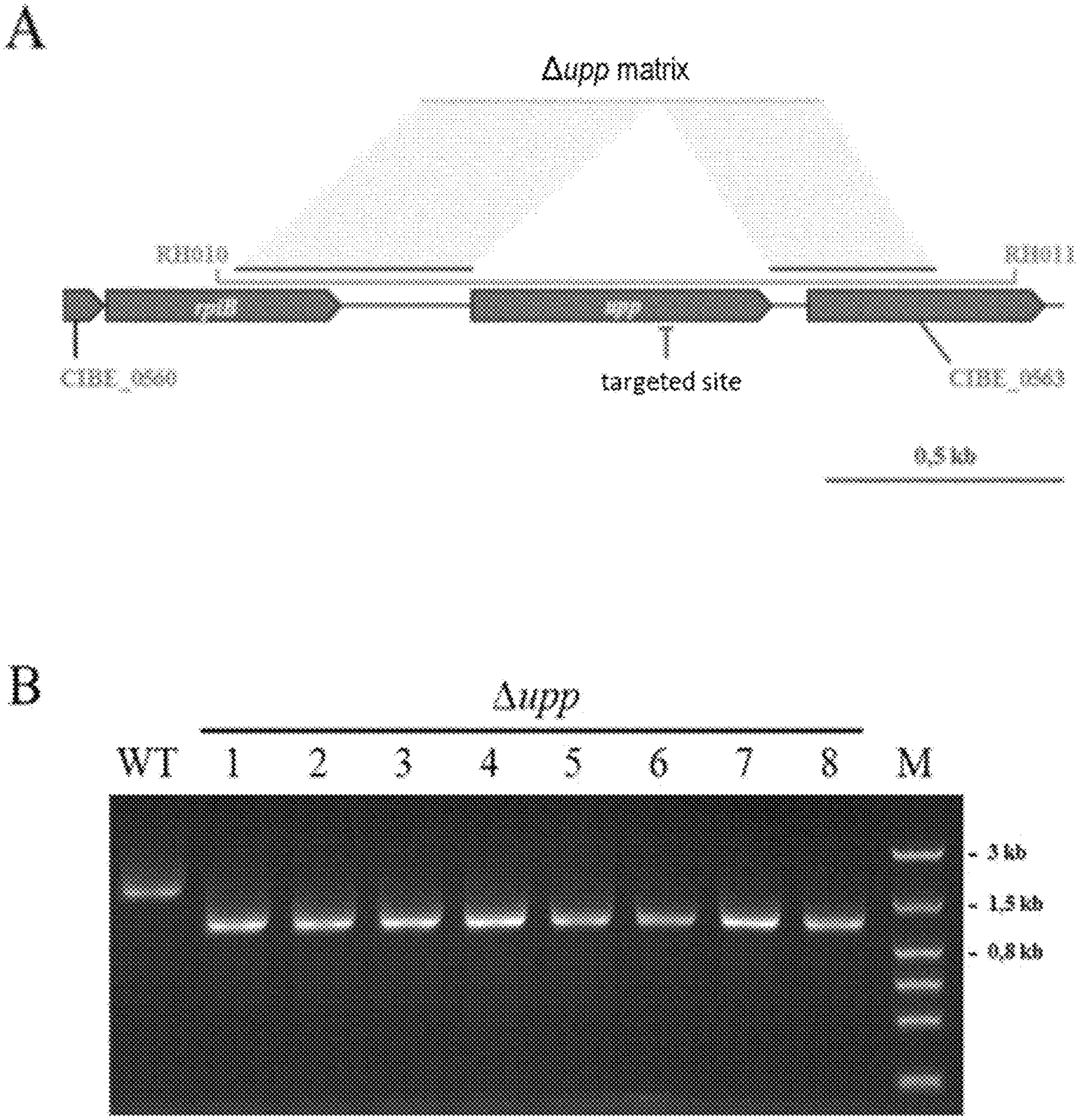

For each clone, two colonies resistant to aTc were tested by colony PCR with primers intended for amplifying the locus upp (cf. FIG. 19).

Deletion of the Natural Plasmid pNF2 by the CRISPR-Cas9 Tool in the Strain *C. beijerinckii* DSM 6423 ΔcatB A clone of the strain *C. beijerinckii* DSM 6423 ΔcatB was transformed beforehand with the vector pCas$9_{ind}$ that does not have a methylation at the level of the motifs recognized by methyltransferases of the Dam and Dcm type (prepared from a bacterium *Escherichia coli* having the dam$^-$ dcm genotype). The presence of the plasmid pCas$9_{ind}$ within the strain *C. beijerinckii* DSM6423 was verified by PCR with the primers pCas$9_{ind}$ fwd (SEQ ID NO: 42) and pCas$9_{ind}$_rev (SEQ ID NO: 43) (cf. FIG. 20).

An erythromycin-resistant clone was then used for transforming pGRNA-pNF2, prepared from a bacterium *Escherichia coli* having the dam$^-$ dcm$^-$ genotype.

Several colonies obtained on medium containing erythromycin (20 μg/mL) and thiamphenicol (15 μg/mL) were resuspended in culture medium and diluted in series up to a dilution factor of $10^4$. Height μL of each dilution was deposited on a Petri dish containing erythromycin, thiamphenicol and anhydrotetracycline (200 ng/mL) in order to induce expression of the CRISPR/Cas9 system. Absence of the natural plasmid pNF2 was verified by PCR with the primers pNF2_fwd (SEQ ID NO: 39) and pNF2_rev (SEQ ID NO: 40) (cf. FIG. 21).

Conclusions

In the course of this work, the inventors succeeded in introducing and maintaining various plasmids within the strain *Clostridium beijerinckii* DSM 6423. They succeeded in suppressing the gene catB using a CRISPR-Cas9 tool based on the use of a single plasmid. The thiamphenicol sensitivity of the recombinant strains obtained was confirmed by assays in agar medium.

This deletion enabled them to use the CRISPR-Cas9 tool more efficiently, requiring two plasmids described in patent application FR1854835. Two examples demonstrating the advantage of this application were carried out: deletion of the gene upp and removal of a natural plasmid that is not essential for the strain *Clostridium beijerinckii* DSM 6423.

Results No. 2

Transformation of the Strains of *C. beijerinckii*

The plasmids prepared in the strain of *E. coli* NEB 10-beta are also used for transforming the strain *C. beijerinckii* NCIMB 8052. However, for *C. beijerinckii* DSM 6423, the plasmids are introduced beforehand and replicated in a strain of *E. coli* dam$^-$ dcm$^-$ (INV110, Invitrogen). This makes it possible to remove the methylations of the Dam and Dcm type on the plasmids of interest before introducing them by transformation into the strain DSM 6423.

The transformation is otherwise carried out similarly for each strain, i.e. according to the protocol described by Mermelstein et al. 1992, with the following modifications: the strain is transformed with a larger amount of plasmid (5-20 μg), at an $OD_{600}$ of 0.6-0.8, and the electroporation parameters are 100Ω, 25μF, 1400 V. After 3 h of regeneration in 2YTG, the bacteria are spread on a Petri dish (2YTG agar) containing the desired antibiotic (erythromycin: 20-40 μg/mL; thiamphenicol: 15 μg/mL; spectinomycin: 650 μg/mL).

Comparison of the Transformation Efficiencies of the Strains of *C. beijerinckii* DSM 6423

Transformations were carried out in biological duplicate in the following strains of *C. beijerinckii*: DSM 6423 wild-type, DSM 6423 ΔcatB and DSM 6423 ΔcatB ΔpNF2 (FIG. 30). For this, the vector pCas$9_{ind}$, which is particularly difficult to use for modifying a bacterium as it does not give good transformation efficiencies, was used. It further comprises a gene endowing the strain with resistance to erythromycin, an antibiotic to which the three strains are sensitive.

The results indicate an increase in the transformation efficiency by a factor of about 15-20, attributable to the loss of the natural plasmid pNF2.

The transformation efficiency has also been tested for the plasmid pEC750C, which confers thiamphenicol resistance, only in the strains DSM 6423 ΔcatB (IFP962 ΔcatB) and DSM 6423 ΔcatB ΔpNF2 (IFP963 ΔcatB ΔpNF2), since the wild-type strain is resistant to this antibiotic (FIG. 31). For this plasmid, the gain in transformation efficiency is even more striking (improvement by a factor of about 2000).

Comparison of the Transformation Efficiencies of the Plasmids pNF3 with Other Plasmids In order to determine the transformation efficiency of plasmids containing the replication origin of the natural plasmid pNF2, the plasmids pNF3E and pNF3C were introduced into the strain *C. beijerinckii* DSM 6423 ΔcatB ΔpNF2. The use of vectors containing erythromycin or chloramphenicol resistance genes makes it possible to compare the transformation efficiency of the vector depending on the nature of the resistance gene. The plasmids pFW01 and pEC750C were also transformed. These two plasmids contain resistance genes to different antibiotics (erythromycin and thiamphenicol respectively) and are commonly used for transforming *C. beijerinckii* and *C. acetobutylicum*.

As shown in FIG. 32, the vectors based on pNF3 have an excellent transformation efficiency, and are usable in particular in *C. beijerinckii* DSM 6423 ΔcatB ΔpNF2. In particular, pNF3E (which contains an erythromycin resistance gene) shows an transformation efficiency far greater than that of pFW01, which comprises the same resistance gene. This same plasmid could not be introduced into the wild-type strain *C. beijerinckii* DSM 6423 (0 colonies obtained with 5 μg of plasmids transformed in biological duplicate), which demonstrates the effect of the presence of the natural plasmid pNF2.

Verification of the Transformability of the Plasmids pNF3 in Other Strains/Species To illustrate the possibility of using this new plasmid in other solventogenic strains of *Clostridium*, the inventors carried out a comparative analysis of the transformation efficiencies of the plasmids pFW01, pNF3E and pNF3S in the ABE strain *C. beijerinckii* NCIMB 8052 (FIG. 33). The strain NCIMB 8052 being naturally resistant to thiamphenicol, pNF3S, conferring spectinomycin resistance, was used in place of pNF3C.

The results demonstrate that the strain NCIMB 8052 is transformable with the plasmids based on pNF3, which proves that these vectors are applicable to the species *C. beijerinckii* in the broad sense.

The applicability of the suite of synthetic vectors based on pNF3 was also tested in the reference strain DSM 792 of *C. acetobutylicum*. A transformation test thus showed that it is possible to transform this strain by means of the plasmid pNF3C (Transformation efficiency of 3 colonies observed per μg of DNA transformed against 120 colonies/μg for the plasmid pEC750C).

Verification of the Compatibility of the Plasmids pNF3 with the Genetic Tool Described in Application FR18/73492

Patent application FR18/73492 describes the strain ΔcatB as well as the use of a CRISPR/Cas9 system with two plasmids requiring the use of an erythromycin resistance gene and a thiamphenicol resistance gene. To demonstrate the advantage of the new suite of plasmids pNF3, the vector pNF3C was transformed into the strain ΔcatB already containing the plasmid pCas9$_{acr}$. The transformation, carried out in duplicate, showed an transformation efficiency of 0.625±0.125 colonies/μg of DNA (mean±standard error), which proves that a vector based on pNF3C can be used in combination with pCas9$_{acr}$ in the strain ΔcatB.

In parallel with these results, a part of the plasmid pNF2 comprising its replication origin (SEQ ID NO: 118) could be reused successfully for creating a new suite of shuttle vectors (SEQ ID NO: 119, 123, 124 and 125), modifiable at will, in particular allowing their replication in a strain of *E. coli* as well as their reintroduction in *C. beijerinckii* DSM 6423. These new vectors have advantageous transformation efficiencies for carrying out gene editing for example in *C. beijerinckii* DSM 6423 and derivatives thereof, in particular using the CRISPR/Cas9 tool comprising two different nucleic acids.

These new vectors could also be tested successfully in another strain of *C. beijerinckii* (NCIMB 8052), and *Clostridium* species (in particular *C. acetobutylicum*), demonstrating their applicability in other organisms of the phylum Firmicutes. A test was also carried out on *Bacillus*.

Conclusions

These results demonstrate that suppression of the natural plasmid pNF2 significantly increases the transformation frequencies of the bacterium that contained it (by a factor of about 15 for pFW01 and by a factor of about 2000 for pEC750C). This result is particularly interesting in the case of bacteria of the genus *Clostridium*, which are known to be difficult to transform, and in particular for the strain *C. beijerinckii* DSM 6423, which has a low transformation efficiency naturally (lower than 5 colonies/μg of plasmid).

REFERENCES

Banerjee, A., Leang, C., Ueki, T., Nevin, K. P., & Lovley, D. R. (2014). Lactose-inducible system for metabolic engineering of *Clostridium ljungdahlii. Applied and environmental microbiology,* 80(8), 2410-2416.

Chen J.-S., Hiu S. F. (1986) Acetone-butanol-isopropanol production by *Clostridium beijerinckii* (synonym, *Clostridium butylicum*). Biotechnol. Lett. 8:371-376.

Cui, L., & Bikard, D. (2016). Consequences of Cas9 cleavage in the chromosome of *Escherichia coli. Nucleic acids research,* 44(9), 4243-4251.

Currie, D. H., Herring, C. D., Guss, A. M., Olson, D. G., Hogsett, D. A., & Lynd, L. R. (2013). Functional heterologous expression of an engineered full length CipA from *Clostridium thermocellum* in *Thermoanaerobacterium saccharolyticum. Biotechnology for biofuels,* 6(1), 32.

DiCarlo, J. E., Norville, J. E., Mali, P., Rios, X., Aach, J., & Church, G. M. (2013). Genome engineering in *Saccharomyces cerevisiae* using CRISPR-Cas systems. *Nucleic acids research,* 41(7), 4336-4343.

Dong, H., Tao, W., Zhang, Y., & Li, Y. (2012). Development of an anhydrotetracycline-inducible gene expression system for solvent-producing *Clostridium acetobutylicum*: A useful tool for strain engineering. *Metabolic engineering,* 14(1), 59-67.

Dong, D., Guo, M., Wang, S., Zhu, Y., Wang, S., Xiong, Z., . . . & Huang, Z. (2017). Structural basis of CRISPR-SpyCas9 inhibition by an anti-CRISPR protein. *Nature,* 546(7658), 436.

Dupuy, B., Mani, N., Katayama, S., & Sonenshein, A. L. (2005). Transcription activation of a UV-inducible *Clostridium perfringens* bacteriocin gene by a novel σ factor. *Molecular microbiology,* 55(4), 1196-1206.

Egholm, M., Buchardt, O., Nielsen, P. E., & Berg, R. H. (1992). Peptide nucleic acids (PNA). Oligonucleotide analogs with an achiral peptide backbone. *Journal of the American Chemical Society,* 114(5), 1895-1897.

Fonfara, I., Le Rhun, A., Chylinski, K., Makarova, K. S., Lecrivain, A. L., Bzdrenga, J., . . . & Charpentier, E. (2013). Phylogeny of Cas9 determines functional exchangeability of dual-RNA and Cas9 among orthologous type II CRISPR-Cas systems. *Nucleic acids research,* 42(4), 2577-2590.

Garcia-Doval C, Jinek M. Molecular architectures and mechanisms of Class 2 CRISPR-associated nucleases. Curr Opin Struct Biol. 2017 December; 47:157-166. doi: 10.1016/j.sbi.2017.10.015 Ajouter au projet Citavi par DOI. Epub 2017 Nov. 3. Review.

George H. A., Johnson J. L., Moore W. E. C., Holdeman, L. V., Chen J. S. (1983) Acetone, Isopropanol, and Butanol Production by *Clostridium beijerinckii* (syn. *Clostridium butylicum*) and *Clostridium aurantibutyricum*. Appl. Env. Microbiol. 45:1160-1163.

Gonzales y Tucker R D, Frazee B. View from the front lines: an emergency medicine perspective on clostridial infections in injection drug users. Anaerobe. 2014 December; 30:108-15.

Hartman, A. H., Liu, H., & Melville, S. B. (2011). Construction and characterization of a lactose-inducible promoter system for controlled gene expression in *Clostridium perfringens. Applied and environmental microbiology,* 77(2), 471-478.

Heap, J. T., Ehsaan, M., Cooksley, C. M., Ng, Y. K., Cartman, S. T., Winzer, K., & Minton, N. P. (2012). Integration of DNA into bacterial chromosomes from plasmids without a counter-selection marker. *Nucleic acids research,* 40(8), e59-e59.

Heap, J. T., Kuehne, S. A., Ehsaan, M., Cartman, S. T., Cooksley, C. M., Scott, J. C., & Minton, N. P. (2010). The ClosTron: mutagenesis in *Clostridium* refined and streamlined. *Journal of microbiological methods,* 80(1), 49-55.

Heap, J. T., Pennington, O. J., Cartman, S. T., Carter, G. P., & Minton, N. P. (2007). The ClosTron: a universal gene knock-out system for the genus *Clostridium. Journal of microbiological methods,* 70(3), 452-464.

Heap, J. T., Pennington, O. J., Cartman, S. T., & Minton, N. P. (2009). A modular system for *Clostridium* shuttle plasmids. *Journal of microbiological methods,* 78(1), 79-85.

Hidalgo-Cantabrana, C., O'Flaherty, S., & Barrangou, R. (2017). *CRISPR-based engineering of next-generation lactic acid bacteria*. Current opinion in microbiology, 37, 79-87.

Hiu S. F., Zhu C.-X., Yan R.-T., Chen J.-S. (1987) Butanol-ethanol dehydrogenase and butanol-ethanol-isopropanol dehydrogenase: different alcohol dehydrogenases in two strains of *Clostridium beijerinckii* (*Clostridium butylicum*). Appl. Env. Microbiol. 53:697-703.

Huang, H., Chai, C., Li, N., Rowe, P., Minton, N. P., Yang, S., & Gu, Y. (2016). CRISPR/Cas9-based efficient genome editing in *Clostridium ljungdahlii*, an autotrophic gas-fermenting bacterium. *ACS synthetic biology,* 5(12), 1355-1361.

Huggins, A. S., Bannam, T. L. and Rood, J. I. (1992) Comparative sequence analysis of the catB gene from *Clostridium butylicum*. Antimicrob. Agents Chemother. 36, 2548-2551.

Ismaiel A. A., Zhu C. X., Colby G. D., Chen, J. S. (1993). Purification and characterization of a primary-secondary alcohol dehydrogenase from two strains of *Clostridium beijerinckii*. J. Bacteriol. 175:5097-5105.

Jinek, M., Chylinski, K., Fonfara, I., Hauer, M., Doudna, J. A., & Charpentier, E. (2012). A programmable dual-RNA-guided DNA endonuclease in adaptive bacterial immunity. *Science,* 337(6096), 816-821.

Jones D. T., Woods D. R. (1986) Acetone-butanol fermentation revisited. Microbiological Reviews 50:484-524.

Kolek J., Sedlar K., Provaznik I., Patakova P. (2016). Dam and Dcm methylations prevent gene transfer into *Clostridium pasteurianum* NRRL B-598: development of methods for electrotransformation, conjugation, and sonoporation. Biotechnol Biofuels. 9:14.

Li, Q., Chen, J., Minton, N. P., Zhang, Y., Wen, Z., Liu, J., . . . & Gu, Y. (2016). CRISPR-based genome editing and expression control systems in *Clostridium acetobutylicum* and *Clostridium beijerinckii. Biotechnology journal,* 11(7), 961-972.

Makarova, K. S., Haft, D. H., Barrangou, R., Brouns, S. J., Charpentier, E., Horvath, P., . . . & Van Der Oost, J. (2011). Evolution and classification of the CRISPR-Cas systems. *Nature Reviews Microbiology,* 9(6), 467.

Makarova, K. S., Wolf, Y. I., Alkhnbashi, 0. S., Costa, F., Shah, S. A., Saunders, S. J., . . . & Horvath, P. (2015). An updated evolutionary classification of CRISPR-Cas systems. *Nature Reviews Microbiology,* 13(11), 722.

Marino, N. D., Zhang, J. Y., Borges, A. L., Sousa, A. A., Leon, L. M., Rauch, B. J., . . . & Bondy-Denomy, J. (2018). Discovery of widespread type I and type V CRISPR-Cas inhibitors. *Science,* 362(6411), 240-242.

Máté de Gérando, H., Wasels, F., Bisson, A., Clément, B., Bidard, F., Jourdier E., Lopez-Contreras A., Lopes Ferreira N. (2018). Genome and transcriptome of the natural isopropanol producer *Clostridium beijerinckii* DSM 6423. BMC genomics. 19:242.

Mearls, E. B., Olson, D. G., Herring, C. D., & Lynd, L. R. (2015). Development of a regulatable plasmid-based gene expression system for *Clostridium thermocellum. Applied microbiology and biotechnology,* 99(18), 7589-7599.

Mermelstein, L. D., & Papoutsakis, E. T. (1993). In vivo methylation in *Escherichia coli* by the *Bacillus subtilis* phage phi 3T I methyltransferase to protect plasmids from restriction upon transformation of *Clostridium acetobutylicum* ATCC 824. *Applied and environmental microbiology,* 59(4), 1077-1081.

Mermelstein L. D., Welker N. E., Bennett G. N., Papoutsakis E. T. (1992). Expression of cloned homologous fermentative genes in *Clostridium acetobutylicum* ATCC 824 10:190-195.

Mermelstein L. D., Welker N. E., Bennett G. N., Papoutsakis E. T. (1993). Expression of cloned homologous fermentative genes in *Clostridium acetobutylicum* ATCC 824 10:190-195.

Moon H G, Jang Y S, Cho C, Lee J, Binkley R, Lee S Y. One hundred years of clostridial butanol fermentation. FEMS Microbiol Lett. 2016 February; 363(3).

Nagaraju, S., Davies, N. K., Walker, D. J. F., Kopke, M., & Simpson, S. D. (2016). Genome editing of *Clostridium autoethanogenum* using CRISPR/Cas9. *Biotechnology for biofuels,* 9(1), 219.

Nariya, H., Miyata, S., Kuwahara, T., & Okabe, A. (2011). Development and characterization of a xylose-inducible gene expression system for *Clostridium perfringens. Applied and environmental microbiology,* 77(23), 8439-8441.

Newcomb, M., Millen, J., Chen, C. Y., & Wu, J. D. (2011). Co-transcription of the celC gene cluster in *Clostridium thermocellum. Applied microbiology and biotechnology,* 90(2), 625-634.

Pawluk, A., Davidson, A. R., & Maxwell, K. L. (2018). Anti-CRISPR: Discovery, mechanism and function. *Nature Reviews Microbiology,* 16(1), 12

Poehlein A., Solano J. D. M., Flitsch S. K., Krabben P., Winzer K., Reid S. J., Jones D. T., Green E., Minton N. P., Daniel R., Dürre P. (2017). Microbial solvent formation revisited by comparative genome analysis. Biotechnol Biofuels. 10:58.

Pyne, M. E., Bruder, M. R., Moo-Young, M., Chung, D. A., & Chou, C. P. (2016). Harnessing heterologous and endogenous CRISPR-Cas machineries for efficient markerless genome editing in *Clostridium. Scientific reports,* 6.

Rauch, B. J., Silvis, M. R., Hultquist, J. F., Waters, C. S., McGregor, M. J., Krogan, N. J., & Bondy-Denomy, J. (2017). Inhibition of CRISPR-Cas9 with bacteriophage proteins. *Cell,* 168(1-2), 150-158.

Rajewska M., Wegrzyn K, Konieczny I., FEMS Microbiol Rev. 2012 March; 36(2). *AT-rich region and repeated sequences—the essential elements of replication origins of bacterial replicons:*408-34.

Ransom, E. M., Ellermeier, C. D., & Weiss, D. S. (2015). Use of mCherry red fluorescent protein for studies of protein localization and gene expression in *Clostridium difficile. Applied and environmental microbiology,* 81(5), 1652-1660.

Rogers P., Chen J.-S., Zidwick M. (2006) in The prokaryotes. 3rd edition, Vol. 1, edited by Dworkin M (Springer, New York, USA, 2006). 3rd edition, Vol. 1, pp. 672-755.

Schwarz S, Kehrenberg C, Doublet B, Cloeckaert A. Molecular basis of bacterial resistance to chloramphénicol and florfenicol. FEMS Microbiol Rev. 2004 November; 28(5):519-42.

Stella S, Alcón P, Montoya G. Class 2 CRISPR-Cas RNA-guided endonucleases: Swiss Army knives of genome editing. Nat Struct Mol Biol. 2017 November; 24(11): 882-892. doi: 10.1038/nsmb.3486.

Wang, S., Dong, S., Wang, P., Tao, Y., & Wang, Y. (2017). Genome Editing in *Clostridium saccharoperbutylacetonicum* N1-4 with the CRISPR-Cas9 System. *Applied and Environmental Microbiology,* 83(10), e00233-17.

Wang Y, Li X, Milne C B, et al. Development of a gene knockout system using mobile group II introns (Targetron) and genetic disruption of acid production pathways in *Clostridium beijerinckii. Appl Environ Microbiol.* 2013; 79(19): 5853-63.

Wang, Y. et al. Markerless chromosomal gene deletion in *Clostridium beijerinckii* using CRISPR/Cas9 system. *J. Biotechnol.* 2015. 200: 1-5.

Wang, Y., Zhang, Z. T., Seo, S. O., Lynn, P., Lu, T., Jin, Y. S., & Blaschek, H. P. (2016). Bacterial genome editing with CRISPR-Cas9: deletion, Integration, single nucleotide modification, and desirable "clean" mutant selection in *Clostridium beijerinckii* as an example. *ACS synthetic biology,* 5(7), 721-732.

Wasels, F., Jean-Marie, J., Collas, F., López-Contreras, A. M., & Ferreira, N. L. (2017). A two-plasmid inducible CRISPR/Cas9 genome editing tool for *Clostridium acetobutylicum*. Journal of microbiological methods. 140:5-11.

Xu, T., Li, Y., Shi, Z., Hemme, C. L., Li, Y., Zhu, Y., . . . & Zhou, J. (2015). Efficient genome editing in *Clostridium cellulolyticum* via CRISPR-Cas9 nickase. *Applied and environmental microbiology,* 81(13), 4423-4431.

Yadav, R., Kumar, V., Baweja, M., & Shukla, P. (2018). *Gene editing and genetic engineering approaches for advanced probiotics*: A Review. Critical reviews in food science and nutrition, 58(10), 1735-1746.

Yue Chen, Bruce A. McClane, Derek J. Fisher, Julian I. Rood, Phalguni Gupta; Construction of an Alpha Toxin Gene Knockout Mutant of *Clostridium perfringens* Type A by Use of a Mobile Group II Intron; Appl. Environ. Microbiol. November 2005, 71 (11) 7542-7547; DOI: 10.1128/AEM.71.11.7542-7547.2005.

Zhang, J., Liu, Y. J., Cui, G. Z., & Cui, Q. (2015). A novel arabinose-inducible genetic operation system developed for *Clostridium cellulolyticum. Biotechnology for biofuels,* 8(1), 36.

Zhang C., Tinggang L. Jianzhong H. (2018) Characterization and genome analysis of a butanol-isopropanol-producing *Clostridium beijerinckii* strain BGS1. Biotechnol Biofuels (2018) 11:280.

Zhong, J., Karberg, M., & Lambowitz, A. M. (2003). Targeted and random bacterial gene disruption using a group II intron (targetron) vector containing a retrotransposition-activated selectable marker. *Nucleic acids research,* 31(6), 1656-1664.

The invention claimed is:

1. A bacterium *C. beijerinckii* deposited under deposit number LMG P-31277 with BCCM-LMG or a genetically modified version thereof, wherein said genetically modified version is sensitive to an amphenicol and lacks pNF2.

2. The bacterium according to claim 1, wherein said bacterium is *C. beijerinckii* deposited under deposit number LMG P-31277 with BCCM-LMG.

3. The bacterium according to claim 1, wherein said bacterium is a genetically modified version of *C. beijerinckii* deposited under deposit number LMG P-31277 with BCCM-LMG, wherein said genetically modified version is sensitive to an amphenicol and lacks pNF2.

* * * * *